United States Patent
Arvela et al.

(10) Patent No.: US 9,533,952 B2
(45) Date of Patent: Jan. 3, 2017

(54) N-PROP-2-YNYL CARBOXAMIDE DERIVATIVES AND THEIR USE AS TRPA1 ANTAGONISTS

(71) Applicant: Orion Corporation, Espoo (FI)

(72) Inventors: Riina Arvela, Turku (FI); Terhi Heikkinen, Lieto (FI); Patrik Holm, Lielahti (FI); Peteris Prusis, Turku (FI); Mattias Roslund, Turku (FI); Harri Salo, Turku (FI)

(73) Assignee: ORION CORPORATION, Espoo (FI)

( * ) Notice: Subject to any disclaimer, the term of this patent is extended or adjusted under 35 U.S.C. 154(b) by 0 days.

(21) Appl. No.: 14/674,940

(22) PCT Filed: Sep. 30, 2013

(86) PCT No.: PCT/FI2013/000034
§ 371 (c)(1),
(2) Date: Mar. 31, 2015

(87) PCT Pub. No.: WO2014/053694
PCT Pub. Date: Apr. 10, 2014

(65) Prior Publication Data
US 2015/0376130 A1    Dec. 31, 2015

Related U.S. Application Data

(60) Provisional application No. 61/708,330, filed on Oct. 1, 2012.

(51) Int. Cl.
| | | |
|---|---|---|
| C07C 237/30 | (2006.01) |
| C07D 317/58 | (2006.01) |
| C07D 417/12 | (2006.01) |
| C07C 323/63 | (2006.01) |
| C07D 213/82 | (2006.01) |
| C07D 209/08 | (2006.01) |
| C07D 319/18 | (2006.01) |
| A61K 31/166 | (2006.01) |
| C07C 255/58 | (2006.01) |
| C07D 333/38 | (2006.01) |
| C07C 237/44 | (2006.01) |
| C07D 239/42 | (2006.01) |
| C07D 213/81 | (2006.01) |
| C07D 215/48 | (2006.01) |
| C07D 405/12 | (2006.01) |
| A61K 31/277 | (2006.01) |
| A61K 31/357 | (2006.01) |
| A61K 31/4439 | (2006.01) |
| A61K 31/444 | (2006.01) |
| A61K 31/455 | (2006.01) |
| A61K 31/472 | (2006.01) |
| A61K 31/505 | (2006.01) |
| A61K 31/5377 | (2006.01) |
| C07C 255/60 | (2006.01) |
| C07D 217/02 | (2006.01) |
| C07D 401/12 | (2006.01) |

(52) U.S. Cl.
CPC .......... *C07D 213/82* (2013.01); *A61K 31/166* (2013.01); *A61K 31/277* (2013.01); *A61K 31/357* (2013.01); *A61K 31/444* (2013.01); *A61K 31/4439* (2013.01); *A61K 31/455* (2013.01); *A61K 31/472* (2013.01); *A61K 31/505* (2013.01); *A61K 31/5377* (2013.01); *C07C 237/30* (2013.01); *C07C 237/44* (2013.01); *C07C 255/58* (2013.01); *C07C 255/60* (2013.01); *C07C 323/63* (2013.01); *C07D 209/08* (2013.01); *C07D 213/81* (2013.01); *C07D 215/48* (2013.01); *C07D 217/02* (2013.01); *C07D 239/42* (2013.01); *C07D 317/58* (2013.01); *C07D 319/18* (2013.01); *C07D 333/38* (2013.01); *C07D 401/12* (2013.01); *C07D 405/12* (2013.01); *C07D 417/12* (2013.01); *C07C 2101/02* (2013.01); *C07C 2101/04* (2013.01); *C07C 2101/14* (2013.01)

(58) Field of Classification Search
CPC .. A61K 31/277; A61K 31/455; A61K 31/357; C07D 319/18; C07D 213/82; C07D 217/02
USPC ......................................................... 546/297
See application file for complete search history.

(56) References Cited

FOREIGN PATENT DOCUMENTS

| WO | WO 2004/060286 A2 | 7/2004 |
| WO | WO 2009/118596 A2 | 10/2009 |

(Continued)

OTHER PUBLICATIONS

Chemical Abstracts STN Registry Database record for RN 141278-35-5, entered May 15, 1992.*

(Continued)

*Primary Examiner* — Noble Jarrell
*Assistant Examiner* — Daniel Carcanague
(74) *Attorney, Agent, or Firm* — Finnegan, Henderson, Farabow, Garrett & Dunner, L.L.P.

(57) ABSTRACT

Compounds of formula I, wherein A, B, X, Z and $R_1$-$R_6$, are as defined in the claims, exhibit TRPA 1 activity and are thus useful as TRPA1 modulators.

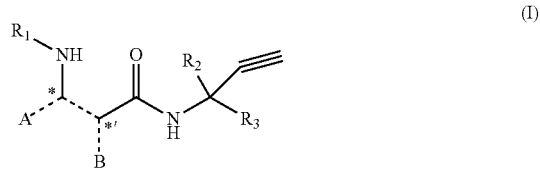

(I)

17 Claims, No Drawings

(56) References Cited

FOREIGN PATENT DOCUMENTS

| | | |
|---|---|---|
| WO | WO 2009/144548 A1 | 12/2009 |
| WO | WO 2009/147079 A1 | 12/2009 |
| WO | WO 2010/004390 A1 | 1/2010 |
| WO | WO 2010/075353 A1 | 7/2010 |
| WO | WO 2010/109287 A1 | 9/2010 |
| WO | WO 2010/109328 A1 | 9/2010 |
| WO | WO 2010/109329 A1 | 9/2010 |
| WO | WO 2010/109334 A2 | 9/2010 |
| WO | WO 2010/125469 A1 | 11/2010 |
| WO | WO 2010/132838 A1 | 11/2010 |
| WO | WO 2010/138879 A1 | 12/2010 |
| WO | WO 2010/141805 A1 | 12/2010 |
| WO | WO 2011/043954 A1 | 4/2011 |
| WO | WO 2011/114184 A1 | 9/2011 |
| WO | WO 2011/132017 A1 | 10/2011 |
| WO | WO 2012/085662 A1 | 6/2012 |
| WO | WO2015144976 * | 10/2015 |
| WO | WO2015144977 * | 10/2015 |

OTHER PUBLICATIONS

Reisch; Monatshefte fur Chemie 1992, 123, 247-250.*
Reisch; J Het Chem 1989, 26, 1495.*
Brederson; European Journal of Pharmacology 2013, 716, 61-76.*
Radresa; The Open Pain Journal, 2013, 6, Suppl1 M14, 137-153.*
Bautista; Annu. Rev. Physiol. 2013, 75, 181-200.*
Rech; Future Med Chem. 2010, 2, 843-858.*
Cao; PLoS One 2012, 7, e38005, 1-10.*
Chaplan, S. R. et al.; "Quantitative Assessment of Tactile Allodynia in The Rat Paw"; Journal of Neuroscience Methods; vol. 53, pp. 55-63; 1994.
Da Costa, D. S. M. et al.; "The Involvement of the Transient Receptor Potential A1 (TRPA1) In the Maintenance of Mechanical and Cold Hyperalgesia in Persistent Inflammation"; PAIN; vol. 148, pp. 431-437; 2010.
Dixon, W. J.; "Efficient Analysis of Experimental Observations"; Ann. Rev. Pharmacol. Toxicol.; vol. 20, pp. 441-462; 1980.
Kopka, I. E. et al.; "Preparation of a Series of Highly Hindered Secondary Amines, Including Bis(triethylcarbinyl)amine"; Journal of Organic Chemistry; vol. 45, pp. 4616-4622; 1980.
Petrus, M. et al.; "A Role of TRPA1 in Mechanical Hyperalgesia is Revealed by Pharmacological Inhibition"; Molecular Pain; vol. 3, p. 40; 2007.
Wei, H. et al.; "Attenuation of Mechanical Hypersensitivity by an Antagonist of The TRPA1 Ion Channel in Diabetic Animals"; Anesthesiology; vol. 111. No. 1, pp. 147-154; 2009.
Reisch, J. et al., "Reaction of N-Methylisatoic Anhydride With Acetylenic Amines: Formation of Oxazoles and Quinazolinones," *Pharmazie* (1992) 47:18-20.
Vallin, Karl S. A., et al.: "N-1-Alkyl-2-oxo-2-aryl amides as novel antagonists of the TRPA1 receptor"; Bioorganic & Medicinal Letters; vol. 22, No. 17; pp. 5485-5492; Sep. 1, 2012.
International Search Report for International Application No. PCT/FI2013/000034, mailed Jan. 14, 2014.

* cited by examiner

N-PROP-2-YNYL CARBOXAMIDE DERIVATIVES AND THEIR USE AS TRPA1 ANTAGONISTS

This is a national stage application under §371 of International Patent Application No. PCT/FI2013/000034, filed Sep. 30, 2013, which claims the benefit of U.S. Provisional Patent Application No. 61/708,330, filed Oct. 1, 2012, both of which are incorporated herein by reference.

TECHNICAL FIELD

The present disclosure relates to pharmacologically active arylamide derivatives, or pharmaceutically acceptable salts and esters thereof, as well as to pharmaceutical compositions comprising them and to their use in the treatment of diseases linked to the activation of the TRPA1 (Transient Receptor Potential subfamily A, member 1) receptors.

BACKGROUND OF THE INVENTION

Human TRPA1 was first cloned from lung fibroblasts. TRPA1 was functionally characterized as a calcium permeable nonselective cation channel that is selectively localized to pain sensing peptidergic unmyelinated sensory neurons, which coexpress TRPV1, substance P and CGRP. TRPA1 exists in both peripheral and central terminals of sensory neurons Amino acid sequence comparison revealed that TRPA1 is a member of the transient receptor potential ion channel superfamily. A recent study finds a somewhat broader expression of TRPA1 even in myelinated fibers.

Studies in healthy animals suggest that TRPA1 is not activated under physiological conditions. Acute administration of TRPA1 agonists such as mustard oil and cinnamaldehyde to the skin causes acute pain and nocifensive behavior in healthy animals and man. Several pathophysiological conditions such as acute and chronic neuropathic pain, diabetes, cancer, inflammation, asthma, arthritis, migraine, osteoarthritis, sleep deprivation, and bladder dysfunction are known to have increased production of endogenous reactive compounds such as 4-hydroxynonenal, acetaldehyde, hydrogen peroxide, prostaglandin J2, prostaglandin A2, methylglyoxal, which are known to act as TRPA1 agonists. Interestingly, several TRPA1 agonists also can be produced through an oxidative stress-related non-enzymatic route.

TRPA1 is a nonselective catkin channel With substantial calcium permeability. TRPA1 is activated through an unusual mechanism in which reactive compounds bind covalently to cysteine and lysine amino acid residues in the N-terminus of the channel protein. Pathophysiological sustained TRPA1 activation by reactive agonists in sensory neurons may result in axoplasmic calcium dysregulation which causes peripheral axonopathy. Axonopathy is a common diagnostic finding in chronic pain patients and patients suffering from work-related exposure to neurotoxic compounds. Axonopathy of sensory neurons is often diagnosed in diabetic patients, who suffer from chronic pain, mechanical hypersensitivity, erectile dysfunction, impaired wound healing, numbness, and at later stage, from leg amputations.

Activation of presynaptic TRPA1 facilitates glutamate release from axon terminals of sensory neurons in the spinal cord. Enhanced glutamate release is shown to cause central pain and secondary mechanical hypersensitivity. Spontaneous pain, secondary mechanical hypersensitivity, and mechanical hyperalgesia are common symptoms of neuropathic pain patients. Recently, human TRPA1 gain-of-function mutation carriers were discovered and shown to have enhanced secondary hyperalgesia to peripheral TRPA1 stimulation, which confirms the role of spina TRPA1 in processing of secondary hyperalgesia. A recent study revealed that spinal TRPA1 plays a key role in neurogenic inflammation reflex, which is evoked by peripheral injury. Neurogenic inflammation is enhanced in several diseases such as fibromyalgia, migraine, complex regional pain syndromes, pain in and around the eye, and urticaria.

TRPA1 activation in the gastrointestinal tract has been shown to release serotonin from enterochromaffin cells. Increased serotonin release induces hypermotility of the gut. Treatment of cancer with reactive compounds increases plasma serotonin level, which is well known to induce nausea and vomiting. TRPA1 activation in airways has been shown to contribute to sensory neuronal hypersensitivity in several airway diseases such as chronic cough, asthma, and chronic obstructive pulmonary disease. TRPA1 activation has been shown to release noradrenaline from superior cervical ganglion sympathetic neurons. Several cardiovascular disorders such as cardiac dysrhythmias and high blood pressure, are well known to be caused by increased plasma noradrenaline level. TRPA1 has been shown to play a critical role in histamine-independent itch transduction. TRPA1 activation has been shown to result in cold hypersensitivity. Cold pain is a common symptom present in several disease conditions such as dental pain, fibromyalgia, complex regional pain, syndrome, cancer pain, and neuropathic pain. Selective TRPA1 modulators can be used for treatment of a large number of acute and chronic TRPA1 activation-dependent diseases and symptoms.

Various TRPA1 modulators have been described earlier, for example, in the international publications WO 2009/118596, WO 2009/144548, WO 2009/147079, WO 2010/004390, WO 2010/075353, WO 2010/109287, WO 2010/109329, WO 2010/109328, WO 2010/109334, WO 2010/125469, WO 2010/132838, WO 2010/138879, WO 2010/141805, WO 2011/043954, WO2011/132017, WO2011/114184 and WO2012/085662. WO2004/060286 discloses certain benzamide derivatives for the treatment of pain and traumatic injury.

SUMMARY OF THE INVENTION

An object of the present disclosure is to provide novel TRPA1 modulators that can be used for the treatment of disorders, conditions, or diseases mediated by TRPA1 activity. Accordingly, an object of the present disclosure is to provide further compounds to be used as TRPA1 modulators in the treatment of mammals. Furthermore, pharmaceutical compositions comprising the presently disclosed compounds are also provided.

The TRPA1 modulators of the present disclosure have an enhanced potency and/or improved metabolic stability and/or improved solubility.

DETAILED DESCRIPTION OF THE INVENTION

The present disclosure relates to novel TRPA1 modulators having the general formula I,

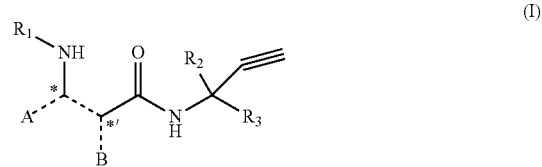

wherein

A and B form, together with the atoms to which they are attached,

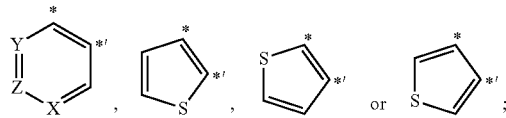

wherein the atoms marked with * and *' are bonded to the parent molecular moiety;

X is $CR_5$ or N;
Y is $CR_6$ or N;
Z is $CR_4$ or N, provided that when Y or X is N, then Z is not N;
$R_1$ is $(C_1-C_6)$alkyl, cyclo$(C_3-C_6)$alkyl, halo$(C_1-C_6)$alkyl, $(C_1-C_6)$alkoxy$(C_1-C_6)$alkyl, halo$(C_1-C_6)$alkoxy$(C_1-C_6)$alkyl, $(C_1-C_5)$alkyl-S—$(C_1-C_6)$alkyl, heterocyclyl, heterocyclyl$(C_1-C_3)$alkyl, phenyl, phenyl$(C_1-C_3)$alkyl, or phenoxy$(C_1-C_6)$alkyl, wherein said cyclo$(C_3-C_6)$alkyl, heterocyclyl, or phenyl is unsubstituted or substituted with 1 or 2 substituent(s) each independently being halogen, $(C_1-C_5)$alkyl, halo$(C_1-C_5)$alkyl, $(C_1-C_5)$alkoxy, cyclo$(C_3-C_6)$alkyl, CN, halo$(C_1-C_5)$alkoxy, $(C_1-C_5)$alkyl-S—, $(C_1-C_5)$alkyl-(S=O)—, $(C_1-C_5)$alkyl-(O=S=O)—, $(C_1-C_3)$alkylamino or di$(C_1-C_3)$alkylamino;
$R_2$ is $(C_1-C_6)$alkyl;
$R_3$ is $(C_1-C_6)$alkyl;
$R_4$ is H, halogen, $(C_1-C_6)$alkyl, $(C_1-C_6)$alkoxy, halo$(C_1-C_6)$alkyl, halo$(C_1-C_6)$alkoxy, $(C_1-C_6)$alkoxy$(C_1-C_6)$alkoxy, $(C_1-C_6)$alkyl-S—, $(C_1-C_6)$alkylamino, halo$(C_1-C_6)$alkylamino, $(C_1-C_6)$alkyl(C=O), CN, or heterocyclyl;
$R_5$ is H, halogen, $(C_1-C_6)$alkyl, cyclo$(C_3-C_6)$alkyl, $(C_1-C_6)$alkoxy, halo$(C_1-C_6)$alkyl, $(C_1-C_6)$alkoxy$(C_1-C_6)$alkyl, halo$(C_1-C_6)$alkoxy, $(C_1-C_6)$alkoxy$(C_1-C_6)$alkoxy, $(C_1-C_6)$alkyl-S—, $(C_1-C_6)$alkyl-(S=O)—, $(C_1-C_6)$alkyl-(O=S=O)—, halo$(C_1-C_6)$alkyl-S—, halo$(C_1-C_6)$alkylamino, $(C_1-C_6)$alkyl-(C=O), or CN; and
$R_6$ is H, halogen, $(C_1-C_6)$alkyl, or halo$(C_1-C_6)$alkyl;
or $R_1$ and $R_6$ form, together with the atoms to which they are attached, a condensed 5 or 6 membered saturated or unsaturated heterocyclic ring containing, in addition to the nitrogen atom to which $R_1$ is attached, 0 or 1 further heteroatom selected from N, O, and S, wherein said heterocyclic ring is unsubstituted or substituted with 1 or 2 substituent(s) each independently being $(C_1-C_2)$alkyl or halogen;
or $R_4$ and $R_5$ form, together with the carbon ring atoms to which they are attached, a condensed 5, 6, or 7 membered saturated or unsaturated carbocyclic ring or a condensed 5, 6, or 7 membered saturated or unsaturated heterocyclic ring containing 1 or 2 heteroatom(s) selected from N, O, and S, wherein said carbocyclic or heterocyclic ring is unsubstituted or substituted with 1 or 2 substituent(s) each independently being $(C_1-C_2)$alkyl or halogen;
or a pharmaceutically acceptable salt or ester thereof;
with the proviso that the compound is not 2-(methylamino)-N-(2-methylbut-3-yn-2-yl)benzamide or N-(2-methylbut-3-yn-2-yl)-2-(propylamino)benzamide.

In at least one embodiment,
A and B form, together with the atoms to which they are attached,

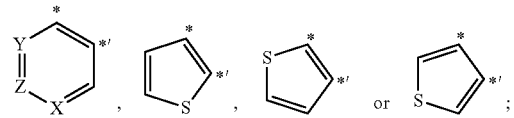

wherein,
X is $CR_5$ or N;
Y is $CR_6$ or N;
Z is $CR_4$ or N;
$R_1$ is $(C_1-C_6)$alkyl, cyclo$(C_3-C_6)$alkyl, halo$(C_1-C_6)$alkyl, $(C_1-C_6)$alkoxy$(C_1-C_6)$alkyl, halo$(C_1-C_6)$alkoxy$(C_1-C_6)$alkyl, heterocyclyl, heterocyclyl$(C_1-C_3)$alkyl, phenyl, phenyl$(C_1-C_3)$alkyl, or phenoxy$(C_1-C_6)$alkyl, wherein said cyclo$(C_3-C_6)$alkyl, heterocyclyl, or phenyl is unsubstituted or substituted with 1 or 2 substituent(s) each independently being halogen, $(C_1-C_3)$alkyl, halo$(C_1-C_3)$alkyl, $(C_1-C_3)$alkoxy, cyclo$(C_3-C_6)$alkyl, or CN;
$R_2$ is $(C_1-C_6)$alkyl;
$R_3$ is $(C_1-C_6)$alkyl;
$R_4$ is H, halogen, $(C_1-C_6)$alkyl, $(C_1-C_6)$alkoxy, halo$(C_1-C_6)$alkyl, CN, or heterocyclyl;
$R_5$ is H, halogen, $(C_1-C_6)$alkyl, $(C_1-C_6)$alkoxy, halo$(C_1-C_6)$alkyl, halo$(C_1-C_6)$alkoxy, $(C_1-C_6)$alkyl-S—, or CN; and
$R_6$ is H or halogen;
or $R_1$ and $R_6$ form, together with the atoms to which they are attached, a condensed 5 or 6 membered saturated or unsaturated heterocyclic ring containing, in addition to the nitrogen atom to which $R_1$ is attached, 0 further heteroatoms, wherein said heterocyclic ring is unsubstituted or substituted with 2 substituent(s) each independently being $(C_1-C_2)$alkyl;
or $R_4$ and $R_5$ form, together with the carbon ring atoms to which they are attached, a condensed 5, 6, or 7 membered saturated heterocyclic ring containing 1 or 2 heteroatom(s) which are O, wherein said heterocyclic ring is unsubstituted.

In another embodiment, A and B form, together with the atoms to which they are attached,

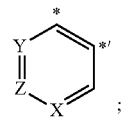

wherein,
X is $CR_5$ or N;
Y is $CR_6$ or N;
Z is $CR_4$ or N;
$R_1$ is $(C_1-C_6)$alkyl, cyclo$(C_3-C_6)$alkyl, halo$(C_1-C_6)$alkyl, $(C_1-C_6)$alkoxy$(C_1-C_6)$alkyl, halo$(C_1-C_6)$alkoxy$(C_1-C_6)$alkyl, heterocyclyl, heterocyclyl$(C_1-C_3)$alkyl, phenyl, phenyl$(C_1-C_3)$alkyl, or phenoxy$(C_1-C_6)$alkyl, wherein said cyclo$(C_3-C_6)$alkyl, heterocyclyl, or phenyl is unsubstituted or substituted with 1 or 2 substituent(s) each independently being halogen, $(C_1-C_3)$alkyl, halo$(C_1-C_3)$alkyl, $(C_1-C_3)$alkoxy, or cyclo$(C_3-C_6)$alkyl;
$R_2$ is $(C_1-C_6)$alkyl;
$R_3$ is $(C_1-C_6)$alkyl;
$R_4$ is H, halogen, $(C_1-C_6)$alkyl, $(C_1-C_6)$alkoxy, halo$(C_1-C_6)$alkyl, CN or heterocyclyl;
$R_5$ is H, halogen, $(C_1-C_6)$alkyl, $(C_1-C_6)$alkoxy, halo$(C_1-C_6)$alkyl, halo$(C_1-C_6)$alkoxy, $(C_1-C_6)$alkyl-S—, or CN; and $R_6$ is H or halogen;

or $R_1$ and $R_6$ form, together with the atoms to which they are attached, a condensed 5 or 6 membered saturated or unsaturated heterocyclic ring containing, in addition to the nitrogen atom to which $R_1$ is attached, 0 further heteroatoms, wherein said heterocyclic ring is unsubstituted or substituted with 2 substituent(s) each independently being $(C_1-C_2)$alkyl;

or $R_4$ and $R_5$ form, together with the carbon ring atoms to which they are attached, a condensed 5, 6 or 7 membered saturated heterocyclic ring containing 1 or 2 heteroatom(s) which are O, wherein said heterocyclic ring is unsubstituted.

In another embodiment,

X is $CR_5$ or N;
Y is $CR_6$ or N;
Z is $CR_4$;
$R_1$ is $(C_1-C_6)$alkyl, cyclo$(C_3-C_6)$alkyl, halo$(C_1-C_6)$alkyl, $(C_1-C_6)$alkoxy$(C_1-C_6)$alkyl, halo$(C_1-C_6)$alkoxy$(C_1-C_6)$alkyl, or phenyl, wherein said cyclo$(C_3-C_6)$alkyl, or phenyl is unsubstituted or substituted with 1 or 2 substituent(s) each independently being halogen, $(C_1-C_3)$alkyl, or $(C_1-C_3)$alkoxy;
$R_2$ is $(C_1-C_3)$alkyl;
$R_3$ is $(C_1-C_3)$alkyl;
$R_4$ is H, halogen, $(C_1-C_4)$alkoxy, or halo$(C_1-C_4)$alkyl;
$R_5$ is H, halogen, $(C_1-C_4)$alkyl, $(C_1-C_4)$alkoxy, halo$(C_1-C_4)$alkyl, halo$(C_1-C_4)$alkoxy or $(C_1-C_4)$alkyl-S—; and
$R_6$ is H or halogen;

In another embodiment,

X is $CR_5$ or N;
Y is $CR_6$ or N;
Z is $CR_4$;
$R_1$ is, $(C_1-C_6)$alkyl, cyclo$(C_3-C_6)$alkyl, halo$(C_1-C_6)$alkyl, or phenyl, wherein said cyclo$(C_3-C_6)$alkyl; or phenyl is unsubstituted or substituted with 1 or 2 substituent(s) each independently being halogen, $(C_1-C_3)$alkyl, or $(C_1-C_3)$alkoxy;
$R_2$ is $(C_1-C_3)$alkyl;
$R_3$ is $(C_1-C_3)$alkyl;
$R_4$ is H, halogen, $(C_1-C_4)$alkoxy or halo$(C_1-C_4)$alkyl;
$R_5$ is H, halogen, $(C_1-C_4)$alkyl, $(C_1-C_4)$alkoxy, halo$(C_1-C_4)$alkyl, halo$(C_1-C_4)$alkoxy or $(C_1-C_4)$alkyl-S—; and
$R_6$ is H or halogen.

In another embodiment,

X is $CR_5$;
Y is $CR_6$;
Z is $CR_4$;
$R_1$ is, $(C_1-C_6)$alkyl, cyclo$(C_3-C_6)$alkyl, halo$(C_1-C_6)$alkyl, or phenyl, wherein said cyclo$(C_3-C_6)$alkyl, or phenyl is unsubstituted or substituted with 1 or 2 substituent(s) each independently being halogen, $(C_1-C_2)$alkyl, or $(C_1-C_2)$alkoxy;
$R_2$ is $(C_1-C_2)$alkyl;
$R_3$ is $(C_1-C_2)$alkyl;
$R_4$ is H, halogen; $(C_1-C_2)$alkoxy or halo$(C_1-C_2)$alkyl;
$R_5$ is H, halogen, $(C_1-C_2)$alkyl, $(C_1-C_2)$alkoxy, halo$(C_1-C_2)$alkyl, halo$(C_1-C_2)$alkoxy or $(C_1-C_2)$alkyl-S—; and
$R_6$ is H or halogen.

In another embodiment,

X is $CR_5$;
Y is N;
Z is $CR_4$;
$R_1$ is, $(C_1-C_6)$alkyl, cyclo$(C_3-C_6)$alkyl, halo$(C_1-C_6)$alkyl, or phenyl, wherein said cyclo$(C_3-C_6)$alkyl, or phenyl is unsubstituted or substituted with 1 or 2 substituent(s) each independently being halogen, $(C_1-C_2)$alkyl, or $(C_1-C_2)$alkoxy;
$R_3$ is $(C_1-C_2)$alkyl;
$R_4$ is H, halogen, $(C_1-C_2)$alkoxy or halo$(C_1-C_2)$alkyl; and
$R_5$ is H, halogen, $(C_1-C_2)$alkyl, $(C_1-C_2)$alkoxy, halo$(C_1-C_2)$alkyl, halo$(C_1-C_2)$alkoxy or $(C_1-C_2)$alkyl-S—.

In another embodiment,

X is $CR_5$ or N;
Y is $CR_6$ or N;
Z is $CR_4$;
$R_1$ is phenyl, wherein said phenyl is unsubstituted or substituted with 1 or 2 substituent(s) each independently being halogen, $(C_1-C_3)$alkyl or $(C_1-C_3)$alkoxy;
$R_2$ is $(C_1-C_3)$alkyl;
$R_3$ is $(C_1-C_3)$alkyl;
$R_4$ is H, halogen, $(C_1-C_4)$alkoxy, or halo$(C_1-C_4)$alkyl;
$R_5$ is H, halogen, $(C_1-C_4)$alkyl, $(C_1-C_4)$alkoxy, halo$(C_1-C_4)$alkyl, halo$(C_1-C_4)$alkoxy, or $(C_1-C_4)$alkyl-S—; and
$R_6$ is H or halogen.

In yet another embodiment,

X is $CR_5$;
Y is N;
Z is $CR_4$;
$R_1$ is phenyl, wherein said phenyl is unsubstituted or substituted with 1 or 2 substituent(s) each independently being halogen, $(C_1-C_2)$alkyl or $(C_1-C_2)$alkoxy;
$R_2$ is $(C_1-C_2)$alkyl;
$R_3$ is $(C_1-C_2)$alkyl;
$R_4$ is H, halogen, $(C_1-C_2)$alkoxy or halo$(C_1-C_2)$alkyl; and
$R_5$ is H, halogen, $(C_1-C_2)$alkyl, $(C_1-C_2)$alkoxy, halo$(C_1-C_2)$alkyl, halo$(C_1-C_2)$alkoxy or $(C_1-C_2)$alkyl-S—.

In a further embodiment, X is $CR_5$, Y is N, and Z is $CR_4$.
In another embodiment, X is $CR_5$, Y is $CR_6$, and Z is $CR_4$.

In yet another embodiment, the compound of formula I is 5-fluoro-(2-methylbut-3-yn-2-yl)-2-(3,3,3-trifluoropropylamino)nicotinamide, N-(2-methylbut-3-yn-2-yl)-5-(trifluoromethyl)-2-(3,3,3-trifluoropropylamino)nicotinamide, 5-chloro-N-(2-methylbut-3-yn-2-yl)-2-(propylamino)benzamide, 5-chloro-2-(isopropylamino)-N-(2-methylbut-3-yn-2-yl)benzamide, 5-chloro-2-(2,2-trifluoroethylamino)-N-(2-methylbut-3-yn-2-yl)benzamide, N-(2-methylbut-3-yn-2-yl)-7-(3,3,3-trifluoropropylamino)-2,3-dihydrobenzo[b][1,4]dioxine-6-carboxamide, 6-(isobutylamino)-N-(2-methylbut-3-yn-2-yl)benzo[d][1,3]dioxole-5-carboxamide, 8-(isobutylamino)-N-(2-methylbut-3-yn-2-yl)-3,4-dihydro-2H-benzo[b][1,4]dioxepine-7-carboxamide, 7-(isobutylamino)-N-(2-methylbut-3-yn-2-yl)-2,3-dihydrobenzo[b][1,4]dioxine-6=arboxamide, 2-(2,2-difluoroethylamino)-N-(2-methylbut-3-yn-2-yl)-5-(trifluoromethyl)benzamide, N-(2-methylbut-3-yn-2-yl)-2-(trifluoromethyl)-4-(3,3,3-trifluoropropylamino)pyrimidine-5-carboxamide, N-(2-methylbut-3-yn-2-yl)-5-(trifluoromethyl)-2-(3,3,3-trifluoropropylamino)benzamide, 4-chloro-N-(2-methylbut-3-yn-2-yl)-2-(propylamino)benzamide, 5-chloro-N-(2-methylbut-3-yn-2-yl)-2-(2,2,2-trifluoroethylamino)benzamide, 3-fluoro-N-(2-methylbut-3-yn-2-yl)-2-(3,3,3-trifluoropropylamino)benzamide, 3-fluoro-N-(2-methylbut-3-yn-2 yl)-2-(propylamino)-benzamide, 2-(cyclobutylamino)-4,5-difluoro-N-(2-methylbut-3-yn-2-yl)benzamide, N-(2-methylbut-3-yn-2-yl)-2-(2,2,3,3,3-pentafluoropropylamino)-5-(trifluoro methyl)benzamide, N-(2-methylbut-3-yn-2-yl)-2-(2,2,3,3,3-pentafluoropropylamino)benzamide, 2-(2,2-difluoroethylamino)-5-fluoro-N-(3-methylpent-1-yn-3-yl)nicotinamide, 2-(cyclobutylamino)-3-fluoro-N-(2-methylbut-3-yn-2-yl)benzamide, 5-fluoro-N-(2-methylbut-3-yn-2-yl)-2-(2,2,2-trifluoroethylamino)

benzamide, 2-(cyclobutylamino)-N-(2-methylbut-3-yn-2-yl)-5-(trifluoromethyl)benzamide, 2-(cyclobutylamino)-5-fluoro-N-(2-methylbut-3-yn-2-yl)benzamide, 2-(cyclobutylamino)-5-fluoro-N-(2-methylbut-3-yn-2-yl)nicotinamide, 5-chloro-2-(isopropylamino)-N-(2-methylbut-3-yn-2-yl)nicotinamide, 5-chloro-2-(cyclobutylamino)-N-(2-methylbut-3-yn-2-yl)nicotinamide, 2-(isopropylamino)-N-(2-methylbut-3-yn-2-yl)-5-(trifluoromethyl)nicotinamide, 5-fluoro-N-(2-methylbut-3-yn-2-yl)-2-(2,2,3,3,3-pentafluoropropylamino)nicotinamide, 5-methyl-N-(2-methylbut-3-yn-2-yl)-2-(2,2,3,3,3-pentafluoropropylamino)benzamide, 5-fluoro-N-(2-methylbut-3-yn-2-yl)-2-(2,2,3,3,3-pentafluoropropylamino)benzamide, 5-chloro-2-(2,2-difluoroethylamino)-N-(2-methylbut-3-yn-2-yl)nicotinamide, 5-fluoro-N-(2-methylbut-3-yn-2-yl)-2-(2,2,2-trifluoroethylamino)nicotinamide, 5-chloro-N-(2-methylbut-3-yn-2-yl)-2-(2,2,2-trifluoroethylamino)nicotinamide, N-(2-methylbut-3-yn-2-yl)-2-(2,2,2-trifluoroethylamino)-5-(trifluoromethyl)nicotinamide, 5-cyano-2-(cyclobutylamino)-N-(2-methylbut-3-yn-2-yl)benzamide, 4-cyano-2-(cyclobutylamino)-N-(2-methylbut-3-yn-2-yl)benzamide, 4,5-difluoro-N-(2-methylbut-3-yn-2-yl)-2-(2,2,2-trifluoroethylamino)benzamide, N-(2-methylbut-3-yn-2-yl)-2-(2,2,2-trifluoroethylamino)-5-(trifluoromethyl)benzamide, 5-methyl-N-(2-methylbut-3-yn-2-yl)-2-(2,2,2-trifluoroethylamino)benzamide, 5-chloro-N-(2-methylbut-3-yn-2-yl)-2-(3,3,3-trifluoropropylamino)nicotinamide, 2-(butylamino)-4,5-difluoro-N-(2-methylbut-3-yn-2-yl)benzamide, 5-bromo-N-(3-ethylpent-1-yn-3-yl)-2-(2-methoxyethylamino)benzamide, 5-chloro-N-(3-ethylpent-1-yn-3-yl)-2-(2-methoxyethylamino)benzamide, N-(3-ethylpent-1-yn-3-yl)-4,5-difluoro-2-(2-methoxyethylamino)benzamide, N-(3-ethylpent-1-yn-3-yl)-2-(2-methoxyethylamino)-5-(trifluoromethyl)benzamide, N-(3-ethylpent-1-yn-3-yl)-5-iodo-2-(2-methoxyethylamino)-benzamide, 2-(2-methoxyethylamino)-N-(2-methylbut-3-yn-2-yl)-5-(trifluoromethyl)-benzamide, 2-(butylamino)-5-fluoro-N-(2-methylbut-3-yn-2-yl)benzamide, 5-iodo-2-(2-methoxyethylamino)-N-(2-methylbut-3-yn-2-yl)benzamide, 5-fluoro-2-(isobutylamino)-N-(2-methylbut-3-yn-2-yl)nicotinamide, 5-fluoro-2-(isopentylamino)-N-(2-methylbut-3yn-2-yl)nicotinamide, 5-fluoro-N-(2-methylbut-3-yn-2-yl)-2-(2-(trifluoromethoxy)ethylamino)-benzamide, 5-fluoro-N-(2-methylbut-3-yn-2-yl)-2-(4,4,4-trifluorobutylamino)benzamide, 3,5-difluoro-N-(2-methylbut-3-yn-2-yl)-2-(3,3,3-trifluoropropylamino)benzamide, 2-(2,2-difluoroethylamino)-N-(2-methylbut-3-yn-2-yl)-5-(trifluoromethyl)nicotinamide, 2-(2,2-difluoropropylamino)-5-fluoro-N-(2-methylbut-3-yn-2-yl)nicotinamide, 2-(3,3-difluoropropylamino)-N-(2-methylbut-3-yn-2-yl)-5-(trifluoromethyl)nicotinamide, 5-chloro-2-(2,2-difluoropropylamino)-N-(2-methylbut-3-yn-2-yl)nicotinamide, 5-chloro-2-(3,3-difluoropropylamino)-N-(2-methylbut-3-yn-2-yl)nicotinamide, 4,5-difluoro-N-(2-methylbut-3-yn-2-yl)-2-(neopentylamino)benzamide, 4,5-difluoro-2-(isobutylamino)-N-(2-methylbut-3-yn-2-yl)benzamide, 4,5-difluoro-N-(2-methylbut-3-yn-2-yl)-2-(propylamino)benzamide, 2-(butylamino)-N-(2-methylbut-3-yn-2-yl)benzamide, 2-(ethylamino)-4,5-difluoro-N-(2-methylbut-3-yn-2-yl)benzamide, 4,5-difluoro-N-(2-methylbut-3-yn-2-yl)-2-(3,3,3-trifluoropropylamino)benzamide, 4,5-difluoro-2-(isopropylamino)-N-(2-methylbut-3-yn-2-yl)benzamide, N-(3,5-dimethylhex-1-yn-3-yl)-4,5-difluoro-2-(isobutylamino)benzamide, N-(3,4-dimethylpent-1-yn-3-yl)-4,5-difluoro-2-(isobutylamino)benzamide, 4,5-difluoro-2-(isobutylamino)-N-(3-methylhex-1-yn-3-yl)benzamide, 4-fluoro-N-(2-methylbut-3-yn-2-yl)-2-(3,3,3-trifluoropropylamino)benzamide, N-(2-methylbut-3-yn-2-yl)-4-(trifluoromethyl)-2-(3,3,3-trifluoropropylamino)benzamide, 4-methoxy-N-(2-methylbut-3-yn-2-yl)-2-(3,3,3-trifluoropropylamino) benzamide, 4-methoxy-N-(2-methylbut-3-yn-2-yl)-2-(propylamino)-benzamide, N-(2-methylbut-3-yn-2-yl)-5-(trifluoromethoxy)-2-(3,3,3-trifluoropropylamino)-benzamide, 5-methoxy-N-(2-methylbut-3-yn-2-yl)-2-(3,3,3-trifluoropropylamino)-benzamide, 5-methyl-N-(2-methylbut-3-yn-2-yl)-2-(3,3,3-trifluoropropylamino) benzamide, N-(2-methylbut-3-yn-2-yl)-5-(methylthio)-2-(3,3,3-trifluoropropylamino)benzamide, N-(2-methylbut-3-yn-2-yl)-2-(3,3,3-trifluoropropylamino)benzamide, 2-(isobutylamino)-N-(2-methylbut-3-yn-2-yl)benzamide, N-(2-methylbut-3-yn-2-yl)-2-(neopentylamino)benzamide, 2-(tert-butylamino)-4,5-difluoro-N-(2-methylbut-3-yn-2-yl)benzamide, 4-fluoro-2-(isopropylamino)-N-(2-methylbut-3-yn-2-yl)benzamide, 2-(methylamino)-N-(2-methylbut-3-yn-2-yl)-4-(trifluoromethyl)benzamide, 2-(methylamino)-N-(2-methylbut-3-yn-2-yl)-5-(trifluoromethoxy)benzamide, 2-(cyclopropylamino)-4,5-difluoro-N-(2-methylbut-3-yn-2-yl)benzamide, N-(3,4-dimethylpent-1-yn-3-yl)-2-(ethylamino)-4,5-difluorobenzamide, 2-(isobutylamino)-4,5-dimethoxy-N-(2-methylbut-3-yn-2-yl)benzamide, 2-(2-methoxy-ethylamino)-N-(2-methylbut-3-yn-2-yl)-4-(trifluoromethyl)benzamide, 2-(cyclopropyl-amino)-4-fluoro-N-(2-methylbut-3-yn-2-yl)benzamide, 2-(cyclopropylamino)-5-fluoro-N-(2-methylbut-3-yn-2-yl)benzamide, 5-fluoro-2-(isopropylamino)-N-(2-methylbut-3-yn-2-yl)benzamide, 2-(isopropylamino)-5-methyl-N-(2-methylbut-3-yn-2-yl)benzamide, 4-methyl-N-(2-methylbut-3-yn-2-yl)-2-(3,3,3-trifluoropropylamino)benzamide, 5-chloro-3-fluoro-2-(isopropylamino)-N-(2-methylbut-3-yn-2-yl)benzamide, 5-methoxy-N-(2-methylbut-3-yn-2-yl)-2-(4,4,4-trifluorobutylamino)benzamide, 2-(3-methoxybenzylamino)-N-(2-methylbut-3-yn-2-yl)nicotinamide, 2-(3-fluorobenzylamino)-N-(2-methylbut-3-yn-2-yl)nicotinamide, N-(2-methylbut-3-yn-2-yl)-2-(propylamino)-6-(trifluoromethyl)-nicotinamide, 2-(butylamino)-N-(2-methylbut-3-yn-2-yl)nicotinamide, 2-(tert-butylamino)-N-(2-methylbut-3-yn-2-yl)nicotinamide, 2-(butylamino)-5-fluoro-N-(3-methylpent-1-yn-3-yl)benzamide, 2-(ethylamino)-N-(3-ethylpent-1-yn-3-yl)-5-fluorobenzamide, 5-fluoro-N-(2-methylbut-3-yn-2-yl)-2-(3,3,3-trifluoropropylamino)benzamide, 2-(isobutylamino)-N-(2-methylbut-3-yn-2-yl)-6-(trifluoromethyl)nicotinamide, 2-(isopropylamino)-N-(2-methylbut-3-yn-2-yl)-6-(trifluoromethyl)nicotinamide, 2-(ethylamino)-N-(2-methylbut-3-yn-2-yl)-6-(trifluoromethyl)nicotinamide, 4-(tert-butylamino)-N-(2-methylbut-3-yn-2-yl)-2-(trifluoro-methyl)pyrimidine-5-carboxamide, N-(2-methylbut-3-yn-2-yl)-4-(tert-pentylamino)-2-(trifluoromethyl)pyrimidine-5-carboxamide, 4-(isopropylamino)-N-(2-methylbut-3-yn-2-yl)-2-(trifluoromethyl)pyrimidine-5-carboxamide, 2-(tert-butylamino)-N-(2-methylbut-3-yn-2-yl)-6-(trifluoromethyl)nicotinamide, 6-chloro-2-(isopropylamino)-N-(2-methylbut-3-yn-2-yl)nicotinamide, 6-chloro-2-(ethylamino)-N-(2-methylbut-3-yn-2-yl)nicotinamide, 5-fluoro-2-(isopropylamino)-N-(2-methylbut-3-yn-2-yl)-6-morpholinonicotinamide, N-(2-methylbut-3-yn-2-yl)-2-(tetrahydro-2H-pyran-4-ylamino)-6-(trifluoromethyl)nicotinamide, N-(2-methylbut-3-yn-2-yl)-2-((tetrahydro-2H-pyran-4-yl)methylamino)-6-(trifluoromethyl)-nicotinamide, 2-(cyclopropylamino)-N-(2-methylbut-3-yn-2-yl)-6-(trifluoromethyl)-nicotinamide, 2,3-dimethyl-N-(2-methylbut-3-yn-2-yl)-1H-indole-7-carboxamide, N-(3-ethylpent-1-yn-3-yl)-1H-indole-7-carboxamide, N-(3-ethylpent-1-yn-3-yl)-

1,2,3,4-tetrahydroquinoline-8-carboxamide, 2-(3-fluorophenylamino)-N-(2-methylbut-3-yn-2-yl)nicotinamide, 2-(2-fluorophenylamino)-N-(2-methylbut-3-yn-2-yl)nicotinamide, 2-(4,4-difluorocyclohexylamino)-N-(2-methylbut-3-yn-2-yl)nicotinamide, 5-bromo-N-(2-methylbut-3-yn-2-yl)-2-(propylamino)benzamide, N-(2-methylbut-3-yn-2-yl)-2-(1,1,1-trifluoro-2-methylpropan-2-ylamino)nicotinamide, N-(2-methylbut-3-yn-2-yl)-4-(propylamino)thiophene-3-carboxamide, N-(2-methylbut-3-yn-2-yl)-2-(phenylamino)-nicotinamide, 2-(tert-butylamino)-N-(2-methylbut-3-yn-2-yl)-5-(trifluoromethyl)-nicotinamide, 5-chloro-N-(2-methylbut-3-yn-2-yl)-2-(phenylamino)nicotinamide, 2-(butylamino)-N-(2-methylbut-3-yn-2-yl)thiophene-3-carboxamide, 2-(4-fluorophenyl-amino)-N-(2-methylbut-3-yn-2-yl)nicotinamide, N-(2-methylbut-3-yn-2-yl)-4-(2,2,3,3,3-pentafluoropropylamino)pyrimidine-5-carboxamide, 2-(3,3-difluorocyclobutylamino)-N-(2-methylbut-3-yn-2-yl)nicotinamide, 3-((4-chlorophenyl)amino)-N-(2-methylbut-3-yn-2-yl)isonicotinamide, 2-(3,3-difluoropropylamino)-3,5-difluoro-N-(2-methylbut-3-yn-2-yl)benzamide, 3-(isobutylamino)-N-(2-methylbut-3-yn-2-yl)thiophene-2-carboxamide, 5-fluoro-N-(2-methylbut-3-yn-2-yl)-2-(3-methylisothiazol-5-ylamino)nicotinamide, 5-chloro-N-(2-methylbut-3-yn-2-yl)-2-(pyridin-3-ylamino)nicotinamide, 5-chloro-2-(3,3-difluorocyclobutylamino)-N-(2-methylbut-3-yn-2-yl)nicotinamide, 2-(6-cyclopentylpyridin-3-ylamino)-5-fluoro-N-(2-methylbut-3-yn-2-yl)nicotinamide, 2-(3,3-difluorocyclo-butylamino)-N-(2-methylbut-3-yn-2-yl)-5-(trifluoromethyl)nicotinamide, N-(2-methylbut-3-yn-2-yl)-2-(phenethylamino)nicotinamide, N-(2-methylbut-3-yn-2-yl)-2-(3-phenylpropyl-amino)nicotinamide, 5-fluoro-2-(3-(4-fluorophenoxy)propylamino)-N-(2-methylbut-3-yn-2-yl)nicotinamide, 5-fluoro-2-(2-(4-fluorophenoxy)ethylamino)-N-(2-methylbut-3-yn-2-yl)nicotinamide, 5-chloro-2-(3-ethoxypropylamino)-N-(2-methylbut-3-yn-2-yl)nicotinamide, 2-(2-tert-butoxyethylamino)-5-chloro-N-(2-methylbut-3-yn-2-yl)nicotinamide, 5-chloro-2-(2-ethoxyethylamino)-N-(2-methylbut-3-yn-2-yl)nicotinamide, 2-(3-fluoro-4-methyl-phenylamino)-N-(2-methylbut-3-yn-2-yl)nicotinamide, 2-(3-chloro-4-methoxyphenyl-amino)-N-(2-methylbut-3-yn-2-yl)nicotinamide, 2-(3,5-difluorophenylamino)-N-(2-methylbut-3-yn-2-yl)nicotinamide, 2-(3,3-difluorocyclobutylamino)-5-(difluoromethyl)-N-(2-methylbut-3-yn-2-yl)nicotinamide, 5-bromo-2-(ethylamino)-N-(2-methylbut-3-yn-2-yl)nicotinamide, 5-ethoxy-N-(2-methylbut-3-yn-2-yl)-2-(propylamino)benzamide, 2-(tert-butylamino)-5-chloro-N-(2-methylbut-3-yn-2-yl)nicotinamide, 2-(3,3-difluorocyclobutyl-amino)-5-fluoro-N-(2-methylbut-3-yn-2-yl)nicotinamide, 5-fluoro-2-(4-fluorophenylamino)-N-(2-methylbut-3-yn-2-yl)nicotinamide, 5-fluoro-N-(2-methylbut-3-yn-2-yl)-2-(1,1,1-trifluoropropan-2-ylamino)nicotinamide, 4-(4-chlorophenylamino)-N-(2-methylbut-3-yn-2-yl)nicotinamide, 5-fluoro-N-(2-methylbut-3-yn-2-yl)-2-(phenylamino)nicotinamide, N-(2-methylbut-3-yn-2-yl)-4-(4-(trifluoromethyl)phenylamino)pyrimidine-5-carboxamide, 2-(tert-butylamino)-5-fluoro-N-(2-methylbut-3-yn-2-yl)nicotinamide, 2-(3,3-difluorocyclobutyl-amino)-N-(3-ethylpent-1-yn-3-yl)-5-fluoronicotinamide, 2-(3,3-difluorocyclobutylamino)-5-fluoro-N-(3-methylpent-1-yn-3-yl)nicotinamide, 2-(3-fluoro-5-methoxyphenylamino)-N-(2-methylbut-3-yn-2-yl)nicotinamide, 2-(3-fluoro-5-methoxyphenylamino)-N-(3-methylpent-1-yn-3-yl)nicotinamide, 2-(3-chloro-5-methoxyphenylamino)-N-(2-methylbut-3-yn-2-yl)nicotinamide, 2-(3-chloro-5-methoxyphenylamino)-N-(3-methylpent-1-yn-3-yl)-nicotinamide, 2-(2-fluoro-3-methoxyphenylamino)-N-(2-methylbut-3-yn-2-yl)nicotinamide, 2-(2-fluoro-3-methoxyphenylamino)-N-(3-methylpent-1-yn-3-yl) nicotinamide, 5-fluoro-2-(4-fluorophenylamino)-N-(3-methylpent-1-yn-3-yl)nicotinamide, 5-fluoro-N-(3-methylpent-1-yn-3-yl)-2-(phenylamino)nicotinamide, 2-(2,4-difluorophenylamino)-N-(2-methylbut-3-yn-2-yl)nicotinamide, 2-(2,4-difluorophenylamino)-N-(3-methylpent-1-yn-3-yl)-nicotinamide, 5-fluoro-2-(3-fluorophenylamino)-N-(2-methylbut-3-yn-2-yl)nicotinamide, 5-fluoro-2-(3-fluorophenylamino)-N-(3-methylpent-1-yn-3-yl)nicotinamide, 5-chloro-2-(3,3-difluorocyclobutylamino)-N-(3-methylpent-1-yn-3-yl)nicotinamide, 2-(3-cyanophenyl-amino)-5-fluoro-N-(3-methylpent-1-yn-3-yl)nicotinamide, 2-(2-fluoro-5-methoxyphenyl-amino)-N-(2-methylbut-3-yn-2-yl)nicotinamide, 2-(2-fluoro-5-methoxyphenylamino)-N-(3-methylpent-1-yn-3-yl)nicotinamide, 2-(3-cyano-4-fluorophenylamino)-N-(2-methylbut-3-yn-2-yl)nicotinamide, 2-(3-cyano-4-fluorophenylamino)-N-(3-methylpent-1-yn-3-yl)-nicotinamide, 2-(3-cyano-5-fluorophenylamino)-N-(2-methylbut-3-yn-2-yl)nicotinamide, 2-(3-fluorophenylamino)-N-(3-methylpent-1-yn-3-yl)nicotinamide, 2-(2-fluorophenylamino)-N-(3-methylpent-1-yn-3-yl)nicotinamide, 2-(3,5-difluorophenylamino)-N-(3-methylpent-1-yn-3-yl) nicotinamide, 2-(3-cyano-5-fluorophenylamino)-N-(3-methylpent-1-yn-3-yl)-nicotinamide, 2-(2-chloro-5-methoxyphenylamino)-N-(2-methylbut-3-yn-2-yl) nicotinamide, 2-(2-chloro-5-methoxyphenylamino)-N-(3-methylpent-1-yn-3-yl)nicotinamide, N-(3-methylpent-1-yn-3-yl)-2-(phenylamino)nicotinamide, 2-(4,4-difluorocyclohexylamino)-N-(3-methylpent-1-yn-3-yl) nicotinamide, 2-(3-chloro-4-methoxyphenylamino)-N-(3-methylpent-1-yn-3-yl)nicotinamide, 2-(4-fluoro-3-methoxyphenylamino)-N-(2-methylbut-3-yn-2-yl) nicotinamide, 2-(4-fluoro-3-methoxyphenylamino)-N-(3-methylpent-1-yn-3-yl)nicotinamide, 2-(3,4-difluorophenylamino)-N-(3-methylpent-1-yn-3-yl) nicotinamide, 2-(4-chloro-3-methoxyphenylamino)-N-(2-methylbut-3-yn-2-yl)nicotinamide, 2-(4-chloro-3-methoxyphenylamino)-N-(3-methylpent-1-yn-3-yl) nicotinamide, or 2-(4-fluorophenylamino)-N-(3-methylpent-1-yn-3-yl)nicotinamide.

The terms employed herein have the meanings indicated below. The term "at least one" employed in the meanings below refers to one or several, such as one. For example, the term "at least one fluorine" refers to one or several fluorines, for example three, two, or one fluorines, such as three fluorines.

The term "halo" or "halogen", as employed herein as such or as part of another group, refers to fluorine, chlorine, bromine, or iodine.

The term "$(C_1-C_2)$alkyl", as employed herein as such or as part of another group, refers to a saturated hydrocarbon group having a straight or branched moiety, containing 1 or 2 carbon atom(s). Representative examples of $(C_1-C_2)$alkyl include methyl and ethyl.

The term "$(C_1-C_3)$alkyl", as employed herein as such or as part of another group, refers to a saturated hydrocarbon group having a straight or branched moiety, containing 1, 2, or 3 carbon atom(s). Representative examples of $(C_1-C_3)$alkyl include methyl, ethyl, n-propyl and isopropyl.

The term "$(C_1-C_4)$alkyl", as employed herein as such or as part of another group, refers to a saturated hydrocarbon group having a straight or branched moiety, containing 1, 2, 3, or 4 carbon atom(s). Representative examples of $(C_1-C_4)$ alkyl include methyl, ethyl, n-propyl, isopropyl, n-butyl, isobutyl, sec-butyl and tert-butyl.

The term "$(C_1-C_5)$alkyl", is employed herein as such or as part of another group, refers to a saturated hydrocarbon group having a straight or branched moiety, containing 1, 2, 3, 4, or 5, carbon atom(s). Representative examples of $(C_1-C_5)$alkyl include, but are not limited to, methyl, ethyl, n-propyl, isopropyl, n-butyl, isobutyl, sec-butyl, tert-butyl, n-pentyl, isopentyl, tert-pentyl, and neopentyl.

The term "$(C_1-C_6)$alkyl", as employed herein as such or as part of another group, refers t a saturated hydrocarbon group having a straight or branched moiety, containing 1, 2, 3, 4, 5, or 6 carbon atom(s). Representative examples of $(C_1-C_6)$alkyl include, but are not limited to, methyl, ethyl, n-propyl, isopropyl, i-butyl, isobutyl, sec-butyl, tert-butyl, n-pentyl, isopentyl, tert-pentyl, neopentyl and n-hexyl.

The term "cyclo$(C_3-C_6)$alkyl", as employed herein as such or as part of another group, refers to a saturated hydrocarbon group having cyclic moiety, containing 3, 4, 5, or 6 carbon atom(s). Representative examples of cyclo$(C_3-C_6)$alkyl include, but are not limited to cyclopropyl, cyclobutyl, cyclopentyl and cyclohexyl.

The term "$(C_1-C_2)$alkoxy", as employed herein as such or as part of another group, refers to an $(C_1-C_2)$alkyl group, as defined herein, bonded to an oxygen atom. Representative examples of $(C_1-C_2)$alkoxy include methoxy and ethoxy.

The term "$(C_1-C_3)$alkoxy", as employed herein as such or as part of another group, refers to an $(C_1-C_3)$alkyl group, as defined herein, bonded to an oxygen atom. Representative examples of $(C_1-C_3)$alkoxy include, but are not limited to, methoxy, ethoxy, and n-propoxy.

The term "$(C_1-C_4)$alkoxy", as employed herein as such or as part of another group, refers to an $(C_1-C_4)$alkyl group, as defined herein, bonded to an oxygen atom. Representative examples of $(C_1-C_4)$alkoxy include, but are not limited to, methoxy, ethoxy, n-propoxy, n-butoxy, isobutoxy, sec-butoxy, and tert-butoxy.

The term "$(C_1-C_5)$alkoxy", as employed herein as such or as part of another group, refers to an $(C_1-C_5)$alkyl group, as defined herein, bonded to an oxygen atom. Representative examples of $(C_1-C_5)$alkoxy include, but are not limited to, methoxy, ethoxy, n-propoxy, n-butoxy, isobutoxy, sec-butoxy, tert-butoxy, 2,2-dimethylpropoxy, and 3-methylbutoxy.

The term "$(C_1-C_6)$alkoxy", as employed herein as such or as part of another group, refers to an $(C_1-C_6)$alkyl group, as defined herein, bonded to an oxygen atom. Representative examples of $(C_1-C_6)$alkoxy include, but are not limited to, methoxy, ethoxy, n-propoxy, n-butoxy, isobutoxy, sec-butoxy, tert-butoxy, 2,2-dimethylpropoxy, 3-methylbutoxy, and n-hexoxy.

The terms "$(C_1-C_2)$alkyl S—", "$(C_1-C_4)$alkyl-S—", "$(C_1-C_5)$alkyl-S—", or "$(C_1-C_6)$alkyl-S—", as employed herein as such or as part of another group, refer to an $(C_1-C_2)$alkyl, $(C_1-C_4)$alkyl, $(C_1-C_5)$alkyl, or $(C_1-C_4)$alkyl group, as defined herein, bonded to a sulfur atom. Representative examples of $(C_1-C_2)$alkyl-S—, $(C_1-C_4)$alkyl-S—, $(C_1-C_5)$alkyl-S—, or $(C_1-C_6)$alkyl-S— include, but are not limited to, thiomethyl, thioethyl, thiopropyl, and thiobutyl.

The term "$(C_1-C_6)$alkyl(C=O)", as employed herein as such or as part of another group, refers to a $(C_1-C_6)$alkyl group, as defined herein, bonded to a carbonyl group. Representative examples include, but are not limited to, acetyl, ethylcarbonyl, propylcarbonyl, and isopropylcarbonyl.

The term "$(C_1-C_6)$alkoxy$(C_1-C_6)$alkyl", as employed herein as such or as part of another group, refers to at least one $(C_1-C_6)$alkoxy group, as defined herein, bonded to an $(C_1-C_6)$alkyl group, as defined herein. When there are several $(C_1-C_6)$alkoxy groups, the $(C_1-C_6)$alkoxy groups can be identical or different. Representative examples of $(C_1-C_6)$alkoxy$(C_1-C_6)$alkyl include, but are not limited to, methoxymethyl, ethoxymethyl, propoxymethyl, 2-methoxyethyl, 2-ethoxyethyl, 2,2-dimethoxyethyl, i-methyl-2-propoxyethyl, 1-methoxy-1-methylethyl, and 4-methoxybutyl.

The term "$(C_1-C_6)$alkyl-S—$(C_1-C_6)$alkyl," as employed herein as such or as part of another group, refers to at least one $(C_1-C_6)$alkyl-S— group, as defined herein, bonded to a $(C_1-C_6)$alkyl group, as defined herein. Representative examples of $(C_1-C_6)$alkyl-S—$(C_1-C_6)$alkyl include, but are not limited to, methylthiomethyl, ethylthiomethyl, propylthiomethyl, 2-methylthioethyl, 2-ethylthioethyl, 2,2-dimethylthioethyl, 1-methyl-2-propylthioethyl, 1-methylthio-1-methylethyl, and 4-methylthiobutyl.

The terms "$(C_1-C_5)$alkyl-(S=O)—" or "$(C_1-C_6)$alkyl-(S=O)—", as employed herein a such or as part of another group, refers to a $(C_1-C_5)$alkyl or $(C_1-C_6)$alkyl group, as defined herein, bonded to a sulfoxide group. Representative examples of $(C_1-C_5)$alkyl-(S=O)— or $(C_1-C_6)$alkyl-(S=O)— include, but are not limited to, methylsulfoxide, ethylsulfoxide, propylsulfoxide, and isopropylsulfoxide.

The terms "$(C_1-C_5)$alkyl-(O=S=O)—" or "$(C_1-C_6)$alkyl-(O=S=O)—", as employed herein as such or as part of another group, refers to a $(C_1-C_5)$alkyl or $(C_1-C_6)$alkyl group, as defined herein, bonded to a sulfone group. Representative examples of $(C_1-C_5)$alkyl-(O=S=O) or $(C_1-C_6)$alkyl-(O=S=O)— include, but are not limited to, methylsulfone, ethylsulfone, propylsulfone, and isopropylsulfone.

The terms "halo$(C_1-C_2)$alkyl", "halo$(C_1-C_3)$alkyl", "halo$(C_1-C_4)$alkyl", "halo$(C_1-C_5)$alkyl", or "halo$(C_1-C_6)$alkyl", as employed herein as such or as part of another group, refer to at least one halogen, as defined herein, bonded to a $(C_1-C_2)$alkyl, $(C_1-C_3)$alkyl, $(C_1-C_4)$alkyl, $(C_1-C_5)$alkyl, or $(C_1-C_6)$alkyl group, as defined herein. When there are several halogens, the halogens can be attached to the same or different carbon atom and the halogens can be identical or different. Representative examples of halo$(C_1-C_2)$alkyl, halo$(C_1-C_3)$alkyl, halo$(C_1-C_4)$alkyl, halo$(C_1-C_5)$alkyl, or halo$(C_1-C_6)$alkyl include, but are not limited to, fluoromethyl, difluoromethyl, trifluoromethyl, 2-fluoroethyl, 2,2-difluoroethyl, 2,2,2-trifluoroethyl, 1,2,2-trifluoroethyl, 3-fluoropropyl, 1,1-difluoropropyl, 1,3-difluoropropyl, 2,2-difluoropropyl, 3,3-difluoropropyl, 3,3,3-trifluoropropyl, 2,2,3,3,3-pentafluoropropyl, 4,4,4-trifluorobutyl, 1,1-trifluoro-2-methylpropanyl, and 1,1,1-trifluoropropan-2-yl.

The term "halo$(C_1-C_6)$alkyl-S-", as employed herein as such or as part of another group, refers to a halo$(C_1-C_6)$alkyl group, as defined herein, bonded to a sulfur atom. Representative examples of halo$(C_1-C_6)$alkyl-S— include, but are not limited to, fluoromethanethiol, 1-fluoroethanethiol, 2-fluoroethanethiol, and 1-fluoropropane-2-thiol.

The terms "halo$(C_1-C_2)$alkoxy", "halo$(C_1-C_4)$alkoxy", "halo$(C_1-C_5)$alkoxy" or "halo$(C_1-C_6)$alkoxy", as employed herein as such or as part of another group, refer to at least one halogen bonded to a $(C_1-C_2)$alkoxy, $(C_1-C_4)$alkoxy, $(C_1-C_5)$alkoxy, or $(C_1-C_6)$alkoxy group, as defined herein. When there are several halogens, the halogens can be attached to the same or different carbon atom and the halogens can be identical or different. Representative examples of halo$(C_1-C_2)$alkoxy, halo$(C_1-C_4)$alkoxy, halo$(C_1-C_5)$alkoxy, or halo$(C_1-C_6)$alkoxy include, but are not limited to, fluoromethoxy, difluoromethoxy, trifluoromethoxy, 2-fluoromethoxy, 2,2,2-trifluoroethoxy, 3-fluoropropoxy, 3,3,3-trifluoropropoxy, and 4-fluorobutoxy.

The term "halo($C_1$-$C_6$)alkoxy($C_1$-$C_6$)alkyl", as employed herein as such or as part of another group, refers to at least one halo($C_1$-$C_6$)alkoxy group, as defined herein, bonded to a ($C_1$-$C_6$)alkyl group, as defined herein. When there are several halo($C_1$-$C_6$)alkoxy groups, the halo($C_1$-$C_6$)alkoxy groups can be attached to the same or different carbon atom and the halo($C_1$-$C_6$)alkoxy groups can be identical or different. Representative examples of halo($C_1$-$C_6$)alkoxy($C_1$-$C_6$)alkyl include, but are not limited to, fluoromethoxymethyl, difluoromethoxymethyl, trifluoromethoxymethyl, and 2-trifluoromethoxyethyl.

The term "($C_1$-$C_6$)alkoxy($C_1$-$C_6$)alkoxy", as employed herein as such or as part of another group, refers to at least one ($C_1$-$C_6$)alkoxy group, as defined herein, bonded to a ($C_1$-$C_6$)alkoxy group, as defined herein. When there are several ($C_1$-$C_6$)alkoxy groups, the ($C_1$-$C_6$)alkoxy groups can be attached to the same or different carbon atom and the ($C_1$-$C_6$)alkoxy groups can be identical or different. Representative examples of ($C_1$-$C_6$)alkoxy-($C_1$-$C_6$)alkoxy include, but are not limited to, methoxymethoxy, propoxymethoxy, 2-methoxyethoxy, 2-ethoxyethoxy, 2-butoxyethoxy, 2,2-dimethoxyethoxy, 1-methyl-2-propoxyethoxy, 2-methoxypropoxy, and 4-methoxybutoxy.

The term "($C_1$-$C_6$)alkylamino", as employed herein as such or as part of another group, refers to one or two ($C_1$-$C_6$)alkyl group(s), as defined herein, bonded to an amino group. When there are two ($C_1$-$C_6$)alkyl groups, the ($C_1$-$C_6$)alkyl groups can be identical or different. Representative examples of ($C_1$-$C_6$)alkylamino include, but are not limited to, N-methylamino, N-ethylamino, N-butylamino, N,N-dimethylamino, and N,N-diethylamino.

The term "halo($C_1$-$C_6$)alkylamino", as employed herein as such or is part of another group, refers to one or two halo($C_1$-$C_6$)alkyl group(s), as defined herein, bonded to an amino group. When there are two halo($C_1$-$C_6$)alkyl groups, the halo($C_1$-$C_6$)alkyl groups can be identical or different. When there is one halo($C_1$-$C_6$)alkyl group, the other group bonded to an amino group can be H or ($C_1$-$C_6$)alkyl. Representative examples of halo($C_1$-$C_6$)alkylamino include, but are not limited to, 3,3,3-trifluoropropylamino and 2,2-difluoroethyl(methyl)amino.

The terms "heterocyclyl" or "heterocyclic ring", as employed herein as such or as part of another group, refer to a 5, 6, or 7 membered saturated or unsaturated monocyclic group containing 1 or 2 ring heteroatom(s) each independently selected from N, O, and S or to an 8, 9, or 10 membered saturated or unsaturated bicyclic group containing 1 or 2 ring heteroatom(s) each independently selected from N, O, and S. Representative examples of heterocyclyl include, but are not limited to, pyrrolidin-1-yl, piperidin-1-yl, 3,6-dihydro-2H-pyran-4-yl, tetrahydro-2H-pyran-4-yl, morpholino, pyridin-3-yl, and 2,3-dihydrobenzofuran-5-yl.

The term "heterocyclyl($C_1$-$C_3$)alkyl", as employed herein as such or as part of another group, refers to a heterocyclyl group, as defined herein, bonded to a ($C_1$-$C_3$)alkyl group, as defined herein. Representative examples of heterocyclyl($C_1$-$C_3$)alkyl include, but are not limited to, (tetrahydro-2H-pyran-4-yl)methyl, morpholinomethyl, and 3-(pyrrolidin-1-yl)propyl.

The term "phenyl($C_1$-$C_3$)alkyl", as employed herein as such or as part of another group, refers to a phenyl group, bonded to a ($C_1$-$C_3$)alkyl group, as defined herein. Representative examples of phenyl($C_1$-$C_3$)alkyl include, but are not limited to, benzyl and phenethyl.

The term "phenyl($C_1$-$C_3$)alkoxy", as employed herein as such or as part of another group, refers to a phenyl group, bonded to a ($C_1$-$C_3$)alkoxy group, as defined herein. Representative examples of phenyl($C_1$-$C_3$)alkoxy include, but are not limited to, phenoxy.

The term "phenyl($C_1$-$C_6$)alkoxy($C_1$-$C_6$)alkyl", as employed herein as such or as part of another group, refers to at least one phenyl($C_1$-$C_6$)alkoxy group, as defined herein, bonded to a ($C_1$-$C_6$)alkyl group, as defined herein. Representative examples of phenyl($C_1$-$C_6$)alkoxy($C_1$-$C_6$)alkyl include, but are not limited to, phenylmethoxymethyl, phenylmethoxyethyl, phenylethoxyethyl, phenylmethoxypropyl, and phenyletoxyethyl.

The term "phenoxy", as employed herein as such or as part of another group, refer to an phenyl group, as defined herein, bonded to an oxygen atom.

The term "phenoxy($C_1$-$C_3$)alkyl", as employed herein as such or as part of another group, refers to a phenoxy group, bonded to a ($C_1$-$C_3$)alkyl group, as defined herein. Representative examples of phenoxy($C_1$-$C_3$)alkyl include, but are not limited to, phenoxymethyl, phenoxyethyl, and phenoxypropyl.

The expression "compound of the present disclosure" as employed herein refers to the compounds of formula I.

The "pharmaceutically acceptable salts" according to the present disclosure include therapeutically active, non-toxic, base and acid salt forms, which the compounds of formula I are able to form with both organic and inorganic bases and acids. Representative examples of pharmaceutically acceptable base addition salt forms, for example, metal or amine salts, include, but are not limited to, ammonium salts, lithium, sodium, potassium, calcium, magnesium, aluminum and zinc salts, salts with organic bases, such as N-methyl-D-glucamine, hydrabamine salts and salts with amino acids, such as arginine, lysine, and the like. Representative examples of pharmaceutically acceptable acid addition salts include, but are not limited to, chlorides, bromides, sulfates, nitrates, phosphates, sulfonates, methane sulfonates, formates, tartrates, maleates, citrates, benzoates, salicylates, ascorbates, acetates and oxalates, fumarates, and succinates.

Pharmaceutically acceptable esters, when applicable, may be prepared by known methods using pharmaceutically acceptable acids that are conventional in the field of pharmaceuticals and that retain the pharmacological properties of the free form. Non-limiting examples of these esters include esters of aliphatic or aromatic alcohols. Representative examples of pharmaceutically acceptable esters include, but are not limited to, methyl, ethyl, n-propyl, isopropyl, n-butyl, isobutyl, sec-butyl, tert-butyl, and benzyl esters.

The present disclosure includes all the possible geometric isomers, for example Z and E isomers (cis and trans isomers), of the compounds, as well as all the possible optical isomers, such as diastereomers and enantiomers, of the compounds. Furthermore, the present disclosure includes both the individual isomers and any mixtures thereof, such as racemic mixture. The individual isomers may be obtained using the corresponding isomeric forms of the starting material or they may be separated after the preparation of the end compound according to conventional separation methods. For the separation of optical isomers, such as enantiomers, from the mixture thereof, conventional resolution methods, for example fractional crystallization or preparative chiral chromatography, may be used.

The compounds of formula I can be prepared by a variety of synthetic routes analogously to, or according to methods known in the literature using suitable starting matetials.

Referring to Scheme 1, the compounds of formula I can be prepared from suitably substituted aromatic 1-amino-2-carboxylic esters (1) Or aromatic 1-halo-2-carboxylic esters (2). Referring to Scheme 2, the same compounds can be prepared from the corresponding carboxylic acids. The substitutent of the amine, $R_1$, can be attached to the aromatic core, for example, using some of the methods A-F.

A. Reductive amination, using a suitable aldehyde and a reducing agent, such as sodium tris(acetoxy)borohydride or sodium cyanoborohydride.

B. Using a two step procedure where the amine is acylated using a suitable acylation method, and subsequently reduced with a suitable reducing agent, such as borane dimethyl sufide complex.

C. When starting material is an ester: alkylation, rising a suitable alkylating agent, such as an alkyl halide or alkyl sulfonate ester.

D. The conditions of the Buchwald-Hartwig reaction, using a suitable amine and a suitable Pd-catalyst system.

E. Aromatic substitution, using a suitable amine, especially when Y is N, and W is F or Cl.

F. The conditions of the copper mediated Ullman reaction, using a suitable amine and a source of Cu(I), when W is Cl, Br, I, or other suitable leaving group.

G. In those cases where an ester is used, the ester is hydrolysed to give the corresponding acid.

H. The carboxylic acid can be converted to an amide using a suitable amine and some of the known amide coupling methods, or by converting the carboxylic acid to the corresponding acyl chloride, to form the amides of formula I.

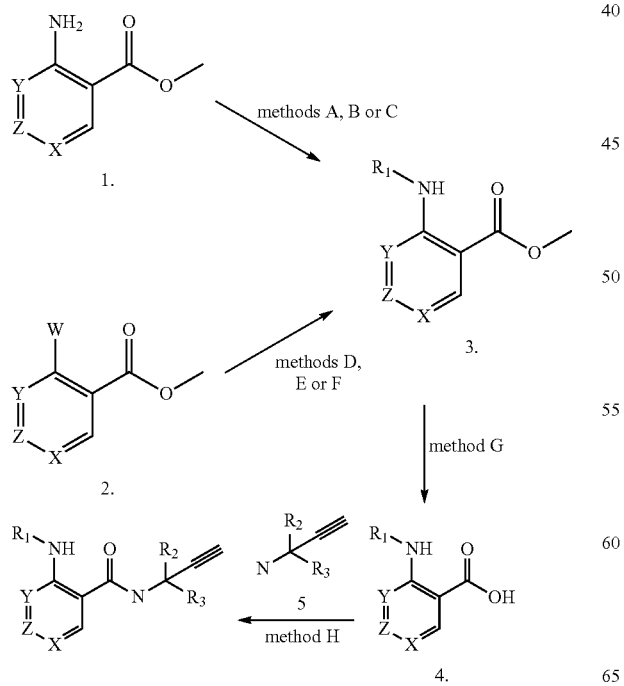

Scheme 1.

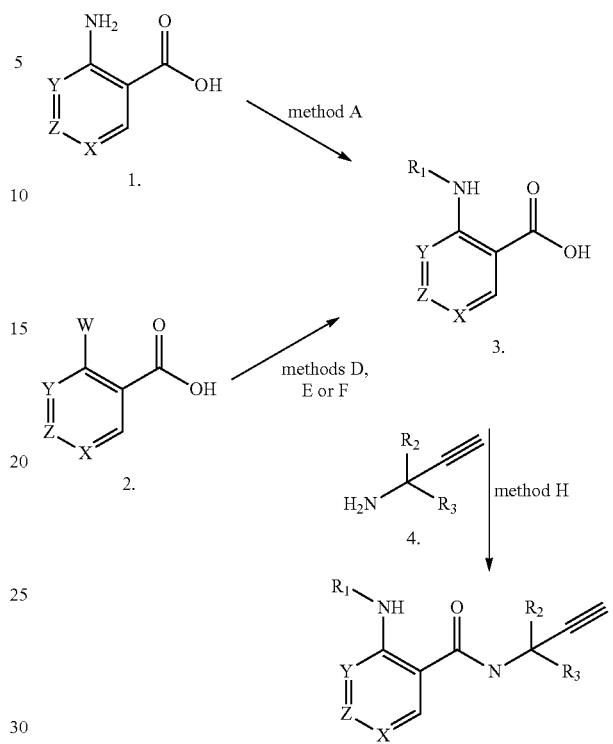

Scheme 2.

Alternatively, the amide coupling reaction can be performed prior to the construction of the aromatic ring substitution pattern and the attachment of the suitable amine substituent.

In similar manner, the above mentioned strategies can be applied when the aromatic core is a five membered heterocycle, such as a tiophene, pyrrole, tiazole, oxazole or pyrazole.

The starting materials depicted above, of formulae I and 2, are commercially available or can be prepared via synthetic routes known in the literature. The required amines of formula 4, branched at the α-position, are commercially available or can be prepared using the method illustrated in Scheme 3. (Kopka et al., *Journal of Organic Chemistry*, 1980, vol. 45, 4616-4622).

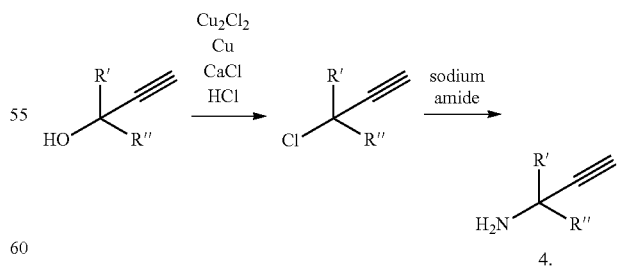

Scheme 3.

A person skilled in the art realizes that any starting material or intermediate in the reactions described above can be protected, if necessary, in a manner known in the art. Any protected functionality can subsequently be deprotected in a manner known in the art.

The synthetic routes described above are meant to illustrate the preparation of the compounds of formula I and the preparation is by no means limited thereto, that is, there are also other possible synthetic methods which are within the general knowledge of a person skilled in the art.

The compounds of formula I may be converted, if desired, into their pharmaceutically acceptable salt or ester forms using methods known in the art.

The present disclosure will be explained in more detail by the following examples. The examples are meant for illustrating purposes only and do not limit the scope of the invention defined in the claims.

Normal phase and reverse phase flash chromatography was performed using CombiFlash instruments together with disposable Redisep columns (Teledyne ISCO). Preparative HPLC purifications were performed with a Waters preparative HPLC/MS autopurification system equipped with an XBridge Prep C18 (5 μm, 30×150 mm) column. Typically, a gradient of water/acetonitrile with 0.1% formic acid was used as eluent. Microwave heating was performed using microwave reactors from Biotage. The structures of the products were confirmed by $^1$H NMR. The spectra were measured with a Bruker Avance 400 instrument. LC-MS analyses were performed using a Waters Acquity UPLC/MS with an SQD or TQ detector, a Waters 2690 Micromass ZQ4000 or an Agilent 1100 Series LC/MS instrument.

The following general abbreviations are used: EDCI=1-(3-dimethylaminopropyl)-3-ethylcarbodiimide hydrochloride, DIPEA=N,N-disopropylethylamine, HOBt=1-hydroxybenzotriazole, DCM=dichloromethane, EtOAc=ethyl acetate, DMF=N,N-dimethylformamide, DCE=1,2-dichloroethane, NMP=N-methylpyrrolidone, MeOD-d=deuterated methanol, CDCl$_3$-d=deuterated chloroform, HATU=(1-[Bis (dimethylamino)-methylene]-1H-1,2,3-triazolo[4,5-b]pyridinium 3-oxid hexafluorophosphate), ACN=acetonitrile, LiHMDS=lithium hexamethyl-disilazide, THF=tetrahydrofuran, BH$_3$-DMS=borane dimethylsulfide.

PREPARATION OF THE COMPOUNDS OF THE PRESENT DISCLOSURE

Example 1

5-Fluoro-N-(2-methylbut-3-yn-2-yl)-2-(3,3,3-trifluoropropylamino)-nicotinamide

Step 1: 5-Fluoro-2-(3,3,3-trifluoropropylamino)nicotinic acid

2-Chloro-5-fluoropyridine-3-carboxylic acid (0.800 g, 4.56 mmol), 3,3,3-trifluoropropylamine hydrochloride (1.022 g, 6.84 mmol), potassium carbonate (1.071 g, 7.75 mmol), copper(I) bromide (0.33 g, 0.228 mmol), copper (0.017 g, 0.273 mmol) and N,N-dimethyl formamide (13 ml) were added to a microwave vial. The reaction mixture was irradiated at 150° C. for 60 minutes at high absorbance. DCM and water were added to the reaction mixture and the mixture was acidified with HCl. The layers were separated and the organic phase was washed twice with water. The organic phase was evaporated to dryness to yield 1.054 g of the title compound.

$^1$H NMR (400 MHz, MeOD-d) δ ppm 2.36-2.61 (m, 2 H) 3.77 (t, 2 H) 7.92-8.12 (m, 1 H) 8.17-8.30 (m, 1 H).

Step 2: 5-Fluoro-N-(2-methylbut-3-yn-2-yl)-2-(3,3,3-trifluoropropylamino) nicotinamide 5-Fluoro-2-(3,3,3-trifluoropropylamino)nicotinic acid (1000 mg, 3.97 mmol), dichloromethane (30 ml), 1-(3-dimethylaminopropyl)-3-ethylcarbodiimide hydrochloride (912 mg, 4.76 mmol), 1-hydroxybenzotriazole (536 mg, 3.97 mmol), N,N-diisopropylethylamine; DIPEA (0.424 mil, 2.432 mmol) and 1,1-dimethylpropargylamine (1.381 ml, 7.93 mmol) were stirred at room temperature for 3 hours. The reaction mixture was washed once with 1M NaOH, 1M HCl and water. The organic phase was dried and evaporated to dryness. The product was purified by flash chromatography to yield 673 mg of the title compound.

$^1$H NMR (400 MHz, CDCl$_3$-d) δ ppm 1.67-1.80 (s, 6 H) 2.34-2.57 (m, 2 H) 2.41 (s, 1 H) 3.62-3.76 (m, 2 H) 5.97 (br. s., 1 H) 7.32 (dd, 1 H) 8.00 (br. s., 1 H) 8.13 (d, 1 H).

Example 2

N-(2-Methylbut-3-yn-2-yl)-5-(trifluoromethyl)-2-(3,3,3-trifluoropropylamino) nicotinamide Step 1: 5-(Trifluoromethyl)-2-(3,3,3-trifluoropropylamino)nicotinic acid A mixture of 2-chloro-5-(trifluoromethyl)pyridine-3-carboxylic acid (0.32 g, 1.42 mmol), 3,3,3-trifluoropropylamine hydrochloride (0.36 g, 2.41 mmol), copper (5.4 mg, 0.085 mmol), copper(I)bromide (10.2 mg, 0.071 mmol) and potassium carbonate (0.32 g, 2.41 mmol) in DMF (2 ml) was heated in a microwave reactor at 150° C. for 2 h. The mixture was diluted with ethyl acetate and washed with 0.5 M citric acid solution. The organic layer was dried over anhydrous sodium sulphate and evaporated. The crude was purified by, reverse phase column chromatography. Yield: 0.102 g.

$^1$H NMR (400 MHz, CD$_3$OD) δ ppm 2.57 (qt, 2 H), 3.86 (t, 2 H), 8.36 d, 1 H), 8.53 (d, 1H).

Step 2: N-(2-Methylbut-3-yn-2-yl)-5-(trifluoromethyl)-2-(3,3,3-trifluoropropylamino)-nicotinamide A mixture of 5-(trifluoromethyl)-2-(3,3,3-trifluoropropylamino)nicotinic acid (102 mg, 0.34 mmol), 1,1-dimethylpropargylamine (0.039 ml, 0.37 mmol), EDCI (78 n g, 0.405), DIPEA (0.12 ml, 0.68 mmol) and HOBt (23 mg, 0.17 mmol) in DME (2 ml) was stirred overnight. The mixture was diluted with water and extracted with EtOAc. The organic layer was washed with 2 M Na$_2$CO$_3$, evaporated to dryness and purified by preparative HPLC. Yield: 61 mg.

$^1$H NMR (400 MHz, CDCl$_3$) δ ppm 1.75 (s, 6 H), 2.40-2.54 (m, 2 H), 2.42 (s, 1H), 3.72-3.81 (m, 2 H), 6.19 (bs, 1 H), 7.68 (d, 1 H), 8.43 (dd, 1 H), 8.62 (t, 1 H).

Example 3

5-Chloro-N-(2-methylbut-3-yn-2-ylbut-3)-2-(propylamino)benzamide

Step 1: 5-Chloro-2-(propylamino)benzoic acid

2-Amino-5-chlorobenzoic acid (1.166 mmol, 0.2 g) was dissolved in dry DCE, propionaldehyde (1.224 mmol, 0.089 ml) and glacial acetic acid (2.91 mmol, 0.167 ml) were added at 0° C. Sodium triacetoxy borohydride (2.331 mmol, 0.494 g) was added in one portion and the reaction mixture was stirred over-night. The reaction mixture was extracted with water and the water-phase was washed with EtOAc. The combined organic-phases were extracted with aqueous Na$_2$CO$_3$ and NaCl and finally dried over Na$_2$SO$_4$, filtered and evaporated. The product was purified by flash chromatography to yield 71 mg of the title compound.

$^1$H NMR (400 MHz, CDCl$_3$) δ ppm 1.03 (t, 3 H) 1.71 (tq, 2 H) 3.17 (t, 2 H) 6.64 (d, 1 H) 7.32 (dd, 1 H) 7.93 (d, 1 H).

Step 2: 5-Chloro-N-(2-methylbut-3-yn-2-yl)-2-(propylamino)benzamide

5-Chloro-2-(propylamino)benzoic acid (0.332 mmol, 71 mg), DIPEA (0.399 mmol, 0.069 ml), HOBT (0.432 mmol, 58.4 mg), 1,1-dimethylpropargylamine (0.399 mmol, 0.042 ml), And EDCI (0.432 mmol, 83 mg) were dissolved in 5 ml DCM. Reaction was stirred over-night and extracted three times with 1 M NaOH. The organic-phase was evaporated to dryness and purified by preparative HPLC to give 35 mg of the title compound.

$^1$H NMR (400 MHz, CDCl$_3$) δ ppm 0.99 (t, 3 H) 1.66 (tq, 2 H) 1.73 (s, 6 H) 2.39 (s, 1 H) 3.07 (t, 2 H) 6.03 (br. s., 1 H) 6.59 (d, 1 H) 7.20 (dd, 1 H) 7.24 (d, 1 H) 7.45 (d, 1 H).

Example 4

5-Chloro-2-(isopropylamino)-N-(2-methylbut-3-yn-2-yl)benzamide

Step 1: 5-Chloro-2-(isopropylamino)benzoic acid 2,5-Dichlorobenzoic acid (1.309 mmol, 250 mg), propan-2-amine (2.62 mmol, 0.223 ml), potassium acetate (2.62 mmol, 257 mg), copper(II) acetate monohydrate (0.131 mmol, 26.1 mg) and triethylamine (1.571 mmol, 0.219 ml) in 3 ml DMF were heated to 180° C. for 50 min using a microwave reactor. Water was added to the reaction mixture and the solution was made acidic with HCl and extracted two times with EtOAc. The organic phase was dried over Na$_2$SO$_4$, filtered and evaporated and used as such without any further purification.

$^1$H NMR (400 MHz, CD$_3$OD) δ ppm 1.25 (d, 6 H) 3.73 (spt, 1 H) 6.75 (d, 1 H) 7.29 (dd, 1 H) 7.81 (d, 1 H).

Step 2: 5-Chloro-2-(isopropylamino)-N-(2-methylbut-3-yn-2-yl)benzamide 405 mg of the 5-chloro-2-(propylamino)benzoic acid reaction mixture, DIPEA (0.682 mmol, 0.119 ml), HOBT (0.739 mmol, 100 mg), 1,1-dimethylpropargylamine (0.682 mmol, 0.072 ml), and EDCI (0.739 mmol, 142 mg) were dissolved in 5 ml DCM. Reaction was stirred over-night, diluted with DCM and extracted three times with 1 M NaOH. The organic-phase was dried over Na$_2$SO$_4$, filtered, evaporated to dryness and purified by preparative HPLC to give 4 mg of the title compound.

$^1$H NMR (400 MHz, CDCl$_3$) δ ppm 1.23 (d, 6 H) 1.73 (s, 6 H) 2.39 (s, 1 H) 3.61 (spt, 1 H) 6.00 (br. s., 1 H) 6.62 (d, 1 H) 7.20 (dd, 1 H) 7.24 (d, 1 H).

Example 5

5-Chloro-2-(2,2-difluoroethylamino)-N-(2-methylbut-3-yn-2-yl)benzamide

Step 1: 5-Chloro-2-(2,2-difluoroethylamino)benzoic acid

Methyl 2,5-dichlorobenzoate (0.975 mmol, 0.2 g), 2,2-difluoroethylamine (1.951 mmol, 0.138 ml), potassium acetate (1.951 mmol, 191 mg), copper(II) acetate monohydrate, (0.098 mmol, 0.019 g) and triethylamine (1.171 mmol, 0.163 ml) in 4 ml DMF were heated to 180° C. for 45 min. using a microwave reactor. The reaction mixture was purified with preparative HPLC to give 84.1 mg of title compound.

$^1$H NMR (400 MHz, CD$_3$OD) δ ppm 3.67 (td, 2 H) 6.01 (tt, 1 H) 6.86 (d, 1 H) 7.34 (dd, 1 H) 7.85 (d, 1 H).

Step 2: 5-Chloro-2-(2,2-difluoroethylamino)-N-(2-methylbut-3-yn-2-yl)benzamide

5-Chloro-2-(2,2-difluoroethylamino)benzoic acid (0.357 mmol, 84.1 mg), DIPEA (0.428 mmol, 0.075 ml), HOBT (0.464 mmol, 62.7 mg), 1,1-dimethylpropargylamine (0.428 mmol, 0.45 ml), and EDCI (0.464 mmol, 89 mg) were dissolved in 5 ml DCM. The reaction mixture was stirred over-night, diluted with DCM and extracted twice with 1 M NaOH. The organic-phase was dried Over Na$_2$SO$_4$, filtered, evaporated to dryness and purified by column chromatography to give 95 mg of the title compound.

$^1$H NMR (400 MHz, CD$_3$OD) δ ppm 1.68 (s, 6 H) 2.67 (s, 1 H) 3.61 (td, 2 H) 6.00 (tt, 1 H) 6.83 (d, 1 H) 7.28 (dd, 1 H) 7.48 (d, 1 H).

Example 6

N-(2-Methylbut-3-yn-2-yl)-7-(3,3,3-trifluoropropylamino)-2,3-dihydrobenzo[b][1,4]dioxine-6-carboxamide Step 1: 7-(3,3,3-Trifluoropropylamino)-2,3-dihydrobenzo[b][1,4]dioxine-6-carboxylic acid 7-Amino-2,3-dihydrobenzo[b][1,4]dioxine-6-carboxylic acid (0.512 mmol, 100 mg) was dissolved in 7 ml dry DCE. 3,3,3-Trifluoropropanal (0.666 mmol, 0.057 ml) and glacial acetic acid (1.281 mmol, 0.073 mil) were added at 0° C. Sodium triacetoxy borohydride (1.025 mmol, 0.217 g) was added in one portion and the reaction mixture was stirred over-night. The reaction mixture was extracted with acidic water and brine, dried over Na$_2$SO$_4$, filtered and evaporated to dryness. The product was used directly without any further purification. The title compound was obtained in quantitative yield.

$^1$H NMR (400 MHz, CD$_3$OD) δ ppm 2.50 (qt, 2 H) 3.44 (t, 2 H) 4.17-4.20 (m, 2 H) 4.27-4.31 (m, 2 H) 6.19 (s, 1 H) 7.41 (s, 1 H).

Step 2: N-(2-Methylbut-3-yn-2-yl)-7-(3,3,3-trifluoropropylamino)-2,3-dihydrobenzo[b][1,4]dioxine-6-carboxamide 7-(3,3,3-Trifluoropropylamino)-2,3-dihydrobenzo[b][1,4]dioxine-6-carboxylic acid (0.512 mmol, 149 mg) DIPEA (0.614 mmol, 0.107 ml), HOBT (0.665 mmol, 90 mg), 1,1-dimethylpropargylamine (0.614 mmol, 0.065 ml), and EDCI (0.665 mmol, 128 nit) were dissolved in 5 nil DCM. Reaction was stirred over-night and extracted twice with 1 M NaOH. The organic-phase was isolated with a phase-separator, evaporated to dryness and purified by column chromatography to give 126 mg of the title compound.

$^1$H NMR (460 MHz, CD$_3$OD) δ ppm 1.66 (s, 6 H) 2.49 (qt, 2 H) 2.64 (s, 1 H) 3.37 (t, 2 H) 4.15-4.21 (m, 2 H) 4.23-4.32 (m, 2 H) 6.21 (s, 1 H) 7.07 (s, 1 H).

Example 7

6-(Isobutylamino)-N-(2-methylbut-3-yn-2-yl)benzo[d][1,3]dioxole-5-carboxamide Step 1: 6-(Isobutylamino)benzo[d][1,3]dioxole-5-carboxylic acid 6-Aminobenzo[d][1,3]dioxole-5-carboxylic acid (0.828 mmol, 150 mg) was dissolved in 7 ml dry DCE. Isobutyraldehyde (0.994 mmol, 0.091 ml) and glacial acetic acid. (2.07 mmol, 0.1 J9 ml), were added at 0° C. Sodium triacetoxy borohydride (1.656 mmol, 351 mg) was added in one portion and the reaction mixture was stirred over-night. The reaction mixture was diluted with DCM, extracted with acidic water and brine and finally dried over $Na_2SO_4$, filtered and evaporated. 143 mg of the title compound was obtained.

$^1$H NMR (400 MHz, $CD_3OD$) δ ppm 1.03 (d, 6 H) 1.93 (spt, 1 H) 2.99 (d, 2 H) 5.89 (s, 2 H) 6.30 (s, 1 H) 7.28 (s, 1 H).

Step 2: 6-(Isobutylamino)-N-(2-methylbut-3-yn-2-yl)benzo[d][1,3]dioxole-5-carboxamide 6-(Isobutylamino)benzo[d][1,3]dioxole-5-carboxylic acid (0.603 mmol, 143 mg), DIPEA (0.723 mmol, 0.126 ml), HOBT (0.784 mmol, 106 mg), 1,1-dimethyl-propargylamine (0.723 mmol, 0.076 ml), and EDCI (0.784 mmol, 150 mg) were dissolved in 5 ml DCM. Reaction was stirred over-night and extracted twice with 1 M NaOH. The organic-phase was isolated with a phase-separator, evaporated to dryness and purified by column chromatography to give 106 mg of the title compound in 58% yield.

$^1$H NMR (400 MHz, $CD_3OD$) δ ppm 1.02 (d, 6 H) 1.66 (s, 6 H) 1.91 (tspt, 1 H) 2.63 (s, 1 H) 2.93 (d, 2 H) 5.87 (s, 2 H) 6.31 (s, 1 H) 7.02 (s, 1 H).

Example 8

8-(Isobutylamino)-N-(2-methylbut-3 yn-2-yl)-3,4-dihydro-2H-benzo[b][1,4]dioxepine-7-carboxamide Step 1: 8-(Isobutylamino)-3,4-dihydro-2H-benzo[b][1,4]dioxepine-7-carboxylic acid 8-Amino-3,4-dihydro-2H-benzo[b][1,4]dioxepine-7-carboxylic acid (0.717 mmol, 150 mg) was dissolved in 7 ml dry DCE. Isobutyraldehyde (0.860 mmol, 0.079 ml) and glacial acetic acid (1.793 mmol, 0.103 ml) were added at 0° C. Sodium triacetoxy borohydride (1.434 mmol, 304 mg) was added in one portion and the reaction mixture was stirred over-night. The reaction mixture was diluted with DCM, extracted with acidic water and brine and finally dried over $Na_2SO_4$, filtered and evaporated. The product was used directly without any further purification. The title compound was obtained in quantitative yield.

$^1$H NMR (400 MHz, $CD_3OD$) δ ppm 1.02 (d, 6 H) 1.92 (tspt, 1 H) 2.00 (s, 1 H) 2.14 (m, 2H) 2.95 (d, 2 H) 4.06 (m, 2 H) 4.21 (m, 2 H) 6.26 (s, 1 H) 7.51 (s, 1 H).

Step 2: 8-(Isobutylamino)-N-(2-methylbut-3-yn-2-yl)-3,4-dihydro-2H-benzo[b][1,4]dioxepine-7-carboxamide 8-(Isobutylamino)-3,4-dihydro-2H-benzo[b][1,4]dioxepine-7-carboxylic acid (0.716 mmol 190 mg), DIPEA (0.859 mmol, 0.150 ml), HOBT (0.931 mmol, 126 mg), 1,1-dimethylpropargylamine (0.859 mmol, 0.090 ml), and EDCI (0.931 mmol, 178 mg) were dissolved in 5 ml DCM. Reaction was stirred over-night and extracted twice with 1 M NaOH. The organic-phase was isolated with a phase-separator, evaporated to dryness and purified by column chromatography and preparative HPLC to give 129.2 mg of the title compound.

$^1$H NMR (400 MHz, $CDCl_3$) δ ppm 0.97 (d, 6 H) 1.71 (s, 6 H) 1.92 (tspt, 1 H) 2.11-2.23 (m, 2 H) 2.36 (s, 1 H) 2.88 (dd, 2 H) 4.04-4.14 (m, 2H) 4.16-4.25 (m, 2 H) 5.92 (s, 1 H) 6.26 (s, 1 H) 6.99 (s, 1 H) 7.49 (br. t., 1 H).

Example 9

7-(Isobutylamino)-N-(2-methylbut-3-yn-2-yl)-2,3-dihydrobenzo[b][1,4]dioxine-6-carboxamide Step 1: 7-(Isobutylamino)-2,3-dihydrobenzo[b][1,4]dioxine-6-carboxylic acid 7-Amino-2,3-dihydrobenzo[b][1,4]dioxine-6-carboxylic acid (0.769 mmol, 150 mg) was dissolved in 7 ml dry DCE. Isobutyraldehyde (0.922 mmol, 0.084 ml) and glacial acetic acid (1.921 mmol, 0.110 ml) were added at 0° C. Sodium triacetoxy borohydride (1.537 mmol, 326 mg) was added in one portion and the reaction mixture was stirred over-night. The reaction mixture was diluted with DCM, extracted with acidic water and brine and finally dried over $Na_2SO_4$, filtered and evaporated. The product was used directly without any further purification. The title compound was obtained in quantitative yield.

$^1$H NMR (400 MHz, $CD_3OD$) δ ppm 1.02 (d, 6 H) 1.92 (tspt, 1 H) 2.93 (d, 2 H) 4.12-4.20 (m, 2 H) 4.23-4.31 (m, 2 H) 6.15 (s, 1 H) 7.38 (s, 1 H).

Step 2: 7-(Isobutylamino)-N-(2-methylbut-3-yn-2-yl)-2,3-dihydrobenzo[b][1,4]dioxine-6-carboxamide 7-(Isobutylamino)-2,3-dihydrobenzo[b][1,4]dioxine-6-carboxylic acid (0.768 mmol, 193 mg), DIPEA (0.922 mmol, 0.161 ml), HOBT (0.998 mmol, 135 mg), 1,1-dimethylpropargylamine (0.922 mmol, 0.097 ml), and EDCI (0.998 mmol, 191 mg) were dissolved in 5 ml DCM. Reaction was stirred over-night and extracted twice with 1 M NaOH. The organic-phase was isolated with a phase-separator, evaporated to dryness and purified by flash chromatography to give 178 mg of the title compound.

$^1$H NMR (400 MHz, $CD_3OD$) δ ppm 1.01 (d, 6 H) 1.66 (s, 6 H) 1.90 (tspt, 1 H) 2.63 (s, 1 H) 2.87 (d, 2 H) 4.14-4.20 (m, 2 H) 4.22-4.27 (m, 2 H) 6.16 (s, 1 H) 7.03 (s, 1 H).

Example 10

2-(2,2-Difluoroethylamino)-N-(2-methylbut-3yn-2-yl)-5-(trifluoromethyl)benzamide Step 1: 2-(2,2-Difluoroethylamino)-5-(trifluoromethyl)benzoic acid 2-Chloro-5-(trifluoromethyl)benzoic acid (1.781 mmol, 0.40 g), 2,2-difluoro-ethanamine (3.56 mmol, 0.251 ml), potassium acetate (3.56 mmol, 0.350 g), copper(II) acetate monohydrate (0.178 mmol, 36 mg), triethylamine (1.781 mmol, 0.248 ml) in 6 ml DMF were heated to 180° C. for 25 min using a microwave reactor. Water was added to the reaction mixture and the solution was extracted twice with EtOAc. The organic-phase was dried over $Na_2SO_4$, filtered, evaporated and purified by flash chromatography to give 238 mg of the title compound in 50% yield.

$^1$H NMR (400 MHz, $CDCl_3$ and $CD_3OD$) δ ppm 3.68 (td, 2 H) 5.94 (tt, 1 H) 6.81 (d, 1 H) 7.58 (dd, 1 H) 8.25 (d, 1 H).

Step 2: 2-(2,2-Difluoroethylamino)-N-(2-methylbut-3-yn-2-yl)-5-(trifluoromethyl)-benzamide 2-(2,2-Difluoroethylamino)-5-(trifluoromethyl)benzoic acid (0.884 mmol, 238 mg), DIPEA (1.061 mmol, 0.185 ml), HOBt (1.149 mmol, 155 mg), 1,1-dimethyl-propargylamine (1.061 mmol, 0.112 ml), and EDCI (1.149 mmol, 220 mg) were dissolved in 5 ml DCM. Reaction was stirred overnight and diluted with DCM, extracted three times 1 M NaOH. The organic-phase was dried over $Na_2SO_4$, filtered, evaporated to dryness and purified by preparative HPLC to give 104.5 mg of the title compound in 35% yield.

$^1$H NMR (400 MHz, $CDCl_3$) δ ppm 1.75 (s, 6 H) 2.41 (s, 1 H) 3.62 (tdd, 2 H) 5.89 (tt, 1 H) 6.16 (br. s., 1 H) 6.79 (d, 1 H) 7.47-7.57 (m, 2 H) 8.32 (br. t., 1 H).

Example 11

N-(2-Methylbut-3-yn-2-yl)-2-(trifluoromethyl)-4-(3,3,3-trifluoropropylamino)pyrimidine-5-carboxamide Step 1: Ethyl 2-(trifluoromethyl)-4-(3,3,3-trifluoropropylamino)pyrimidine-5-carboxylate Ethyl 4-chloro-2-(trifluoromethyl)pyrimidine-5-carboxylate (1.178 mmol, 0.3 g), 3,3,3-trifluoropropylamine hydrochloride (2.357 mmol, 0.352 g) and triethylamine (2.357 mmol, 0.328 ml) in 2 ml EtOH were heated to 160° C. for 30 minutes using a microwave reactor. Solvents were removed under reduced pressure and the water-phase was extracted with EtOAc four times. The combined organic phases were dried over $Na_2SO_4$, filtered and evaporated to dryness to give 349 mg of the title compound.

$^1$H NMR (400 MHz, DMSO-$d_6$) δ ppm 1.34 (t, 3 H) 2.55-2.74 (m, 2 H) 3.80 (td, 2 H) 4.36 (q, 2 H) 8.77 (t, 1 H) 8.89 (d, 1 H).

Step 2: 2-(Trifluoromethyl)-4-(3,3,3-trifluoropropylamino)pyrimidine-5-carboxylic acid Ethyl 2-(trifluoromethyl)-4-(3,3,3-trifluoropropylamino) pyrimidine-5-carboxylate (1.054 mmol, 349 mg), was dissolved in 10 ml THF and 1 ml of a 5M aqueous NaOH solution. The reaction mixture was refluxed for 2 h. THF was removed under reduced pressure and the solution was made acidic and extracted with DCM three times. The organic-phase was dried over $Na_2SO_4$, filtered and evaporated to dryness to give 287 mg of the title compound.

$^1$H NMR (400 MHz, DMSO-$d_6$) δ ppm 2.55-2.73 (m, 2 H) 3.79 (td, 2 H) 8.86 (s, 1 H) 8.90 (t, 1 H) 13.99 (br. s., 1 H).

Step 3: N-(2-Methylbut-3-yn-2-yl)-2-(trifluoromethyl)-4-(3,3,3-trifluoropropylamino)pyrimidine-5-carboxamide 2-(Trifluoromethyl)-4-(3,3,3-trifluoropropylamino)pyrimidine-5-carboxylic acid (0.947 mmol, 287 mg), DIPEA (1.893 mmol, 0.33 ml), HOBt (1.041 mmol, 141 mg), 1,1-dimethylpropargylamine (1.893 mmol, 0.110 ml), and EDCI (1.041 mmol, 210 mg) were dissolved in 5 ml DCM. Reaction was stirred over-night and was then heated to 50° C. for 2 h. The reaction mixture was diluted with DCM, extracted twice with 1 M NaOH. The organic-phase was dried over $Na_2SO_4$, filtered, evaporated to dryness and purified by flash chromatography to give 179.1 mg of the title compound.

$^1$H NMR (400 MHz, $CDCl_3$) δ ppm 1.75 (s, 6 H) 2.43 (s, 1 H) 2.44-2.56 (m, 2 H) 3.82 (dt, 1H) 6.14 (br. s., 1 H) 8.43 (s, 1 H) 8.98 (br. t, 1 H).

Example 12

N-(2-Methylbut-3-yn-2-yl)-5-(trifluoromethyl)-2-(3,33-trifluoropropylamino) benzamide Step 1: 2-Amino-N-(2-methylbut-3-yn-2-yl)-5-(trifluromethyl)benzamide A mixture of 2-amino-5-(trifluoromethyl)benzoic acid (0.25 g, 1.22 mmol), EDCI (0.28 g, 1.46 mmol), DIPEA (0.425 ml, 2.44 mmol) and HOBt (82 mg, 0.609 mmol) in DCM (10 ml) was stirred for 30 minutes. 1,1-Dimethylpropargylamine (0.141 ml, 1.34 mmol) was added. The mixture was stirred for one day, washed with 2M $Na_2CO_3$, dried and evaporated and purified by flash chromatography to give 0.25 g of the title compound.

$^1$H NMR (400 MHz, $CDCl_3$) δ ppm 1.76 (s, 6 H), 2.41 (s, 1 H), 5.94 (bs, 2 H), 6.05 (bs, 1 H), 6.67-6.73 (m, 1 H), 7.38-7.44 (m, 1 H), 7.47-7.51 (m, 1 H).

Step 2: N-(2-Methylbut-3-yn-2-yl)-5-(trifluoromethyl)-2-(3,3,3-trifluoropropylamino) benzamide To a stirred solution of 2-amino-N-(2-methylbut-3-yn-2-yl)-5-(trifluoromethyl)benzamide (0.25 g, 0.92 mmol), 3,3,3-trifluoropropanal (0.15 ml, 1.8 mmol) and glacial acetic acid (0.318 ml, 5.55 mmol) in 1,2-dichloroethane (10 ml) was added sodium triacetoxy borohydride (0.55 g, 2.6 mmol) under $N_2$ atmosphere. The resulting mixture was stirred overnight and neutralized by adding saturated aqueous sodium bicarbonate to pH 7. The mixture was extracted with ethyl acetate. The organic layer was dried over anhydrous sodium sulphate and evaporated. The crude was purified using preparative HPLC to give 88 mg of the title compound.

$^1$H NMR (400 MHz, $CDCl_3$) δ ppm 1.75 (s, 6 H), 2.41 (s, 1 H), 2.41-2.52 (m, 2 H), 3.46-3.53 (m, 2 H), 6.01-6.12 (m, 1 H), 6.69 (d, 1 H), 7.52 (d, 1 H), 8.15 (t, 1 H).

Example 13

4-Chloro-N-(2-methylbut-3-yn-2-yl)-2-(propylamino)benzamide

Step 1: Methyl 4-chloro-2-(propylamino)benzoate

Methyl 2-amino-4-chlorobenzoate (0.5 g, 2.7 mmol), propionaldehyde (0.373 ml, 5.1 mmol) and acetic acid (0.925 ml, 16 mmol) were dissolved in 1,2-dichloroethane (15 ml). Sodium triacetoxy borohydride (1.599 g, 7.54) was added and the mixture was stirred overnight. The reaction was quenched with saturated $NaHCO_3$-solution and extracted with EtOAc. The combined organic layers were dried and evaporated to give 0.621 g of the title compound.

$^1$H NMR (400 MHz, $CDCl_3$) δ ppm 1.02 (t, 3 H), 1.70 (m, 2 H), 3.11 (td, 2 H), 3.83 (s, 3 H), 6.50 (dd, 1 H), 6.63 (d, 1 H), 7.78 (d, 2 H).

Step 2: 4-Chloro-2-(propylamino)benzoic acid

A solution of NaOH (0.1 g, 2.6 mmol) in water (0.5 ml) was added to a solution of methyl 4-chloro-2-(propylamino) benzoate (0.3 g, 1.3 mmol) in THF (3 ml) and heated to 50° C. for 4 h. The solvents were evaporated under reduced pressure. The crude product was diluted with water and extracted with Et$_2$O. The aqueous layer was acidified with dilute HCl solution and stirred for 20 min. The solid precipitate was filtered off and dried. Yield: 0.28 g.

$^1$H NMR (400 MHz, CDCl$_3$) δ ppm 1.03 (t, 3 H), 1.72 (m, 2 H), 3.15 (td, 2 H), 6.5 (dd, 1 H), 6.67 (d, 1 H), 7.88 (d, 1 H).

Step 3: 4-Chloro-N-(2-methylbut-3-yn-2-yl)-2-(propylamino)benzamide

4-Chloro-2-(propylamino)benzoic acid (70 mg, 0.33 mmol), 1,1-dimethylpropargylamine (0.038 ml, 0.36 mmol), EDCI (75 mg, 0.39 mmol), DIPEA (0.114 ml, 0.66 mmol) and HOBt (22 mg, 1.64 mmol) in 5 ml DCM were mixed overnight. The mixture was washed with 2 M Na$_2$CO$_3$, evaporated and purified by preparative HPLC. Yield 29 mg.

$^1$H NMR (400 MHz, CDCl$_3$) δ ppm 1.00 (t, 3 H), 1.62-1.70 (m, 2 H), 1.72 (s, 6 H), 2.38 (s, 1 H), 3.06 (td, 2 H), 6.02 (bs, 1 H), 6.48 (dd, 1 H), 6.62 (d, 1 H), 7.20 (d, 1 H), 7.71 (bs, 1H).

Example 14

5-Chloro-N-(2-methylbut-3-yn-2-yl)-2-(2,2,2-trifluoroethylamino)-benzamide

Step 1: Methyl 5-chloro-2-(2,2,2-trifluoroethylamino)benzoate

Trifluoroacetic acid (1.3 ml, 17.5 mmol) was added to a cold solution of methyl 2 amino-5-chlorobenzoate (0.25 g, 1.35 mmol) and sodium cyanoborohydride (0.18 g, 2.8 mmol) in DCM (4 ml). The temperature was kept below 5° C. Trifluoroacetaldehyde hydrate (0.27 ml, 3.4 mmol) was added drop-wise. The mixture was stirred at room temperature for 2 days. The mixture was slowly poured onto cold saturated sodium bicarbonate solution. The pH was adjusted to 7 by adding solid sodium bicarbonate in portions. The resulting mixture was stirred for 30 min and extracted with DCM, dried over anhydrous sodium sulphate and evaporated. The crude product was purified by flash column chromatography to afford 0.102 g of the title compound.

$^1$H NMR (400 MHz, CDCl$_3$) δ ppm 3.80-3.88 (m, 2 H), 3.88 (s, 3 H), 6.73 (d, 1 H), 7.34 (ddd, 1 H), 7.91 (dd, 1 H), 8.15 (t, 1 H).

Step 2: 5-Chloro-2-(2,2,2-trifluoroethylamino)benzoic acid

A mixture of methyl 5-chloro-2-(2,2,2-trifluoroethylamino)benzoate (0.4 g, 0.38 mmol) in THF (5 ml) with 1 M NaOH (2 ml) was stirred at 60° C. for 3 h. Further 2 ml of 1 M NaOH solution was added. The mixture was stirred overnight. The solvents were evaporated under reduced pressure. The crude product was diluted with t-butyl methyl ether and acidified with dilute HCl solution. The solution was then extracted with DCM (2×10 ml), washed with water, dried and evaporated. Yield: 91 mg.

$^1$H NMR (400 MHz, CDCl$_3$) δ ppm 3.88 (q, 2 H), 6.76 (d, 1 H), 7.39 (dd, 1 H), 7.98 (d, 1H), 8.03 (t, 1 H).

Step 3: 5-Chloro-N-(2-methylbut-3-yn-2-yl)-2-(2,2,2-trifluoroethylamino)benzamide A mixture of 5-chloro-2-(2,2,2-trifluoroethylamino)benzoic acid (90 mg, 0.36 mmol), 1,1-dimethylpropargylamine (0.042 ml, 0.40 mmol), EDCI (83 mg, 0.43 mmol), DIPEA (0.12 ml, 0.72 mmol) and HOBt (24 mg, 0.18 mmol) in DCM (5 ml) was stirred overnight. The mixture was washed with 2 M Na$_2$CO$_3$, evaporated and purified by preparative HPLC.

Yield: 47 mg.

$^1$H NMR (400 MHz, CDCl$_3$) δ ppm 1.74 (s, 6 H), 2.41 (s, 1 H), 3.79 (qd, 2 H), 6.05 (bs, 1H), 6.74 (d, 1 H), 7.27 (dd, 1 H), 7.29-7.30 (m, 2 H), 8.04 (t, 1 H).

Example 15

3-Fluoro-N-(2-methylbut-3-yn-2-yl)-2-(3,3,3-trifluoropropylamino)-benzamide

Step 1: 2-Amino-3-fluoro-N-(2-methylbut-3-yn-2-yl)benzamide

A mixture of 1,1-dimethylpropargylamine (0.3 ml, 2.84 mmol), 2-amino-3-fluorobenzoic acid (0.4 g, 2.58 mmol), EDCI (0.6 g, 3.09 mmol), DIPEA (1.35 ml, 7.74 mmol) and HOBt (174 mg, 1.29 mmol) in DCM (10 ml) was stirred overnight. The mixture was washed with 2 M Na$_2$CO$_3$, evaporated to dryness and purified by flash chromatography. Yield: 0.38 g.

$^1$H NMR (400 MHz, CDCl$_3$) δ ppm 1.75 (s, 6 H), 2.40 (s, 1 H), 5.64 (ts, 2 H), 6.08 (bs, 1H), 6.56 (td, 1 H), 7.01-7.10 (m, 2 H).

Step 2: 3-Fluoro-N-(2-methylbut-3-yn-2-yl)-2-(3,3,3-trifluoropropylamino)benzamide A mixture of 2-amino-3-fluoro-N-(2-methylbut-3-yn-2-yl)benzamide (0.15 g, 0.68 mmol), 3,3,3-trifluoropropanal (0.112 ml, 1.29 mmol) and glacial acetic acid (0.23 ml, 4.1 mmol) in 1,2-dichloroethane (5 ml) was stirred. Sodium triacetoxy borohydride (0.4 g, 1.9 mmol) was added. The mixture was stirred for 6 days. The reaction was quenched with saturated NaHCO$_3$ (aq) and extracted with EtOAc. The combined organic layers were dried and evaporated to dryness. Preparative HPLC gave 6 mg of the title compound.

$^1$H NMR (400 MHz, CDCl$_3$) δ ppm 1.74 (s, 6 H), 2.32-2.45 (m, 3 H), 3.57 (qd, 2 H), 6.50 (bs, 1 H), 6.61 (bs, 1 H), 6.74 (td, 1 H), 7.09 (ddd, 1 H), 7.23-7.25 (m, 1 H).

Example 16

3-Fluoro-N-(2-methylbut-3-yn-2-yl)-2-(propylamino)benzamide

2-Amino-3-fluoro-N-(2-methylbut-3-yn-2-yl)benzamide (0.15 g, 0.68 mmol), propionaldehyde (0.09 ml, 1.3 mmol) and glacial acetic acid (0.23 ml, 4.1 mmol) in 1,2-dichloroethane (5 ml) were stirred. Sodium triacetoxy borohydride (0.4 g, 1.0 mmol) was added and the mixture was stirred for 6 days. NaHCO$_3$ (aq) was added. The mixture was extracted with EtOAc. The organic layers were evaporated to dryness. Purification by flash chromatography and preparative HPLC gave 10 mg of the title compound.

¹H NMR (400 MHz, CDCl₃) ☐ ppm 0.95 (t, 3 H), 1.57-1.64 (m, 2 H), 1.74 (s, 6 H), 2.38 (s, 1 H), 3.16 (qd, 2 H), 5.42 (bs, 1 H), 6.78 (td, 1 H), 7.08 (ddd, 1 H), 7.41 (dt, 1 H), 7.45 (bs 1 H).

Example 17

2-(Cyclobutylamino)-4,5-difluoro-N-(2-methylbut-3-yn-2-yl)benzamide

Step 1: Methyl 2-(cyclobutylamino)-4,5-difluorobenzoate

A mixture of methyl 2-amino-4,5-difluorobenzoate (0.5 g, 2.7 mmol), cyclobutanone (0.383 ml, 5.1 mmol), acetic acid (0.92 ml, 16.0 mmol) in 1,2-dichloroethane (10 ml) was stirred. Sodium triacetoxy borohydride (1.59 g, 7.5 mmol) was added and the mixture was stirred overnight. The reaction was quenched with saturated NaHCO₃ (aq) and extracted with EtOAc. The combined organic layers were dried and evaporated to dryness. Flash chromatography gave 0.30 g of the title compound.

¹H NMR (400 MHz, CDCl₃) δ ppm 1.74-1.99 (m, 4 H), 2.40-2.49 (m, 2 H), 3.78-3.90 (m, 1 H), 3.84 (s, 3 H), 6.27 (dd, 1 H), 7.64-7.72 (m, 1 H), 7.78 (bs, 1 H).

Step 2: 2-(Cyclobutylamino)-4,5-difluorobenzoic acid

A solution of methyl 2-(cyclobutylamino)-4,5-difluorobenzoate (0.3 g, 1.25 mmol) in THF (5 ml) and 1 M NaOH (15 ml) was stirred for one day. The solvents were evaporated under reduced pressure. The crude product was diluted with t-butyl methyl ether and acidified with dilute HCl solution. The solution was then extracted with DCM (2×10 ml), washed with water, dried and evaporated. Yield: 0.23 g.

¹H NMR (400 MHz, CDCl₃) δ ppm 1.77-2.03 (m, 4 H), 2.41-2.52 (m, 2 H), 3.82-3.94 (m, 1 H), 6.31 (dd, 1 H), 7.76 (dd, 1 H).

Step 3: 2-(Cyclobutylamino)-4,5-difluoro-N-(2-methylbut-3-yn-2-yl)benzamide

A mixture of 2-(cyclobutylamino)-4,5-difluorobenzoic acid (100 mg, 0.44 mmol), 1,1-dimethylpropargylamine (0.051 ml, 0.48 mmol), EDCI (101 mg, 0.53 mmol), DIPEA (0.15 ml, 0.88 mmol) and HOBt (30 mg, 0.22 mmol) in 10 ml DCM was stirred overnight. The mixture was washed with 2 M Na₂CO₃, evaporated to dryness and purified by preparative HPLC. Yield: 78 mg.

¹H NMR (400 MHz, CDCl₃) δ ppm 1.73 (m, 6H), 1.76-2.01 (m, 4 H), 2.36-2.46 (m, 2 H), 2.40 (s, 1H), 3.74-3.85 (m, 1 H), 5.87 (bs, 1 H), 6.29 (dd, 1 H), 7.12 (dd, 1 H), 7.67 (bs, 1 H).

Example 18

N-(2-Methylbut-3-yn-2-yl)-2-(2,2,3,3,3-pentafluoropropylamino)-5-(trifluoromethyl)benzamide Step 1: 2-(2,2,3,3,3-Pentafluoropropylamino)-5-(trifluoromethyl)benzoic acid 2-Chloro 5-(trifluoromethyl)benzoic acid (0.3 g, 1.34 mmol), 2,2,3,3,3-pentafluoropropylamine (0.28 ml, 2.67 mmol), potassium acetate (0.26 g, 2.67 mmol), copper(II) acetate monohydrate (27 mg, 0.134 mmol) and triethylamine (0.22 ml, 1.6 mmol) in DMF (5 ml) were heated at 180° C. for 2 h using a microwave reactor. The mixture diluted with ethyl acetate and neutralized with dilute HCl solution. The layer were separated and the aqueous layer was extracted with ethyl acetate. The organic layer was dried over anhydrous sodium sulphate and evaporated. The material was purified by flash chromatography. Yield: 0.10 g.

¹H NMR (400 MHz, CDCl₃) δ ppm 3.99 (td, 2 H), 6.87 (d, 1 H), 7.66 (dd, 1 H), 8.27-8.31 (m, 1 H), 8.39 (t, 1 H).

Step 2: N-(2-Methylbut-3-yn-2-yl)-2-(2,2,3,3,3-pentafluoropropylamino)-5-(trifluoromethyl)benzamide A mixture of 2-(2,2,3,3,3-pentafluoropropylamino)-5-(trifluoromethyl)benzoic acid (70 mg, 1 eq), 1,1-dimethylpropargylamine (0.024 ml, 1.1 eq), EDCI (48 mg, 1.2 eq), DIPEA (0.07 ml, 2 eq) and HOBt (14 mg, 0.5 eq) in 10 ml DCM was stirred overnight. The mixture was washed with 2 M Na₂CO₃, evaporated to dryness and purified by preparative HPLC. Yield: 39 mg.

¹H NMR (400 MHz, CDCl₃) δ ppm 1.76 (s, 6 H), 2.42 (s, 1 H), 3.90 (td, 2 H), 6.13 (bs, 1 H), 6.82 (d, 1 H), 7.50-7.59 (m, 2 H), 8.43 (t, 1 H).

Example 19

N-(2-Methylbut-3-yn-2-yl)-2-(2,2,3,3,3-pentafluoropropylamino)-benzamide

Step 1: 2-(2,2,3,3,3-Pentafluoropropylamino)benzoic acid

2-Bromobenzoic acid (0.5 g, 2.49 mmol), 2,2,3,3,3-pentafluoropropylamine (0.53 ml, 5.0 mmol), potassium acetate (5.0 mmol), copper(II)acetate monohydrate (50 mg, 0.25 mmol) and triethylamine (0.42 ml, 3.0 mmol) in DMF (5 ml) were heated at 180° C. for 30 minutes using a microwave reactor. The mixture was neutralised with diluted HCl and extracted with EtOAc. The organic phase was dried, evaporated and purified by flash chromatography to give 72 mg of the title compound.

¹H NMR (400 MHz, CDCl₃) δ ppm 3.95 (td, 2 H), 6.73-6.82 (m, 2H), 7.46 (ddd, 1 H), 7.98-8.07 (m, 2 H).

Step 2: N-(2-Methylbut-3-yn-2-yl)-2-(2,2,3,3,3-pentafluoropropylamino)benzamide

A mixture of 2-(2,2,3,3,3-pentafluoropropylamino)benzoic acid (70 mg, 1 eq), 1,1-dimethylpropargylamine (0.03 ml, 1.1 eq), EDCI (60 mg, 1.2 eq), DIPEA (0.09 ml, 2 eq) and HOBt (18 mg, 0.5 eq) in 10 nil DCM was stirred overnight. The mixture was washed with 2 M Na₂CO₃, evaporated to dryness and purified by preparative HPLC. Yield: 33 mg.

¹H NMR (400 MHz, CDCl₃) δ ppm 1.74 (s, 6 H), 2.39 (s, 1 H), 3.86 (td, 2 H) 6.12 (bs, 1H), 6.70 (ddd, 1 H), 6.78 (d, 1 H), 7.29-7.37 (m, 2 H), 8.06 (t, 1 H).

Example 20

2-(2,2-Difluoroethylamino)-5-fluoro-N-(3-methylpent-1-yn-3-yl)nicotinamide

Step 1: 2-(2,2-Difluoroethylamino)-5-fluoronicotinic acid

2-Chloro-5-fluoropyridine-3-carboxylic acid (0.199 ml, 1.709 mmol), 2,2-difluoroethylamine (0.205 ml, 2.91 mmol), copper powder. (6.5 mg, 0.03 mmol), copper(I) bromide (12.0 mg, 0.085 mmol), potassium carbonate (0.283 g, 2.051 mmol) and dry DMF (2 ml) were heated by microwave irradiation at 150° C. for 1 h. Some EtOAc was added and organic phase was washed 2 times with 0.5 M citric acid, dried over Na$_2$SO$_4$ filtered and evaporated. 0.335 g of the title compound was obtained.

$^1$H NMR (400 MHz, CDCl$_3$) δ ppm 3.88 (td, 2 H) 5.81-6.13 (m, 1 H) 7.95 (dd, 1 H) 7.99 (br. s, 1 H) 8.16 (d, 1 H)

Step 2: 2-(2,2-Difluoroethylamino)-5-fluoro-N-(3-methylpent-1-yn-3-yl)nicotinamide 2-(2,2-Difluoroethylamino)-5-fluoronicotinic acid (0.100 g, 0.454 mmol), 3-amino-3-methyl-1-pentyne hydrochloride (0.061 g, 0.454 mmol), 1-hydroxybenzotriazole (0.068 g, 0.500 mmol), 1-(3-dimethylaminopropyl)-3-ethylcarbodiimide hydrochloride (0.096 g, 0.500 mmol) and N,N-diisopropylethylamine (0.166 ml, 0.954 mmol) in DCM (5 ml) were stirred at room temperature overnight. Some DCM was added and organic phase was washed with 1 M HCl and 1 M Na$_2$CO$_3$, dried over Na$_2$SO$_4$, filtered and evaporated. The crude product was purified by preparative HPLC. 0.024 g of the title compound was obtained.

$^1$H NMR (400 MHz, CDCl$_3$) δ ppm 1.06 (t, 3 H) 1.72 (s, 3 H) 1.90 (dq, 1 H) 2.16 (dq, 1 H) 2.44 (s, 1 H) 3.82 (tdd, 2 H) 5.79-6.13 (m, 2 H) 7.32-7.39 (m, 1 H) 8.04 (t, 1 H) 8.10 (d, 1 H)

Example 21

2-(Cyclobutylamino)-3-fluoro-N-(2-methylbut-3-yin-2-yl)benzamide

A mixture of 2-amino-3-fluoro-N-(2-methylbut-3-yn-2-yl)benzamide (75 mg, 034 mmol), cyclobutanone (0.05 ml, 0.7 mmol), glacial acetic acid (0.117 ml, 2.0 mmol) in 1,2-dichloroethane (4 ml) was stirred. Sodium triacetoxy borohydride (0.20 g, 0.95 mmol) was added and the mixture was stirred for two days. The reaction was quenched with saturated NaHCO$_3$ (aq) and extracted with EtOAc. The combined organic layers were dried and evaporated to dryness. Preparative HPLC gave 1.5 mg of the title compound.

$^1$H NMR (400 MHz, CDCl$_3$) δ ppm 1.55-1.71 (m, 2 H), 1.73 (s, 6 H), 1.84-1.97 (m, 2 H), 2.25-2.35 (m, 2 H), 2.38 (s, 1 H), 3.87-3.97 (m, 1 H), 5.46 (d, 1 H), 6.80 (td, 1 H), 7.07 (ddd, 1 H), 7.42-7.45 (m, 1 H), 7.55 (bs, 1 H).

Example 22

5-Fluoro-N-(2-methylbut-3-yn-2-yl)-2-(2,2,2-trifluoroethylamino)-benzamide

Step 1: Methyl 5-fluoro-2-(2,2,2-trifluoroethylamino)benzoate

A mixture of methyl 2-amino-5-fluorobenzoate (0.5 g, 2.96 mmol), sodium cyanoborohydride (0.39 g, 6.2 mmol) and DCM (8 ml) was stirred at 0° C. Trifluoroacetic acid (2.85 ml, 38.4 mmol) was added. Trifluoroacetaldehyde hydrate (0.59 ml, 2.5 equiv) was added dropwise. The mixture was stirred for 7 days. The mixture was filtrated and the filtrate was purified by flash chromatography. Yield: 18 mg.

$^1$H NMR (400 MHz, CDCl$_3$) δ ppm 3.82-3.87 (m, 2 H), 3.89 (s, 3 H), 6.74 (dd, 1 H), 7.16 (dddd, 1 H), 7.61-7.66 (m, 1 H), 7.99 (t, 1 H).

Step 2:
5-Fluoro-2-(2,2,2-trifluoroethylamino)benzoic acid

A solution of methyl 5-fluoro-2-(2,2,2-trifluoroethylamino)benzoate (18 mg, 0.07 mmol) in THF (3 ml) with 1M NaOH (2 ml) was stirred for 3 h at room temperature. The solvent was evaporated. The crude was treated with diluted HCl and the solid separated was dried under vacuum. The crude product, containing salts, was used as such in the next step.

$^1$H NMR (400 MHz, D$_2$O) δ ppm 3.86 (q, 2 H), 6.87 (dd, 1 H), 7.09 (td, 1 H), 7.43 (dd, 1 H).

Step 3: 5-Fluoro-N-(2-methylbut-3-yn-2-yl)-2-(2,2,2-trifluoroethylamino)benzamide A mixture of 5-fluoro-2-(2,2,2-trifluoroethylamino)benzoic acid (30 mg, 1 eq), 1,1-dimethylpropargylamine (0.015 ml, 1.1 eq), EDCI (29 mg, 1.2 eq), DIPEA (0.066 ml, 3 eq) and HOBt (8.55 mg, 0.5 eq) in 5 ml DCM was stirred overnight. The mixture was washed with 2 M Na$_2$CO$_3$, evaporated to dryness and purified by preparative HPLC. Yield: 2.3 mg.

$^1$H NMR (400 MHz, CDCl$_3$) δ ppm 1.74 (s, 6 H), 2.41 (s, 1 H), 3.78 (qd, 2 H), 6.04 (bs, 1 H), 6.75 (dd, 1 H), 7.04-7.08 (m, 2 H), 7.80 (t, 1 H).

Example 23

2-(Cyclobutylamino)-N-(2-methylbut-3-yn-2-yl)-5-(trifluoromethyl)-benzamide

2-Amino-N-2-ethylbut-3-yn-2-yl)-5-(trifluoromethyl) benzamide (150 mg, 0.55 mmol), cyclobutanone (0.079 ml, 1.055; mmol)), glacial acetic acid (0.191 ml, 3.33 mmol) and 1,2-dichloroethane (4 ml) were charged in a flask. Sodium triacetoxy borohydride (0.33 g, 2.8 1.6 mmol) was added and the mixture stirred overnight. The reaction was quenched with saturated NaHCO3 (aq) and extracted with EtOAc. The combined organic layers were dried and evaporated to dryness. Purification by preparative HPLC gave 66 mg of the title compound.

$^1$H NMR (400 MHz, CDCl$_3$) δ ppm 1.75 (s, 6H), 1.78-2.03 (m, 4 H), 2.37-2.49 (m, 2 H), 2.41 (s, 1 H), 3.86-3.99 (m, 1 H), 6.09 (bs, 1 H), 6.55 (d, 1 H), 7.40-7.46 (m, 1 H), 7.47-7.50 (m, 1 H), 8.08 (d, 1 H).

Example 24

2-(Cyclobutylamino)-5-fluoro-N-(2-methylbut-3-yn-2-yl)benzamide

Step 1: Methyl 2-(cyclobutylamino)-5-fluorobenzoate

Methyl 2-amino-5-fluorobenzoate (0.5 g, 3.0 mmol), cyclobutanone (0.42 ml, 5.6 mmol), glacial acetic acid (1.0 ml, 17.7 mmol) and 1,2-dichloroethane (10 ml) were charged in a flask. Sodium triacetoxy borohydride (1.75 g, 8.3 mmol) was added and the mixture stirred overnight. The reaction was quenched with saturated NaHCO$_3$ (aq) and extracted with EtOAc. The combined organic layers were dried and evaporated to dryness. The crude product was used in the next step.

$^1$H NMR (400 MHz, CDCl$_3$) δ ppm 1.75-1.99 (m, 4 H), 2.40-2.48 (m, 2 H), 3.85 (s, 3 H), 3.88-3.97 (m, 1 H), 6.49 (dd, 1 H), 7.08 (ddd, 1 H), 7.54-7.64 (m, 2 H).

Step 2: 2-(Cyclobutylamino)-5-fluorobenzoic acid

A solution of methyl 2-(cyclobutylamino)-5-fluorobenzoate (0.7 g, 3.13 mmol) in THF (3 ml) with 1M NaOH (14 ml) was stirred at 60° C. for 4 h. The solvents were evaporated and the residue was diluted with tert-butyl methyl ether. The mixture was acidified by adding 2M HCl. The solvent was evaporated, and the residue washed with heptane-DCM to give 1.33 g of a crude product.

$^1$H NMR (400 MHz, CDCl$_3$) δ ppm 1.78-2.12 (m, 2 H), 2.27-2.41 (m, 2 H), 2.56-2.71 (m, 2 H), 4.04 (quin, 1 H), 7.44 (ddd, 1 H), 7.67 (dd, 1 H), 7.90 (dd, 1 H), 11.24 (bs, 2 H).

Step 3: 2-(Cyclobutylamino)-5-fluoro-N-(2-methylbut-3-yn-2-yl)benzamide

A mixture of 2-(cyclobutylamino)-5-fluorobenzoic acid (100 mg, 0.48 mmol), 1,1-dimethylpropargylamine (0.055 ml, 0.53 mmol), EDCI (110 mg, 0.57 mmol), DIPEA (0.17 ml, 0.96 mmol) and HOBt (32 mg, 0.24 mmol) in DMF (3 mil) was shaken overnight. Water (3 ml) was added. The aqueous mixture was extracted with EtOAc (3 ml). The organic layer was washed with 2M Na$_2$CO$_3$, evaporated to dryness and purified by preparative HPLC.

Yield: 40 mg.

$^1$H NMR (400 MHz, CDCl$_3$) δ ppm 1.73 (s, 6H), 1.75-1.98 (m, 4 H), 2.35-2.44 (m, 2 H), 2.40 (s, 1H), 3.79-3.90 (m, 1 H), 6.09 (bs, 1 H), 6.48 (dd, 1 H), 6.95-7.06 (m, 2 H), 7.29 (bs, 1 H).

Example 25

2-(Cyclobutylamino)-5-fluoro-N-(2-methylbut-3-yn-2-yl)nicotinamide

Step 1: 2-(Cyclobutylamino)-5-fluoronicotinic acid

A mixture of 2-chloro-5-fluoropyridine-3-carboxylic acid (0.13 ml, 1.14 mmol), cyclobutylamine (0.14 g, 1.94 mmol), copper powder (4.34 mg, 0.068 mmol), copper(I)bromide (8.17 mg, 0.057 mmol), potassium carbonate (0.19 g, 1.37 mmol) in DMF (1 ml) was heated at 150° C. for 4 h using a microwave reactor. The mixture was diluted with ethyl acetate and washed with 0.5M citric acid solution. The organic layer was dried over anhydrous sodium sulphate and evaporated. The crude product was purified by reverse phase column chromatography. Yield: 0.171 g.

$^1$H NMR (400 MHz, CDCl$_3$) δ ppm 1.73-1.83 (m, 2 H), 1.88-2.00 (m, 2 H), 2.39-2.50 (m, 2 H), 4.54-4.59 (m, 1 H) 789 (dd, 1 H), 8.23 (d, 1 H).

Step 2: 2-(Cyclobutylamino)-5-fluoro-N-(2-methylbut-3-yn-2-yl)nicotinamide

A mixture of 2-(cyclobutylamino)-5-fluoronicotinic acid (170 mg, 0.81 mmol, 1,1-dimethylpropargylamine (0.094 ml, 0.90 mmol), EDCI (187 mg, 0.98 mmol), DIPEA (0.28 ml, 1.6 mmol) and HOBt (0.41 mmol) in 3 ml DMF was shaken overnight. Water (3 ml) was added. The aqueous mixture was extracted with EtOAc (3 ml). The organic layer was washed with 2M Na$_2$CO$_3$, evaporated to dryness and purified by preparative HPLC. Yield: 139 mg.

$^1$H NMR (400 MHz, CDCl$_3$) δ ppm 1.66-1.79 (m, 2 H), 1.73 (s, 6H), 1.83-1.96 (m, 2 H), 2.33-2.42 (m, 2 H), 2.42 (s, 1H), 4.39-4.50 (m, 1 H), 6.26 (s, 1 H), 7.34 (dd, 1 H), 7.90 (d, 1 H), 8.06 (d, 1 H).

Example 26

5-Chloro-2-(isopropylamino)-N-(2-methylbut-3-yn-2-yl)-nicotinamide

Step 1: 5-Chloro-2-(isopropylamino)nicotinic acid 2,5-Dichloronicotinic acid (0.2 g, 1.04 mmol), isopropylamine (0.1 g, 1.77 mmol), copper powder (3.97 ng, 0.063 mmol), copper(I)bromide (7.47 mg, 0.052 mmol), potassium carbonate (0.17 g, 1.25 mmol) in DMF (1 ml) were irradiated at 150° C. for 4 h using microwaves. The mixture was diluted with ethyl acetate and washed with 0.5M citric acid solution. The organic layer was dried over anhydrous sodium sulphate and evaporated. The crude was purified by reverse phase column chromatography. Yield: 133 mg.

$^1$H NMR (400 MHz, CDCl$_3$) δ ppm 1.27 (d, 6 H), 4.28-4.37 (m, 1 H), 7.68 (bs, 1 H), 8.12 (d, 1 H), 8.26 (d, 1 H).

Step 2: 5-Chloro-2-(isopropylamino)-N-(2-methylbut-3-yn-2-yl)nicotinamide

5-Chloro-2-(isopropylamino)nicotinic acid (133 mg, 0.62 mmol), 1,1-dimethylpropargylamine (0.072 ml, 0.68 mmol), EDCI (143 mg, 0.74 mmol), DIPEA (0.22 ml, 1.24 mmol) and HOBt (42 mg, 0.31 mmol) in 3 ml DMF was shaken overnight. Water (10 ml) was added. The aqueous mixture was extracted with EtOAc (15 ml). The organic layer was washed with 2 M Na$_2$CO$_3$, evaporated to dryness and purified by preparative HPLC. Yield: 98 mg.

$^1$H NMR (400 MHz, CDCl$_3$) δ ppm 2.02 (d, 6 H), 2.81 (s, 1 H), 4.42-4.54 (m, 1 H), 8.11 (d, 1 H), 8.38 (d, 1 H).

Example 27

5-Chloro-2-(cyclobutylamino)-N-(2-methylbut-3-yn-2-yl)nicotinamide

Step 1: 5-Chloro-2-(cyclobutylamino)nicotinic acid 2,5-dichloronicotinic acid (0.2 g, 1.04 mmol), cyclobutylamine (0.13 g, 1.77 mmol), copper powder (3.97 rag, 0.063 mmol), copper(I)bromide (7.47 mg, 0.052 mmol), potassium, carbonate (0.17 g, 1.25 mmol) and DMF (1 ml) were placed in microwave reaction vial and irradiated at 150° C. for 4 h. The mixture was diluted with ethyl acetate and washed with 0.5M citric acid solution. The organic layer was dried over anhydrous sodium sulphate and evaporated. The crude was purified by reverse phase flash chromatography. Yield: 0.11 g.

$^1$H NMR (400 MHz, CDCl$_3$) δ ppm 1.73-1.82 (m, 2 H), 1.87-1.99 (m, 2 H), 2.39-2.48 (m, 2 H), 4.51-4.62 (m, 1 H), 8.09 (d, 1 H), 8.24 (d, 1 H).

Step 2: 5-Chloro-2-(cyclobutylamino)-N-(2-methylbut-3-yn-2-yl)nicotinamide

A mixture of 5-chloro-2-(cyclobutylamino)nicotinic acid (110 mg, 0.48 mmol), 1,1-dimethylpropargylamine (0.056 ml, 0.53 mmol), EDCI (112 mg, 0.58 mmol), DIPEA (0.17 ml, 0.97 mmol) and HOBt (33 mg, 0.24 mmol) in DMF (3 ml) was shaken overnight. Water (3 ml) was added. The aqueous mixture was extracted with EtOAc (3 ml). The organic layer was washed With 2M $Na_2CO_3$, evaporated to dryness and purified by preparative HPLC.

Yield: 79 mg.

$^1$H NMR (400 MHz, $CDCl_3$) δ ppm 1.69-1.78 (m, 2 H), 1.74 (s, 6H), 1.86-1.99 (m, 2 H), 2.34-2.41 (m, 2 H), 2.42 (s, 1 H), 4.40-4.55 (m, 1 H), 6.16 (bs, 1 H), 7.48 (d, 1 H), 8.09 (d, 1 H), 8.12 (d, 1 H).

Example 28

2-(Isopropylamino)-N-(2-methylbut-3-yn-2-yl)-5-(trifluoromethyl)-nicotinamide

Step 1:
2-(Isopropylamino)-5-(trifluoromethyl)nicotinic acid

2-Chloro-5-(trifluoromethyl)pyridine-3-carboxylic acid (0.2 g, 0.89 mmol), isopropylamine (89 mg, 1.5 mmol), copper powder (3.38 mg, 0.053 mmol), copper(I)bromide (6.36 mg, 0.044 mmol), potassium carbonate (0.15 g, 1.06 mmol) and DMF (1 ml) were placed in microwave reaction vial and irradiated at 150° C. for 4 h. The mixture was diluted with ethyl acetate and washed with 0.5M citric acid solution. The organic layer was dried over anhydrous sodium sulphate and evaporated. The crude was purified by reverse phase flash chromatography. Yield: 98 mg.

$^1$H NMR (400 MHz, $CD_3OD$) δ ppm 1.29 (d, 6 H), 4.39 (spt, 1 H), 8.33 (dd, 1 H), 8.45-8.49 (m, 1 H).

Step 2: 2-(isopropylamino)-N-(2-methylbut-3-yn-2-yl)-5-(trifluoromethyl)nicotinamide A mixture of 2-(isopropylamino)-5-(trifluoromethyl)nicotinic acid (98 mg, 0.40 mmol), 1,1-dimethylpropargylamine (0.046 ml, 0.43 mmol), EDCI (91 mg, 0.47 mmol), DIPEA (0.14 ml, 0.79 mmol) and HOBt (27 mg, 0.20 mmol) in 3 ml DMF was stirred overnight. Water (3 ml) was added. The aqueous mixture was extracted with EtOAc (3 ml). The Organic layer was washed with 2M $Na_2CO_3$, evaporated to dryness and purified by preparative HPLC. Yield: 61 mg.

$^1$H NMR (400 MHz, $CDCl_3$) δ ppm 1.25 (d, 6 H), 1.75 (s, 6 H), 2.42 (s, 1 H), 4.27-4.41 (m, 1 H), 6.15 (bs, 1 H), 7.65 (d, 1 H), 8.32 (d, 1 H), 8.41 (dd, 1 H).

Example 29

5-Fluoro-N-(2-methylbut-3-yn-2-yl)-2-(2,2,3,3-pentafluoropropyl-amino)nicotinamide Step 1: 5-Fluoro-2-(2,2,3,3-pentafluoropropylamino)nicotinic acid 2-Chloro-5-fluoropyridine-3-carboxylic acid (0.2 ml, 1.71 mmol), 2,2,3,3,3-pentafluoropropylamine (0.43 g, 2.91 mmol), copper powder (6.52 mg, 0.1 mmol), copper(I) bromide (12 mg, 0.085 mmol), potassium carbonate (0.28 g, 2.05 mmol) and DMF (2 ml) were placed in microwave reaction vial and irradiated at 150° C. for 4 h. The mixture was diluted with ethyl acetate and washed with 0.5M citric acid solution. The organic layer was dried over anhydrous sodium sulphate and evaporated. The crude was purified by reverse phase flash chromatography. Yield: 80 mg.

$^1$H NMR (400 MHz, $CD_3OD$) δ ppm 4.38-4.47 (td, 2 H), 8.01 (dd, 1 H), 8.23 (d, 1 H).

Step 2: 5-Fluoro-N-(2-methylbut-3-yn-2-yl)-2-(2,2,3,3,3-pentafluoropropylamino) nicotinamide A mixture of 5-fluoro-2-(2,2,3,3,3-pentafluoropropylamino)nicotinic acid (80 mg, 0.28 mmol), 1,1-dimethylpropargylamine (0.032 ml, 0.30 mmol), EDCI (64 mg, 0.33 mmol), DIPEA (0.097 ml, 0.56 mmol) and HOBt (19 mg, 0.14 mmol) in 3 ml DMF was shaken overnight. Water (5 ml) was added. The aqueous mixture was extracted with EtOAc (10 ml). The organic layer was washed with 2M $Na_2CO_3$, evaporated to dryness and purified by preparative HPLC. Yield: 33 mg.

$^1$H NMR (400 MHz, $CDCl_3$) δ ppm 1.74 (s, 6 H), 2.42 (s, 1 H), 4.28 (tdd, 2 H), 6.07 (bs, 1H), 7.36 (dd, 1 H), 8.12 (d, 1 H), 8.17 (t, 1 H).

Example 30

5-Methyl-N-(2-methylbut-3-yn-2-yl)-2-(2,2,3,3,3-pentafluoropropyl-amino)benzamide Step 1: 5-Methyl-2-(2,2,3,3,3-pentafluoropropylamino)benzoic add 2-Bromo-5-methylbenzoic acid (0.5 g), 2,2,3,3,3-pentafluoropropylamine (0.49 ml), potassium acetate (0.46 g), copper(I)acetate monohydrate (46 mg) and triethylamine (0.39 ml) in DMF (2 ml) were placed in a microwave reaction vial and irradiated at 180° C. for 2 h. The mixture was cooled, diluted with ethyl acetate and neutralized with dilute HCl solution. The layers were separated and the aqueous layer was extracted with ethyl acetate. The organic layer was dried over anhydrous sodium sulphate and evaporated. The material was purified by flash chromatography. Yield: 46 mg.

$^1$H NMR (400 MHz, $CDCl_3$) δ ppm 2.26 (s, 3 H), 3.91 (t, 2 H), 6.70 (d, 1 H), 7.26-7.29 (m, 1 H), 7.83 (m, 2 H).

Step 2: 5-Methyl-N-(2-methylbut-3-yn-2-yl)-2-(2,2,3,3,3-pentafluoropropyl-amino)benzamide A mixture of 5-methyl-2-(2,2,3,3,3-pentafluoropropylamino)benzoic acid (42 mg, 0.15 mmol), 1,1-dimethylpropargylamine (0.02 ml, 0.16 mmol), EDCI (34 mg, 0.18 mmol), DIPEA (0.05 ml, 0.30 mmol) and HOBt (10 mg, 0.07 mmol) in 2 ml DMF was shaken overnight. Water (3 ml) was added. The aqueous mixture was extracted with EtOAc (3 ml). The organic layer was washed with 2M $Na_2CO_3$, evaporated to dryness and purified by preparative HPLC. Yield: 16 mg.

$^1$H NMR (400 MHz, $CDCl_3$) δ ppm 1.74 (s, 6 H), 2.26 (s, 3 H), 2.39 (s, 1 H), 3.77-3.90 (m, 2 H), 6.11 (bs, 1 H), 6.69 (d, 1 H), 7.10-7.18 (m, 2 H), 7.81 (t, 1 H).

Example 31

5-Fluoro-N-(2-methylbut-3-yn-2-yl)-2-(2,2,3,3,3-pentafluoropropylamino) benzamide Step 1: 5-Fluoro-2-(2,2,3,3,3-pentafluoropropylamino)benzoic acid Methyl 2-bromo-5-fluorobenzoate (0.32 ml), 2,2,3,3,3-pentafluoropropylamine (0.46 ml), potassium acetate (0.42 g), copper(III)acetate monohydrate (43 mg) and triethylamine (0136 ml) and DMF (2 ml) were placed in a microwave reaction vial and irradiated at 180° C. for 2 h. The mixture was cooled, diluted with ethyl acetate and neutralized with dilute HCl solution. The layers were separated and the aqueous layer was extracted with ethyl acetate. The organic layer was dried over anhydrous sodium sulphate and evaporated. The product was purified by reverse phase flash column chromatography. Yield: 69 mg.

$^1$H NMR (400 MHz, CD$_3$OD) δ ppm 4.06 (t, 2 H), 6.89 (dd, 1 H), 7.19 (ddd, 1 H), 7.61 (dd, 1 H).

Step 1: 5-Fluoro-N-(2-methylbut-3-yn-2-yl)-2-(2,2,3,3,3-pentafluoropropylamino)-benzamide A mixture of 5-fluoro-2-(2,2,3,3,3-pentafluoropropylamino)benzoic acid (60 mg, 0.24 mmol), 1,1-dimethylpropargylamine (0.028 ml, 0.26 mmol), EDCI (55 mg, 0.29 mmol), DIPEA (0.084 ml, 0.48 mmol) and HOBt (16 mg, 0.12 mmol) in DMF (2 ml) was shaken overnight. Water (5 ml) was added. The aqueous mixture was extracted with EtOAc (5 ml). The organic layer was washed with 2M Na$_2$CO$_3$, evaporated to dryness and purified by preparative HPLC. Yield: 27 mg.

$^1$H NMR (400 MHz, CDCl$_3$) δ ppm 1.74 (s, 6 H), 2.40 (s, 1 H), 3.83 (td, 2 H), 6.08 (bs, 1H), 6.72 (dd, 1 H), 7.03-7.11 (m, 2 H), 7.72 (t, 1 H).

Example 32

5-Chloro-2-(2,2-difluoroethylamino)-N-(2-methylbut-3-yn-2-yl)nicotinamide

Step 1:
5-Chloro-2-(2,2-difluoroethylamino)nicotinic acid 2,5-Dichloronicotinic acid (0.3 g, 1 eq), 2,2-difluoroethylamine (0.19 ml, 1.7 eq), copper powder (5.96 mg, 0.06 eq), copper(I)bromide (11 mg, 0.05 eq), potassium carbonate (0.26 g, 1.2 eq) and DMF (1 ml) were placed in microwave reaction vial and irradiated at 150° C. for 4 h. The mixture was diluted with ethyl acetate and washed with 0.5M citric acid solution. The organic layer was dried over anhydrous sodium sulphate and evaporated. The crude product was purified by reverse phase column chromatography. Yield: 0.176 g.

$^1$H NMR (400 MHz, CD$_3$OD) δ ppm 3.91 (td, 2 H), 6.03 (tt, 1 H), 8.15 (d, 1 H), 8.24 (d, 1H).

Step 2: 5-Chloro-2-(2,2-difluoroethylamino)-N-(2-methylbut-3-yn-2-yl)nicotinamide A mixture of 5-chloro-2-(2,2-trifluoroethylamino)nicotinic acid (176 mg, 0.74 mmol), 1,1-dimethylpropargylamine (0.086 ml, 0.82 mmol), EDCI (171 mg, 0.89 mmol), DIPEA (0.26 ml, 1.49 mmol) and HOBt (50 mg, 0.37 mmol) in 2 ml DMF was shaken overnight. Water (3 ml) was added. The aqueous mixture was extracted with EtOAc (3 ml. The organic layer was washed with 2M Na$_2$CO$_3$, evaporated to dryness and purified by preparative HPLC. Yield: 33 mg.

$^1$H NMR (400 MHz, CDCl$_3$) δ ppm 1.74 (s, 6 H), 2.42 (s, 1 H), 3.83 (tdd, 2 H), 5.96 (tt, 1H), 6.06 (bs, 1H), 7.52 (dd, 1 H), 8.14 (d, 1 H), 8.28 (t, 1 H).

Example 33

5-Fluoro-N-(2-methylbut-3-yn-2-yl)-2-(2,2,2-trifluoroethylamino)-nicotinamide

Step 1:
5-Fluoro-2-(2,2,2-trifluoroethylamino)nicotinic acid

2-Chloro-5-fluoropyridine-3-carboxylic acid (0.2 ml, 1 eq), 2,2,2-trifluoroethylamine (0.23 ml, 1.7 eq), copper (6.52 mg, 0.06 eq), copper(I)bromide (12 mg, 0.05 eq), potassium carbonate (0.28 g, 1.2 eq) and DMF (1 ml) were placed in microwave reaction vial and irradiated at 150° C. for 4 h. The mixture was diluted with ethyl acetate and washed with 0.5M citric acid solution. The organic layer was dried over anhydrous sodium sulphate and evaporated. The crude was purified by reverse phase column chromatography. Yield: 0.41 g.

$^1$H NMR (400 MHz, CD$_3$OD) δ ppm 4.32 (q, 2 H), 7.99 (dd, 1 H), 8.22 (d, 1 H).

Step 2: 5-Fluoro-N-(2-methylbut-3-yn-2-yl)-2-(2,2,2-trifluoroethylamino)nicotinamide A mixture of 5-fluoro-2-(2,2,2-trifluoroethylamino)nicotinic acid (100 mg, 0.42 mmol), 1,1-dimethylpropargylamine (0.05 ml, 0.46 mmol), EDCI (97 mg, 0.50 mmol), DIPEA (0.15 ml, 0.84 mmol) and HOBt (28 mg, 0.21 mmol) in 2 ml DMF was shaken overnight. Water (5 ml) was added. The aqueous mixture was extracted with EtOAc (5 ml). The organic layer was washed with 2M Na$_2$CO$_3$, evaporated to dryness and purified by flash chromatography. Yield: 60 mg.

$^1$H NMR (400 MHz, CDCl$_3$) δ ppm 1.75 (s, 6 H), 2.42 (s, 1 H), 4.21 (qd, 2 H), 6.05 (bs, 1H), 7.36 (dd, 1 H), 8.13 (d, 1 H), 8.22 (t, 1 H).

Example 34

5-Chloro-N-(2-methylbut-3-yn-yl)-2-(2,2,2-trifluoroethylamino)-nicotinamide

Step 1: Ethyl-2-(2,2,2-trifluoroethylamino)nicotinate

Ethyl-2-chloronicotinate (0.803 ml, 5.39 mmol) and 2,2,2-trifluoroethylamine (1.291 ml, 16.16 mmol) were added to a microwave vial. The reaction mixture was irradiated at 150° C. for 3 hours, at high absorbance. The reaction mixture was diluted with DCM and washed once with water. The organic phase was dried and evaporated to dryness to yield 1.275 g of the title compound.

$^1$H NMR (400 MHz, CDCl$_3$) δ ppm 1.39 (t, 3 H) 4.23-4.43 (m, 4 H) 6.66 (dd, 1 H) 8.17 (dd, 1 H) 8.29 (m, 2 H)

Step 2: Ethyl-5-chloro-2-(2,2,2-trifluoroethylamino)nicotinate

Ethyl-2-(2,2,2-trifluoroethylamino)nicotinate (3.45 g, 13.90 mmol), N-chlorosuccinimide (2.227 g, 16.68 mmol) and N,N-dimethylformamide (15 ml) were stirred at room temperature overnight. Water was added to the reaction mixture and the mixture was acidified with 1 M HCl solution. The acidic water phase was extracted three times with ethyl acetate and once with DCM. The organic phase was evaporated to dryness and DCM was added. The organic phase was washed three times with water, dried and evaporated to dryness td yield 4.0 g of the title compound.

¹H NMR (400 MHz, CCDl₃-d) δ ppm 1.34-1.47 (t, 3 H) 4.19-4.45 (m, 4 H) 8.08-8.18 (m, 1 H) 8.20-8.35 (m, 2 H).

Step 3:
5-Chloro-2-(2,2,2-trifluoroethylamino)nicotinic acid

The mixture of ethyl-5-chloro-2-(2,2,2-trifluoroethylamino)nicotinate (5.25 g, 18.68 mmol), potassium hydroxide (3.14 g, 56.0 mmol), methanol (25 ml) and water (5 ml) was stirred at room temperature overnight. The solvent was evaporated, water was added to the evaporation residue and the mixture was acidified with 5M HCl solution. The formed precipitation was filtered and washed once with water. The precipitation was dried in a vacuum oven at 40° C. overnight to yield 4.4 g of the title compound.
¹H NMR (400 MHz, MeOD-d) δ ppm 4.34 (q, 2 H) 8.18 (d, 1 H) 8.26 (d, 1 H)

Step 4: 5-Chloro-N-(2-methylbut-3-yn-2-yl)-2-(2,2,2-trifluoroethylamino)nicotinamide 5-Chloro-2-(2,2,2-trifluoroethylamino)nicotinic acid (2.2 g, 8.66 mmol), DCM (15 ml), EDCI (1.992 g, 10.39 mmol), HOBt (1.17 g, 8.66 mmol), DIPEA (3.02 ml, 17.32 mmol) and 1,1-dimethylpropargylamine (1.185 ml, 11.26 mmol) were stirred at room temperature overnight. The reaction mixture was washed once with 1M NaOH solution, once with 1M HCl solution and once with water. The organic phase was dried and evaporated to dryness. The product was purified by flash chromatography to yield 1.6 g of the title compound.
¹H NMR (400 MHz, CDCl₃-d) δ ppm 1.75 (s, 6 H) 2.42 (s, 1 H) 4.22 (m, 2 H) 6.04 (br. s., 1H) 7.54 (d, 1 H) 8.18 (d, 1 H) 8.42 (br. s., 1 H)

Example 35

N-(2-Methylbut-3-yn-2-yl)-2-(2,2,2-trifluoroethylamino)-5-(trifluoromethyl)nicotinamide Step 1: 2-(2,2,2-Trifluoroethylamino)-5-(trifluoromethyl)nicotinic acid 2-Chloro-5-(trifluoromethyl)pyridine-3-carboxylic acid (0.3 g, 1 eq), 2,2,2-trifluoroethylamine-amine (0.18 ml, 1.7 eq, copper (5.07 mg, 0.06 eq), copper(I)bromide (9.5 mg, 0.05 eq), potassium carbonate (0.22 g, 1.2 eq) in DMF (1 ml) were placed in a microwave reaction vial and irradiated at 150° C. for 4 h. The mixture was diluted with ethyl acetate and washed with 0.514 citric acid solution. The organic layer was dried over anhydrous sodium sulphate and evaporated. The crude product was purified by reverse phase column chromatography. Yield: 42 mg.
¹H NMR (400 MHz, DMSO-d₆) δ ppm 4.47 (q, 2 H), 8.31 (d, 1 H), 8.67 (d, 1 H), 8.90 (bs, 1 H).

Step 2: N-(2-Methylbut-3-yn-2-yl)-2-(2,2,2-trifluoroethylamino)-5-(trifluoromethyl) nicotinamide A mixture of 2-(2,2,2-trifluoroethylamino)-5-(trifluoromethyl)nicotinic acid (42 mg, 0.146 mmol), 1,1-dimethylpropargylamine (0.017 ml, 0.16 mmol), EDCI (33 mg, 0.18 mmol), DIPEA (0.05 ml, 0.29 mmol) and HOBt (9.85 mg, 0.07 mmol) in 1 ml DMF was shaken overnight. Water (5 ml) was added. The aqueous mixture was extracted with EtOAc (5 ml). The organic layer was washed with 2M Na₂CO₃, evaporated to dryness and purified by preparative HPLC. Yield: 21 mg.
¹H NMR (400 MHz, CDCl₃) δ ppm 1.77 (s, 6 H), 2.44 (s, 1 H), 4.29 (qd, 2 H), 6.14 (bs, 1 H), 7.73 (d, 1 H), 8.47 (dd, 1 H), 8.87 (t, 1 H).

Example 36

5-Cyano-2-(cyclobutylamino)-N-(2-methylbut-3-yn-2-yl)benzamide

Step 1: Methyl 5-cyano-2-(cyclobutylamino)benzoate

Ethyl 2-amino-5-cyanobenzoate (0.3 g, 1.7 mmol), cyclobutanone (0.24 ml, 3.2 mmol) and glacial acetic acid (0.58 ml, 10.2 mmol) in 1,2-Dichloroethane (5 ml) were stirred under N₂. Sodium triacetoxy borohydride (1.011 g, 4.77 mmol) was added and the mixture was stirred overnight. NaHCO₃ (aq) vas added. The mixture with extracted with EtOAC, the organic layers were dried and evaporated. Flash chromatography gave 0.114 g of the title compound.
1H NMR (400 MHz, CDCl₃) δ ppm 1.80-2.05 (m, 4 H), 2.43-2.53 (m, 2 H), 3.88 (s, 3H), 3.95-4.03 (m, 1 H), 6.55 (d, 1 H), 7.49 ddd 1 H), 8.19 (dd, 1 H), 8.39 (d, 1 H).

Step 2: 5-Cyan-2-(cyclobutylamino)benzoic acid

A solution of methyl 5-cyano-2-(cyclobutylamino)benzoate (0.114 g, 0.50 mmol) in THF (3 ml) and 1M NaOH (3 ml) was stirred overnight. The solvents were evaporated under reduced pressure. The crude was diluted with t-butyl methyl ether and acidified with dilute HCl solution. Solvents were evaporated. The crude product was used as such.
¹H NMR (400 MHz, DMSO-d₆) δ ppm 1.72-1.95 (m, 4 H), 2.39-147 (m, 2 H) 4.03-4.10 (m, 1 H), 6.13 (d, 1 H), 7.68 (dd, 1 H), 8.09 (d, 1 H), 8.55 (bs, 1 H), 13.30 (bs, 1H).

Step 3: 5-Cyano-2-(cyclobutylamino)-N-(2-methylbut-3-yn-2-yl)benzamide

A mixture of 5-cyano-2-(cyclobutylamino)benzoic acid (100 mg, 0.46 mmol), 1,1-dimethylpropargylamine (0.054 ml, 0.51 mmol), EDCI (106 mg, 0.56 mmol), DIPEA (0.24 ml, 1.39 mmol) and HOBt (31 mg, 0.23 mmol) in 2 ml DMF was shaken overnight. Water (3 ml) was added. The aqueous mixture was extracted with EtOAc (3 ml). The organic layer was washed with 2M Na₂CO₃, evaporated to dryness and purified by preparative HPLC. Yield: 61 mg.
¹H NMR (400 MHz, CDCl₃) δ ppm 1.74 (d, 6 H), 1.77-2.06 (m, 4 H), 2.41 (s, 1H), 2.36-2.49 (m, 2 H), 3.92 (sxt, 1 H), 6.50 (dd, 1 H), 6.55 (bs, 1H), 7.42 (d, 1 H), 7.76 (d, 1 H), 8.49 (d, 1H).

Example 37

4-Cyano-2-(cydclobutylamino)-N-(2-methylbut-3-yn-2-yl)benzamide

Step 1: Methyl-4-cyano-2-(cyclobutylamino)benzoate

Methyl-2-amino-4-cyanobenzoate (0.3 g, 1.70 mmol), cyclobutanone (0.24 ml, 3.24 mmol) and glacial acetic acid (0.585 ml, 10.22 mmol) in 1,2-dichloroethane (5 ml) were stirred under N₂. Sodium triacetoxy borohydride (1.011 g, 4.77 mmol) was added and the mixture was stirred for two days. NaHCO$_3$ (aq) was added. The mixture with extracted with EtOAc, the organic layers were dried and evaporated. Flash chromatography gave 0.152 g of the title compound.

$^1$H NMR (490 MHz, CDCl$_3$) δ ppm 1.80-2.02 (m, 4 H), 2.44-2.53 (m, 2 H), 3.88 (s, 3 H), 3.90-3.96 (m, 1 H), 6.77-6.81 (m, 2 H), 7.93 (dd, 1 H), 7.97 (bs, 1 H).

Step 2: 4-Cyano-2-(cyclobutylamino)benzoic acid

A solution of methyl-4-cyano-2-(cyclobutylamino)benzoate (0.152 g, 0.66 mmol) in THF (3 ml) and 1M NaOH (4 ml) was stirred overnight. The solvents were evaporated under reduced pressure. The solution was diluted with t-butyl methyl ether and acidified with dilute HCl solution. The solution was evaporated. The crude product was used as such.

$^1$H NMR (400 MHz, DMSO-d$_6$) δ ppm 1.69-1.90 (m, 4 H), 2.39-2.48 (m, 2 H), 3.99-4.09 (m, 1 H), 6.9 (dd, 1 H), 7.02 (d, 1 H), 7.90 (d, 1 H), 8.09 (bs, 1H) 13.33 (bs, 1 H).

Step 3: 4-Cyano-2-(cyclobutylamino)-N-(2-methylbut-3-yn-2-yl)benzamide

A mixture of 4-cyano-2-(cyclobutylamino)benzoic acid (150 mg, 0.69 mmol), 1,1-dimethylpropargylamine (0.080 ml, 0.76 mmol), EDCI (160 mg, 0.83 mmol), DIPEA (0.36 ml, 2.08 mmol) and HOBt (47 mg, 0.35 mmol) in 2 ml DMF was shaken overnight. Water (3 ml) was added. The aqueous mixture was extracted with EtOAc. The organic layer was washed with 2M Na$_2$CO$_3$, evaporated to dryness and purified by preparative HPLC. Yield: 68 mg.

$^1$H NMR (400 MHz, CDCl$_3$) δ ppm 1.74 (s, 6 H), 1.77-1.99 (m, 4 H), 2.41 (s, 1H), 2.38-2.50 (m, 2 H), 3.79-3.91 (m, 1 H), 6.27 (bs, 1 H), 6.71 (d, 1 H), 6.73-6.78 (m, 1 H), 7.37 (d, 1 H), 7.75 (d, 1 H).

Example 38

4,5-Difluoro-N-(2-methylbut-3-yn-2-yl)-2-(2,2,2-trifluoroethylamino)-benzamide

Step 1:
4,5-Difluoro-2-(2,2,2-trifluoroethylamino)benzoic aid

A mixture of 2-bromo-4,5-difluorobenzoic acid (2 g, 8.4 mmol), 2,2,2-trifluoroethylamine (1.15 ml, 14.3 mmol), copper (32 mg, 0.0.5.1 mmol), copper(I)bromide (61 mg, 0.42 mmol), potassium carbonate (1.4 g, 10.1 mmol) in DMF (5 ml) was heated in a microwave reactor at 150° C. for, 0.5 h. The reaction mixture was diluted with ethyl acetate and, washed with 0.5 M citric acid solution. The organic layer was dried over anhydrous sodium sulphate and evaporated. The crude was purified by reverse phase column chromatography. Yield: 0.60 g.

$^1$H NMR (400 MHz, CD$_3$OD) δ ppm 4.03 (q, 2 H), 6.86 (dd, 1 H), 7.79 (dd, 1 H).

Step 2: 4,5-Difluoro-N-(2-methylbut-3-yn-2-yl)-2-(2,2,2-trifluoroethylamino)benzamide A mixture of 4,5-difluoro-2-(2,2,2-trifluoroethylamino) benzoic acid (1.2 g, 4.70 mmol), 1,1-dimethylpropargylamine (0.54 ml, 5.2 mmol), EDCI (1.08 g, 5.64 mmol), DIPEA (1.64 ml, 9.4 mmol) and HOBt (0.32 g, 2.35 mmol) in DCM (20 ml) and DMF (2 ml) vas stirred for one day. The mixture was diluted with water and extracted with EtOAc. The organic layer was washed with 2M Na$_2$CO$_3$; evaporated to dryness and purified by preparative flash chromatography. Yield: 1.27 g.

$^1$H NMR (400 MHz, CDCl$_3$) δ ppm 1.74 (s, 6 H), 2.41 (s, 1 H), 3.74 (qd, 2 H), 5.93, (bs, 1 H), 6.56 (dd, 1 H), 7.18 (dd, 1 H), 8.16 (t, 1 H).

Example 39

N-(2-Methylbut-3-yn-2-yl)-2-(2,2,2-trifluoroethylamino)-5-(trifluoromethyl) benzamide Step 1: 2-(2,2,2-Trifluoroethylamino)-5-(trifluoromethyl)benzoic acid A mixture of 2-chloro-5-(trifluoromethyl)benzoic acid (0.4 g, 1.78 mmol), 2,2,2-trifluoroethylamine (0.24 ml, 3.03 mmol), copper (6.8 mg, 0.11 mmol), copper(I)bromide (13 mg, 0.089 mmol), potassium carbonate (0.29 g, 2.1 mmol) and DMF (1 ml) was heated in a microwave reactor at 150° C. for 2 h. The mixture was diluted with ethyl acetate and washed with 0.5M citric acid solution. The organic layer was dried over anhydrous sodium sulphate and evaporated. The crude was purified by reverse phase column chromatography. Yield: 30 mg.

$^1$H NMR (400 MHz, DMSO-d$_6$) δ ppm 4.28-4.39 (m, 2 H), 7.21 (d, 1 H), 7.71 (dd, 1 H), 8.08 (d, 1 H), 8.65 (bs, 1 H), 13.49 (s, 1 H).

Step 2: N-(2-Methylbut-3-yn-2-yl)-2-(2,2,2-trifluoroethylamino)-5-(trifluoroethyl)-benzamide A mixture of 2-(2,2,2-trifluoroethylamino)-5-(trifluoromethyl)benzoic acid (30 mg, 0.10 mmol), 1,1-dimethylpropargylamine (0.012 ml, 0.12 mmol), EDCI (24 mg, 0.12 mmol) DIPEA (004 ml, 0.21 mmol) and HOBt (7 mg, 0.05 mmol) in 2 ml was shaken overnight. Water (3 ml) was added. The aqueous mixture was extracted with EtOAc (3 ml). The organic layer was washed with 2M Na$_2$CO$_3$, evaporated to dryness and purified by preparative HPLC. Yield: 17 mg.

$^1$H NMR (400 MHz, CDCl$_3$) δ ppm 1.76 (s, 6 H), 2.42 (s, 1 H), 3.85 (qd, 2 H) 6.15 (bs, 1 H, 6.84 (d, 1 H), 7.50-7.58 (m, 2 H), 8.48 (t, 1 H).

Example 40

5-Methyl-N-(2-methylbut-3-yn-2-yl)-2-(2,2,2-trifluoroethylamino)-benzamide

Step 1:
5-Methy-2-(2,2,2-trifluoroethylamino)benzoic acid

A mixture of 2-bromo-5-methylbenzoic acid (0.4 g, 1.86 mmol), 2,2,2-trifluoroethylamine (0.25 ml, 3.16 mmol), copper (7.1 mg, 0.11 mmol), copper(I)bromide (13 mg, 0.09 mmol) and potassium carbonate (0.3 g, 2.23 mmol) and DMF (1 ml) was heated in a microwave reactor at 150° C. for 2 h. The mixture was diluted with ethyl acetate and washed with 0.5M citric acid solution. The organic layer was dried over anhydrous sodium sulphate and evaporated. The crude was purified by reverse phase column chromatography. Yield: 135 mg.

$^1$H NMR (406 MHz, DMSO-d$_6$) δ ppm 4.11-4.22 (m, 2 H), 6.91 (d, 1 H), 7.23 (dd, 1 H), 763 (d, 1 H), 8.02 (t, 1 H), 12.82 (bs, 1 H).

Step 2: 5-Methyl-N-(2-methylbut-3-yn-2-yl)-2-(2,2,2-trifluoroethylamino)benzamide A mixture of 5-methyl-2-(2,2,2-trifluoroethylamino)benzoic acid (135 mg, 0.58 mmol), 1,1-dimethylpropargylamine (0.07 ml, 0.64 mmol), EDCI (133 mg, 0.70 mmol), DIPEA (0.2 ml, 1.16 mmol) and HOBt (39 mg, 0.29 mmol) in DMF (2 ml) was stirred overnight. The mixture was diluted with water and extracted with EtOAc. The organic layer was washed with 2M $Na_2CO_3$, evaporated to dryness and purified by preparative HPLC. Yield: 83 mg.

$^1$H NMR (400 MHz, $CDCl_3$) δ ppm 1.73 (s, 6 H), 2.23 (s, 3 H), 2.39 (s, 1 H), 3.75 (qd, 2 H), 6.18 (bs, 1 H), 6.68 (d, 1 H), 7.07-7.16 (m, 2 H), 7.85 (t, 1 H).

Example 41

5-Chloro-N-(2-methylbut-3yn-2-yl)-2-(3,3,3-trifluoropropylamino)-nicotinamide

Step 1: 5-Chloro-2-(3,3,3-trifluoropropylamino)nicotinic acid

A mixture of 2,5-dichloronicotinic acid (0.25 g, 1.30 mmol), 3,3,3-trifluoropropylamine hydrochloride (0.33 g, 2.21, mmol), copper (4.96 mg, 0.078 mmol), copper(I) bromide (9.3 m g, 0.065 mmol), potassium carbonate (0.3 g, 2.21 mmol) and DMF (2ml) was heated in a microwave reactor at 150° C. for 2 h. The mixture was diluted with ethyl acetate and washed with 0.5M citric acid solution. The organic layer was dried over anhydrous sodium sulphate and evaporated. The crude was purified by reverse phase column chromatography. Yield: 58 mg.

$^1$H NMR (400 MHz, DMSO-4) δ ppm 2.53-2.65 (m, 2 H), 3.70 (q, 2 H), 8.04 (d, 1 H), 8.30 (bs, 1 H), 8.32 (d, 1 H), 13.52 (bs, 1 H).

Step 2: 5-Chloro-N-(2-methylbut-3-yn-2yl)-2-(3,3,3-trifluoropropylamino) nicotinamide A mixture of 5-chloro-2-(3,3,3-trifluoropropylamino) nicotinic acid (58 mg, 0.22 mmol), 1,1-dimethylpropargylamine (0.025 ml, 0.24 mmol), EDCI (50 mg, 0.26 mmol), DIPEA (0.075 ml, 0.43 mmol) and HOBt (15 mg, 0.11 mmol) in 2 ml DMF was stirred overnight. The mixture was diluted with water and extracted with EtOAc. The organic layer was washed With 2M $Na_2CO_3$, evaporated to dryness and purified by preparative HPLC. Yield: 57 mg.

$^1$H NMR (400 MHz, $CDCl_3$) δ ppm 1.73 (s, 6 H), 2.41 (s, 1 H), 2.42-2.51 (m, 2 H), 3.66-3.73 (m, 2 H), 6.08 (bs, 1 H), 7.50 (d, 1 H), 8.14 (d, 1 H), 8.17 (t, 1 H).

Example 42

2-(Butylamino)-4,5-difluoro-N-(2-methylbut-3-yn-2-yl)benzamide

Step 1: 2-(Butylamino)-4,5-difluorobenzoic acid

Butyraldehyde (0.164 ml, 1.820 mmol) and acetic acid, glacial (0.248 ml, 4.33 mmol) were added to 2-amino-4,5-difluorobenzoic acid (0.3 g, 1.733 mmol) in 1,2-dichloroethane (10 ml) at 0° C. Sodium triacetoxy borohydride (0.735 g, 3.47 mmol) was added and the mixture was stirred at room temperature for 2 h. Reaction was quenched with 10 ml of water and resulting layers were separated. The organic phase was washed with 1M $Na_2CO_3$ and brine, dried over $Na_2SO_4$, filtered and evaporated. 0.374 g of the title compound was obtained.

$^1$H NMR (400 MHz, $CDCl_3$) δ ppm 0.98 (t, 3 H) 1.46 (dq, 2 H) 1.67 (quin, 2 H) 3.14 (t, 2 H) 6.42 (dd, 1 H) 7.30-7.83 (m, 2 H).

Step 2: 2-(Butylamino)-4,5-difluoro-N-(2-methylbut-3-yn-2-yl)benzamide 2-(Butylamino)-4,5-difluorobenzoic acid (0.100 g, 0.436 mmol), 2-methylbut-3-yn-2-amine (0043 ml, 0.436 mmol), HOBt (0.065 g, 0.480 mmol), EDCI (0.092 g, 0.480 mmol) and DIPEA (0.084 ml, 0.480 mmol) in DCM (5 ml) were stirred at room temperature for 2 h. Some DCM was added and organic phase was washed with 1M HCl and 1M $Na_2CO_3$, dried over $Na_2SO_4$, filtered and evaporated. The crude product was purified by preparative HPLC. 0.029 g of the title compound was obtained.

$^1$H NMR (400 MHz, $CDCl_3$) δ ppm 0.95 (t, 3 H) 1.37-1.50 (m, 2 H) 1.58-1.68 (m, 2 H) 1.72 (s, 6 H) 2.40 (s, 1H) 3.05 (t, 2 H) 5.90 (br. s., 1 H) 6.40 (dd, 1 H) 7.13 (dd, 1 H) 7.50 (br. s, 1 H).

Example 43

5-Bromo-(3-ethylpent-1-yn-3yl)-2-(2-methoxyethylamino)-benzamide

Step 1: 5-Bromo-2-(2-methoxyethylamino)benzoic acid 1,1,2-Trimethoxyethane (0.268 ml, 2.081 mmol), trifluoroacetic acid (0.2 ml, 2.69 mmol) and water (0.2 ml) were heated at 50° C. for 10 min. The cooled mixture, together with acetic acid, glacial (0.298 ml, 5.20 mmol) was added slowly to 2-amino-5-bromobenzoic acid (0.450 g, 2.081 mmol) in 1,2-dichloroethane (10 ml) at 0° C. Sodium triacetoxy borohydride (0.882 g, 4.16 mmol) was added and the mixture was stirred at room temperature overnight. The reaction was quenched with 10 ml of water. Layers were separated and the organic phase was extracted with 1M $Na_2CO_3$. Resulting aqueous phase was acidified by 2M HCl and extracted 3 times with DCM. Combined organic phases were dried over $Na_2SO_4$, filtered and evaporated. The crude product was purified by reverse phase chromatography. 0.180 g of the title compound was obtained.

$^1$H NMR (400 MHz, $CDCl_3$) δ ppm 3.39 (t, 2 H) 3.43 (s, 3 H) 3.64 (t, 2 H) 6.62 (d, 1 H) 7.44 (dd, 1 H) 8.06 (d, 1 H).

Step 2: 5-Bromo-N-(3-ethylpent-1-yn-3-yl)-2-(2-methoxyethylamino)benzamide 5-Bromo-2-(2-methoxyethylamino)benzoic acid (0.100 g, 0.365 mmol), 3-ethylpent-1-yn-3-amine hydrochloride (0.078 g, 0.474 mmol), HOBt (0.054 g, 0.401 mmol), EDCI (0.077 g, 0.401 mmol) and DIPEA (0.070 ml, 0.401 mmol) in DCM (5 ml) were stirred at room temperature over weekend. Some DCM was added and the organic phase was washed with 1M HCl and 1M $Na_2CO_3$, dried over $Na_2SO_4$, filtered and evaporated. The crude product was purified by preparative HPLC. 0.044 g of the title compound was obtained.

$^1$H NMR (400 MHz, $CDCl_3$) δ ppm 1.04 (t, 6 H) 1.84-1.96 (m, 2 H) 2.26 (dq, 2 H) 2.41 (s, 1 H) 3.31 (q, 2 H)

3.39 (s, 3 H) 3.58 (t, 2 H) 5.91 (br. s., 1 H) 6.60 (d, 1 H) 730-7.37 m, 2 H) 7.39 (d, 1 H).

Example 44

5-Chloro-N-(3-ethylpent-1-yn-3yl)-2-(2-methoxy-ethylamino)-benzamide

Step 1: 5-Chloro-2-(2-methoxyethylamino)benzoic add 1,1,2-Trimethoxyethane (0.268 ml, 2.081 mmol), trifluoroacetic acid (0.2 ml, 2.69 mmol) and water (0.2 ml) were heated at 50° C. for 10 min. The cooled mixture, together with acetic acid, glacial (0.298 ml, 5.20 mmol) was added slowly to 2-amino-5-chlorobenzoic acid (0.357 g, 2.081 mmol) in 1,2-dichloroethane (10 ml) at 0° C. Sodium triacetoxy borohydride (1.323 g, 6.24 mmol) was added and the mixture was stirred at room temperature for 2 h. The reaction was quenched with 10 ml of water. Layers were separated and organic phase was dried over $Na_2SO_4$, filtered and evaporated. The crude product was purified by reverse phase chromatography. 0.044 g of the title compound was obtained.

$^1$H NMR (400 MHz, $CDCl_3$) δ ppm 3.41 (t, 2 H) 3.44 (s, 3 H) 3.66 (t, 2 H) 6.68 (d, 1 H) 7.34 (dd, 1 H) 7.93 (d, 1 H).

Step 2: 5-Chloro-N-(3-ethylpent-1-yn-3-yl)-2-(2-methoxyethylamino)benzamide

5-Chloro-2-(2-methoxyethylamino)benzoic acid (0.044 g, 0.192 mmol), 3-ethylpent-1-yn-3-amine hydrochloride (0.041 g, 0.249 mmol), HOBt (0.028 g, 0.211 mmol), EDCI (0.040 g, 0.211 mmol) and DIPEA (0.037 ml, 0.211 mmol) in DCM (5 ml) were stirred at room temperature overnight. Some DCM was added and organic phase was washed with 1M HCl and 1M $Na_2CO_3$, dried over $Na_2SO_4$, filtered and evaporated. The crude product was purified by preparative HPLC. 0.012 g of the title compound was obtained.

$^1$H NMR (400 MHz, $CDCl_3$) δ ppm 1.04 (t, 6 H) 1.85-1.96 (m, 2 H) 2.21-2.31 (m, 2 H) 2.42 (s, 1 H) 3.31 (q, 2 H) 3.38 (s, 3 H) 3.59 (t, 2 H) 5.93 (br. s., 1 H) 6.64 (d, 1 H) 7.22 (dd, 1 H) 7.25-7.33 (m, 2 H).

Example 45

N-(3-Ethylpent-1-yn-3-yl)-4,5-difluoro-2-(2-methoxyethylamino)-benzamide

Step 1: 4,5-Difluoro-2-(2-methoxyethylamino)benzoic acid 1,1,2-Trimethoxyethane (0.268 ml, 2.081 mmol), trifluoroacetic acid (0.2 ml, 2.69 mmol) and water (0.2 ml) were heated at 50° C. for 10 min. The cooled mixture, together with acetic acid, glacial (0.298 ml, 5.20 mmol) was added slowly to 2-amino-4,5-difluorobenzoic acid (0.360 g, 2.81 mmol) in 1,2-dichloroethane (10 ml) at 0° C. Sodium triacetoxy borohydride (1.323 g, 6.24 mmol) was added and the mixture was stirred at room temperature for 2 h. Reaction was quenched with 10 ml of water. Layers were separated and organic phase was dried over $Na_2SO_4$, filtered and evaporated. The crude product was purified by reverse phase chromatography. 0.188 g of the title compound was obtained.

$^1$H NMR (400 MHz, $CDCl_3$) δ ppm 3.36 (t, 2 H) 3.43 (s, 3 H) 3.65 (t, 2 H) 6.48 (dd, 1 H) 7.54-8.00 (n, 2 H).

Step 2: N-(3-Ethylpent-1-yn-3-yl)-4-difluoro-2-(2-methoxyethylamino)benzamide 4,5-Difluoro-2-(2-methoxyethylamino)benzoic acid (0.100 g, 0.433 mmol, 3-ethylpent-1-yn-3-amine hydrochloride (0.092 g, 0.562 mmol), HOBt (0.064 g, 0.476 mmol), EDCI (0.091 g, 0.476 mmol) and DIPEA (0.083 ml, 0.476 mmol) in DCM (5 ml) were stirred at room temperature overnight. Some DCM was added and organic phase was washed with 1M HCl and 1M $Na_2CO_3$; dried over $Na_2SO_4$, filtered and evaporated. The crude product was purified by preparative HPLC. 0.079 g of the title compound was obtained.

$^1$H NMR (400 MHz, $CDCl_3$) δ ppm 1.03 (t, 6 H) 1.84-1.95 (m, 2 H) 2.24 (dq, 2H) 2.42 (s, 1 H) 3.26 (q, 2 H) 3.39 (s, 3 H) 3.59 (t, 2 H) 5.86 (br. s., 1 H) 6.47 (dd, 1 H) 7.16 (dd, 1 H) 7.35 (br. s., 1 H).

Example 46

N-(3-Ethylpent-1-yn-3-yl)-2-(2-methoxyethyl-amino)-5-(trifluoro-methyl)benzamide Step 1: 2-(2-Methoxyethylamino)-5-(trifluoromethyl)benzoic acid 1,1,2-Trimethoxyethane (0.268 ml, 2.081 mmol), trifluoroacetic acid (0.2 ml, 2.69 mmol) and water (0.2 ml) were heated at 50° C. for 10 min. Cooled mixture together with acetic acid, glacial (0.298 ml, 5.20 mmol) was added slowly to 2-amino-5-(trifluoromethyl)benzoic acid (0.427 g, 2.081 mmol) in 1,2-dichloroethane (10 ml) at 0° C. Sodium triacetoxy borohydride (1.323 g, 6.24 mmol) was added and the mixture was stirred at room temperature for 4 h. Reaction was quenched with 10 ml of water and solvents were evaporated. The crude product was purified by reverse phase chromatography. 0.253 g of the title compound was obtained.

$^1$H NMR (400 MHz, DMSO-$d_6$) δ ppm 3.30 (s, 3 H) 3.39-3.46 (m, 2 H) 3.51-3.62 (m, 2 H) 6.93 (d, 1 H) 7.63 (dd, 1 H) 8.03 (dd, 1 H) 8.38 (br. s., 1 H) 13.22, (br. s, 1 H).

Step 2: N-(3-Ethylpent-1-yn-3-yl)-2-(2-methoxyethylamino)-5-(trifluoromethyl)-benzamide 2-(2-Methoxyethylamino)-5-(trifluoromethyl)benzoic acid (0.100 g, 0.380 mmol), 3-ethylpent-1-yn-3-amine hydrochloride (0.081 g, 0.494 mmol), HOBt (0.056 g, 0.418 mmol), EDCI (0.080 g, 0.418 mmol) and DIPEA (0.139 ml, 0.798 mmol) in DCM (5 ml) were stirred at room temperature over Weekend. Some DCM was added and organic phase was washed with 1M HCl and 1M $Na_2CO_3$, dried over $Na_2SO_4$, filtered and evaporated. The crude product was purified by preparative HPLC. 0.069 g of the title compound was obtained.

$^1$H NMR (400 MHz, $CDCl_3$) δ ppm 1.05 (t, 6 H) 1.86-1.98 (m, 2 H) 2.21-2.32 (m, 2 H) 2.44 (s, 1 H) 3.34-3.43 (m, 5 H) 3.61 (t, 2 H) 6.01 (br. s, 1 H) 6.73 (d, 1 H) 7.44-7.55 (m, 2 H) 7.81 (t, 1 H).

Example 47

N-(3-Ethylpent-1-yn-3-yl)-5-iodo-2-(2-methoxyethylamino)benzamide

Step 1: 5-Iodo-2-(2-methoxyethylamino)benzoic acid 1,1,2-Trimethoxyethane (0.268 ml, 2.081 mmol), trifluoroacetic acid (0.2 ml, 2.69 mmol) and water (0.2 ml) were heated at 50° C. for 10 min. The cooled mixture together with acetic acid, glacial (0.298 ml, 5.20 mmol) was added slowly to 2-amino-5-iodobenzoic acid (0.547 g, 2.081 mmol) in 1,2-dichloroethane (10 ml) at 0° C. Sodium triacetoxy borohydride (1.323 g, 6.24 mmol) was added and the mixture was stirred at room temperature for 4 h. Reaction was quenched with 10 ml of water and solvents were evaporated. The crude product was purified by reverse phase chromatography. 0.206 g of the title compound was obtained.

$^1$H NMR (400 MHz, DMSO-$d_6$) δ ppm 3.29 (s, 3 H) 3.30-3.37 (m, 2 H) 3.49-3.59 (m, 2H) 6.64 (d, 1 H) 7.59 (dd, 1 H) 7.69-8.29 (m, 2 H) 12.84 (br. s, 1 H).

Step 2: N-(3-Ethylpent-1-yn-3-yl)-5-iodo-2-(2-methoxyethylamino)benzamide 5-iodo-2-(2-methoxyethylamino)benzoic acid (0.100 g, 0.311 mmol), 3-ethylpent-1-yl-3-amine hydrochloride (0.066 g, 0.405 mmol), HOBt (0.046 g, 0.343 mmol), EDCI (0.066 g, 0.343 mmol) and DIPEA (0.114 ml, 0.654 mmol) ii DCM (5 nil) were stirred at room temperature over the weekend. Some DCM was added and the organic phase was washed with 1M HCl and 1M Na$_2$CO$_3$, dried over Na$_2$SO$_4$, filtered and evaporated. The crude product was purified by preparative HPLC. 0.076 g of the title compound was obtained.

$^1$H NMR (400 MHz, CDCl$_3$) δ ppm 1.03 (t, 6 H) 1.85-1.96 (m, 2 H) 2.25 (dq, 2 H) 2.42 (s, 1 H) 3.27-3.34 (m, 2 H) 3.38 (s, 3 H) 3.58 (t, 2 H) 5.90 (br. s, 1 H) 6.49 (d, 1 H) 7.36 (br. s., 1 H) 7.50 (dd, 1 H) 7.53 (d, 1 H).

Example 48

2-(2-Methoxyethylamino)-N-(2-methylbut-3-yn-2-yl)-5-(trifluoromethyl)benzamide 2-(2-Methoxyethylamino)-5-(trifluoromethyl)benzoic acid (0.100 g, 0.380 mmol), 1,1-dimethylpropargylamine (0.044 ml, 0.418 mmol), HOBt (0.056 g, 0.418 mmol), EDCI (0.080 g, 0.418 mmol) and DIPEA (0.073 ml, 0.418 mmol) in DCM (5 ml) were stirred at room temperature over weekend. Some DCM was added and organic phase was washed with 1M HCl and 1M Na$_2$CO$_3$, dried over Na$_2$SO$_4$, filtered and evaporated. The crude product was purified by preparative HPLC. 0.080 g of the title compound was obtained.

$^1$H NMR (400 MHz, CDCl$_3$) δ ppm 1.75 (s, 6 H) 2.40 (s, 1 H) 3.34-3.42 (m, 5 H) 3.59-3.64 (m, 2 H) 6.10 (br. s., 1 H) 6.73 (d, 1 H) 7.44-7.52 (m, 1 H) 8.02 (t, 1 H).

Example 49

2-(Butylamino)-5-fluoro-N-(2-methylbut-3-yn-2-yl)benzamide

Step 1: 2-(Butylamino)-5-fluorobenzoic acid

Butyraldehyde (0.168 ml, 1.862 mmol) and acetic acid, glacial (0.254 ml, 4.43 mmol) were added to methyl-2-amino-5-fluorobenzoate (0.3 g, 1.774 mmol) in 1,2-dichloroethane (10 ml) at 0° C. Sodium triacetoxy borohydride (0.752 g, 3.55 mmol) was added and the mixture was stirred at room temperature for 2.5 h. The reaction was quenched with 10 ml of water and resulting layers were separated. The organic phase was washed with 1M Na$_2$CO$_3$ and brine, dried over Na$_2$SO$_4$, filtered and evaporated. The crude compound was purified by flash chromatography. 0.289 g of the title compound was obtained.

$^1$H NMR (400 MHz, CDCl$_3$) δ ppm 0.97 (t, 3 H) 1.41-1.52 (m, 2 H) 1.62-1.71 (m, 2 H) 3.16 (q, 2 H) 3.85 (s, 3 H) 6.58-6.64 (m, 1 H) 7.10 (dddd, 1 H) 7.47 (br. s., 1 H) 7.55-7.60 (dd, 1 H).

Step 2: 2-(Butylamino)-5-fluorobenzoic acid

Lithium hydroxide (0.061 g, 2.57 mmol) was added to methyl 2-(butylamino)-5-fluorobenzoate (0.289 g, 1.283 mmol) in THF (8 ml) and water (2 ml) at 0° C. The reaction mixture was refluxed for 8 h. THF was evaporated and residue was dissolved in water And washed once with DCM. Thereafter the water phase was acidified with 5M HCl and extracted 3 times with EtOAc. The organic phase was dried over Na$_2$SO$_4$, filtered and evaporated. 0.253 g of the title compound was obtained.

$^1$H NMR (400 MHz, DMSO-$d_6$) δ ppm 0.92 (t, 3 H) 1.32-1.45 (m, 2 H) 1.51-1.62 (m, 2 H) 3.15 (t, 2 H) 6.74 (dd, 1 H) 7.27 (ddd, 1 H) 7.48 (dd, 1 H) 10.20 (br. s, 1 H).

Step 3: 2-(Butylamino)-5-fluoro-N-(2-methylbut-3-yn-2-yl)benzamide 2-(Butylamino)-5-fluorobenzoic acid (0.100 g, 0.473 mmol), 1,1-dimethylpropargylamine (0.055 ml, 0.521 mmol), HOBt (0.070 g, 0.521 mmol), EDCI (0.100 g, 0.521 mmol) and DIPEA (0.091 ml, 0.521 mmol) in DCM (5 ml) were stirred at room temperature overnight. Some DCM was added and organic phase was washed with 1M HCl and 1M Na$_2$CO$_3$, dried over Na$_2$SO$_4$, filtered and evaporated. The crude product was purified by preparative HPLC. 0.037 g of the title compound was obtained.

$^1$H NMR (400 MHz, CDCl$_3$) δ ppm 0.95 (t, 3 H) 1.37-1.50 (m, 2 H) 1.56-1.69 (m, 2 H) 1.74 (s, 6 H) 2.39 (s, 1 H) 3.10 (t, 2 H) 6.05 (br. s., 1 H) 6.58-6.65 (m, 1 H) 7.00-7.07 (m, 2 H) 7.12 (br. s., 1 H).

Example 50

5-Iodo-2-(2-methoxyethylamino)-N-(2-methylbut-3-yn-2-yl)benzamide

5-Iodo-2-(2-methoxyethylamino)benzoic acid (0.100 g, 0.311 mmol), 1,1-dimethylpropargylamine (0.036 ml, 0.343 mmol), HOBt (0.046 g, 0.343 mmol), EDCI (0.066 g, 0.343 mmol) and DIPEA (0.060 ml, 0.343 mmol) in DCM (5 ml) were stirred at room temperature overnight. Some DCM was added and organic phase was washed with 1M HCl and 1M Na$_2$CO$_3$, dried over Na$_2$SO$_4$, filtered and evaporated. The crude product was purified by preparative HPLC. 0.071 g of the title compound was obtained.

$^1$H NMR (400 MHz, CDCl$_3$) δ ppm 1.72 (s, 6 H) 2.38 (s, 1 H) 3.26-3.33 (m, 2 H) 3.37 (s, 3 H) 3.57 (t, 2 H) 6.08 (br. s, 1 H) 6.47 (d, 1 H) 7.47 (dd, 1 H) 7.50-7.62 (m, 2 H).

Example 51

5-Fluoro-2-(isobutylamino)-N-(2-methylbut-3-yn-2-yl)nicotinamide

Step 1: 5-Fluoro-2-(isobutylamino)nicotinic acid

Methyl 2-chloro-5-fluoronicotinate (0.4 g, 2.1.1 mmol), isobutylamine (1.258 ml, 12.66 mmol) and ethanol (4 ml) were heated by microwave irradiation at 160° C. for 30 min. After concentration to dryness, the crude mixture was purified by flash chromatography to give a mixture of methyl and ethyl esters. This mixture was dissolved in THF (3 ml), 2 M aqueous sodium hydroxide (1.0 ml, 2.0 mmol) was added and it was heated at 50° C. for 5 h. THF was evaporated and residue was acidified with 1M HCl. The solids were filtered off and dried under reduced pressure. 0.072 g of the title compound, was obtained.

$^1$H NMR (400 MHz, DMSO-$d_6$) δ ppm 0.91 (d, 6 H) 1.80-1.93 (m, 1 H) 3.26 (d, 2 H) 7.89 (dd, 1 H) 8.07 (br. s., 1 H) 8.29 (d, 1 H) 13.35 (br. s, 1 H).

Step 2: 5-Fluoro-2-(isobutylamino)-N-(2-methylbut-3-yn-2-yl)nicotinamide

5-Fluoro-2-(isobutylamino)nicotinic acid (0.072 g, 0.339 mmol), 1,1-dimethylpropargylamine (0.037 ml, 0.373 mmol), HOBt (0.050 g, 0.373 mmol), EDCI (0.072 g, 0.373 mmol) and DIPEA (0.065 ml, 0.373 mmol) in DCM (5 ml) were stirred at room temperature overnight. Some DCM was added and organic phase was washed with 1M HCl and 1M Na$_2$CO$_3$, dried over Na$_2$SO$_4$, filtered and evaporated. The crude product was purified by flash chromatography. 0.080 g of the title compound was obtained.

$^1$H NMR (400 MHz, CDCl$_3$) δ ppm 0.98 (d, 6H) 1.75 (s, 6 H) 1.92 (dquin, 1 H) 2.41 (s, 1 H) 3.26 (dd, 2 H) 5.95 (br. s., 1 H) 7.28-7.32 (m, 1 H) 7.87 (br. s, 1 H) 8.11 (d, 1 H).

Example 52

5-Fluoro-2-(isopentylamino)-N-(2-methylbut-3-yn-2-yl)nicotinamide

Step 1: 5-Fluoro-2-(isopentylamino)nicotinic acid

Methyl 2-chloro-5-fluoronicotinate (0.266 g, 1.403 mmol), isoamylamine (0.980 ml, 8.42 mmol) and ethanol (2 ml) were heated by microwave irradiation at 160° C. for 30 min. The solvent was evaporated and residue was dissolved in THF (5 ml). 2M aqueous sodium hydroxide (2.105 ml, 4.21 mmol) was added and the mixture was heated at 50° C. for 2.5 h. After stirring at room temperature overnight, THF was evaporated and the residue was acidified with 1M HCl. Solids were filtered off and dried under reduced pressure. 0.152 g of the title compound was obtained.

$^1$H NMR (400 MHz, CDCl$_3$) δ ppm 0.93 (d, 6 H) 1.48-1.58 (m, 2 H) 1.70 (m, 1 H) 3.44-3.52 (m, 2 H) 7.81-7.99 (m, 2 H) 8.16 (d, 1 H).

Step 2: 5-Fluoro-2-(isopentylamino)-N-(2-methylbut-3-yn-2-yl)nicotinamide

5-Fluoro-2-(isopentylamino)nicotinic acid (0.100 g, 0.442 mmol), 1,1-dimethylpropargyl-amine (0.048 ml, 0.486 mmol), HOBt (0.066 g, 0.486 mmol), EDCI (0.093 g, 0.486 mmol) and DIPEA (0.085 ml, 0.486 mmol) in DCM (5 ml) were stirred at room temperature overnight. Some DCM was added and organic phase was washed with 1M HCl and 1M Na$_2$CO$_3$; dried over Na$_2$SO$_4$, filtered and evaporated. The crude product was purified by flash chromatography. 0.081 g of the title compound was obtained.

$^1$H NMR (400 MHz, CDCl$_3$) δ ppm 0.94 (d, 6 H) 1.48-1.58 (m, 2 H) 1.65-1.76 (m, 7 H) 2.41 (s, 1 H) 3.39-3.46 (m, 2 H) 5.94 (br. s., 1 H) 7.29 (dd, 1 H) 7.73 (br. s., 1 H) 8.12 (d, 1 H).

Example 53

5-Fluoro-N-(2-methylbut-3-yn-2-yl)-2-(2-(trifluoromethoxy)-ethylamino)benzamide

Step 1: S,S'-Dimethyl O,O-2,2'-oxybis(ethane-2,1-diyl) dicarbonodithioate

Aqueous sodium hydroxide (50%, 97.0 ml, 1844 mmol) was added slowly to diethyleneglycol (7.0 ml, 73.7 mmol) and tetrabutylammonium sulfate (50%, 5.30 ml, 4.61 mmol). After 10 min of stirring at room temperature, carbon disulfide (97 ml, 1605 ml) was slowly added. Finally, iodomethane (10.10 ml, 162 mmol) was added and the mixture was stirred for 4.5 h at ambient temperature. 20 ml of water was cautiously added and the mixture was stirred well. Phases were separated and water phase was extracted three times with DCM. Combined organic phases were washed 2 times with brine, dried over Na$_2$SO$_4$, filtered and evaporated. The crude product was purified by flash chromatography. 15.07 g of the title compound was obtained.

$^1$H NMR (400 MHz, CDCl$_3$) δ ppm 2.58 (s, 6 H) 3.86-3.90 (m, 4 H) 4.74-4.78 (m, 4 H).

Step 2: 1-(Trifluoromethoxy)-2-(2-(trifluoromethoxy)ethoxy)ethane

HF-pyridine complex (70%, 45.5 ml, 1750 mmol) was added to 1,3-dibromo-5,5-dimethylhydantoin (55.4 g, 194 mmol) in dry DCM (170 ml) at −78° C. under N$_2$ atmosphere. S,S-dimethyl O,O-2,2'-oxybis(ethane-2,1-diyl) dicarbonodithioate (9.1 g, 31.8 mmol) in dry DCM (60 ml) was added dropwise and reaction mixture was left to warm slowly to room temperature. The mixture was poured into crushed ice and saturated with NaCl. Aqueous saturated NaHSO$_3$ solution was added until the colour changed to light yellow followed by phase separation. Water phase was further extracted twice with DCM. Combined organic phases were washed with cold aqueous saturated NaHSO$_3$ and brine, dried over Na$_2$SO$_4$, filtered and evaporated. The residue was purified by distillation. 3.874 g of the title compound was obtained.

$^1$H NMR (400 MHz, CDCl$_3$) δ ppm 3.73-3.78 (m, 4 H) 4.09-4.13 (m, 4 H).

Step 3: 2-(Trifluoromethoxy)ethyl trifluoromethanesulfonate 1-(Trifluoromethoxy)-2-(2-(trifluoromethoxy)ethoxy) etharie (3.874 g, 16.00 mmol), trifluoromethanesulfonic anhydride (10.50 ml, 62.4 mmol) and triflic acid (0.382 ml, 4.32 mmol) were heated for 2 days at 60° C. under N$_2$ atmosphere. The volatiles were removed under reduced pressure and the residue was dissolved in DCM and washed with water. The organic phase was dried over Na$_2$SO$_4$, filtered and evaporated. The residue was purified by distillation. 4.222 g of the title compound was obtained.

¹H NMR (400 MHz, CDCl₃) δ ppm 4.25-4.31 (m, 2 H) 4.67-4.72 (m, 2 H).

Step 4:
5-Fluoro-2-(2-(trifluoromethoxy)ethylamino)benzoic acid

2-Amino-5-fluorobenzoic acid (0.100 g, 0.645 mmol) and triethylamine (0.180 ml, 1.289 mmol) were added to 2-(trifluoromethoxy)ethyl trifluoromethanesulfonate (0.376 g, 1.289 mmol) in THF (10 ml) under N₂ atmosphere. The mixture was' stirred at room temperature over weekend after which 0.100 g (0.343 mmol) of 2-(trifluoromethoxy)ethyl-trifluoro-methanesulfonate was added and reaction mixture was heated at 40° C. for 4 h, 5 ml of water was added and pH was adjusted to 4. The mixture was extracted 3 times with EtOAc and combined organic phases were dried over Na₂SO₄, filtered and evaporated. The residue was purified by flash chromatography to give 2-(trifluoromethoxy)ethyl-5-fluoro-2-((2-(trifluoromethoxy)ethyl)amino)benzoate as an intermediate. To 2-(trifluoromethoxy)ethyl 5-fluoro-2-((2-(trifluoromethoxy)ethyl)amino)benzoate in THF (5 ml) was added 2M aqueous sodium hydroxide (0.645 ml, 1.289 mmol) and the resulting mixture was heated at 50° C. for 5 h. THF was evaporated and the residue was acidified with 1M HCl. The solids was filtered off and dried under reduced pressure. 0.073 g of the title compound was obtained.

¹H NMR (400 MHz, MeOD) δ ppm 3.58 (t, 2 H) 4.22 (t, 2 H) 6.81 (dd, 1 H) 7.19 (ddd, 1 H) 7.60 (dd, 1 H).

Step 5: 5-Fluoro-N-(2-methylbut-3-yn-2-yl)-2-(2-(trifluoromethoxy)ethylamino)-benzamide 5-Fluoro-2-(2-(trifluoromethoxy)ethylamino)benzoic acid (0.075 g, 0.281 mmol), 1,1-dimethylpropargylamine (0.032 ml, 0.309 mmol), HOBt (0.042 g, 0.309 mmol), EDCI (0.059 g, 0.309 mmol) and DIPEA (0.054 ml, 0.486 mmol) in DCM (5 ml) were stirred at room temperature overnight. Some DCM was added and organic phase was washed with 1M HCl and 1M Na₂CO₃, dried over Na₂SO₄, filtered and evaporated. The crude product was purified by flash chromatography. 0.045 g of the title compound was obtained.

¹H NMR (400 MHz, CDCl₃) δ ppm 1.74 (s, 6 H) 2.39 (s, 1 H) 3.49 (q, 2 H) 4.10 (t, 2 H) 6.07 (br. s., 1 H) 6.65 (dd, 1 H) 7.02-7.12 (m, 2 H) 7.32-7.42 (m, 1 H).

Example 54

5-Fluoro-N-(2-methylbut-3-yn-2-yl)-2-(4,4,4-trifluorobutylamino)-benzamide

Step 1:
5-Fluoro-2-(4,4,4-trifluorobutylamino)benzoic acid 4,4,4-Trifluorobutyraldehyde (0.305 ml, 2.90 mmol) and trifluoroacetic acid (0.215 ml, 2.90 mmol) were added to 2-amino-5-fluorobenzoic acid (0.3 g, 1.934 mmol) in dry DCM (5 ml) at 0° C. Sodium triacetoxy borohydride (0.615 g, 2.90 mmol) was added and the mixture was stirred at room temperature for 2 h. Reaction was quenched with 10 ml of water and resulting layers were separated. Organic phase was washed with 1M Na₂CO₃ and brine, dried over Na₂SO₄, filtered and evaporated. The crude product was purified by flash chromatography. 0.299 g of the title compound was obtained.

¹H NMR (400 MHz, CDCl₃) δ ppm 1.91-2.01 (m, 2 H) 2.16-2.31 (m, 2 H) 3.31 (t, 2 H) 6.64 (dd, 1 H) 7.19 (ddd, 1 H) 7.68 (dd, 1 H).

Step 2: 5-Fluoro-N-(2-methylbut-3-yn-2-yl)-2-(4,4,4-trifluorobutylamino)benzamide 5-Fluoro-2-(4,4,4-trifluorobutylamino)benzoic acid (0.100 g, 0.377 mmol), 1,1-dimethylpropargylamine (0.044 ml, 0.415 mmol), HOBt (0.056 g, 0.415 mmol), EDCI (0.080 g, 0.415 mmol) and DIPEA (0.072 ml, 0.415 mmol) in DCM (5 ml) were stirred at room temperature overnight. Some DCM was added and organic phase was washed with 1M HCl and 1M Na₂CO₃, dried over Na₂SO₄, filtered and evaporated. The crude product was purified by preparative HPLC. 0.078 g of the title compound was obtained.

¹H NMR (400 MHz, CDCl₃) δ ppm 1.73 (s, 6 H) 1.84-1.96 (m, 2 H) 2.12-2.28 (m, 2 H) 2.40 (s, 1 H) 3.21 (t, 2 H) 6.03 (br. s., 1 H) 6.56-6.65 (m, 1 H) 7.00-7.09 (m, 2 H) 7.12-7.47 (n, 1 H).

Example 55

3,5-Difluoro-N-(2-methylbut-3-yn-2-yl)-2-(3,3,3-trifluoropropylamino)-benzamide

Step 1:
3,5-Difluoro-2-(3,3,3-trifluoropropylamino)benzoic acid 3,3,3-Trifluoropropanal (0.224 ml, 2.60 mmol) and trifluoroacetic acid (0.193 ml, 2.60 mmol) were added to 2-amino-3,5-difluorobenzoic acid (0.3 g, 1.733 mmol) in dry DCM (5 ml) at 0° C. Sodium triacetoxy borohydride (0.551 g, 2.60 mmol) was added and the mixture was stirred at room temperature for 2 h. Reaction was quenched with 10 ml of water and resulting layers were separated. Organic phase was washed with 1M Na₂CO₃ and brine, dried over Na₂SO₄, filtered and evaporated. The crude product was purified by flash chromatography. 0.414 g of the title compound was obtained.

¹H NMR (400 MHz, CDCl₃) δ ppm 2.36-2.50 (m, 2 H) 3.67 (td, 2 H) 7.04 (ddd, 1 H) 7.55 (ddd, 1 H).

Step 2: 3,5-Difluoro-N-(2-methylbut-3-yn-2-yl)-2-(3,3,3-trifluoropropylamino)-benzamide 3,5-Difluoro-2-(3,3,3-trifluoropropylamino)benzoic acid (0.100 g, 0.372 mmol), 1,1-dimethylpropargylamine (0.043 ml, 0.409 mmol), HOBt (0.055 g, 0.409 mmol), EDCI (0.078 g, 0.409 mmol) and DIPEA (0.071 ml, 0.409 mmol) in DCM (5 ml) were stirred at room temperature overnight. Some DCM was added and organic phase was washed with 1M HCl and 1M Na₂CO₃, dried over Na₂SO₄, filtered and evaporated. The crude product was purified by preparative HPLC. 0.084 g of the title compound was obtained.

¹H NMR (400 MHz, CDCl₃) δ ppm 1.74 (s, 6 H) 2.31-2.46 (m, 3 H) 3.41 (td, 2 H) 5.29 (br. s., 1 H) 6.93 (ddd, 1 H) 7.22 (ddd, 1 H) 7.52 (br. s., 1 H).

Example 56

2-(2,2-Difluoroethylamino)-N-(2-methylbut-3-yn-2-yl)-5-(trifluoromethyl)nicotinamide Step 1: 2-(2,2-Difluoroethylamino)-5-(trifluoromethyl)nicotinic acid 2-Chloro-5-(trifluoromethyl)pyridine-3-carboxylic, acid (0.3 g, 1.330 mmol), 2,2-difluoroethylamine (0.159 ml, 2.261 mmol), copper powder (5.1 mg, 0.080 mmol), copper (I) bromide (9.5 mg, 0.067 mmol), potassium carbonate (0.221 g, 1.596 mmol) and dry DMF (1 ml) were heated by microwave irradiation at 150° C. for 1 h. Some EtOAc was added and the organic phase was washed 2 times with 0.5M citric acid, dried over $Na_2SO_4$, filtered and evaporated. The crude product was purified by flash chromatography. 0.164 g of the title compound was obtained.

$^1$H NMR (400 MHz, MeOD) δ ppm 3.99 (td, 2 H) 5.88-6.23 (m, 1 H) 8.37 (dd, 1 H) 8.50-8.55 (m, 1 H).

Step 2: 2-(2,2-Difluoroethylamino)-N-(2-methylbut-3-yn-2-yl)-5-(trifluoromethyl)nicotinamide 2-(2,2-Difluoroethylamino)-5-(trifluoromethyl)nicotinic acid (0.164 g, 0.607 mmol), 1,1-dimethylpropargylamine (0.070 ml, 0.668 mmol), HOBt (0.090 g, 0.668 mmol), EDCI (0.128 g, 0.668 mmol) and DIPEA (0.116 ml, 0.668 mmol) in DCM (5 ml) were stirred at room temperature for 2.5 h. Some DCM was added and organic phase was washed with 1M HCl and 1M $Na_2CO_3$, dried over $Na_2SO_4$, filtered and evaporated. The crude product was purified by preparative HPLC. 0.059 g of the title compound was obtained.

$^1$H NMR (400 MHz, $CDCl_3$) δ ppm 1.76 (s, 6 H) 2.43 (s, 1 H) 3.91 (tdd, 2 H) 5.78-6.22 (m, 2 H) 7.70 (d, 1 H) 8.44 (dd, 1 H) 8.75 (br. s., 1 H).

Example 57

2-(2,2-Difluoropropylamino)-5-fluoro-N-(2-methyl-but-3-yn-2-yl)nicotinamide

Step 1: 2-(2,2-Difluoropropylamino)-5-fluoronicotinic acid

2-Chloro-5-fluoropyridine-3-carboxylic acid (0.3 g, 1.709 mmol), 2,2-difluoropropylamine hydrochloride (0.225 g, 1.709 mmol), copper powder (6.5 mg, 0.103 mmol), copper (I) bromide (12.0 mg, 0.085 mmol), potassium carbonate (0.638 g, 4.61 mmol) and dry DMF (2 ml) were heated by microwave irradiation at 140° C. for 30 min. 0.225 g (1.709 mmol) of 2,2-difluoropropylamine hydrochloride was added and microwave irradiation was continued at 140° C. for 30 min. Some EtOAc was added and organic phase was washed 2 times with 0.5M citric acid, dried over $Na_2SO_4$, filtered and evaporated. The crude product was purified by flash chromatography. 0.076 g of the title compound was obtained.

$^1$H NMR (400 MHz, MeOD) δ ppm 1.62 (t, 3 H) 3.99 (t, 2 H) 7.98 (dd, 1 H) 8.19 (d, 1 H).

Step 2: 2-(2,2-Difluoropropylamino)-5-fluoro-N-(2-methylbut-3-yn-2-yl)nicotinamide 2-(2,2-Difluoropropylamino)-5-fluoronicotinic acid (0.076 g, 0.325 mmol), 1,1-dimethylpropargylamine (0.038 ml, 0.357 mmol), HOBt (0.048 g, 0.357 mmol), EDCI (0.068 g, 0.357 mmol) and DIPEA (0.062 ml, 0.357 mmol) in DCM (5 ml) were stirred at room temperature for 2.5 h. Some DCM was added and organic phase was washed with 1M HCl and 1M $Na_2CO_3$, dried over $Na_2SO_4$, filtered and evaporated. The crude product was purified by preparative HPLC. 0.061 g of the title compound was obtained.

$^1$H NMR (400 MHz, $CDCl_3$) δ ppm 1.62 (t, 3 H) 1.75 (s, 6 H) 2.42 (s, 1 H) 3.94 (td, 2 H) 5.99 (br. s., 1 H) 7.34 (dd, 1 H) 8.07-8.15 (m, 2 H).

Example 58

2-(3,3-Difluoropropylamino)-N-(2-methylbut-3-yn-2-yl)-5-(trifluoromethyl)nicotinamide Step 1: 2-(3,3-Difluoropropylamino)-5-(trifluoromethyl)nicotinic acid 2-Chloro-5-(trifluoromethyl)pyridine-3-carboxylic acid (0.12 g, 0.532 mmol), 3,3-difluoropropan-1-amine hydrochloride (0.117 g, 0.532 mmol), copper powder (2.0 mg, 0.032 mmol), copper(I) bromide (3.8 mg, 0.027 mmol), potassium carbonate (0.162 g, 1.170 mmol) and dry DMF (1 ml) were heated by microwave irradiation at 150° C. for 1 h. Some EtOAc was added and organic phase was washed 2 times with 0.5M citric acid, dried over $Na_2SO_4$, filtered and evaporated. The crude product was purified by flash chromatography. 0.043 g of the title compound was obtained.

$^1$H NMR (400 MHz, MeOD) δ ppm 2.16-2.26 (m, 2 H) 3.73 (t, 2 H) 5.76-6.11 (m, 1 H) 8.34 (dd, 1 H) 8.45-8.49 (m, 1 H).

Step 2: 2-(3,3-Difluoropropylamino)-N-(2-methyl-but-3-yn-2-yl)-5-(trifluoromethyl)-nicotinamide 2-(3,3-Difluoropropylamino)-5-(trifluoromethyl)nicotinic acid (0.043 g, 0.151 mmol), 1,1-dimethylpropargylamine (0.018 ml, 0.166 mmol), HOBt (0.022 g, 0.166 mmol), EDCI (0.032 g, 0.166 mmol) and DIPEA (0.029 ml, 0.166 mmol) in DCM (5 ml) were stirred at room temperature overnight. Some DCM was added and organic phase was washed with 1M HCl and 1M $Na_2CO_3$, dried over $Na_2SO_4$, filtered and evaporated. The crude product was purified by preparative HPLC. 0.030 g of the title compound was obtained.

$^1$H NMR (400 MHz, $CDCl_3$) δ ppm 1.75 (s, 6 H) 2.13-2.28 (m, 2 H) 2.43 (s, 1 H) 3.70 (q, 2 H) 5.76-6.18 (m, 2 H) 7.67 (d, 1 H) 8.44 (dd, 1 H) 8.53-8.68 (m, 1 H).

Example 59

5-Chloro-2-(2,2-difluoropropylamino)-N-(2-methyl-but-3-yn-2-yl)nicotinamide

Step 1: 5-Chloro-2-(2,2-difluoropropylamino)nicotinic acid 2,5-Dichloronicotinic acid (0.3 g, 1.564 mmol), 2,2-difluoropropylamine hydrochloride (0.121 g, 0.920 mmol), copper powder (3.5 mg, 0.055 mmol), copper(I) bromide (6.6 mg, 0.046 mmol), potassium carbonate (0.343 g, 2.483 mmol), and dry DMF (2 ml) were heated by microwave irradiation at 140° C. for 30 min. 0.10 g (0.760 mmol) of 2,2-difluoropropylamine hydrochloride and 1 ml of DMF was added and microwave irradiation was continued for 1 h at 170° C. and for 2 h at 180° C. Some EtOAc was added and organic phase was washed 2 times with 0.5M citric acid, dried over $Na_2SO_4$, filtered and evaporated. The crude product was purified by flash chromatography. 0.061 g of the title compound was obtained.

$^1$H NMR (400 MHz, $CDCl_3$) δ ppm 1.62 (t, 3 H) 3.99 (t, 2 H) 8.15 (d, 1 H) 8.21 (d, 1 H).

Step 2: 5-Chloro-2-(2,2-difluoropropylamino)-N-(2-methylbut-3-yn-2'-yl)nicotinamide 5-Chloro-2-(2,2-difluoropropylamino)nicotinic acid (0.061 g, 0.243 mmol), 1,1-dimethylpropargylamine (0.028 ml, 0.268 mmol), HOBt (0.036 g, 0.268 mmol), EDCI (0.051 g, 0.268 mmol) and DIPEA (0.047 ml, 0.268 mmol) in DCM (5 ml) were stirred at room temperature overnight. Some DCM was added and the organic phase was washed with 1M HCl and 1M $Na_2CO_3$, dried over $Na_2SO_4$, filtered and evaporated. The crude product was purified by preparative HPLC. 0.015 g of the title compound was obtained.

$^1$H NMR (400 MHz, $CDCl_3$) δ ppm 1.61 (t, 3 H) 1.74 (s, 6 H) 2.42 (s, 1 H) 3.94 (td, 2 H) 6.06 (br. s., 1 H) 7.52 (d, 1 H) 8.14 (d, 1 H) 8.30 (t, 1 H).

Example 60

5-Chloro-2-(3,3-difluoropropylamino)-N-(2-methylbut-3-yn-2-yl)nicotinamide

Step 1:
5-Chloro-2-(3,3-difluoropropylamino)nicotinic acid 2,5-Dichloronicotinic acid (0.166, g, 0.867 mmol), 3,3-difluoropropan-1-amine hydrochloride (0.190 g, 0.867 mmol), copper powder (3.3 mg, 0.052 mmol), copper(I) bromide (6.2 mg, 0.043 mmol), potassium carbonate (0.263 g, 1.906 mmol) and dry DMF (2 ml) were heated by microwave irradiation at 170° C. for 2 h. Some EtOAc was added and organic phase was washed 2 times with 0.5 M citric acid, dried over $Na_2SO_4$, filtered and evaporated. The crude product was purified by flash chromatography. 0.029 g of the title compound was obtained.

$^1$H NMR (400 MHz, $CDCl_3$) δ ppm 2.20 (ttd, 2 H) 3.68 (t, 2 H) 5.75-6.17 (m, 1 H) 8.13 (d, 1 H) 8.21 (d, 1 H).

Step 2: 5-Chloro-2-(3,3-difluoropropylamino)-N-(2-methylbut-3-yn-2-yl)nicotinamide 5-Chloro-2-(3,3-difluoropropylamino)nicotinic acid (0.029 g, 0.116 mmol), 1,1-dimethylpropargylamine (0.013 ml, 0.127 mmol), HOBt (0.017 g, 0.127 mmol), EDCI (0.024 g, 0.127 mmol) and DIPEA (0.022 ml, 0.127 mmol) in DCM (5 ml) were stirred at room temperature overnight. Some DCM was added and the organic phase was washed with 1M HCl and 1M $Na_2CO_3$, dried over $Na_2SO_4$, filtered and evaporated. The crude product was purified by preparative HPLC. 0.015 g of the title compound was obtained.

$^1$H NMR (400 MHz, $CDCl_3$) δ ppm 1.74 (s, 6 H) 2.18 (ttd, 2 H) 2.42 (s, 1 H) 3.63 (td, 2 H) 5.75-6.13 (m, 2 H) 7.49 (dd, 1 H) 8.08-8.24 (m, 2 H).

Example 61

4,5-Difluoro-N-(2-methylbut-3-yn-2-yl)-2-(neopentylamino) benzamide

Step 1: 4,5-Difluoro-2-(neopentylamino)benzoic acid 4,5-Difluoroanthranilic acid (0.5 g, 2.89 mmol) and 1,2-dichloroethane (10 ml) were cooled down to 0° C. Trimethylacetaldehyde (0.329 ml, 3.03 mmol) and acetic acid, glacial (0.413 ml, 7.22 mmol) were added slowly. Sodium triacetoxy borohydride (1.224 g, 5.78 mmol) was added and the reaction mixture was stirred at room temperature overnight. The reaction mixture was cooled down to 0° C., DCM was added and the organic phase was washed with water. The organic phase was extracted with 1M $Na_2CO_3$ and brine. The basic water phases were combined and acidified with HCl. The acidic water phase was extracted twice with DCM and the combined DCM phases were dried and evaporated to dryness to yield 0.556 g of the title compound.

$^1$H NMR (400 MHz, $CDCl_3$-d) δ ppm 1.04 (s, 9 H) 2.92 (s, 2 H) 6.32-6.53 (m, 1 H) 7.77 (m, 2 H).

Step 2: 4,5-Difluoro-N-(2-methylbut-3-yn-2-yl)-2-(neopentylamino)benzamide 4,5-Difluoro-2-(neopentylamino)benzoic acid (100 mg, 0.411 mmol), DCM (3 ml), EDCI (95 mg, 0.493 mmol), HOBt (27.8mg, 0.206 mmol), DIPEA (0.143 ml, 0.822 mmol) aid 1,1-dimethylpropargylamine (0.048 ml, 0.452 mmol) were stirred at room temperature overnight. The reaction mixture was washed twice with 1M NaOH and once with 1M HCl. The organic phase was dried and evaporated to dryness. The product was purified by flash chromatography to yield 80 mg of the title compound.

$^1$H NMR (400 MHz, $CDCl_3$-d) δ ppm 0.93-1.06 (m, 9 H) 1.73 (s, 6 H) 2.38 (s, 1 H) 2.84 (d, 2 H) 5.74-5.99 (m, 1 H) 6.42 (dd, 1 H) 7.04-7.18 (m, 1 H) 7.56 (br. s., 1 H).

Example 62

4,5-Difluoro-2-(isobutylamino)-N-(2-methylbut-3-yn-2-yl)benzamide

Step 1: 4,5-Difluoro-2-(isobutylamino)benzoic acid 4,5-Difluoroanthranilic acid (0.5 g, 2.89 mmol) and 1,2-dichloroethane (10 ml) were cooled down to 0° C. Isobutyraldehyde (0.277 ml, 3.03 mmol) and acetic acid, glacial (0.413 ml, 7.22 mmol) were added slowly. Sodium triacetoxy borohydride (1.224 g, 5.78 mmol) was added and the reaction mixture was stirred at room temperature overnight. The reaction mixture was cooled down to 0° C., DCM was added and the organic phase was washed with water. The organic phase was extracted with 1M $Na_2CO_3$ and brine. The basic water phases were combined and acidified with HCl. The acidic water phase was extracted twice with DCM and the combined DCM phases were dried and evaporated to dryness to yield to yield 0.593 g of the title compound.

$^1$H NMR (400 MHz, $CDCl_3$-d) δ ppm 0.97-1.08 (s, 6 H) 1.97 (dt, 1 H) 2.97 (d, 2 H) 6.42 (dd, 1 H) 7.77 (dd, 2 H).

Step 2: 4,5-Difluoro-2-(isobutylamino)-N-(2-methylbut-3-yn-2-yl)benzamide 4,5-Difluoro-2-(isobutylamino)benzoic acid (100 mg, 0.436 mmol), DCM (3 ml), EDCI (100 mg, 0.523 mmol), HOBt (29.5 mg, 0.218 mmol), DIPEA (0.152 ml, 0.873 mmol) and 1,1-dimethylpropargylamine (0.050 ml, 0.480 mmol) were stirred at room temperature overnight. The reaction mixture was washed twice with 1M NaOH and once with 1M HCl. The organic phase was dried and evaporated to dryness. The product was purified by flash chromatography to yield 87 mg of the title compound.

$^1$H NMR (400 MHz, $CDCl_3$-d) δ ppm 0.93-1.05 (s, 6 H) 1.73 (s, 6 H) 1.92 (dt, 1 H) 2.39 (s, 1 H) 2.87 (dd, 2 H) 5.88 (br. s., 1 H) 6.28-6.48 (m, 1 H) 7.03-7.20 (m, 1 H) 7.60 (br. s., 1 H).

Example 63

4,5-Difluoro-N-(2-methylbut-3-yn-2-yl)-2-(propylamino)benzamide

Step 1: 2-Amino-4,5-difluoro-N-(2-methylbut-3-yn-2-yl)benzamide 4,5-Difluoroanthranilic acid (100 mg, 0.578 mmol), DCM (3 ml), EDCI (133 mg, 0.693 mmol), HOBt (39.0 mg, 0.289 mmol), DIPEA (0.201 ml, 1.155 mmol) and 1,1-dimethyl-propargylamine (0.067 ml, 0.635 mmol) were stirred at room temperature overnight. The reaction mixture was washed twice with 1M NaOH and once with 1M HCl. The organic phase was dried and evaporated to dryness. The product was purified by flash chromatography to yield 64 mg of the title compound.

$^1$H NMR (400 MHz, CDCl$_3$-d) δ ppm 1.73 (s, 6 H) 2.40 (s, 1 H) 5.52 (br. s., 2 H) 5.91 (br. s., 1 H) 6.44 (dd, 1 H) 7.11 (dd, 1 H).

Step 2: 4,5-Difluoro-N-(2-methylbut-3-yn-2-yl)-2-(propylamino)benzamide

2-Amino-4,5-difluoro-N-(2-methylbut-3-yn-2-yl)benzamide (64 mg, 0.269 mmol) and 1,2-dichloroethane (5 ml) were cooled down to 0° C. Propionaldehyde (0.021 ml, 0.282 mmol) and acetic acid, glacial (0.038 ml, 0.672 mmol) were added slowly. Sodium triacetoxy borohydride (114 mg, 0.537 mmol) was added and the reaction mixture was stirred at room temperature overnight. The reaction mixture was cooled down to 0° C. and the mixture was washed with water, 1M Na$_2$CO$_3$ and brine. The organic phase was dried and evaporated to dryness. The product was purified by flash chromatography to yield 44 mg of the title compound.

$^1$H NMR (400 MHz, CDCl$_3$-d) δ ppm 1.00 (t, 3 H) 1.61-1.70 (m, 2 H) 1.73 (s, 6 H) 2.39 (s, 1 H) 3.03 (td, 2 H) 5.87 (br. s., 1 H) 6.40 (dd, 1 H) 7.12 (dd, 1 H) 7.53 (d, 1 H).

Example 64

2-(Butylamino)-N-(2-methylbut-3-yn-2-yl)benzamide

Step 1: 2-Amino-N-(2-methylbut-3-yn-2-yl)benzamide

Anthranilic acid (100 mg, 0.729 mmol), DCM (3 ml), EDCI (168 mg, 0.875 mmol), HOBt (49.3 mg, 0.365 mmol), DIPEA (0.254 ml, 1.458 mmol) and 1,1-dimethylpropargylamine (0.084 ml, 0.802 mmol) were stirred at room temperature overnight. The reaction mixture was washed twice with 1M NaOH and once with 1M HCl. The organic phase was dried and evaporated to dryness. The product was purified by flash chromatography to yield 69 mg of the title compound.

$^1$H NMR (400 MHz, CDCl$_3$-d) δ ppm 1.69-1.82 (s, 6 H) 2.38 (s, 1 H) 5.53 (br. s., 2 H) 6.08 (br. s., 1 H) 6.57-6.72 (m, 2 H) 7.16-7.30 (m, 2 H).

Step 2: 2-(Butylamino)-N-(2-methylbut-3-yn-2-yl)benzamide

2-Amino-N-(2-methylbut-3-yn-2-yl)benzamide (69 mg, 0.341 mmol) and 1,2-dichloroethane (5 ml) were cooled down to 0° C. Butyraldehyde (0.032 ml, 0.358 mmol) and acetic acid, glacial (0.049 ml, 0.853 mmol) were added slowly. Sodium triacetoxy borohydride (145 mg, 0.682 mmol) was added and the reaction mixture was stirred at room temperature overnight. The reaction mixture was cooled down to 0° C. and the mixture was washed with water, 1M Na$_2$CO$_3$ and brine. The organic phase was dried and evaporated to dryness. The product was purified by flash chromatography to yield 58 mg of the title compound.

$^1$H NMR (400 MHz, CDCl$_3$-d) δ ppm 0.95 (t, 3 H) 1.44 (dq, 2 H) 1.59-1.69 (m, 2 H) 1.73 (s, 6 H) 2.38 (s, 1 H) 3.13 (td, 2 H) 6.06 (br. s., 1 H) 6.54 (td, 1 H) 6.67 (d, 1 H) 7.27-7.31 (m, 2 H) 7.42-7.58 (m, 1 H).

Example 65

2-(Ethylamino)-4,5-difluoro-N-(2-methylbut-3-yn-2-yl)benzamide

2-Amino-4,5-difluoro-N-(2-methylbut-3-yn-2-yl)benzamide (100 mg, 0.420 mmol) and 1,2-dichloroethane (5 ml) were cooled down to 0° C. Acetaldehyde (0.026 ml, 0.462 mmol) and acetic acid, glacial (0.060 ml, 1.049 mmol) were added slowly. Sodium triacetoxy borohydride (178 mg, 0.840 mmol) was added and the reaction mixture was stirred at room temperature overnight. The reaction mixture was cooled down to 0° C. and the mixture was washed with water, 1M Na$_2$CO$_3$ and brine. The organic phase was dried and evaporated to dryness. The product was purified by preparative HPLC to yield 69 mg of the title compound.

$^1$H NMR (400 MHz, CDCl$_3$-d) δ ppm 1.28 (t, 3 H) 1.65-1.80 (s, 6 H) 2.40 (s, 1 H) 3.10 (qd, 2 H) 5.89 (br. s., 1 H) 6.40 (dd, 1 H) 7.13 (dd, 1 H) 7.47 (br. s., 1 H).

Example 66

4,5-Difluoro-N-(2-methylbut-3-yn-2-yl)-2-(3,3,3-trifluoropropylamino)-benzamide

Step 1: 4,5-Difluoro-N-(2-methylbut-3-yn-2-yl)-2-(3,3,3-trifluoropropylamino) benzamide 4,5-Difluoroanthranilic acid (5 g, 28.9 mmol) and dichloromethane (75 ml) were cooled down to 0° C. 3,3,3-Trifluoropropanal (3.73 ml, 43.3 mmol) and acetic acid, glacial (4.13 ml, 72.2 mmol) were added slowly. Sodium triacetoxy borohydride (12.24 g, 57.8 mmol) was added and the reaction mixture was stirred at room temperature for four hours. The reaction mixture was washed three times with water. The organic phase was dried and evaporated to dryness to yield 7.64 g of the title compound.

LC/MS [M+1] 270.1

Step 2: 4,5-Difluoro-N-(2-methylbut-3-yn-2-yl)-2-(3,3,3-trifluoropropylamino) benzamide 4,5-Difluoro-2-(3,3,3-trifluoropropylamino)benzoic acid (7.64 g, 28.4 mmol), dichloromethane (100 ml), EDCI (6.53 g, 34.1 mmol), HOBt (3.84 g, 28.4 mmol), DIPEA (12.36 ml, 71.0 mmol) and 1,1-dimethylpropargylamine (3.88 ml, 36.9 mmol) were stirred at room temperature over night. The reaction mixture was washed twice with 1M NaOH and 1M HCl and once with water. The organic phase was dried and evaporated to dryness. The product was crystallised from isopropanol/heptane mixture to yield 5.58 g of the title compound.

$^1$H NMR (400 MHz, CDCl$_3$-d) δ ppm 1.68-1.78 (m, 6 H) 2.35-2.52 (m, 2 H) 2.40 (s, 1H) 3.39 (td, 2 H) 5.90 (br. s., 1 H) 6.41 (dd, 1 H) 7.16 (dd, 1 H) 7.75 (br. s., 1 H).

Example 67

4,5-Difluoro-2-(isopropylamino)-N-(2-methylbut-3-yn-2-yl)benzamide

2-Amino-4,5-difluoro-N-(2-methylbut-3-yn-2-yl)benzamide (100 mg, 0.420 mmol) and 1,2-dichloroethane (5 ml) were cooled down to 0° C. Acetone (0.037 ml, 0.504 mmol)

and acetic acid, glacial (0.072 ml, 1.259 mmol) were added slowly. Sodium triacetoxy borohydride (356 mg, 1.679 mmol) was added and the reaction mixture was stirred at room temperature over four nights. The reaction mixture was cooled down to 0° C. and the mixture was washed with water and brine. The organic phase was dried and evaporated to dryness. The product was purified by preparative HPLC to yield 15 mg of the title compound.

$^1$H NMR (400 MHz, CDCl$_3$-d) δ ppm 1.23 (d, 6 H) 1.73 (s, 6 H) 2.39 (s, 1 H) 3.51 (dq, 1 H) 5.89 (br. s., 1 H) 6.42 (dd, 1 H) 7.12 (dd, 1 H) 7.40 (d, 1 H).

Example 68

N-(3,5-Dimethylhex-1-yn-3-yl)-4,5-difluoro-2-(isobutylamino)-benzamide

Step 1: 3-Chloro-3,5-dimethylhex-1-yne

Copper(I) chloride (3.14 g, 31.7 mmol, calcium chloride anhydrous (4.40 g, 39.6 mmol) and copper-tin alloy (40 mg, 79 mmol) were cooled down to 0° C. and cold conc. hydrogen chloride (33.4 ml, 396 mmol) was added. 3,5-Dimethyl-1-hexyn-3-ol (11.64 ml, 79 mmol) was added slowly and the reaction mixture was stirred at 0° C. for two hours. The layers were separated and the product phase was washed twice with 5M HCl and once with water. The product was vacuum distilled to yield 7.72 g of the title compound.

$^1$H NMR (400 MHz, CDCl$_3$-d) δ ppm 1.04 (dd, 6 H) 1.77-1.96 (m, 5 H) 1.97-2.11 (m, 1 H) 2.65 (s, 1 H).

Step 2: 3,5-Dimethylhex-1-yn-3-amine hydrochloride

Iron(III) chloride (0.086 g, 0.532 mmol) was added to cold (−78° C.) liquid ammonia (ca 25 ml). More ammonia (ca 60 ml) was added and sodium (1.285 g, 55.9 mmol) was added carefully in small pieces. The reaction mixture was stirred at −78° C. for 15 minutes and 3-chloro-3,5-dimethylhex-1-yne (7.7 g, 53.2 mmol) in diethyl ether (20 ml) was added slowly. The reaction mixture was stirred at −78° C. for 3 hours, diluted with diethyl ether (75 ml) and the mixture was stirred overnight at room temperature. The reaction mixture was cooled down to 0° C., cold water (70 ml) was added carefully drop by drop and stirred for 20 minutes. The layers were separated and the water phase was extracted with diethyl ether. The organic phases were combined, washed twice with water, dried over Na$_2$SO$_4$ and evaporated to dryness. 10% HCl/EtOAc (32.3 ml, 80 mmol) was added to evaporation residue, the mixture was stirred for a while and evaporated to dryness. The evaporation residue was triturated with diethyl ether and the solid precipitate was filtered and dried in a vacuum oven at 40° C. overnight to yield 6.15 g of the title compound.

$^1$H NMR (400 MHz, CDCl$_3$-d) δ ppm 1.05 (t, 6 H) 1.71 (s, 3 H) 1.72-2.03 (m, 3 H) 2.64 (s, 1 H).

Step 3: N-(3,5-Dimethylhex-1-yn-3-yl)-4,5-difluoro-2-(isobutylamino)benzamide 4,5-Difluoro-2-(isobutylamino)benzoic acid (100 mg, 0.436 mmol), DCM (3 ml), EDCI (100 mg, 0.523 mmol), HOBt (29.5 mg, 0.218 mmol), DIPEA (0.228 ml, 1.309 mmol) and 3,5-dimethylhex-1-yn-3-amine hydrochloride (92 mg, 0.567 mmol) were stirred at room temperature overnight. The reaction mixture was washed twice with 1M NaOH and once with 1M HCl. The organic phase was dried and evaporated to dryness. The product was purified at first by flash chromatography and finally by preparative HPLC to yield 81 mg of the title compound.

$^1$H NMR (400 MHz, CDCl$_3$-d) δ ppm 0.93-1.07 (m, 12 H) 1.68-1.81 (m, 4 H) 1.93 (tt, 2 H) 2.10 (dd, 1 H) 2.43 (s, 1 H) 2.87 (dd, 2 H) 5.88 (s, 1 H) 6.39 (dd, 1 H) 7.09 (dd, 1 H) 7.43-0.7.57 (m, 1 H).

Example 69

N-(3,4-Dimethylpent-1-yn-3-yl)-4,5-difluoro-2-(isobutylamino)-benzamide

Step 1: 3-Chloro-3,4-dimethylpent-1-yne

Copper(I) chloride (3.32 g, 33.5 mmol, calcium chloride anhydrous (4.65 g, 41.9 mmol) and copper-tin alloy (40 mg, 84 mmol) were cooled down to 0° C. and cold conc. hydrogen chloride (35.4 ml, 419 mmol) was added. 3,5-Dimethyl-1-pentyn-3-ol (11.49 ml, 84 mmol) was added slowly and the reaction mixture was stirred at 0° C. for two hours. The layers were separated and the product phase was washed twice with 5M HCl and once with water. The product was vacuum distilled to yield 7.25 g of the title compound.

$^1$H NMR (400 MHz, CDCl$_3$-d) δ ppm 1.13 (dd, 6 H) 1.81 (s, 3 H) 2.06 (dt, 1 H) 2.64 (s, 1 H).

Step 2: 3,4-Dimethylpent-1-yn-3-amine hydrochloride

Iron(III) chloride (0.089 g, 0.551 mmol) was added to cold (−78° C.) liquid ammonia (ca 25 ml). More ammonia (ca 60 ml) was added and sodium (1.331 g, 57.9 mmol) was added carefully in small pieces. The reaction mixture was stirred at −78° C. for 15 minutes and 3-chloro-3,4-dimethylpent-1-yne (7.2 g, 55.1 mmol) in diethyl ether (20 ml) was added slowly. The reaction mixture was stirred at −78° C. for 3 hours, diluted with diethyl ether (75 ml) and the mixture was stirred overnight at room temperature. The reaction mixture was cooled down to 0° C., cold water (70 ml) was added carefully drop by drop and stirred for 20 minutes. The layers were separated and the water phase was extracted with diethyl ether. The organic phases were combined, washed twice with water, dried over Na$_2$SO$_4$ and evaporated to dryness. 10% HCl/EtOAc (32.3 ml, 80 mmol) was added to evaporation residue, the mixture was stirred for a while and evaporated to dryness. The evaporation residue was triturated with diethyl ether and the solid precipitate was filtered and dried in a vacuum oven at 40° C. overnight to yield 6.15 g of the title compound.

$^1$HNMR (400 MHz, MeOD-d) δ ppm 1.13 (dd, 6 H) 1.61 (s, 3 H) 2.05 (m, 1 H) 3.31 (s, 1 H).

Step 3: N-(3,4-Dimethylpent-1-yn-3-yl)-4,5-difluoro-2-(isobutylamino)benzamide 4,5-Difluoro-2-(isobutylamino)benzoic acid (100 mg, 0.436 mmol), DCM (3 ml), EDCI (100 mg, 0.524 mmol), HOBt (29.5 mg, 0.218 mmol), DIPEA (0.228 ml, 1.309 mmol) and 3,4-dimethylpent-1-yn-3-amine hydrochloride (84 mg, 0.567 mmol) were stirred at room temperature overnight. The reaction mixture was washed twice with 1M NaOH and once with 1M HCl. The organic phase was dried and evaporated to dryness. The product was purified by flash chromatography to yield 86 mg of the title compound.

$^1$H NMR (400 MHz, CDCl$_3$-d) δ ppm 0.92-1.14 (m, 12 H) 1.71 (d, 3 H) 1.85-2.02 (m, 1 H) 2.41 (s, 1 H) 2.54 (m, 1 H) 2.81-2.94 (m, 2 H) 5.87 (br. s., 1 H) 6.31-6.49 (m, 1 H) 7.02-7.20 (m, 1H) 7.48 (br. s., 1H).

Example 70

4,5-Difluoro-2-(isobutylamino)-N-(3-methylhex-1-yn-3-yl)benzamide

Step 1: 3-Chloro-3-methylhex-1-yne

Copper(I) chloride (3.53 g, 35.7 mmol, calcium chloride anhydrous (4.95 g, 44.6 mmol) and copper-tin alloy (40 mg, 89 mmol) were cooled down to 0° C. and cold conc. hydrogen chloride (37.6 ml, 446 mmol) was added. 3-Methyl-1-hexyn-3-ol (11.19 ml, 89 mmol) was added slowly and the reaction mixture was stirred at 0° C. for two hours. The layers were separated and the product phase was washed twice with 5M HCl and once with water. The product was vacuum distilled to yield 7.24 g of the title compound.

$^1$H NMR (400 MHz, CDCl$_3$-d) δ ppm 0.98 (t, 3 H) 1.58-1.72 (m, 2 H) 1.81-1.85 (s, 3 H) 1.86-1.96 (m, 2 H) 2.63 (s, 1 H).

Step 2: 3-Methylhex-1-yn-3-amine hydrochloride

Iron(III) chloride (0.089 g, 0.551 mmol) was added to cold (−78° C.) liquid ammonia (ca 25 ml). More ammonia (ca 60 ml) was added and sodium (1.331 g, 57.9 mmol) was added carefully in small pieces. The reaction mixture was stirred at −78° C. for 15 minutes and 3-chloro-3-methylhex-1-yne, (7.2 g, 55.1 mmol) in diethyl ether (20 ml) was added slowly. The reaction mixture was stirred at −78° C. for 4 hours, diluted with diethyl ether (75 ml) aid the mixture was stirred overnight at room temperature. The reaction mixture was cooled down to 0° C., cold water (70 ml) was added carefully drop by drop and stirred for 20 minutes. The layers Were separated and the water phase was extracted with diethyl ether. The organic phases were combined, washed twice with water, dried over Na$_2$SO$_4$ and evaporated to dryness. 10% HCl/EtOAc (33.5 ml, 83 mmol) was added to evaporation residue, the mixture was stirred for a while and evaporated to dryness. The evaporation residue was triturated with diethyl ether and the solid precipitate was filtered and dried in a vacuum oven at 40° C. overnight to yield 6.32 g of the title compound.

$^1$H NMR (400 MHz, MeOD-d) δ ppm 1.04 (t, 3 H) 1.52-1.65 (m, 5 H) 1.71-1.93 (m, 2 H) 3.30 (s, 1 H).

Step 3: 4,5-Difluoro-2-(isobutylamino)-N-(3-methylhex-1-yn-3-yl)benzamide 4,5-Difluoro-2-(isobutylamino)benzoic acid (100 mg, 0.436 mmol), DCM (3 ml), EDCI (100 mg, 0.524 mmol), HOBt (29.5 mg, 0.218 mmol), DIPEA (0.228 ml, 1.309 mmol) and 3-methylhex-1-yn-3-amine hydrochloride (84 mg, 0.567 mmol) were stirred at room temperature overnight. The reaction mixture was washed twice with 1M NaOH and once with 1M HCl. The organic phase was dried and evaporated to dryness. The product was purified by flash chromatography to yield 90 mg of the title compound.

$^1$H NMR (400 MHz, CDCl$_3$-d) δ ppm 094-1.03 (m, 9 H) 1.45-1.59 (m, 2 H) 1.72 (s, 3 H) 1.76-1.98 (m, 2 H) 2.10 (m, 1 H) 2.40 (s, 1 H) 2.87 (dd, 2 H) 5.83 (s, 1 H) 6.39 (dd, 1 H) 7.11 (dd, 1 H) 7.51 (d, 1 H).

Example 71

4-Fluoro-N-(2-methylbut-3-yn-2-yl)-2-(3,3,3-trifluoropropylamino) benzamide

Step 1:
4-Fluoro-2-(3,3,3-trifluoropropylamino)benzoic acid

2-Amino-4-fluorobenzoic acid (200 mg, 1.289 mmol) and 1,2-dichloroethane (5 ml) were cooled down to 0° C. 3,3,3-Trifluoropropanal (0.144 ml, 1.676 mmol) and acetic acid, glacial (0.148 ml, 2.58 mmol) were added slowly. Sodium triacetoxy borohydride (683 mg, 3.22 mmol) was added and the reaction mixture was stirred at room temperature overnight. The reaction mixture was cooled down to 0° C., DCM was added and the organic phase Was washed once with water and once with brine. The organic phase was dried and evaporated to dryness to yield to yield 172 mg of the title compound.

$^1$H NMR (400 MHz, CDCl$_3$-d) δ ppm 2.39-2.55 (m, 2 H) 3.50 (m, 2 H) 6.24-6.45 (m, 2 H) 7.88-8.06 (m, 2 H).

Step 2: 4-Fluoro-N-(2-methylbut-3-yn-2-yl)-2-(3,3,3-trifluoropropylamino)benzamide 4-Fluoro-2-(3,3,3-trifluoropropylamino)benzoic acid (170 mg, 0.677 mmol), DCM (3 ml), EDCI (156 mg, 0.812 mmol), HOBt (91 mg, 0.677 mmol), DIPEA (0.236 ml, 1.354 mmol) and 1,1-dimethylpropargylamine (0.093 ml, 0.880 mmol) were stirred at room temperature overnight. The reaction mixture was washed once with 1M NaOH and once with 1M HCl. The organic phase was dried and evaporated to dryness. The product Was purified at first by flash chromatography and finally by preparative HPLC to yield 59 mg of the title compound.

$^1$H NMR (400 MHz, CDCl$_3$-d) δ ppm 1.73 (s, 6 H) 2.39 (s, 1 H) 2.40-2.54 (m, 2 H) 3.34-3.50 (m, 2 H) 5.98 (br. s., 1 H) 6.23-6.39 (m, 2 H) 7.28-7.34 (m, 1 H) 8.05 (br. s., 1 H).

Example 72

N-(2-methylbut-3-yn-2-yl)-4-(trifluoromethyl)-2-(3,3,3-trifluoropropyl-amino)benzamide Step 1: 2-Amino-N-(2-methylbut-3-yn-2-yl)-4-(trifluoromethyl)benzamide 2-Amino-4-(trifluoromethyl)benzoic acid (1 g, 4.87 mmol), DCM (30 ml), EDCI (1.121 g, 5.85 mmol), HOBt (0.659 g, 4.87 mmol), DIPEA (1.698 ml, 9.75 mmol) and 1,1-dimethylpropargylamine (0.667 ml, 6.34 mmol) were stirred at room temperature over three nights. The reaction mixture was washed twice with water. The organic phase was dried and evaporated to dryness to yield 1.519 g of the title compound.

$^1$H NMR (400 MHz, CDCl$_3$-d) δ ppm 1.74 (s, 6 H) 2.40 (s, 1 H) 5.72 (br. s., 2 H) 6.27 (s, 1 H) 6.74-6.83 (m, 1 H) 6.87 (m, 1 H) 7.37 (d, 1 H).

Step 2: N-(2-Methylbut-3-yn-2-yl)-4-(trifluoromethyl)-2-(3,3,3-trifluoropropylamino)-benzamide 2-Amino-N-(2-methylbut-3-yn-2-yl)-4-(trifluoromethyl)benzamide (100 mg, 0.370 mmol) and 1,2-dichloroethane (5 ml) were cooled down to 0° C. 3,3,3-Trifluoropropanal (0.041 ml, 0.481 mmol) and acetic acid, glacial (0.042 ml, 0.740 mmol) were added slowly. Sodium triacetoxy borohydride (196 mg, 0.925 mmol) was added and the reaction mixture was stirred at room temperature overnight. 3,3,3-Trifluoropropanal (0.041 ml) was added and the reaction mixture was stirred for four hours. 3,3,3-Trifluoropropanal (0.041 ml) was added and the reaction mixture was stirred at room temperature overnight. The reaction mixture was cooled down to 0° C., DCM was added and the mixture was washed with water. The organic phase was dried and evaporated to dryness. The product was purified at first by preparative HPLC and finally by flash chromatography to yield 36 mg of the title compound.

$^1$H NMR (400 MHz, CDCl$_3$-d) δ ppm 1.74 (s, 6 H) 2.40 (s, 1 H) 2.42-2.53 (m, 2 H) 3.48 (td, 2 H) 6.09 (br. s., 1 H) 6.78-6.93 (m, 2 H) 7.41 (d, 1 H) 7.75-7.91 (m, 1 H).

Example 73

4-Methoxy-N-(2-methylbut-3-yn-2-yl)-2-(3,3,3-trifluoropropylamino)-benzamide

Step 1: 4-Methoxy-2-(3,3,3-trifluoropropylamino)benzoic acid

2-Amino-4-methoxybenzoic acid (200 mg, 1.196 mmol) and 1,2-dichloroethane (5 ml) were cooled down to 0° C. 3,3,3-Trifluoropropanal (0.134 ml, 1.555 mmol) and acetic acid, glacial (0.137 ml, 2.393 mmol) were added slowly. Sodium triacetoxy borohydride (634 mg, 2.99 mmol) was added and the reaction mixture was stirred at room temperature overnight. The reaction mixture was cooled down to 0° C., DCM was added and the organic phase was washed once with water and once with brine. The organic phase was dried and evaporated to dryness to yield to yield 154 mg of the title compound.

$^1$H NMR (400 MHz, CDCl$_3$-d) δ ppm 2.40-2.55 (mr, 2 H) 3.51 (t, 2 H) 3.85 (s, 3 H) 6.09 (m, 1 H) 6.26 (m, 1 H) 7.80-7.95 (m, 2 H).

Step 2: 4-Methoxy-N-(2-methylbut-3-yn-2-yl)-2-(3,3-trifluoropropylamino) benzamide 4-Methoxy-2-(3,3,3-trifluoropropylamino)benzoic acid (150 mg, 0.570 mmol), DCM (3 ml), EDCI (131 mg, 0.684 mmol), HOBt (77 mg, 0.570 mmol), DIPEA (0.199 ml, 1.140 mmol) and 1,1-dimethylpropargylamine (0.078 ml, 0.741 mmol) were stirred at room temperature overnight. The reaction mixture was washed once with 1M NaOH. The organic phase was dried and evaporated to dryness. The product was purified by flash chromatography to yield 63 mg of the title compound.

$^1$H NMR (400 MHz, CDCl$_3$-d) δ ppm 1.72 (s, 6 H) 2.38 (s, 1 H) 2.39-2.53 (m, 2 H) 3.35-3.51 (m, 2 H) 3.82 (s, 3 H) 5.95 (br. s., 1 H) 6.12 (d, 1 H) 6.17 (dd, 1 H) 8.09 (t, 1 H).

Example 74

4-Methoxy-N-(2-methylbut-3-yn-2-yl)-2-(propylamino)benzamide

Step 1: 4-Methoxy-2-(propylamino)benzoic acid

2-Amino-4-methoxybenzoic acid (200 mg, 1.196 mmol) and 1,2-dichloroethane (5 ml) were cooled down to 0° C. Propionaldehyde (0.113 ml, 1.555 mmol) and acetic acid, glacial (0.137 ml, 2.393 mmol) were added slowly. Sodium triacetoxy borohydride (634 mg, 2.99 mmol) was added and the reaction mixture was stirred at room temperature overnight. The reaction mixture was cooled down to 0° C., DCM was added and the organic phase was washed once with water and once with brine. The organic phase was dried and evaporated to dryness to yield to yield 116 mg of the title compound.

$^1$H NMR (400 MHz, CDCl$_3$-d) δ ppm 1.03 (t, 3 H) 1.72 (m, 2 H) 3.15 (m, 2 H) 3.84 (s, 3 H) 6.10 (d, 1 H) 6.19 (dd, 1 H) 7.92 (m, 2 H).

Step 2: 4-Methoxy-N-(2-methylbut-3-yn-2-yl)-2-(propylamino)benzamide

4-Methoxy-2-(propylamino)benzoic acid (116 mg, 0.554 mmol), DCM (3 ml), EDCI (128 mg, 0.665 mmol), HOBt (74.9 mg, 0.554 mmol), DPEA (0.193 ml, 1.109 mmol) and 1,1-dimethylpropargylamine (0.076 ml, 0.721 mmol) were stirred at room temperature overnight. The reaction mixture was washed once with 1M NaOH and once with 1M HCl. The organic phase was dried and evaporated to dryness. The product was purified at first by flash chromatography and finally by preparative HPLC to yield 43 mg of the title compound.

$^1$H NMR (400 MHz, CDCl$_3$-d) δ ppm 1.00 (t, 3 H) 1.62-1.80 (m, 8 H) 2.37 (s, 1 H) 3.02-3.17 (m, 2 H) 3.81 (s, 3 H) 5.92 (br. s., 1 H) 6.04-6.17 (min, 2 H) 7.18-7.31 (m, 1 H) 7.88 (br. s., 1 H).

Example 75

N-(2-Methylbut-3-yn-2-yl)-5-(trifluoromethoxy)-2-(3,3,3-trifluoropropylamino)benzamide Step 1: 2-Amino-N-(2-methylbut-3-yn-2-yl)-5-(trifluoromethoxy)benzamide 2-Amino-5-(trifluoromethoxy)benzoic acid (500 mg, 2.261 mmol), DCM (15 ml), EDCI (520 mg, 2.71 mmol), HOBt (306 mg, 2.261 mmol), DIPEA (0.788 ml, 4.52 mmol) and 1,1-dimethylpropargylamine (0.309 ml, 2.94 mmol) were stirred at room temperature over three nights. The reaction mixture was washed twice with water. The organic phase was dried and evaporated to dryness to yield 563 mg of the title compound.

$^1$H NMR (400 MHz, MeOD-d) δ ppm 1.74 (s, 6 H) 2.24 (br. s 2 H) 2.41 (s, 1 H) 5.56 (d, 1 H) 6.65 (d, 1 H) 7.03-7.12 (m, 1 H) 7.17 (d, 1 H).

Step 2: N-(2-Methylbut-3-yn-2-yl)-5-(trifluoromethoxy)-2-(3,3,3-trifluoropropyl-amino)benzamide 2-Amino-N-(2-methylbut-3yn-2-yl)-4-(trifluoromethoxy)benzamide (100 mg, 0.349 mmol) and 1,2-dichloroethane (5 ml) were cooled down to 0° C. 3,3,3-Trifluoropropanal (0.039 ml, 0.454 mmol) and acetic acid, glacial (0.040 ml, 0.699 mmol) were added slowly. Sodium triacetoxy borohydride (185 mg, 0.873 mmol) was added and the reaction mixture was stirred at room temperature overnight. 3,3,3-Trifluoropropanal (0.039 ml) was added and the reaction mixture was stirred for four hours. 3,3,3-Trifluoropropanal (0.039 ml) was added and the reaction mixture was stirred at room temperature overnight. The reaction mixture was cooled down to 0° C., DCM was added and the mixture was washed with water. The organic phase was dried and evaporated to dryness. The product was purified by flash chromatography and twice by preparative HPLC to yield 15 mg of the title compound.

$^1$H NMR (400 MHz, CDCl$_3$-d) δ ppm 1.74 (s, 6 H) 2.41-2.51 (m, 2 H) 3.37-3.52 (m, 2 H) 5.99 (br. s., 1 H) 6.55-6.71 (m, 1 H) 7.11-7.24 (m, 2 H) 7.70 (br. s., 1 H).

Example 76

5-Methoxy-N-(2-methylbut-3-yn-2-yl)-2-(3,3,3-trifluoropropyl-amino)benzamide

Step 1: 2-Amino-5-methoxy-N-(2-methylbut-3-yn-2-yl)benzamide

2-Amino-5-methoxybenzoic acid (500 mg, 2.99 mmol), DCM (15 ml), EDCI (688 mg, 3.59 mmol), HOBt (404 mg, 2.99 mmol), DIPEA (1.042 ml, 5.98 mmol) and 1,1-dimethylpropargylamine (0.409 ml, 3.89 mmol) were stirred at room temperature over three nights. The reaction mixture was washed twice with water. The organic phase was dried and evaporated to dryness. The product was purified by flash chromatography to yield 165 mg of the title compound.

$^1$H NMR (400 MHz, CDCl$_3$-d) δ ppm 1.74 (s, 6 H) 2.39 (s, 1 H) 3.76 (s, 3 H) 5.12 (br. s., 2 H) 6.22 (br. s., 1 H) 6.63-6.68 (m, 1 H) 6.84-6.90 (m, 2 H).

Step 2: 5-Methoxy-N-(2-methylbut-3-yn-2-yl)-2-(3,3,3-trifluoropropylamino)-benzamide 2-Amino-5-methoxy-N-(2-methylbut-3-yn-2-yl)benzamide (80 mg, 0.344 mmol) and 1,2-dichloroethane (5 ml) were cooled down to 0° C. 3,3,3-Trifluoropropanal (0.039 ml, 0.448 mmol) and acetic acid, glacial (0.039 ml, 0.689 mmol) were added slowly. Sodium triacetoxy borohydride (182 mg, 0.861 mmol) was added and the reaction mixture was stirred at room temperature overnight. DCM was added to the reaction mixture and the mixture was washed with water. The organic phase was dried and evaporated to dryness. The product was purified at first by flash chromatography and finally by preparative HPLC to yield 61 mg of the title compound.

$^1$H NMR (400 MHz, CDCl$_3$-d) δ ppm 1.73 (s, 6 H) 2.38-2.50 (m, 3 H) 3.42 (t, 2 H) 3.78 (s, 3 H) 6.19 (br. s., 1 H) 6.65 (d, 1 H) 6.88-7.03 (m, 3 H).

Example 77

5-Methyl-N-(2-methylbut-3-yn-2-yl)-2-(3,3,3-trifluoropropylamino)-benzamide

Step 1: 5-Methyl-2-(3,3,3-trifluoropropylamino)benzoic acid

2-Amino-5-methylbenzoic acid (200 mg, 1.196 mmol) and 1,2-dichloroethane (5 ml) were cooled down to 0° C. 3,3,3-Trifluoropropanal (0.148 ml, 1.720 mmol) and acetic acid, glacial (0.151 ml, 2.65 mmol) were added slowly. Sodium triacetoxy borohydride (701 mg, 3.31 mmol) was added and the reaction mixture was stirred at room temperature overnight. The reaction mixture was cooled down to 0° C., DCM was added and the organic phase was washed once with water and once with brine. The organic phase was dried and evaporated to dryness to yield 308 mg of the title compound.

$^1$H NMR (400 MHz, CDCl$_3$-d) δ ppm 2.26 (s, 3 H) 2.37-2.57 (m, 2 H) 3.46-3.59 (m, 2 H) 6.61 (d, 1 H) 7.25-7.29 (m, 1 H) 7.77-7.86 (m, 1 H).

Step 2: 5-Methyl-N-(2-methylbut-3-yn-2-yl)-2-(3,3,3-trifluoropropylamino)benzamide 5-Methyl-2-(3,3,3-trifluoropropylamino)benzoic acid (308 mg, 1.246 mmol), DCM (3 ml), EDCI (287 mg, 1.495 mmol), HOBt (168 mg, 1.246 mmol), DIPEA (0.434 ml, 2.492 mmol) and 1,1-dimethylpropargylamine (0.170 ml, 1.620 mmol) were stirred at room temperature overnight. The reaction mixture was washed once with 1M NaOH and once with 1M HCl. The organic phase was dried and evaporated to dryness. The product was purified at first by flash chromatography and finally by preparative HPLC to yield 195 mg of the title compound.

$^1$H NMR (400 MHz, CDCl$_3$-d) δ ppm 1.68-1.80 (m, 6 H) 2.25 (s, 3 H) 2.32-2.54 (m, 3 H) 3.35-3.51 (m, 2 H) 6.08 (br. s., 1 H) 6.59 (d, 1 H) 7.07-7.19 (m, 2 H) 7.42-7.52 (m, 1 H).

Example 78

N-(2-Methylbut-3-yn-2-yl)-5-(methylthio)-2-(3,3,3-trifluoropropyl-amino)benzamide Step 1: 5-(Methylthio)-2-(3,3,3-trifluoropropylamino)benzoic acid 2-Amino-5-methylmercaptobenzoic acid (146 mg, 0.797 mmol) and 1,2-dichloroethane (5 ml) were cooled down to 0° C. 3,3,3-Trifluoropropanal (0.089 ml, 1.036 mmol) and acetic acid, glacial (0.091 ml, 1.594 mmol) were added slowly. Sodium triacetoxy borohydride (422 mg, 1.992, mmol) was added and the reaction mixture was stirred at room temperature overnight. The reaction mixture was cooled down to 0° C., DCM was added and the organic phase was washed once with water and once with brine. The organic phase was dried and evaporated to dryness to yield to yield 186 mg of the title compound.

$^1$H NMR (400 MHz, CDCl$_3$-d) δ ppm 2.37-2.60 (m, 2 H) 2.44 (s, 3 H) 3.55 (t, 2 H) 6.66 (d, 1 H) 7.48 (dd, 1 H) 7.60-7.89 (m, 1 H) 8.04 (d, 1 H).

Step 2: N-(2-Methylbut-3-yn-2-yl)-5-(methylthio)-2-(3,3,3-trifluoropropylamino)-benzamide 4-(Methylthio)-2-(3,3,3-trifluoropropylamino)benzoic acid (186 mg, 0.666 mmol), DCM (3 ml), EDCI (153 mg, 0.799 mmol), HOBt (90 mg, 0.666 mmol), DIPEA (0.232 ml, 1.332 mmol) and 1,1-dimethylpropargylamine (0.091 ml, 0.866 mmol) were stirred at room temperature overnight. The reaction mixture was washed once with 1M NaOH and once with 1M HCl. The organic phase was dried and evaporated to dryness. The product was purified at first by flash chromatography and finally by preparative HPLC to yield 123 mg of the title compound.

$^1$H NMR (400 MHz, CDCl$_3$-d) δ 1.73 (s, 6 H) 2.35-2.52 (m, 6 H) 3.45 (t, 2 H) 6.08 (br. s., 1 H) 6.58-6.69 (m, 1 H) 7.35-7.43 (m, 2 H) 7.68-7.84 (m, 1 H).

Example 79

N-(2-Methylbut-3-yn-2-yl)-2-(3,3,3-trifluoropropylamino)benzamide

Step 1: 2-(3,3,3-Trifluoropropylamino)benzoic acid

Anthranilic acid (250 mg, 1.823 mmol) and 1,2-dichloroethane (5 ml) were cooled down to 0° C. 3,3,3-Trifluoropropanal (0.204 ml, 2.370 mmol) and acetic acid, glacial (0.261 ml, 4.56 mmol) were added slowly. Sodium triacetoxy borohydride (773 mg, 3.65 mmol) was added and the reaction mixture was stirred at room temperature overnight. The reaction mixture was cooled down to 0° C., DCM was added and the organic phase was washed three times with water. The organic phase was dried and evaporated to dryness to yield to yield 410 mg of the title compound.

$^1$H NMR (400 MHz, CDCl$_3$-d) δ ppm 2.39-2.56 (m, 2 H) 3.55 (t, 2 H) 6.64-6.76 (m, 2 H) 7.44 (m, 1 H) 7.55-7.90 (m, 1 H) 8.02 (dd, 1 H).

Step 2: N-(2-Methylbut-3-yn-2-yl)-2-(3,3,3-trifluoropropylamino)benzamide 2-(3,3,3-Trifluoropropylamino)benzoic acid (410 mg, 1.758 mmol), DCM (3 ml), EDCI (404 mg, 2.110 mmol), HOBt (238 mg, 1.758 mmol), DIPEA (0.613 ml, 3.52 mmol) and 1,1-dimethylpropargylamine (0.241 ml, 2.286 mmol) were stirred at room temperature overnight. The reaction mixture was washed once with 1M NaOH and once with 1M HCl. The organic phase was dried and evaporated to dryness. The product was purified at first by flash chromatography and finally by preparative HPLC to yield 221 mg of the title compound.

$^1$H NMR (400 MHz, CDCl$_3$-d) δ ppm 1.73 (s, 6 H) 2.39 (s, 1 H) 2.40-2.51 (m, 2 H) 3.36-3.55 (m, 2 H) 6.08 (br. s., 1 H) 6.57-6.74 (m, 2 H) 7.28-7.36 (m, 2 H) 7.74 (t, 1 H).

Example 80

2-(Isobutylamino)-N-(2-methylbut-3-yn-2-yl)benzamide

Step 1: 2-(Isobutylamino)benzoic acid

Anthranilic acid (250 mg, 1.823 mmol) and 1,2-dichloroethane (10 ml) were cooled down to 0° C. Isobutyraldehyde (0.216 ml, 2.370 mmol) and acetic acid, glacial (0.313 ml, 5.47 mmol) were added slowly. Sodium triacetoxy borohydride (1545 mg, 7.29 mmol) was added and the reaction mixture was stirred at room temperature overnight. The reaction mixture was cooled down to 0° C., DCM was added and the organic phase was washed three times with water. The organic phase was dried and evaporated to dryness to yield to yield 439 mg of the title compound.

$^1$H NMR (400 MHz, CDCl$_3$-d) δ ppm 0.98-1.09 (m, 6 H) 1.98 (dt, 1 H) 3.03 (d, 2H) 6.51-6.71 (m, 2 H) 7.37 (m, 1 H) 7.92-8.06 (m, 1 H).

Step 2: 2-(Isobutylamino)-N-(2-methylbut-3-yn-2-yl)benzamide 2-(Isobutylamino)benzoic acid (352 mg, 1.822 mmol), DCM (3 ml), EDCI (419 mg, 2.186 mmol), HOBt (246 mg, 1.822 mmol), DIPEA (0.635 ml, 3.64 mmol) and 1,1-dimethylpropargylamine (0.249 ml, 2.368 mmol) were stirred at room temperature overnight. The reaction mixture was washed once with 1M NaOH and once with 1M HCl. The organic phase was dried and evaporated to dryness. The product was purified by flash chromatography to yield 244 mg of the title compound.

$^1$H NMR (400 MHz, CDCl$_3$-d) δ ppm 0.99 (d, 6 H) 1.73 (s, 6 H) 1.86-2.03 (m, 1 H) 2.38 (s, 1 H) 2.95 (dd, 2 H) 6.05 (br. s., 1 H) 6.47-6.58 (m, 1 H) 6.66 (dd, 1 H) 7.24-7.31 (m, 2 H) 7.60 (br. s., 1 H).

Example 81

N-(2-Methylbut-3-yn-2-yl)-2-(neopentylamino)benzamide

Step 1: 2-(Neopentylamino)benzoic acid

Anthranilic acid (250 mg, 1.823 mmol) and 1,2-dichloroethane (5 ml) were cooled down to 0° C. Trimethylacetaldehyde (0.257 ml, 2.370 mmol) and acetic acid, glacial (0.261 ml, 4.56 mmol) were added slowly. Sodium triacetoxy borohydride (773 mg, 3.65 mmol) was added and the reaction mixture was stirred at room temperature overnight. The reaction mixture was cooled down to 0° C., DCM was added and the organic phase was washed three times with water. The organic phase was dried and evaporated to dryness to yield to yield 387 mg of the title compound.

$^1$H NMR (400 MHz, CDCl$_3$-d) δ ppm 1.05 (s, 9 H) 2.99 (s, 2 H) 6.57 (m, 1 H) 6.70 (dd, 1 H) 7.37 (m, 1 H) 7.93-8.02 (m, 1 H).

Step 2: N-(2-Methylbut-3-yn-2-yl)-2-(neopentylamino)benzamide 2-(Neopentylamino)benzoic acid (378 mg, 1.824 mmol), DCM (3 ml), EDCI (420 mg, 2.188 mmol), HOBt (246 mg, 1.824 mmol), DIPEA (0.635 ml, 3.65 mmol) and 1,1-dimethylpropargylamine (0.249 ml, 2.371 mmol) were stirred at room temperature overnight. The reaction mixture was washed once with 1M NaOH and once with 1M HCl. The organic phase was dried and evaporated to dryness. The product was purified at first by flash chromatography and finally by preparative HPLC to yield 272 mg of the title compound.

$^1$H NMR (400 MHz, CDCl$_3$-d) δ ppm 0.96-1.07 (m, 9 H) 1.68-1.80 (m, 6 H) 2.37 (s, 1 H) 2.92 (d, 2 H) 6.04 (br. s., 1 H) 6.46-6.58 (m, 1 H) 6.69 (dd, 1 H) 7.18-7.38 (m, 2 H) 7.52 (d, 1 H).

Example 82

2-(tert-Butylamino)-4,5-difluoro-N-(2-methylbut-3-yn-2-yl)benzamide

Step 1: 2-(tert-Butylamino)-4,5-difluorobenzoic acid

2-Bromo-4,5-difluorobenzoic acid (250 mg, 1.055 mmol), tert-butylamine (0.222 ml, 2.110 mmol), potassium acetate (207 mg, 2.110 mmol), copper(II) acetate monohydrate (21.06 mg, 0.105 mmol), triethylamine (0.176 ml, 1.266 mmol) and N,N-dimethyl formamide (3 ml) were added to a microwave vial. The reaction mixture was irradiated at 180° C. for 10 minutes at high absorbance. DCM was added to the reaction mixture and the product was extracted twice with water. The water phase was acidified with 1M HCl and extracted with ethyl acetate. The organic phase was dried and evaporated to dryness to yield 223 mg of the title compound.

LC/MS [M−1] 228.0

Step 2: 2-(tert-Butylamino)-4,5-difluoro-N-(2-methylbut-3-yn-2-yl) benzamide 2-(tert-Butylamino)-4,5-difluorobenzoic acid (223 mg, 0.973 mmol), DCM (3 ml), EDCI (224 mg, 1.167 mmol), HOBt (131 mg, 0.973 mmol), DIPEA (0.424 ml, 2.432 mmol) and 1,1-dimethylpropargylamine (0.133 ml, 1.265 mmol) were stirred at room temperature over three nights. The reaction mixture was washed once with water. The organic phase was dried and evaporated to dryness. The product was purified at first by flash chromatography and finally by preparative HPLC to yield 6 mg of the title compound.

$^1$H NMR (400 MHz, CDCl$_3$-d) δ ppm 1.35 (s, 9 H) 1.73 (s, 6 H) 2.38 (s, 1 H) 6.46 (br. s., 1 H) 6.69 (dd, 1 H) 6.88 (s, 1 H) 7.21-7.27 (m, 1 H).

Example 83

4-Fluoro-2-(isopropylamino)-N-(2-methylbut-3-yn-2-yl)benzamide

Step 1: 2-Amino-4-fluoro-N-(2-methylbut-3-yn-2-yl)benzamide

2-Amino-4-fluorobenzoic acid (300 mg, 1.934 mmol), DCM (3 ml), EDCI (445 mg, 2.321 mmol), HOBt (261 mg, 1.934 mmol), DIPEA (0.674 ml, 3.87 mmol) and 1,1-dimethylpropargylamine (0.265 ml, 2.51 mmol) were stirred at room temperature overnight. The reaction mixture was washed once with water. The organic phase was dried and evaporated to dryness to yield 325 mg of the title compound.

$^1$H NMR (400 MHz, CDCl$_3$-d) δ ppm 1.74 (s, 6 H) 2.39 (s, 1 H) 5.75 (br. s., 2 H) 5.97 (br. s., 1 H) 6.27-6.43 (m, 2 H) 7.22-7.30 (m, 1 H).

Step 2: 4-Fluoro-2-(isopropylamino)-N-(2-methylbut-3-yn-2-yl)benzamide

2-Amino-4-fluoro-N-(2-methylbut-3-yn-2-yl)benzamide (325 mg, 1.476 mmol) and 1,2-dichloroethane (5 ml) were cooled down to 0° C. Acetone (0.434 ml, 5.90 mmol) and acetic acid, glacial (0.422 ml, 7.38 mmol) were added slowly. Sodium triacetoxy borohydride (938 mg, 4.43 mmol) was added and the reaction mixture was stirred at room temperature overnight. DCM was added to the reaction mixture and the mixture was washed once with water and once with brine. The organic phase was dried and evaporated to dryness. The product was purified by flash chromatography and preparative HPLC to yield 205 mg of the title compound.

$^1$H NMR (400 MHz, CDCl$_3$-d) δ ppm 1.25 (d, 6 H) 1.67-1.80 (m, 6 H) 2.39 (s, 1 H) 3.56 (m, 1 H) 5.94 (br. s., 1 H) 6.15-6.26 (m, 1 H) 6.33 (dd, 1 H) 7.24-7.29 (m, 1 H) 7.73 (d, 1 H).

Example 84

2-(Methylamino)-N-(2-methylbut-3-yn-2-yl)-4-(trifluoromethyl)-benzamide

2-Amino-N-(2-methylbut-3-yn-2-yl)-4-(trifluoromethyl) benzamide (250 mg, 0.925 mmol) and 1,2-dichloroethane (5 ml) were cooled down to 0° C. Paraformaldehyde (55.6 mg, 1.850 mmol) and acetic acid, glacial (0.212 ml, 3.70 mmol) were added slowly. Sodium triacetoxy borohydride (882 mg, 4.16 mmol) was added and the reaction mixture was stirred at room temperature overnight. DCM was added to the reaction mixture and the mixture was, washed twice with water. The organic phase was dried and evaporated to dryness. The product was purified at first by flash chromatography and finally by preparative HPLC to yield 34 mg of the title compound.

$^1$H NMR (400 MHz, CDCl$_3$-d) δ ppm 1.74 (s, 6 H) 2.40 (s, 1 H) 2.88 (d, 3 H) 6.08 (br. s., 1 H) 6.72-6.89 (m, 2 H) 7.37 (d, 1 H) 7.69 (br. s., 1 H).

Example 85

2-(Methylamino)-N-(2-methylbut-3-yn-2-yl)-5-(trifluoromethoxy)-benzamide

2-Amino-N-(2-methylbut-3-yn-2-yl)-5-(trifluoromethoxy)benzamide (150 mg, 0.524 mmol) and 1,2-dichloroethane (5 ml) were cooled down to 0° C. Paraformaldehyde (31.5 mg, 1.048 mmol) and acetic acid, glacial (0.120 ml, 2.096 mmol) were added slowly. Sodium triacetoxy borohydride (500 mg, 2.358 mmol) was added and the reaction mixture was stirred at room temperature overnight. DCM was added to the reaction mixture and the mixture was washed twice with water. The organic phase was dried and evaporated to dryness. The product was purified at by flash chromatography and preparative HPLC to yield 10 mg of the title compound.

$^1$H NMR (400 MHz, CDCl$_3$-d) δ ppm 1.74 (s, 6 H) 2.40 (s, 1 H) 2.85 (d, 3 H) 5.97 (br. s., 1 H) 6.61 (d, 1 H) 7.09-7.23 (m, 2 H) 7.46-7.63 (m, 1 H).

Example 86

2-(Cyclopropylamino)-4,5-difluoro-N-(2-methylbut-3-yn-2-yl) benzamide

Step 1: 2-(Cyclopropylamino)-4,5-difluorobenzoic acid

2-Bromo-4,5-difluorobenzoic acid (250 mg, 1.055 mmol), cyclopropylamine (0.147 ml, 2.110 mmol), potassium acetate (207 mg, 2.110 mmol), copper(II) acetate monohydrate (21.06 mg, 0.105 mmol), triethylamine (0.176 ml, 1.266 mmol) and N,N-dimethyl formamide (3 ml) were added to a microwave vial. The reaction mixture was irradiated at 1.80° C. for 10 minutes. Water was added to the reaction mixture, the mixture was acidified with 1M HCl and extracted twice with ethyl acetate. The organic phase was dried and evaporated to dryness to yield 223 mg of the title compound.

$^1$H NMR (400 MHz, CDCl$_3$-d) δ ppm 0.53-0.64 (m, 2 H) 0.78-0.89 (m, 2 H) 2.44 (dt, 1 H) 6.91 (dd, 1 H) 7.62-7.80 (m, 2 H).

Step 2: 2-(Cyclopropylamino)-4,5-difluoro-N-(2-methylbut-3-yn-2-yl)benzamide 2-(Cyclopropylamino)-4,5-difluorobenzoic acid (223 mg, 1.046 mmol), DCM (3 ml), EDCI (241 mg, 1.255 mmol), HOBt (141 mg, 1.046 mmol), DIPEA (0.456 ml, 2.62 mmol) and 1,1-dimethylpropargylamine (0.143 ml, 1.360 mmol) were stirred at room temperature for three days. The reaction mixture was washed once with water. The organic phase was dried and evaporated to dryness. The product was purified at first by flash chromatography and finally by preparative HPLC to yield 58 mg of the title compound.

$^1$H NMR (400 MHz, CDCl$_3$-d) δ ppm 0.50-0.56 (m, 2 H) 0.72-0.81 (m, 2 H) 1.72 (s, 6 H) 2.31-2.38 (m, 1 H) 2.39 (s, 1 H) 5.86 (br. s., 1 H) 6.90 (dd, 1 H) 7.11 (dd, 1 H) 7.77 (br. s., 1 H).

Example 87

N-(3,4-Dimethylpent-1-yn-3-yl)-2-(ethylamino)-4,5-difluorobenzamide

Step 1: 2-(Ethylamino)-4,5-difluorobenzoic acid 4,5-Difluoroanthranilic acid (500 mg, 2.89 mmol) and 1,2-dichloroethane (5 ml) were cooled down to 0° C. Acetaldehyde (0.221 ml, 3.75 mmol) and acetic acid, glacial (0.33 ml, 5.78 mmol) were added slowly. Sodium triacetoxy borohydride (1530 mg, 7.22 mmol) was added and the reaction mixture was stirred at room temperature overnight. The reaction mixture was cooled down to 0° C., DCM was added and the organic phase was washed once with water and once with brine. The organic phase was dried and evaporated to dryness to yield to yield 550 mg of the title compound.

$^1$H NMR (400 MHz, MeOD-d) δ ppm 1.21-1.36 (m, 3 H) 3.08-3.24 (m, 2 H) 6.40 (dd, 1 H) 7.64-7.82 (m, 1 H).

Step 2: N-(3,4-Dimethylpent-1-yn-3-yl)-2-(ethylamino)-4,5-difluorobenzamide 2-(Ethylamino)-4,5-difluorobenzoic acid (100 mg, 0.497 mmol), DCM (3 ml), EDCI (114 mg, 0.597 mmol), HOBt (67.2 mg, 0.497 mmol), DIPEA (0.216 ml, 1.243 mmol) and 3,4-dimethylpent-1-yn-2-amine hydrochloride (71.8 mg, 0.486 mmol) were stirred at room temperature over three nights. The reaction mixture was washed once with water. The organic phase was dried and evaporated to dryness. The product was purified by flash chromatography to yield 100 mg of the title compound.

$^1$H NMR (400 MHz, CDCl$_3$-d) δ ppm 1.07 (dd, 6 H) 1.28 (t, 3 H) 1.70 (s, 3 H) 2.42 (s, 1 H) 2.51 (m, 1 H) 3.10 (m, 2 H) 5.88 (br. s., 1 H) 6.40 (dd, 1 H) 7.11 (dd, 1 H) 7.35 (br. s., 1 H).

Example 88

2-(Isobutylamino)-4,5-dimethoxy-N-(2-methylbut-3-yn-2-yl)benzamide

Step 1: 2-Amino-4,5-dimethoxy-N-(2-methylbut-3-yn-2-yl)benzamide

2-Amino-4,5-methoxybenzoic acid (300 mg, 1.521 mmol), DCM (3 ml), EDCI (350 mg, 1.826 mmol), HOBt (206 mg, 1.521 mmol), DIPEA (0.530 ml, 3.04 mmol) and 1,1-dimethylpropargylamine (0.208 ml, 1.978 mmol) were stirred at room temperature overnight. The reaction mixture was washed once with water. The organic phase was dried and evaporated to dryness. The product was purified by flash chromatography to yield 265 mg of the title compound.

$^1$H NMR (400 MHz, CDCl$_3$-d) δ ppm 1.74 (s, 6 H) 2.39 (s, 1 H) 3.82 (s, 3 H) 3.85 (s, 3 H) 5.40 (br. s., 2 H) 6.00 (br. s., 1 H) 6.18 (s, 1 H) 6.80 (s, 1 H).

Step 2: 2-(Isobutylamino)-4,5-dimethoxy-N-(2-methylbut-3-yn-2-yl)benzamide

2-Amino-4,5-dimethoxy-N-(2-methylbut-3-yn-2-yl)benzamide (130 mg, 0.496 mmol) and 1,2-dichloroethane (5 ml) Were cooled down to 0° C. Isobutyraldehyde (0.059 ml, 0.664 mmol) and acetic acid, glacial (0.057 ml, 0.991 mmol) were added slowly. Sodium triacetoxy borohydride (263 mg, 1.239 mmol) was added and the reaction mixture was stirred at room temperature overnight. DCM was added to the reaction mixture and the mixture was washed twice with water. The organic phase was dried and evaporated to dryness. The product was purified at first by flash chromatography and finally by preparative HPLC to yield 40 mg of the title compound.

$^1$H NMR (400 MHz, CDCl$_3$-d) δ ppm 1.01 (d, 6 H) 1.73 (s, 6 H) 1.95 (dt, 1 H) 2.38 (s, 1 H) 2.94 (d, 2 H) 3.81 (s, 3 H) 3.89 (s, 3 H) 5.95 (s, 1H) 6.18 (s, 1 H) 6.85 (s, 1 H) 7.52 (br. s., 1 H).

Example 89

2-(2-Methoxyethylamino)-N-(2-methylbut-3-yn-2-yl)-4-(trifluoro-methyl)benzamide

Step 1: 2-(2-Methoxyethylamino)-4-(trifluoromethyl)benzoic acid

The mixture of 1,1,2-trimethoxyethane (0.408 ml, 3.17 mmol), trifluoroacetic acid (0.290 ml, 3.90 mmol) and water (0.4 ml) was stirred at 50° C. for 10 minutes. The reaction mixture was cooled down to 0° C. and 2-amino-4-(trifluoromethyl)benzoic acid (500 mg, 2.437 mmol), 1,2-dichloroethane (10 ml), acetic acid, glacial (0.419 ml, 7.31 mmol) and sodium triacetoxy borohydride (2066 mg, 9.75 mmol) were added. The reaction mixture was stirred at room temperature overnight. DCM and ethyl acetate were added to the reaction mixture and the mixture was washed once with acidic water and once with water. The organic phase was dried and evaporated to dryness to yield 665 mg of the title compound.

$^1$H NMR (400 MHz, CDCl$_3$-d) δ ppm 3.38-3.45 (m, 5 H) 3.67 (t, 2 H) 6.81 (dd, 1 H) 6.90 (m, 1 H) 8.04 (dd, 1 H).

Step 2: 2-(2-Methoxyethylamino)-N-(2-methylbut-3-yn-2-yl)-4-(trifluoromethyl)-benzamide 2-(2-Methoxyethylamino)-4-(trifluoromethyl)benzoic acid (150 mg, 0.570 mmol), DCM (3 ml), EDCI (131 mg, 0.684 mmol), HOBt (77 mg, 0.570 mmol), DIPEA (0.248 ml, 1.425 mmol) and 1,1-dimethylpropargylamine (0.060 ml, 0.570 mmol) were stirred at room temperature overnight. The reaction mixture was washed once with water. The organic phase was dried and evaporated to dryness. The product was purified at first by flash chromatography and finally by preparative HPLC to yield 42 mg of the title compound.

$^1$H NMR (400 MHz, CDCl$_3$-d) δ ppm 1.69-1.79 (m, 6 H) 2.40 (s, 1 H) 3.31-3.45 (m, 5 H) 3.62 (t, 2 H) 6.09 (br. s., 1 H) 6.74-6.85 (m, 1 H) 6.90 (s, 1 H) 7.38 (d, 1 H) 7.68 (br. s., 1 H).

Example 90

2-(Cyclopropylamino)-4-fluoro-N-(2-methylbut-3-yn-2-yl)benzamide

Step 1: 2-(Cyclopropylamino)-4-fluorobenzoic acid

2-Bromo-4-fluorobenzoic acid (150 mg, 0.685 mmol), cyclopropylamine (0.095 ml, 1.370 mmol), potassium acetate (134 mg, 1.370 mmol), copper(II) acetate monohydrate (13.67 mg, 0.068 mmol), triethylamine (0.115 ml, 0.822 mmol) ja N,N-dimethyl formamide (3 ml) were added to a microwave vial. The reaction mixture was irradiated at 180° C. for 10 minutes at high absorbance. Water was added to the reaction mixture, the mixture was acidified with 1M HCl and extracted twice with ethyl acetate. The organic phase was dried and evaporated to dryness to yield 555 mg of the title compound containing also DMF.

$^1$H NMR (400 MHz, CDCl$_3$-d) δ ppm 0.51-0.62 (m, 2 H) 0.74-0.88 (m, 2 H) 2.35-2.50 (m, 1 H) 6.26-6.39 (m, 1 H) 6.71-6.83 (m, 1 H) 7.92 (m, 1 H).

Step 2: 2-(Cyclopropylamino)-4-fluoro-N-(2-methylbut-3-yn-2-yl)benzamide 2-(Cyclopropylamino)-4-fluorobenzoic acid (134 mg, 0.687 mmol), DCM (3 ml), EDCI (158 mg, 0.824 mmol), HOBt (93 mg, 0.687 mmol), DIPEA (0.239 ml, 1.373 mmol) and 1,1-dimethylpropargylamine (0.094 ml, 0.892 mmol) were stirred at room temperature overnight. The reaction mixture was washed once with 1M NaOH and once with water. The organic phase was dried and evaporated to dryness. The product was purified at first by flash chromatography and finally by preparative HPLC to yield 5 mg of the title compound.

$^1$H NMR (400 MHz, CDCl$_3$-d) δ ppm 0.49-0.61 (m, 2 H) 0.71-0.82 (m, 2 H) 1.66-1.77 (s, 6 H) 2.31-2.45 (m, 2 H) 5.95 (br. s., 1 H) 6.22-6.35 (m, 1 H) 6.79 (dd, 1 H) 7.22-7.29 (m, 2 H) 8.02 (br. s., 1 H).

Example 91

2-(Cyclopropylamino)-5-fluoro-N-(2-methylbut-3-yn-2-yl)benzamide

Step 1: 2-(Cyclopropylamino)-5-fluorobenzoic acid

2-Bromo-5-fluorobenzoic acid (150 mg, 0.685 mmol), cyclopropylamine (0.095 ml, 1.370 mmol), potassium acetate (134 mg, 1.370 mmol), copper(II) acetate monohydrate (13.67 mg, 0.068 mmol), triethylamine (0.115 ml, 0.822 mmol) and N,N-dimethyl formamide (3 ml) were added to a microwave vial. The reaction mixture was irradiated at 180° C. for 10 minutes at high absorbance. Water was, added to the reaction mixture, the mixture was acidified with 1M HCl and extracted twice with ethyl acetate. The organic phase was dried and evaporated to dryness to yield 109 mg of the title compound.

LC/MS [M+1] 196.0

Step 2: 2-(Cyclopropylamino)-5-fluoro-N-(2-methylbut-3-yn-2-yl)benzamide 2-(Cyclopropylamino)-5-fluorobenzoic acid (109 mg, 0.558 mmol), DCM (3 ml), EDCI (128 mg, 0.670 mmol), HOBt (75 mg, 0.558 mmol), DIPEA (0.195 ml, 1.117 mmol) and 1,1-dimethylpropargylamine (0.076 ml, 0.726 mmol) were stirred at room temperature overnight. The reaction mixture was washed once with 1M NaOH and once with water. The organic phase was dried and evaporated to dryness. The product was purified at first by flash chromatography and finally by preparative HPLC to yield 9 mg of the title compound.

$^1$H NMR (400 MHz, CDCl$_3$-d) δ ppm 0.47-0.58 (m, 2 H) 0.67-0.80 (m, 2 H) 1.72 (s, 6 H) 2.31-2.42 (m, 2 H) 5.98 (br. s., 1 H) 6.93-7.14 (m, 3 H) 7.48 (br. s., 1 H).

Example 92

5-Fluoro-2-(isopropylamino)-N-(2-methylbut-3-yn-2-yl)benzamide

Step 1: 5-Fluoro-2-(isopropylamino)benzoic acid

2-Bromo-5-fluorobenzoic acid (150 mg, 0.685 mmol), isopropylamine (0.117 ml, 1.370 mmol), potassium acetate (134 mg, 1.370 mmol), copper(II) acetate monohydrate (13.67 mg, 0.068 mmol), triethylamine (0.115 ml, 0.822 mmol) and N,N-dimethyl formamide (3 ml) were added to a microwave vial. The reaction mixture was irradiated at 180° C. for 10 minutes at high absorbance. Water was added to the reaction mixture, the mixture was acidified with 1M HCl and extracted twice with ethyl acetate. The organic phase was dried and evaporated to dryness to yield 108 mg of the title compound.

LC/MS [M+1] 198.0

Step 2: 5-Fluoro-2-(isopropylamino)-N-(2-methylbut-3-yn-2-yl)benzamide

5-Fluoro-2-(isopropylamino)benzoic acid (108 mg, 0.548 mmol), DCM (3 ml), EDCI (126 mg, 0.657 mmol), HOBt (74 mg, 0.548 mmol), DIPEA (0.191 ml, 1.095 mmol) and 1,1-dimethylpropargylamine (0.075 ml, 0.712 mmol) were stirred at room temperature overnight. The reaction mixture was washed once with 1M NaOH and once with water. The organic phase was dried and evaporated to dryness. The product was purified at first by flash chromatography and finally by preparative HPLC to yield 12 mg of the title compound.

$^1$H NMR (400 MHz, CDCl$_3$-d) δ ppm 1.22 (d, 6 H) 1.73 (s, 6 H) 2.39 (s, 1 H) 3.58 (dt, 1 H) 6.15 (br. s., 1 H) 6.56-6.69 (m, 1 H) 6.90 (br. s., 1 H) 6.97-7.09 (m, 2 H).

Example 93

2-(Isopropylamino)-5-methyl-N-(2-methylbut-3-yn-2-yl)benzamide

Step 1: 2-(Isopropylamino)-5-methylbenzoic acid

2-Amino-5-methylbenzoic acid (250 mg, 1.654 mmol) and DCM (2 ml) were cooled down to 0° C. Acetone (0.304 ml, 4.13 mmol) and acetic acid, glacial (0.284 ml, 4.96 mmol) were added slowly. Sodium triacetoxy borohydride (1402 mg, 6.62 mmol) was added and the reaction mixture was stirred at room temperature overnight. The reaction mixture was cooled down to 0° C., DCM was added and the organic phase was washed once with water and once with brine. The organic phase was dried and evaporated to dryness to yield to yield 273 mg of the title compound.

$^1$H NMR (400 MHz, MeOD-d) δ ppm 1.24 (d, 6 H) 2.17-2.26 (m, 3 H) 3.63-3.82 (m, 1 H) 6.60-6.78 (m, 1 H) 7.20 (m, 1 H) 7.65-7.77 (m, 1 H).

Step 2: 2-(Isopropylamino)-5-methyl-N-(2-methylbut-3-yn-2-yl)benzamide 2-(Isopropylamino)-5-methylbenzoic acid (273 mg, 1.413 mmol), DCM (3 ml), EDCI (325 mg, 1.695 mmol), HOBt (191 mg, 1.413 mmol), DIPEA (0.615 ml, 3.53 mmol) and 1,1-dimethylpropargylamine (0.193 ml, 1.837 mmol) were stirred at room temperature over three nights. The reaction mixture was washed once with water. The organic phase was dried and evaporated to dryness. The product was purified at first by flash chromatography and finally by preparative HPLC to yield 22 mg of the title compound.

¹H NMR (400 MHz, CDCl₃-d) δ ppm 1.22 (d, 6 H) 1.73 (s, 6 H) 2.22 (s, 3 H) 2.38 (s, 1 H) 3.61 (m, 1 H) 6.14 (br. s., 1 H) 6.62 (d, 1 H) 6.96-7.15 (m, 3 H).

Example 94

4-Methyl-N-(2-methylbut-3-yn-2-yl)-2-(3,3,3-trifluoropropylamino)-benzamide

Step 1:
4-Methyl-2-(3,3,3-trifluoropropylamino)benzoic acid

2-Amino-4-methylbenzoic acid (150 mg, 0.992 mmol) and DCM (3 ml) were cooled down to 0° C. 3,3,3-Trifluoropropanal (0.111 ml, 1.29 mmol) and acetic acid, glacial (0.114 ml, 1.985 mmol) were added slowly. Sodium triacetoxy borohydride (526 mg, 2.481 mmol) was added and the reaction mixture, was stirred at room temperature overnight. The reaction mixture was cooled down to 0° C., DCM was added and the organic phase was washed once with water and once with brine. The organic phase was dried and evaporated to dryness to yield to yield 233 mg of the title compound.

LC/MS [M+i]248.1

Step 2: 4-Methyl-N-(2-methylbut-3-yn-2-yl)-2-(3,3,3-trifluoropropylamino)benzamide 4-Methyl-2-(3,3,3-trifluoropropylamino)benzoic acid (233 mg, 0.943 mmol), DCM (5 ml), EDCI (217 mg, 1.131 mmol), HOBt (127 mg, 0.943 mmol), DIPEA (0.328 ml, 1.885 mmol) and 1,1-dimethylpropargylamine (0.129-ml, 1.225 mmol) were stirred at room temperature over three nights. The reaction mixture was washed once with water. The organic phase was dried and evaporated to dryness. The product was purified at first by flash chromatography and preparative HPLC to yield 103 mg of the title compound.

¹H NMR (400 MHz, CDCl₃-d) δ ppm 1.72 (s, 6 H) 2.31 (s, 3 H) 2.38 (s, 1 H) 2.40-2.57 (m, 2 H) 3.39-3.51 (i, 2 H) 6.04 (br. s., 1 H) 6.40-6.51 (m, 2 H) 7.21 (d, 1 H) 7.82 (t, 1 H).

Example 95

5-Chloro-3-fluoro-2-(isopropylamino)-N-(2-methylbut-3-yn-2-yl)-benzamide

Step 1: 2-Amino-5-chloro-3-fluorobenzoic acid

2-Amino-3-fluorobenzoic acid (100 mg, 0.645 mmol), N-chlorosuccinimide (103 mg, 0.774 mmol) and N,N-dimethylformamide (3 ml) were stirred at room temperature overnight. Water was added to the reaction mixture, the mixture was acidified with 1M HCl and extracted twice with ethyl acetate. The organic phase was dried and evaporated to dryness to yield 220 mg of the title compound containing also succinimide.

¹H NMR (400 MHz, CDCl₃-d) δ ppm 3.36-3.41 (m, 1 H) 7.13 (m, 1 H) 7.66-7.71 (m, 1 H).

Step 2: 2-Amino-5-chloro-3-fluoro-N-(2-methylbut-3-yn-2-yl)benzamide

2-Amino-5-chloro-3-fluorobenzoic acid (108 mg, 0.570 mmol), DCM (3 ml), EDCI (131 mg, 0.684 mmol), HOBt (77 mg, 0.570 mmol), DIPEA (0.198 ml, 1.139 mmol) and 1,1-dimethylpropargylamine (0.078 ml, 0.741 mmol) were stirred at room temperature over, three nights. The reaction mixture was washed once with water. The organic phase was dried and evaporated to dryness. The product was purified by flash chromatography to yield 123 mg of the title compound.

¹H NMR (400 MHz, CDCl₃-d) δ ppm 1.74 (s, 6 H) 2.41 (s, 1 H) 5.61 (br. s., 2 H) 6.02 (br. s., 1 H) 7.02-7.12 (m, 2 H).

Step 3: 5-Chloro-3-fluoro-2-(isopropylamino)-N-(2-methylbut-3-yn-2-yl)benzamide

2-Amino-5-chloro-3-fluoro-N-(2-methylbut-3-yn-2-yl) benzamide (60 mg, 0.236 mmol) and DCM (3 ml) were charged and acetone (0.069 ml, 0.942 mmol) and trifluoroacetic acid (0.026 ml, 0.353 mmol) were added slowly. Sodium triacetoxy borohydride (74.9 mg, 0.353 mmol) was added and the reaction mixture was stirred at room temperature for two hours. More trifluoroacetic acid (0.05 ml) was added and the mixture was stirred for 90 minutes. Trifluoroacetic acid (0.05 ml) was added once more and the mixture was stirred for 45 minutes. The reaction mixture was diluted with DCM and the mixture was washed once with water and once with brine. The organic phase was dried and evaporated to dryness. The product was purified by flash chromatography to yield to yield 33 mg of the title compound.

¹H NMR (400 MHz, CDCl₃-d) δ ppm 1.16 (dd, 6 H) 1.74 (s, 6 H) 2.39 (s, 1 H) 3.41-3.57 (m, 1 H) 4.36 (br. s., 1 H) 7.12 (dd, 1 H) 7.56 (dd, 1 H) 8.09 (br. s., 1 H).

Example 96

5-Methoxy-N-(2-methylbut-3-yn-2-yl)-2-(4,4,4-trifluorobutylamino)-benzamide

Step 1:
5-Methoxy-2-(4,4,4-trifluorobutylamino)benzoic acid

2-Amino-5-methoxybenzoic acid (250 mg, 1.496 mmol) and DCM (3 ml) were cooled down to 0° C. 4,4,4-Trifluorobutyraldehyde (0.204 ml, 1.944 mmol) and acetic acid, glacial (0.17 ml, 2.99 mmol) were added slowly. Sodium triacetoxy borohydride (792 mg, 3.74 mmol) was added and the reaction mixture was stirred at room temperature for two hours. DCM was added to the reaction mixture and the mixture was washed once with water and once with brine. The organic phase was dried and evaporated to dryness to yield to yield 441 mg of the title compound.

LC/MS [M+1] 278.1

Step 2: 5-Methoxy-N-(2-methylbut-3-yn-2-yl)-2-(4,4,4-trifluorobutylamino)benzamide 5-Methoxy-2-(4,4,4-trifluorobutylamino)benzoic acid (415 mg, 1.497 mmol), DCM (3 ml), EDCI (344 mg, 1.796 mmol), HOBt (202 mg, 1.497 mmol), DIPEA (0.521 ml, 2.99 mmol) and 1,1-dimethylpropargylamine (0.205 ml, 1.946 mmol) were stirred at room temperature overnight. The reaction mixture was washed once with water. The organic phase was dried and evaporated to dryness. The product was purified twice by flash chromatography to yield 134 mg of the title compound.

¹H NMR (400 MHz, MeOD-d) δ ppm 1.69 (s, 6 H) 1.80-1.95 (m, 2 H) 2.20-2.40 (m, 2 H) 2.67 (s, 1 H) 3.22 (t, 2 H) 3.78 (s, 3 H) 6.76 (d, 1 H) 6.98 (dd, 1 H) 7.07 (d, 1 H).

Example 97

2-(3-Methoxybenzylamino)-N-(2-methylbut-3-yn-2-yl)nicotinamide

Step 1: Ethyl 2-(3-methoxybenzylamino)nicotinate

3-Methoxybenzaldehyde (311 mg, 2.287 mmol), ethyl 2-aminopyridine-3-carboxylate (200 mg, 1.204 mmol), acetic acid, glacial (0.413 ml, 7.922 mmol) and 1,2-dichloroethane (10 ml) were stirred at room temperature for 10 minutes. Sodium triacetoxy borohydride (714 mg, 3.737 mmol) was added and the reaction mixture was stirred at room temperature overnight. Methanol was added to the reaction mixture and the mixture was washed once with NaHCO$_3$ solution. The water phase was extracted once with DCM, the organic phases were combined and washed with brine and water. The organic phase was dried and evaporated to dryness. The product was purified by flash chromatography to yield to yield 51 mg of the title compound.
LC/MS [M+1] 287.1

Step 2: 2-(3-Methoxybenzylamino)nicotinic acid

The mixture of ethyl 2-(3-methoxybenzylamino)nicotinate (51 mg, 0.178 mmol), tetrahydrofuran (5 ml) and 2M NaOH solution (0.267 ml, 0.534 mol) was stirred at room temperature overnight. Tho solvent was evaporated, water was added to the evaporation residue and the mixture was washed with DCM. The pH of the water phase was adjusted to 2 using 1M HCl solution and the water phase was extracted three times with ethyl acetate. The organic phase was dried and evaporated to dryness to yield 20 mg of the title compound.
¹H NMR (400 MHz, MeOD-d) δ ppm 3.82 (s, 3 H) 4.88 (s, 2 H) 6.84-6.96 (m, 2 H) 6.97-7.03 (m, 2 H) 7.30 (t, 1 H) 8.29 (dd, 1 H) 8.60 (dd, 1 H).

Step 3: 2-(3-Methoxybenzylamino)-N-(2-methylbut-3-yn-2-yl)nicotinamide 2-(3-Methoxybenzylamino)nicotinic acid (20 nig, 0.077 mmol), DCM (4 ml), EDCI (16 mg, 0.085 mmol), HOBt (12 mg, 0.085 mmol), DIPEA (0.007 ml, 0.039 mmol) and 1,1-dimethylpropargylamnine (0.009 ml, 0.085 mmol) were stirred at room temperature overnight. The reaction mixture was diluted with DCM and washed with Na$_2$CO$_3$ solution, 1M HCl and water. The organic phase was dried and evaporated to dryness to yield 18 mg of the title compound.
¹H NMR (400 MHz, CDCl$_3$-d) δ ppm 1.73 (s, 6 H) 2.38 (s, 1 H) 3.78 (s, 3 H) 4.70 (d, 2 H) 6.14 (br. s., 1 H) 6.50 (dd, 1 H) 6.74-6.82 (m, 1 H) 6.90-7.00 (m, 2H) 7.22 (t, 1 H) 7.57 (dd, 1 H) 8.20 (dd, 1 H) 8.53 (br. s., 1 H).

Example 98

2-(3-Fluorobenzylamino)-N-(2-methylbut-3-yn-2-yl)nicotinamide

Step 1: Ethyl 2-(3-fluorobenzylamino)nicotinate

3-Fluorobenzylamine (0.371 ml, 3.23 mmol), ethyl 2-chloronicotinate (0.161 ml, 1.078 mmol) and ethanol (2 ml) were added to a microwave vial. The reaction mixture was irradiated at 160° C. for 30 minutes at high absorbance. Water was added to the reaction mixture and the mixture was extracted twice with DCM. The organic phase was dried and evaporated to dryness. The product was purified by flash chromatography to yield 196 mg of the title compound.
¹H NMR (400 MHz, CDCl$_3$-d) δ ppm 1.37 (t, 3 H) 4.32 (q, 2 H) 4.76 (d, 2 H) 6.55 (m, 1 H) 6.84-6.98 (m, 1 H) 7.00-7.18 (m, 2 H) 7.20-7.32 (m, 1 H) 8.14 (dd, 1 H) 8.27 (dd, 1 H) 8.37 (br. s., 1 H).

Step 2: 2-(3-Fluorobenzylamino)nicotinic acid

The mixture of ethyl 2-(3-fluorobenzylamino)nicotinate (197 mg, 0.718 mmol), tetrahydrofuran (10 ml) and 2M NaOH solution (1.077 ml, 2.155 mol) was stirred at 50° C. until the starting material was consumed. Solvents were evaporated, water was added to the evaporation residue and water phase was acidified 2 using 1M HCl solution. The water phase was extracted three times with ethyl acetate. The ethyl acetate layers were combined and the organic phase was dried and evaporated to dryness to yield 121 mg of the title compound.
LC/MS [M+1] 247.1

Step 3: 2-(3-Fluorobenzylamino)-N-(2-methylbut-3-yn-2-yl)nicotinamide 2-(3-Fluorobenzylamino)nicotinic acid (50 mg, 0.203 mmol), DCM (5 ml), EDCI (39 mg, 0.203 mmol), HOBt (27 mg, 0.203 mmol) and 1,1-dimethylpropargylamine (0.026 ml, 0.244 mmol) were stirred at room temperature overnight. The reaction mixture was washed with acidic water, NaOH solution and water. The organic phase was dried and evaporated to dryness to yield 19 mg of the title compound.
¹H NMR (400 MHz, CDCl$_3$-d) δ ppm 1.73 (s, 6 H) 2.40 (s, 1 H) 4.71 (d, 2 H) 6.13 (br. s., 1H) 6.51 (dd, 1 H) 6.86-6.94 (n, 1 H) 7.03-7.09 (m, 1 H) 7.10-7.16 (m, 1 H) 7.24 (dd, 1 H) 7.53-7.59 (m, 1 H) 8.20 (dd, 1 H) 8.53 (t, 1 H).

Example 99

N-(2-Methylbut-3-yn-2-yl)-2-(propylamino)-6-(trifluoromethyl)-nicotinamide

Step 1: Ethyl 2-(propylamino)-6-(trifluoromethyl)nicotinate

Propionaldehyde (0.121 ml, 1.665 mmol), ethyl 2-amino-6-(trifluoromethyl)nicotinate (300 mg, 1.281 mmol), acetic acid, glacial (0.440 ml, 7.69 mmol) and 1,2-dichloroethane (10 ml) were stirred at room temperature for 10 minutes. Sodium triacetoxy borohydride (760 mg, 0.359 mmol) was added and the reaction mixture was stirred at room temperature overnight. The mixture was warmed up and stirred at 60° C. for 3 hours to complete the reaction. Methanol was added to the reaction mixture and the mixture was washed once with NaHCO$_3$ solution. The water phase was extracted once with DCM, the organic phases were combined and washed with brine and water. The organic phase was dried and evaporated to dryness. The product was purified by flash chromatography to yield to yield 200 mg of the title compound.
LC/MS [M+1] 277.1

Step 2: 2-(Propylamino)-6-(trifluoromethyl)nicotinic acid

The mixture of ethyl 2-(propylamino)-6-(trifluoromethyl) nicotinate (200 mg, 0.724 mmol), tetrahydrofuran (5 ml) and 2M NaOH solution (1.068 ml, 2.172 mol) was stirred at 50° C. until the starting material was consumed. Solvents were evaporated, water was added to the evaporation residue, and the water phase was acidified using 1M HCl solution. The water phase as extracted three times with ethyl acetate. The ethyl acetate layers were combined and the organic phase was dried and evaporated to dryness to yield 160 mg of the title compound.

$^1$H NMR (400 MHz, CDCl$_3$-d) δ ppm 1.01 (t, 3 H) 1.69 (m, 2 H) 3.42-3.59 (m, 2 H) 6.77-6.95 (m, 1 H) 7.71-8.03 (m, 1 H) 8.32 (d, 1 H) 11.49 (br. s., 1 H).

Step 3: N-(2-Methylbut-3-yn-2-yl)-2-(propylamino)-6-(trifluoromethyl)nicotinamide 2-Propylamino-6-(trifluoromethyl)nicotinic acid (50 mg, 0.201 mmol), DCM (4 ml), EDCI (42 mg, 0.222 mmol), HOBt (30 mg, 0.222 mmol), DIPEA (0.018 ml, 0.101 mmol) and 1,1-dimethylpropargylamine (0.023 ml, 0.222 mmol) were stirred at room temperature overnight. The reaction mixture was diluted with DCM and washed with Na$_2$CO$_3$ solution, 1M HCl solution and water. The organic phase was dried and evaporated to dryness. The product was purified by preparative HPLC to yield 19 mg of the title compound.

$^1$H NMR (400 MHz, CDCl$_3$-d) δ ppm 0.97 (t, 3 H) 1.65 (m, 2 H) 1.74 (s, 6 H) 2.41 (s, 1 H) 3.45 (m, 2 H) 6.07 (br. s., 1 H) 6.76 (d, 1 H) 7.61 (d, 1 H) 8.11 (br. s., 1 H).

Example 100

2-(Butylamino)-N-(2-methylbut-3-yn-2-yl)nicotinamide

Step 1: Ethyl 2-(butylamino)nicotinate

Butylamine (0.802 ml, 8.08 mmol), ethyl 2-chloronicotinate (0.5 g, 2.69 mmol) and ethanol (2 ml) were added to a microwave vial. The reaction mixture was irradiated at 160° C. for 30 minutes. Water was added to the reaction mixture and the mixture was extracted twice with ethyl acetate. The ethyl acetate layers were combined, washed with water, dried and evaporated to dryness to yield 569 mg of the title compound.

$^1$H NMR (400 MHz, CDCl$_3$-d) δ ppm 0.96 (t, 3 H) 1.38 (t, 3 H) 1.41-1.51 (m, 2 H) 1.57-1.71 (m, 2 H) 3.51 (td, 2 H) 4.32 (q, 2 H) 6.49 (m, 1H) 7.97 (br. s., 1 H) 8.11 (dd, 1 H) 8.24-8.33 (m, 1 H).

Step 2: 2-(Butylamino)nicotinic acid

The mixture of ethyl 2-(butylamino)nicotinate (599 mg, 2.69 mmol), tetrahydrofuran (10 ml) and 2M NaOH solution (4.04 ml, 8.08 mol) was stirred at 50° C. for 4.5 hours and at room temperature overnight. 2M NaOH (4.04 ml) was added and the mixture was refluxed for 10 hours and stirred at room temperature over three nights. Solvent was evaporated, water was added to the mixture and the mixture was acidified using 1M HCl. The mixture was extracted three times with ethyl acetate. The ethyl acetate layers were combined, dried and evaporated to dryness to yield 115 mg of the title compound.

$^1$H NMR (400 MHz, DMSO-d) δ ppm 0.84-0.99 (m, 3 H) 1.30-1.42 (m, 2 H) 1.46-1.61 (m, 2 H) 3.43 (m, 2 H) 6.56 (dd, 1 H) 8.04 (dd, 1 H) 8.24 (dd, 1 H).

Step 3: 2-(Butylamino)-N-(2-methylbut-3-yn-2-yl)nicotinamide 2-(Butylamino)nicotinic acid (50 mg, 0.257 mmol), DCM (4 ml), EDCI (54 mg, 0.283 mmol), HOBt (38 mg, 0.283 mmol), DIPEA (0.045 ml, 0.257 mmol) and 1,1-dimethylpropargylamine (0.030 ml, 0.283 mmol) were stirred at room temperature overnight. The reaction mixture was diluted with DCM and washed with Na$_2$CO$_3$ solution, 1M HCl solution and water. The organic phase was dried and evaporated to dryness. The product was purified by preparative HPLC to yield 5 mg of the title compound.

$^1$H NMR (400 MHz, CDCl$_3$-d) δ ppm 0.94 (t, 3 H) 1.37-1.49 (m, 2 H) 1.57-1.68 (m, 2 H) 1.73 (s, 6 H) 2.40 (s, 1 H) 3.45 (m, 2 H) 6.02 (br. s., 1 H) 6.44 (m, 1 H) 7.43-7.56 (dd, 1 H) 7.98-8.13 (m, 1 H) 8.22 (dd, 1 H).

Example 101

2-(tert-Butylamino)-N-(2-methylbut-3-yn-2-yl)nicotinamide

Step 1: Ethyl 2-(tert-butylamino)nicotinate tert-Butylamine (0.510 ml, 4.85 mmol), ethyl 2-chloronicotinate (0.3 g, 1.616 mmol) and ethanol (2 ml) were added to a microwave vial. The reaction mixture was irradiated twice at 160° C. for 60 minutes at high absorbance. tert-Butylamine (0.510 ml) was added and the mixture was irradiated at 160° C. for 90 minutes at high absorbance. tert-Butylamine (0.510 ml) was added and the mixture was irradiated at 160° C. for four hours at high absorbance. The reaction mixture was diluted with water and extracted twice with ethyl acetate. The organic layers were combined, washed with water, dried and evaporated to dryness. The product was purified by flash chromatography to yield 173 mg of the title compound.

$^1$H NMR (400 MHz, DMSO-d) δ ppm 1.30 (t, 3 H) 1.45 (s, 9 H) 4.27 (q, 2 H) 6.58 (dd, 1 H) 8.01-8.13 (m, 2 H) 8.27 (dd, 1 H).

Step 2: 2-(tert-Butylamino)nicotinic acid

The mixture of ethyl 2-(tert-butylamino)nicotinate (173 mg, 0.778 mmol), tetrahydrofuran (4.8 ml), water (4.8 ml) and lithium hydroxide (56 mg, 2.335 mmol) was refluxed for 10 hours. Solvent was evaporated, water was added to the mixture and the mixture was acidified using 1M HCl. The water phase was evaporated to dryness to yield 457 g of the title compound containing salts.

LC/MS [M+1] 195.1

Step 3: 2-(tert-Butylamino)-N-(2-methylbut-3-yn-2-yl)nicotinamide 2-(tert-Butylamino)nicotinic acid (100 mg, 0.257 mmol), DCM (4 ml), EDCI (54 mg, 0.283 mmol), HOBt (38 mg, 0.283 mmol), DIPEA (0.045 ml, 0.257 mmol) and 1,1-dimethylpropargylamine (0.030 ml, 0.283 mmol) were stirred at room temperature overnight. The reaction mixture was diluted with DCM and washed with Na$_2$CO$_3$ solution, 1M HCl solution and water. The organic phase was dried and evaporated to dryness. The product was purified by preparative HPLC to yield 3 mg of the title compound.

¹H NMR (400 MHz, CDCl₃-d) δ ppm 1.48 (s, 9 H) 1.73 (s, 6 H) 2.39 (s, 1 H) 5.99 (br. s., 1 H) 6.40 (dd, 1 H) 7.41-7.54 (m, 1 H) 8.01 (br. s., 1 H) 8.17 (dd, 1 H).

Example 102

2-(Butylamino)-5-fluoro-N-(3-methylpent-1-yn-3-yl)benzamide

Step 1: 3-Chloro-3-methylpent-1-yne

Copper(I) chloride (4.03 g, 40.8 mmol, calcium chloride anhydrous (5.65 g, 50.9 mmol) and copper-tin alloy (40 mg, 102 mmol) were cooled down to 0° C. and cold conc. hydrogen chloride (43.0 ml, 509 mmol) was added. 3-Methyl-1-pentyn-3-ol (11.51 ml, 102 mmol) was added slowly and the reaction mixture was stirred at 0° C. for two hours. The layers were separated and the product phase was washed twice with 5M HCl and once with water. The product was vacuum distilled to yield 8.68 g of the title compound.

¹H NMR (400 MHz, CDCl₃-d) δ ppm 1.15 (t, 3 H) 1.83 (s, 3 H) 1.89-2.06 (m, 2 H) 2.63 (s, 1 H).

Step 2: 3-Methylpent-1-yn-3-amine hydrochloride

Iron(III) chloride (0.120 g, 0.738 mmol) was added to cold (−78° C.) liquid ammonia (ca 25 ml). More ammonia (ca 60 ml) was added and sodium (1.781 g, 77.0 mmol) was added carefully in small pieces. The reaction mixture was stirred at −78° C. for 15 minutes and 3-chloro-3-methylpent-1-yne (8.6 g, 73.8 mmol) in diethyl ether (20 ml) was added slowly. The reaction mixture was stirred at −78° C. for 3 hours, diluted with diethyl ether (75 ml) and the mixture was stirred overnight at room temperature. The reaction mixture was cooled down to 0° C., cold water (70 ml) was added carefully drop by drop and stirred for 20 minutes. The layers were separated and the water phase was extracted with diethyl ether. The organic phases were combined, washed twice with water, dried over Na₂SO₄ and evaporated to dryness. 10% HCl/EtOAc (59.7 ml, 148 mmol) was added to evaporation residue, the mixture was stirred for a while and evaporated to dryness. The evaporation residue was triturated with diethyl ether and the solid precipitate was filtered and dried in a vacuum oven at 40° C. overnight to yield 4.25 g of the title compound.

¹HNMR (400 MHz, CDCl₃-d) δ ppm 1.16 (t, 3 H) 1.73 (s, 3 H) 1.85-1.98 (m, 1 H) 2.02-2.16 (m, 1 H) 2.57 (s, 1 H) 8.90 (br. s., 3 H).

Step 3: Methyl 2-(butylamino)-5-fluorobenzoate

Butyraldehyde (0.168 ml, 1.862 mmol), methyl 2-amino-5-fluorobenzoate (300 mg, 1.774 mmol), acetic acid, glacial (0.254 ml, 4.43 mmol) and 1,2-dichloroethane (10 ml) were stirred at room temperature for 10 minutes. Sodium triacetoxy borohydride (752 mg, 3.55 mmol) was added and the reaction mixture was stirred at room temperature for 2.5 hours. The reaction mixture was cooled down to 0° C., DCM was added and the organic phase was washed with water, 1M Na₂CO₃ and brine. The organic phase was dried and evaporated to dryness. The product was purified by flash chromatography to yield to yield 289 mg of the title compound.

¹H NMR (400 MHz, CDCl₃-d) δ ppm 0.97 (t, 3 H) 1.34-1.55 (m, 2 H) 1.58-1.74 (m, 2 H) 3.16 (td, 2 H) 3.85 (s, 3 H) 6.54-6.67 (m, 1 H) 7.10 (m, 1 H) 7.47 (br. s., 1 H) 7.54-7.63 (m, 1 H).

Step 4: 2-(Butylamino)-5-fluorobenzoic acid

The mixture of methyl 2-(butylamino)-5-fluorobenzoate (289 mg, 1.283 mmol), tetrahydrofuran (8 ml), water (2 ml) and lithium hydroxide (61 mg, 2.57 mmol) was refluxed for 7 hours. Solvent was evaporated, water was added to the mixture and the mixture was washed once with DCM. The water phase was acidified using 1M HCl and extracted three times with ethyl acetate. The ethyl acetate layers were combined, dried and evaporated to dryness to yield 253 mg of the title compound.

¹H NMR (400 MHz, DMSO-d) δ ppm 0.84-0.97 (m, 3 H) 1.30-1.46 (m, 2 H) 1.49-1.63 (m, 2 H) 3.15 (t, 2 H) 6.74 (dd, 1 H) 7.27 (m, 1 H) 7.48 (dd, 1 H)

Step 5: 2-(Butylamino)-5-fluoro-N-(3-methylpent-1-yn-3-yl)benzamide 2-(Butylamino)-5-fluorobenzoic acid (60 mg, 0.284 mmol), DCM (4 ml), EDCI (60 mg, 0.312 mmol), HOBt (42 mg, 0.312 mmol), DIPEA (0.054 ml, 0.312 mmol) and 3-methylpent-1-yn-2-amine hydrochloride (30 mg, 0.225 mmol) were stirred at room temperature for two hours. The reaction mixture was diluted with DCM and washed with Na₂CO₃ solution, 1M HCl solution and water. The organic phase was dried and evaporated to dryness. The product was purified by preparative HPLC to yield 17 mg of the title compound.

¹H NMR (400 MHz, CDCl₃-d) δ ppm 0.94 (t, 3 H) 1.06 (t, 3 H) 1.36-1.49 (m, 2 H) 1.57-1.68 (m, 2 H) 1.71 (s, 3 H) 1.90 (m, 1 H) 2.16 (m, 1 H) 2.41 (s, 1 H) 3.09 (t, 2 H) 5.99 (br. s., 1 H) 6.53-6.68 (m, 1 H) 6.95-7.11 (m, 2 H).

Example 103

2-(Ethylamino)-N-(3-ethylpent-1-yn-3-yl)-5-fluorobenzamide

Step 1: Methyl 2-(ethylamino)-5-fluorobenzoate

Acetaldehyde (0.129 ml, 2.306 mmol), methyl 2-amino-5-fluorobenzoate (300 mg, 1.774 mmol), acetic acid, glacial (0.609 ml, 10.64 mmol) and 1,2-dichloroethane (7.5 ml) were stirred at room temperature for 10 minutes. Sodium triacetoxy borohydride (1052 mg, 4.97 mmol) was added and the reaction mixture was stirred at room temperature over three nights. Methanol was added to the reaction mixture and the mixture was washed once with NaHCO₃ solution. The water phase was extracted once with DCM, the organic phases were combined and washed with brine and water. The organic phase was dried and evaporated to dryness to yield 328 mg of the title compound.

¹H NMR (400 MHz, CDCl₃-d) δ ppm 1.31 (t, 3 H) 3.20 (m, 2 H) 3.85 (s, 3 H) 6.52-6.68 (m, 1 H) 7.04-7.18 (nm, 1 H) 7.39 (br. s., 1 H) 7.53-7.62 (m, 1 H).

Step 2: 2-(Ethylamino)-5-fluorobenzoic acid

The mixture of methyl 2-(ethylamino)-5-fluorobenzoate (350 mg, 1.775 mmol), tetrahydrofuran (5 ml) and 2M NaOH solution (2.66 ml, 5.32 mmol) was stirred at 50° C. until the starting material was consumed. Solvent was evaporated, water was added to the mixture and the mixture was acidified using 1M HCl. The mixture was extracted three times with ethyl acetate. The ethyl acetate layers were combined, dried and evaporated to dryness to yield 256 mg of the title compound.

$^1$H NMR (400 MHz, CDCl$_3$-d) δ ppm 1.33 (t, 3 H) 3.26 (q, 2 H) 6.75 (m, 1 H) 7.18 (m, 1 H) 7.68 (m, 1 H) 8.68 (br. s., 2 H).

Step 3: 2-(Ethylamino)-N-(3-ethylpent-1-yn-3-yl)-5-fluorobenzamide 2-(Ethylamino)-5-fluorobenzoic acid (60 mg, 0.328 mmol), DCM (4 ml), EDCI (69 mg, 0.360 mmol), HOBt (49 mg, 0.360 mmol), DIPEA (0.063 ml, 0.360 mmol) and 3-ethylpent-1-yn-2-amine hydrochloride (48 mg, 0.328 mmol) were stirred at room temperature overnight. The reaction mixture was diluted with DCM and washed with Na$_2$CO$_3$ solution, 1M HCl solution and water. The organic phase was dried and evaporated to dryness. The product was purified by preparative HPLC to yield 19 mg of the title compound.

$^1$H NMR (400 MHz, CDCl$_3$-d) δ ppm 0.91-1.12 (m, 6 H) 1.26 (t, 3 H) 1.90 (m, 2 H) 2.24 (m, 2 H) 2.37-2.48 (s, 1 H) 3.13 (m, 2 H) 5.94 (br. s., 1 H) 6.61 (m, 1 H) 6.87 (br. s., 1 H) 6.97-7.10 (m, 2 H).

Example 104

5-Fluoro-N-(2-methylbut-3-yn-2-yl)-2-(3,3,3-trifluoropropylamino)benzamide

Step 1: Methyl 5-fluoro-2-(3,3,3-trifluoropropylamino)benzoate 3,3,3-Trifluoropropanal (1.77 ml, 20.4 mmol), methyl 2-amino-5-fluorobenzoate (2.88 g, 17 mmol), acetic acid, glacial (5.84 ml, 102 mmol) and 1,2-dichloroethane (70 ml) were stirred at room temperature for 15 minutes. Sodium triacetoxy borohydride (10.1 g, 47.6 mmol) was added and the reaction mixture was stirred at room temperature overnight. Methanol (50 ml) was added. The reaction mixture was washed once with NaHCO$_3$ solution. The water phase was extracted once with DCM, the organic phases were combined and washed with brine and water. The organic phase was dried and evaporated to dryness. The product was purified by flash chromatography to yield 1.6 g of the title compound.

LC/MS [M+1] 266.1

Step 2: 5-Fluoro-2-(3,3,3-trifluoropropylamino)benzoic acid

A mixture of methyl 5-fluoro-2-(3,3,3-trifluoropropylamino)benzoate (2.16 g, 8.16 mmol), tetrahydrofuran (50 ml) and 5 M NaOH solution (16 ml, 80 mmol) was refluxed for 5 h. The solvent was evaporated. Water was added (10 ml) to the mixture and the mixture was acidified using 1M HCl. The formed precipitation was filtered, washed with water and dried in a vacuum oven. Yield 2.019 g.

$^1$H NMR (400 MHz, DMSO-d) δ ppm 2.60 (m, 2 H) 3.47 (t, 2 H) 679 (dd, 1 H) 7.31 (m, 1H) 7.52 (dd, 1 H).

Step 3: 5-Fluoro-N-(2-methylbut-3-yn-2-yl)-2-(3,3,3-trifluoropropylamino)benzamide 5-Fluoro-2-(3,3,3-trifluoropropylamino)benzoic acid (2.0 g, 7.96 mmol), DCM (20 ml), EDCI (1.70 g, 8.76 mmol), HOBt (0.32 g, 2.39 mmol), DIPEA (2.77 ml, 15.9 mmol) and 1,1-dimethylpropargylamine (1.68 g, 8.76 mmol) were stirred at room temperature overnight. The reaction mixture was washed With Na$_2$CO$_3$ solution and water. The organic phase was dried and evaporated to dryness. The product was purified by flash chromatography to yield 1.46 g of the title compound.

$^1$H NMR (400 MHz, MeOD-d) δ ppm 1.68 (s, 6 H) 2.36-2.59 (m, 2 H) 2.67 (s, 1 H) 3.44 (t, 2 H) 6.71 (dd, 1 H) 7.10 (m, 1 H) 7.27 (dd, 1 H) 8.10 (br. s., 1 H).

Example 105

2-(Isobutylamino)-N-(2-methylbut-3-yn-2-yl)-6-trifluoromethyl)-nicotinamide

Step 1: Ethyl 2-(isobutylamino)-6-(trifluoromethyl)nicotinate

Isobutyraldehyde (0.072 ml, 0.790 mmol), ethyl 2-amino-6-(trifluoromethyl)nicotinate (185 mg, 0.790 mmol), acetic acid, glacial (0.271 ml, 4.74 mmol) and 1,2-dichloroethane (5 ml) were stirred at room temperature for 10 minutes. Sodium triacetoxy borohydride (469 mg, 2.212 mmol) was added and the reaction mixture was stirred at room temperature overnight. Isobutyraldehyde (0.072 ml) was added and the mixture was warmed for a day. Isobutyraldehyde was added again and the reaction mixture was warmed until the starting material was consumed. Methanol was added to the reaction mixture and the mixture was washed once with NaHCO$_3$ solution. The water phase was extracted once with DCM, the organic, phases were-combined and washed with brine and water. The organic phase was dried and evaporated to dryness. The product was purified by flash chromatography to yield 87 mg of the title compound.

LC/MS [M+1] 291.1

Step 2: 2-(Isobutylamino)-6-(trifluoromethyl)nicotinic acid

The mixture of ethyl 2-(isobutylamino)-6-(trifluoromethyl)nicotinate (87 mg, 0.300 mmol), tetrahydrofuran (10 ml) and 5M NaOH solution was refluxed for four hours and stirred at room temperature overnight. Solvents were evaporated, water was added to the mixture and the mixture was acidified using 1M HCl. The mixture was extracted three times with DCM. The organic layers were combined, dried and evaporated to dryness to yield 58 mg of the title compound.

$^1$H NMR (400 MHz, CDCl$_3$-d) δ ppm 1.00 (d, 6 H) 1.96 (m, 1 H) 3.42 (t, 2 H) 6.79-6.92 (m, 1 H) 7.98 (br. s., 1 H) 8.33 (d, 1 H).

Step 3: 2-(Isobutylamino)-N-(2-methylbut-3-yn-2-yl)-6-(trifluoromethyl)nicotinamide 2-(Isobutylamino)-6-(trifluoromethyl)nicotinic acid (58 mg, 0.221 mmol), DCM (4 ml), EDCI (47 mg, 0.243 mmol), HOBt (33 mg, 0.243 mmol), DIPEA (0.077 ml, 0.442 mmol) and 1,1-dimethylpropargylamine (20 mg, 0.243 mmol) were stirred at room temperature overnight. The reaction mixture was diluted with DCM and washed with Na$_2$CO$_3$ solution, 1M HCl solution and water. The organic phase was dried and evaporated to dryness. The product was purified by preparative HPLC to yield 26 mg of the title compound.

$^1$H NMR (400 MHz, CDCl$_3$-d) δ ppm 0.97 (d, 6 H) 1.74 (s, 6 H) 1.93 (m, 1 H) 2.41 (s, 1 H) 3.32 (dd, 2 H) 6.05 (br. s., 1 H) 6.76 (d, 1 H) 7.60 (d, 1 H) 8.17 (br. s., 1 H).

Example 106

2-(Isopropylamino)-N-(2-methylbut-3-yn-2-yl)-6-(trifluoromethyl)-nicotinamide

Step 1: Ethyl 2-(isopropylamino)-6-(trifluoromethyl)nicotinate 2,2-Dimethoxypropane (0.630 ml, 5.12 mmol), ethyl 2-amino-6-(trifluoromethyl)nicotinate (200 mg, 0.854 mmol), trifluoroacetic acid (0.127 ml, 1.708 mmol) and DCM (10 ml) were stirred at room temperature for 10 minutes. Sodium triacetoxy borohydride (290 mg, 1.366 mmol) was added and the reaction mixture was stirred at room temperature over three nights. 2,2-Dimethoxypropane (0.63 ml), trifluoroacetic acid (0.127 ml) and sodium triacetoxy borohydride (290 mg) were added and the mixture was stirred at room temperature overnight. 2,2-Dimethoxypropane (1.26 ml) was added and the mixture was stirred overnight. Dimethoxypropane (1.26 ml) and sodium triacetoxy borohydride (54 mg) were added and the mixture was refluxed. 2,2-Dimethoxypropane, sodium triacetoxyborohydride and trifluoroacetic acid were added once more and the reaction mixture was stirred at room temperature overnight. The reaction mixture was diluted with DCM and washed with Na$_2$CO$_3$ solution and brine. The organic phase was dried and evaporated to dryness. Toluene was added to the evaporation residue and solvents were evaporated once more. The product was purified by flash chromatography to yield 140 mg of the title compound.
LC/MS [M+1] 277.0

Step 2: 2-(Isopropylamino)-6-(trifluoromethyl)nicotinic acid

The mixture of ethyl 2-(isopropylamino)-6-(trifluoromethyl)nicotinate (140 mg, 0.507 mmol), tetrahydrofuran (10 mil) and 5M NaOH solution (0.507 ml, 2.53 mmol) was refluxed until the starting material was consumed. Solvents were evaporated, water was added to the mixture and the mixture was acidified using 1M HCl. The mixture was extracted three times with DCM. The organic layers were combined, dried and evaporated to dryness to yield 90 mg of the title compound.
$^1$H NMR (400 MHz, CDCl$_3$-d) δ ppm 1.29 (d, 6 H) 4.32-4.51 (m, 1 H) 6.86 (d, 1 H) 7.73 (br. s., 1 H) 8.27-8.37 (m, 1 H).

Step 3: 2-(Isopropylamino)-N-(2-methylbut-3-yn-2-yl)-6-(trifluoromethyl)nicotinamide 2-(Isopropylamino)-6-(trifluoromethyl)nicotinic acid (81 mg, 0.326 mmol), DCM (4 ml), EDCI (69 mg, 0.359 mmol), HOBt (49 mg, 0.359 mmol), DIPEA (0.114 ml, 0.63 mmol) and 1,1-dimethylpropargylamine (0.038 ml, 0.359 mmol) were stirred at room temperature overnight. The reaction mixture was diluted with DCM and washed with Na$_2$CO$_3$ solution, 1M HCl solution and water. The organic phase was dried and evaporated to dryness. The product was purified by preparative HPLC to yield 47 mg of the title compound.
$^1$H NMR (400 MHz, CDCl$_3$-d) δ ppm 1.25 (d, 6 H) 1.74 (s, 6 H) 2.41 (s, 1 H) 4.31 (m, 1 H) 6.08 (br. s., 1 H) 6.74 (d, 1 H) 7.61 (d, 1 H) 7.94 (d, 1 H).

Example 107

2-(Ethylamino)-N-(2-methylbut-3-yn-2-yl)-6-(trifluoromethyl)-nicotinamide

Step 1: Ethyl 2-(ethylamino)-6-(trifluoromethyl)nicotinate

Acetaldehyde (0.308 ml, 5.52 mmol), ethyl 2-amino-6-(trifluoromethyl)nicotinate (323 mg, 1.379 mmol), trifluoroacetic acid (0.205 ml, 2.76 mmol) and DCM (5 ml) were stirred at room temperature for 10 minutes. Sodium triacetoxy borohydride (819 mg, 3.86 mmol) was added and the reaction mixture was stirred at room temperature overnight. Acetaldehyde (0.5 ml) and sodium triacetoxy borohydride (146 mg) were added and the mixture was stirred at room temperature overnight. Acetaldehyde (0.308 ml) and trifluoroacetic acid (0.205 ml) were added again and the reaction mixture stirred at room temperature overnight. The reaction mixture was diluted with DCM and washed with Na$_2$CO$_3$ solution. The water phase was extracted with DCM, the organic layers were combined, dried and evaporated to dryness. The product was purified by flash chromatography to yield 54 mg of the title compound.
LC/MS [M+1] 263.0

Step 2: 2-(Ethylamino)-6-(trifluoromethyl)nicotinic acid

The mixture of ethyl 2-(ethylamino)-6-(trifluoromethyl)nicotinate (54 mg, 0.206 mmol), tetrahydrofuran (10 ml) and 5M NaOH solution (0.206 ml, 1.030 mmol) was refluxed until the starting material was consumed. Solvent was evaporated, water was added to the mixture and the mixture was acidified using 1M HCl. The mixture was extracted three times with DCM. The organic layers were combined, dried and evaporated to dryness to yield 36 mg of the title compound.
$^1$H NMR (400 MHz, CDCl$_3$-d) δ ppm 1.29 (t, 3 H) 3.61 (m, 2 H) 6.88 (d, 1 H) 7.82 (br. s., 1 H) 8.32 (dd, 1 H).

Step 3: 2-(Ethylamino)-N-(2-methylbut-3-yn-2-yl)-6-(trifluoromethyl)nicotinamide 2-(ethylamino)-6-(trifluoromethyl)nicotinic acid (36 mg, 0.154 mmol), DCM (4 ml), EDCI (32 mg, 0.169 mmol), HOBt (23 mg, 0.169 mmol), DIPEA (0.054 ml, 0.307 mmol) and 1,1-dimethylpropargylamine (0.018 ml, 0.169 mmol) were stirred at room temperature overnight. The reaction mixture was diluted with DCM and washed with Na$_2$CO$_3$ solution, 1M HCl solution and water. The organic phase was dried and evaporated to dryness. The product was purified by preparative HPLC to yield 32 mg of the title compound.
$^1$H NMR (400 MHz, CDCl$_3$-d) δ ppm 1.24 (t, 3 H) 1.74 (s, 6 H) 2.41 (s, 1 H) 3.52 (m, 2 H) 6.06 (br. s., 1 H) 6.77 (d, 1 H) 7.61 (d, 1 H) 8.08 (br. s., 1 H).

Example 108

4-(tert-Butylamino)-N-(2-methylbut-3-yn-2-yl)-2-(trifluoromethyl)pyrimidine-5-carboxamide Step 1: Ethyl 4-(tert-butylamino)-2-(trifluoromethyl)pyrimidine-5-carboxylate tert-Butylamine (1.238 ml, 11.78 mmol), ethyl 4-chloro-2-(trifluoromethyl)pyrimidine-5-carboxylate (0.3 g, 1.178 mmol) and ethanol (2 ml) were added to a microwave vial. The reaction mixture was irradiated at 160° C. for 30 minutes at high absorbance. The reaction mixture was diluted with water and extracted twice with ethyl acetate. The organic layers were combined, washed with water, dried and evaporated to dryness to yield 307 mg of the title compound.

$^1$H NMR (400 MHz, CDCl$_3$-d) δ ppm 1.41 (t, 3 H) 1.53 (s, 9 H) 4.39 (q, 2 H) 8.57 (br. s., 1 H) 8.89 (d, 1 H).

Step 2: 4-(tert-Butylamino)-2-(trifluoromethyl)pyrimidine-5-carboxylic acid

The mixture of ethyl 4-(tert-butylamino)-2-(trifluoromethyl)pyrimidine-5-carboxylate (307 mg, 1.054 mmol), tetrahydrofuran (10 ml) and 5M NaOH solution (1.054 ml, 5.27 mmol) was refluxed until the starting material was consumed. Solvent was evaporated, water Was added to the mixture and the mixture was acidified using 1M HCl. The mixture was extracted three times with DCM. The organic layers were combined, dried and evaporated to dryness. The product was purified by reverse phase flash chromatography to yield 239 mg of the title compound.

$^1$H NMR (400 MHz, MeOD-d) δ ppm 1.54 (s, 9 H) 8.85 (s, 1 H).

Step 3: 4-(tert-Butylamino)-N-(2-methylbut-3-yn-2-yl)-2-(trifluoromethyl)pyrimidine-5-carboxamide 4-(tert-Butylamino)-2-(trifluoromethyl)pyrimidine-5-carboxylic acid (50 mg, 0.190 mmol), DCM (4 ml), EDCI (40 mg, 0.209 mmol), HOBt (28 mg, 0.209 mmol), DIPEA (0.054 ml, 0.307 mmol) and 1,1-dimethylpropargylamine (0.066 ml, 0.380 mmol) were stirred at room temperature overnight. The reaction mixture was diluted with DCM and washed with Na$_2$CO$_3$ solution, 1M HCl solution and water. The organic phase was dried and evaporated to dryness. The product was purified by preparative HPLC to yield 35 mg of the title compound.

$^1$H NMR (400 MHz, CDCl$_3$-d) δ ppm 1.50 (s, 9 H) 1.74 (s, 6 H) 2.43 (s, 1 H) 6.13 (br. s., 1 H) 8.36 (s, 1 H) 8.75 (br. s., 1H).

Example 109

N-(2-Methylbut-3-yn-2-yl)-4-(tert-pentylamino)-2-(trifluoromethyl)-pyrimidine-5-carboxamide Step 1: Ethyl 4-(tert-pentylamino)-2-(trifluoromethyl)pyrimidine-5-carboxylate tert-Amylamine (0.688 ml, 5.89 mmol), ethyl 4-chloro-2-(trifluoromethyl)pyrimidine-5-carboxylate, (0.3 g, 1.178 mmol) and ethanol (2 ml) were added to a microwave vial. The reaction mixture was irradiated at 160° C. for 30 minutes at high absorbance. The reaction mixture was diluted with water and extracted twice with ethyl acetate. The organic layers were combined, washed with water, dried and evaporated to dryness, to yield 292 mg of the title compound.

$^1$H NMR (400 MHz, CDCl$_3$-d) δ ppm 0.91 (t, 3 H) 1.41 (t, 3 H) 1.49 (s, 6 H) 1.91 (m, 2 H) 4.39 (m, 2 H) 8.53 (br. s., 1 H) 8.89 (d, 1 H).

Step 2: 4-(tert-Pentylamino)-2-(trifluoromethyl)pyrimidine-5-carboxylic acid

The mixture of ethyl 4-(tert-pentylamino)-2-(trifluoromethyl)pyrimidine-5-carboxylate (292 mg, 0.956 mmol), tetrahydrofuran (10 ml) and 5M NaOH solution (0.956 ml, 4.87 mmol) was refluxed until the starting material was consumed. Solvent was evaporated, water was added to the mixture and the mixture was acidified using 1M HCl. The mixture was extracted three times with DCM. The organic layers were combined, dried and evaporated to dryness. The product was purified by reverse phase flash chromatography to yield 189 mg of the title compound.

$^1$H NMR (400 MHz, MeOD-d) δ ppm 0.92 (t, 3 H) 1.49 (s, 6) 1.94 (q, 2 H) 8.85 (s, 1 H).

Step 3: N-(2-Methylbut-3-yn-2-yl)-4-(tert-pentylamino)-2-(trifluoromethyl)pyrimidine-5-carboxamide 4-(tert-Pentylamino)-2-(trifluoromethyl)pyrimidine-5-carboxylic acid (50 mg, 0.180 mmol), DCM (4 ml), EDCI (38 mg, 0.198 mmol), HOBt (27 mg, 0.198 mmol), DIPEA (0.063 ml, 0.361 mmol) and 1,1-dimethylpropargylamine (0.021 ml, 0.198 mmol) were stirred at room temperature overnight. The reaction mixture was diluted with DCM and washed with Na$_2$CO$_3$ solution, 1M HCl solution and water. The organic phase was dried and evaporated to dryness. The product was purified by preparative HPLC to yield 23 mg of the title compound.

$^1$H NMR (400 MHz, CDCl$_3$-d) δ ppm 0.88 (t, 3 H) 1.45 (s, 6 H) 1.75 (s, 6 H) 1.88 (q, 2 H) 2.43 (s, 1 H) 6.09 (br. s., 1 H) 8.35 (s, 1 H) 8.66 (br. s., 1 H).

Example 110

4-(Isopropylamino)-N-(2-methylbut-3-yn-2-yl)-2-(trifluoromethyl)-pyrimidine-5-carboxamide Step 1: Ethyl 4-(isopropylamino)-2-(trifluoromethyl)pyrimidine-5-carboxylate Isopropylamine (1.004 ml, 11.78 mmol), ethyl 4-chloro-2-(trifluoromethyl)pyrimidine-5-carboxylate, (0.3 g, 1.178 mmol) and ethanol (2 ml) were added to a microwave vial. The reaction mixture was irradiated at 160° C. for 30 minutes at high absorbance. The reaction mixture was diluted with water and extracted twice with ethyl acetate. The organic layers were combined, washed with water, dried and evaporated to dryness. The product was purified by flash chromatography to yield 174 mg of the title compound.

$^1$H NMR (400 MHz, CDCl$_3$-d) δ ppm 1.29 (d, 6 H) 1.41 (t, 3 H) 4.31-4.53 (m, 3 H) 8.31 (br. s., 1 H) 8.88 (d, 1 H).

Step 2: 4-(Isopropylamino)-2-(trifluoromethyl)pyrimidine-5-carboxylic acid

The mixture of ethyl 4-(isopropylamino)-2-(trifluoromethyl)pyrimidine-5-carboxylate (174 mg, 0.628 mmol), tetrahydrofuran (10 ml) and 5M NaOH solution (0.628 ml, 3.14 mmol) was refluxed until the starting material was consumed. Solvent was evaporated, water was added to the mixture and the mixture was acidified using 1M HCl. The mixture was extracted three times with DCM. The organic layers were combined, dried and evaporated to dryness td yield 0.154 mg of the title compound.

$^1$H NMR (400 MHz, MeOD-d) δ ppm 1.31 (d, 6 H) 4.33-4.51 (m, 1 H) 8.84 (s, 1 H).

Step 3: 4-(Isopropylamino)-N-(2-methylbut-3-yn-2-yl)-2-(trifluoromethyl)pyrimidine-5-carboxamide 4-(Isopropylamino)-2-(trifluoromethyl)pyrimidine-5-carboxylic acid (50 mg, 0.201 mmol), DCM (4 ml), EDCI (42 mg, 0.221 mmol), HOBt (30 mg, 0.221 mmol), DIPEA (0.070 ml, 0.401 mmol) and 1,1-dimethylpropargylamine (0.023 ml, 0.221 mmol) were stirred at room temperature overnight. The reaction mixture was diluted with DCM and washed with Na$_2$CO$_3$ solution, 1M HCl solution and water. The organic phase was dried and evaporated to dryness. The product was purified by preparative HPLC to yield 44 mg of the title compound.

$^1$H NMR (400 MHz, CDCl$_3$-d) δ ppm 1.28 (d, 6 H) 1.75 (s, 6 H) 2.44 (s, 1 H) 4.29-4.51 (m, 1 H) 6.09 (br. s., 1 H) 8.36 (s, 1 H) 8.61 (d, 1 H).

Example 111

2-(tert-Butylamino)-N-(2-methylbut-3-yn-2-yl)-6-(trifluoromethyl)-nicotinamide

Step 1: 2-(tert-Butylamino)-6-(trifluoromethyl)nicotinonitrile tert-Butylamine (1.562 ml, 14.86 mmol), 2-chloro-6-(trifluoromethyl)nicotinonitrile (307 mg, 1.486 mmol) and ethanol (2 ml) were added to a microwave vial. The reaction mixture was irradiated at 160° C. for 30 minutes at. The reaction mixture was diluted with water and extracted twice with ethyl acetate. The organic layers were combined, washed with water, dried and evaporated to dryness. The product was purified by flash chromatography to yield 360 mg of the title compound.

$^1$H NMR (400 MHz, CDCl$_3$-d) δ ppm 1.50 (s, 9 H) 5.25 (br. s., 1 H) 6.90 (d, 1 H) 7.71-7.82 (m, 1 H).

Step 2: 2-(tert-Butylamino)-6-(trifluoromethyl)nicotinic acid 2-(tert-Butylamino)-6-(trifluoromethyl)nicotinonitrile (360 mg, 1.480 mmol), potassium hydroxide 45% aq. solution (5 ml) and 1-propanol (5 ml) were added to a microwave vial. The reaction mixture was irradiated at 150° C. for 45 minutes at high absorbance. The reaction mixture was diluted with water and solvent was evaporated. Water was added to the evaporation residue and the mixture was acidified using concentrated HCl. The formed precipitation was filtered and dried at 40° C. overnight in a vacuum oven to yield the title compound.

$^1$H NMR (400 MHz, CDCl$_3$-d) δ ppm 1.51 (s, 9 H) 6.84 (d, 1 H) 7.99 (br. s., 1 H) 8.30 (dd, 1 H).

Step 3: 2-(tert-Butylamino)-N-(2-methylbut-3-yn-2-yl)-6-(trifluoromethyl)-nicotinamide 2-(tert-Butylamino)-6-(trifluoromethyl)nicotinic acid (50 mg, 0.191 mmol), DCM (4 ml), EDCI (40 mg, 0.210 mmol), HOBt (28 mg, 0.210 mmol), DIPEA (0.066 ml, 0.381 mmol) and 1,1-dimethylpropargylamine (0.022 ml, 0.210 mmol) were stirred at room temperature overnight. The reaction mixture was diluted with DCM and washed with Na$_2$CO$_3$ solution, 1M HCl solution and water. The organic phase was dried and evaporated to dryness. The product was purified by preparative HPLC to yield 22 mg of the title compound.

$^1$H NMR (400 MHz, CDCl$_3$-d) δ ppm 1.48 (s, 9 H) 1.74 (s, 6 H) 2.41 (s, 1 H) 6.03 (br. s., 1 H) 6.74 (d, 1 H) 7.59 (d, 1 H) 8.06 (br. s., 1 H).

Example 112

6-Chloro-2-(isopropylamino)-N-(2-methylbut-3-yn-2-yl)nicotinamide

Step 1: 6-Chloro-2-(isopropylamino)nicotinic acid

Isopropylamine (0.887 ml, 10.42 mmol), 2,6-dichloronicotinic acid (200 mg, 1.042 mmol) and NMP (2 ml) were added to a microwave reaction vial. The reaction mixture was irradiated at 200° C. for 60 minutes at high absorbance. The reaction mixture was diluted with water and acidified using 1M HCl solution. The formed precipitate was filtrated and washed with water. The precipitate was dried at 40° C. overnight in a vacuum oven to yield 19 mg of the title compound.

LC/MS [M+1] 215.0

Step 2: 6-Chloro-2-(isopropylamino)-N-(2-methylbut-3-yn-2-yl)nicotinamide

6-Chloro-2-(isopropylamino)nicotinic acid (19 mg, 0.089 mmol), DCM (4 ml), EDCI (19 mg, 0.097 mmol), HOBt (13 mg, 0.097 mmol), DIPEA (0.031 ml, 0.177 mmol) and 1,1-dimethylpropargylamine (0.014 ml, 0.133 mmol) were stirred at room temperature for few hours. 1,1-Dimethylpropargylamine (0.014 ml) was added and the mixture was stirred for a few more hours. The reaction mixture was diluted with DCM and washed with Na$_2$CO$_3$ solution, 1M HCl solution and water. The organic phase was dried and evaporated to dryness. The product was purified by preparative HPLC to yield 13 mg, of the title compound.

$^1$H NMR (400 MHz, DMSO-d) δ ppm 1.18 (d, 6 H) 1.57 (s, 6 H) 3.13 (s, 1 H) 4.11 (m, 1 H) 6.58 (d, 1 H) 7.98 (d, 1 H) 8.23 (s, 1 H) 8.43 (d, 1 H).

Example 113

6-Chloro-2-(ethylamino)-N-(2-methylbut-3-yn-2-yl)nicotinamide

Step 1: 6-Chloro-2-(ethylamino)nicotinic acid

Ethylamine hydrochloride (0.849 mg, 10.42 mmol), 2,6-dichloronicotinic acid (200 mg, 1.042 mmol), triethylamine (1.452 ml, 10.42 mmol) and NMP (2 ml) were added to a microwave vial. The reaction mixture was irradiated at 200° C. for 30 minutes at high absorbance. The reaction mixture was diluted with water and acidified using 1M HCl solution. The formed precipitate was filtrated and washed with water. The precipitate was dried at 40° C. overnight in a vacuum oven to yield 59 mg of the title compound.

LC/MS [M+1] 201.0

Step 2: 6-Chloro-2-(ethylamino)-N-(2-methylbut-3-yn-2-yl)nicotinamide

6-Chloro-2-(ethylamino)nicotinic acid (50 mg, 0.249 mmol), DCM (4 ml), EDCI (53 mg, 0.274 mmol), HOBt (37 mg, 0.274 mmol), DIPEA (0.087 ml, 0.498 mmol) and 1,1-dimethylpropargylamine (0.029 ml, 0.274 mmol) were stirred at room temperature for few hours. 1,1-Dimethylpropargylamine (0.029 ml) was added and the mixture was stirred few more hours. The reaction mixture was diluted with DCM and washed with Na$_2$CO$_3$ solution, 1M HCl solution and water. The organic phase was dried and evaporated to dryness. The product was purified by preparative HPLC to yield 17 mg of the title compound.

$^1$H NMR (400 MHz, DMSO-d) δ ppm 1.15 (t, 3 H) 1.58 (s, 6 H) 3.12 (s, 1 H) 3.37 (m, 2 H) 6.58 (d, 1 H) 7.96 (d, 1 H) 8.24 (s, 1 H) 8.47 (s, 1 H).

Example 114

5-Fluoro-2-(isopropylamino)-N-(2-methylbut-3-yn-2-yl)-6-morpholinonicotinamide

Step 1:
2-Chloro-5-fluoro-6-morpholinonicotinonitrile

The mixture of 2,6-dichloro-3-cyano-5-fluoropyridine (1.03 g, 5.39 mmol) and acetonitrile (20 ml) was cooled down to 0° C. and morpholine (1.411 ml, 16.18 mmol) and triethylamine (2.255 ml, 16.18 mmol) were added slowly. The reaction mixture was stirred at room temperature for one hour. The mixture was evaporated to dryness, DCM was added and the organic phase was washed once with water and once with brine. The organic phase was dried and evaporated to dryness to yield 1.06 g of the title compound.

$^1$H NMR (400 MHz, DMSO-d) δ ppm 3.64-3.75 (m, 8 H) 8.14 (d, 1 H).

Step 2: 5-Fluoro-2-(isopropylamino)-6-morpholinonicotinonitrile

Isopropylamine (0.705 ml, 8.28 mmol), 2-chloro-5-fluoromorpholinicotinonitrile (200 mg, 0.828 mmol) and NMP (2 ml) were added to a microwave vial. The reaction mixture was irradiated at 200° C. for 60 minutes at high absorbance. The reaction mixture was diluted with DCM and washed several times with water. The product was evaporated to dryness and purified by flash chromatography to yield 174 mg of the title compound.

LC/MS [M+1] 265.1

Step 3:
5-Fluoro-2-(isopropylamino)-6-morpholinonicotinic acid

5-Fluoro-2-(isopropylamino)-6-morpholinonicotinonitrile (174 mg, 0.658 mmol), potassium hydroxide 45% aq. solution (5 ml) and 1-propanol (5 ml) were added to a microwave vial. The reaction mixture was' irradiated at 150° C. for 3 hours at high absorbance. The reaction mixture was diluted with water and solvent was evaporated. Water was added to the evaporation residue and the mixture was acidified using concentrated HCl. The formed precipitation was filtered and dried at 40° C. overnight in a vacuum oven to yield 197 mg of the title compound.

$^1$H NMR (400 MHz, CDCl$_3$-d) δ ppm 1.14-1.31 (m, 6 H) 3.69-3.87 (m, 8 H) 4.09-4.30 (m, 1 H) 7.57 (br. s., 1 H) 7.66 (d, 1 H).

Step 4: 5-Fluoro-2-(isopropylamino)-N-(2-methylbut-3-yn-2-yl)-6-morpholino-nicotinamide 5-Fluoro-2-(isopropylamino)-6-morpholinonicotinic acid (50 mg, 0.141 mmol), DCM (4 ml), EDCI (30 mg, 0.155 mmol), HOBt (21 mg, 0.155 mmol), DIPEA (0.049 ml, 0.282 mmol) and 1,1-dimethylpropargylamine (0.016 ml, 0.155 mmol) were stirred at room temperature overnight. The reaction mixture was diluted with DCM and washed with Na$_2$CO$_3$ solution, 1M HCl solution and water. The organic phase was dried and evaporated to dryness. The product was purified by preparative HPLC to yield 14 mg of the title compound.

$^1$H NMR (400 MHz, CDCl$_3$-d) δ ppm 1.22 (d, 6 H) 1.71 (s, 6 H) 2.38 (s, 1 H) 3.56-3.68 (m, 4 H) 3.72-3.87 (m, 4 H) 4.14 (dd, 1 H) 5.65 (s, 1 H) 7.12 (d, 1 H) 8.08 (d, 1 H).

Example 115

N-(2-Methylbut-3-yn-2-yl)-2-(tetrahydro-2H-pyran-4-ylamino)-6-(trifluoromethyl)nicotinamide Step 1: 2-(Tetrahydro-2H-pyran-4-ylamino)-6-(trifluoromethyl)nicotinonitrile Tetrahydro-pyran-4-ylamine (0.301 ml, 2.90 mmol), 2-chloro-6-(trifluoromethyl)-nicotinonitrile (300 mg, 1.452 mmol) and ethanol (2 ml) were added to a microwave vial. The reaction mixture was irradiated at 160° C. for 30 minutes. The reaction mixture was diluted with ethyl acetate and washed several times with water. The organic phase was evaporated to dryness and purified by flash chromatography to yield 281 mg of the title compound.

$^1$H NMR (400 MHz, CDCl$_3$-d) δ ppm 1.51-1.73 (m, 2 H) 1.99-2.14 (m, 2 H) 3.56 (td, 2 H) 3.97-4.10 (m, 2 H) 4.17-4.35 (m, 1 H) 5.44 (d, 1 H) 6.96 (d, 1 H) 7.78-7.88 (m, 1 H).

Step 2: 2-(Tetrahydro-2H-pyran-4-ylamino)-6-(trifluoromethyl)nicotinic acid 2-(Tetrahydro-2H-pyran-4-ylamino)-6-(trifluoromethyl) nicotinonitrile (141 mg, 0.520 mmol), potassium hydroxide 45% aq. solution (5 ml) and 1-propanol (5 ml) were refluxed for Several hours until the starting material was consumed. The reaction mixture was diluted with water and solvent was evaporated. Water was added to the evaporation residue and the mixture was acidified using concentrated HCl. The formed precipitation was filtered and dried at 40° C. overnight in a vacuum oven to yield 164 mg of the title compound.

LC/MS [M+1] 291.1

Step 3: N-(2-Methylbut-3-yn-2-yl)-2-(tetrahydro-2H-pyran-4-ylamino)-6-(trifluoromethyl)nicotinamide 2-(Tetrahydro-2H-pyran-4-ylamino)-6-(trifluoromethyl) nicotinic acid (81 mg, 0.279 mmol), DCM (4 ml), EDCI (59 mg, 0.307 mmol), HOBt (41 mg, 0.307 mmol), DIPEA (0.097 ml, 0.558 mmol) and 1,1-dimethylpropargylamine (0.032 ml, 0.307 mmol) were stirred at room temperature overnight. The reaction mixture was diluted with DCM and washed with Na$_2$CO$_3$ solution, 1M HCl solution and water. The organic phase was dried and evaporated to dryness. The product was purified by preparative HPLC to yield 43 mg of the title compound.

$^1$H NMR (400 MHz, CDCl$_3$-d) δ ppm 1.51-1.68 (m, 2 H) 1.75 (s, 6 H) 2.04 (m, 2 H) 2.42 (s, 1 H) 3.56 (td, 2 H) 3.98 (m, 2 H) 4.13-4.30 (m, 1 H) 6.11 (br. s., 1 H) 6.80 (d, 1 H) 7.64 (d, 1 H) 8.11 (d, 1 H).

Example 116

N-(2-Methylbut-3-yn-2-yl)-2-((tetrahydro-2H-pyran-4-yl)methyl-amino)-6-(trifluoromethyl)nicotinamide Step 1: 2-((Tetrahydro-2H-pyran-4-yl)methyl-amino)-6-(trifluoromethyl)nicotinonitrile 4-Aminomethyltetrahydropyran hydrochloride (440 mg, 2.90 mmol), 2-chloro-6-(trifluoromethyl)nicotinonitrile (200 mg, 0.968 mmol), triethylamine (0.405 ml, 2.90 mmol) and NMP (2 ml) were added to a microwave vial. The reaction mixture was irradiated at 200° C. for 30 minutes at high absorbance. The reaction mixture was diluted with DCM and washed several times with water. The organic phase was evaporated to dryness and purified by flash chromatography to yield 207 mg of the title compound.

$^1$H NMR (400 MHz, CDCl$_3$-d) δ ppm 1.30-1.52 (m, 2 H) 1.62-1.76 (m, 2 H) 1.83-2.02 (m, 1 H) 3.31-3.52 (m, 4 H) 3.92-4.07 (m, 2 H) 5.63 (t, 1 H) 6.94 (d, 1 H) 7.75-7.86 (m, 1 H).

Step 2: 2-((Tetrahydro-2H-pyran-4-yl)methyl-amino)-6-(trifluoromethyl)nicotinic acid 2-((Tetrahydro-2H-pyran-4-yl)methylamino)-6-(trifluoromethyl)nicotinonitrile (207 mg, 0.726 mmol), potassium hydroxide 45% aq. solution (5 ml) and 1-propanol (5 ml) were refluxed for several hours until the starting material was consumed. The reaction mixture was diluted with water and solvent was evaporated. Water was added to the evaporation residue, the mixture was acidified using concentrated HCl and extracted with ethyl acetate. The organic phase was evaporated to dryness and purified by flash chromatography to yield 44 mg of the title compound.

$^1$H NMR (400 MHz, CDCl$_3$-d) δ ppm 1.36-1.54 (m, 2 H) 1.70 (m, 2 H) 1.83-2.05 (m, 1 H) 3.35-3.56 (m, 4 H) 4.04 (m, 2 H) 6.88 (d, 1 H) 8.06 (t, 1 H) 8.26-8.39 (m, 1 H).

Step 3: N-(2-Methylbut-3-yn-2-yl)-2-((tetrahydro-2H-pyran-4-yl)methylamino)-6-(trifluoromethyl) nicotinamide 2-((Tetrahydro-2H-pyran-4-yl)methylamino)-6-(trifluoromethyl)nicotinic acid (44 mg, 0.145 mmol), DCM (4 ml), EDCI (30 mg, 0.159 mmol), HOBt (21 mg, 0.159 mmol), DIPEA (0.050 ml, 0.289 mmol) and 1,1-dimethylpropargylamine (0.017 ml, 0.159 mmol) were stirred at room temperature overnight. The reaction mixture was diluted with DCM and washed with Na$_2$CO$_3$ solution, 1M HCl solution and water. The organic phase was dried and evaporated to dryness. The product was purified by preparative HPLC to yield 36 mg of the title compound.

$^1$H NMR (400 MHz, CDCl$_3$-d) δ ppm 1.26-1.49 (m, 2 H) 1.63-1.80 (m, 8 H) 1.82-1.96 (m, 1 H) 2.42 (s, 1 H) 3.29-3.49 (m, 4 H) 3.97 (dd, 2 H) 6.09 (br. s., 1 H) 6.79 (d, 1 H) 7.62 (d, 1 H) 8.25 (t, 1 H).

Example 117

2-(Cyclopropylamino)-N-(2-methylbut-3-yn-2-yl)-6-(trifluoromethyl)-nicotinamide

Step 1: 2-(Cyclopropylamino)-6-(trifluoromethyl) nicotinonitrile

Cyclopropylamine (1.011 ml, 14.52 mmol), 2-chloro-6-(trifluoromethyl)nicotinonitrile (300 mg, 1.452 mmol) and ethanol (2 ml) were added to a microwave vial. The reaction mixture was irradiated at 160° C. for 30 minutes at high absorbance. The reaction mixture was diluted with ethyl acetate and washed several times with water. The organic phase was evaporated to dryness and purified by flash chromatography to yield 395 mg of the title compound.

$^1$H NMR (400 MHz, CDCl$_3$-d) δ ppm 0.56-0.69 (m, 2 H) 0.85-0.96 (m, 2 H) 2.92 (m, 1 H) 5.58 (br. s., 1 H) 6.99 (d, 1 H) 7.75-7.87 (m, 1 H).

Step 2: 2-(Cyclopropylamino)-6-(trifluoromethyl)nicotinic acid 2-(Cyclopropylamino)-6-(trifluoromethyl)nicotinonitrile (295 mg, 1.298 mmol), potassium hydroxide 45% aq. solution (10 ml) and 1-propanol (10 ml) were added to a microwave vial. The reaction mixture was irradiated at 155° C. for 30-45 minutes at high absorbance. The reaction mixture was diluted with water and solvent was evaporated. Water was added to the evaporation residue and the mixture was acidified using concentrated HCl. The formed precipitation was filtered and dried at 40° C. overnight in a vacuum oven to yield 315 mg of the title compound.

$^1$H NMR (400 MHz, CDCl$_3$-d) δ ppm 0.49-0.65 (m, 2 H) 0.79-0.94 (m, 2 H) 3.00 (m, 1 H) 6.94 (d, 1 H) 7.91 (br. s., 1 H) 8.31 (dd, 1 H).

Step 3: 2-(Cyclopropylamino)-N-(2-methylbut-3-yn-2-yl)-6-(trifluoromethyl)-nicotinamide 2-(Cyclopropylamino)-6-(trifluoromethyl)nicotinic acid (80 mg, 0.325 mmol), DCM (4 ml), EDCI (69 mg, 0.357 mmol), HOBt (48 mg, 0.357 mmol), DIPEA (0.113 ml, 0.650 mmol) and 1,1-dimethylpropargylamine (0.038 ml, 0.357 mmol) were stirred at room temperature overnight. The reaction mixture was diluted with DCM and washed with Na$_2$CO$_3$ solution, 1M HCl solution and water. The organic phase was dried and evaporated to dryness. The product was purified at first by flash chromatography and finally by preparative HPLC to yield 13 mg of the title compound.

$^1$H NMR (400 MHz, CDCl$_3$-d) δ ppm 0.46-0.61 (m, 2 H) 0.73-0.87 (m, 2 H) 1.73 (s, 6 H) 2.41 (s, 1 H) 2.92 (m, 1 H) 6.06 (br. s., 1 H) 6.84 (d, 1 H) 7.61 (d, 1 H) 8.16 (br. s., 1 H).

Example 118

2,3-Dimethyl-N-(2-methylbut-3-yn-2-yl)-1H-indole-7-carboxamide

Step 1: 2,3-Dimethyl-1H-indole-7-carboxylic acid

2-Butanone (2.375 ml, 26.5 mmol) was added slowly to the mixture of 2-hydrazinobenzoic acid hydrochloride (5 g, 26.5 mmol) and acetic acid (50 ml). The reaction mixture was refluxed for 3.5 hours and cooled down to room temperature. Solvent was evaporated and ethyl acetate (50 ml) and water (50 ml) was added to the mixture. The layers were separated and the organic layer was evaporated to dryness. The product was crystallised from ethanol to yield 1.762 g of the title product.

$^1$H NMR (400 MHz, DMSO-d) δ ppm 2.17 (s, 3 H) 2.37 (s, 3 H) 6.92-7.15 (m, 1 H) 7.63 (d, 2 H) 10.55 (br. s., 1 H) 12.85 (br. s., 1 H).

Step 2: 2,3-Dimethyl-N-(2-methylbut-3-yn-2-yl)-1H-indole-7-carboxamide 2,3-Dimethyl-1H-indole-7-carboxylic acid (100 mg, 0.529 mmol), DCM (4 ml), EDCI (111 mg, 0.581 mmol), HOBt (79 ng, 1.057 mmol), DIPEA (0.184 ml, 1.057 mmol) and 1,1-dimethylpropargylamine (48 nig, 0.581 mmol) were stirred at room temperature overnight. The reaction mixture was diluted with DCM and washed with Na$_2$CO$_3$ solution, 1M HCl solution and water. The organic phase was dried and evaporated to dryness. The product was crystallised from the mixture of acetonitrile and water to yield 43 mg of the title compound.

$^1$H NMR (400 MHz, CDCl$_3$-d) δ ppm 1.79 (s, 6 H) 2.23 (d, 3 H) 2.37 (d, 3 H) 2.41 (s, 1 H) 6.36 (br. s., 1 H) 7.04 (t, 1 H) 7.21 (dd, 1 H) 7.61 (d, 1 H) 9.94 (br. s., 1 H)

Example 119

N-(3-Ethylpent-1-yn-3-yl)-1H-indole-7-carboxamide

Step 1: 5-N-(3-Ethylpent-1-yn-3-yl)-1H-indole-7-carboxamide

1H-Indole-7-carboxylic acid (100 mg, 0.621 mmol), dichloromethane (3 ml), 1-(3-dimethylaminopropyl)-3-ethylcarbodiimide hydrochloride (143 mg, 0.745 mmol), 1-hydroxybenzotriazole (84 mg, 0.621 mmol), N,N-diisopropylethylamine; DIPEA (0.324 ml, 1.862 mmol) and 3-ethylpent-1-yn-3-amine hydrochloride (119 mg, 0.807 mmol) were stirred at room temperature overnight. The reaction mixture was washed once with water. The organic phase was dried and evaporated to dryness. The product was purified by flash chromatography to yield 139 mg of the title compound.

$^1$H NMR (400 MHz, CDCl$_3$-d) δ ppm 1.07 (t, 6 H) 1.98 (m, 2 H) 2.31 (m, 2 H) 2.45 (s, 1 H) 6.29 (br. s., 1 H) 6.56 (dd, 1 H) 7.11 (t, 1 H) 7.28-7.37 (m, 2 H) 7.80 (dt, 1 H) 10.30 (br. s., 1 H).

Example 120

N-(3-Ethylpent-1-yn-3-yl)-1,2,3,4-tetrahydroquinoline-8-carboxamide 1,2,3,4-Tetrahydroquinoline-8-carboxylic acid (100 mg, 0.564 mmol), dichloromethane (3 ml), 1-(3-dimethylaminopropyl)-3-ethylcarbodiimide hydrochloride (130 mg, 0.677 mmol), 1-hydroxybenzotriazole (76 mg, 0.564 mmol), N,N-diisopropylethylamine; DIPEA (0.295 ml, 1.693 mmol) and 3-ethylpent-1-yn-3-amine hydrochloride (108 mg, 0.764 mmol) were stirred at room temperature overnight. The reaction mixture was washed once with water. The organic phase was dried and evaporated to dryness. The product was purified by flash chromatography to yield 80 mg of the title compound.

$^1$H NMR (400 MHz, CDCl$_3$-d) δ ppm 1.03 (t, 6 H) 1.81-2.01 (m, 4 H) 2.24 (m, 2 H) 2.39 (s, 1 H) 2.76 (t, 2 H) 3.28-3.41 (m, 2 H) 5.93 (br. s., 1 H) 6.38-6.48 (m, 1 H) 6.98 (m, 1 H) 7.13 (dd, 1 H) 7.45-7.74 (m, 1 H).

Example 121

2-(3-Fluorophenylamino)-N-(2-methylbut-3-yn-2-yl)nicotinamide

Step 1: Methyl 2-(3-fluorophenylamino)nicotinate

2-Fluoronicotinic acid methyl ester (500 mg, 3.22 mmol) and 3-fluoroaniline (716 mg, 6.45 mmol) were mixed and heated in a microwave oven at 120° C. for 20 minutes. The reaction mixture was then dissolved in DCM and washed with 2×water. The organic phase was dried and concentrated. 639 mg of the title compound was obtained.

$^1$H NMR (400 MHz, CDCl$_3$-d) δ ppm 3.95 (s, 3 H) 6.71-6.77 (m, 1 H) 6.78 (dd, 1 H) 7.23-7.31 (m, 2 H) 7.81-7.87 (m, 1 H) 8.26 (dd, 1 H) 8.42 (dd, 1 H) 10.32 (br. s., 1 H).

Step 2: 2-(3-Fluorophenylamino)nicotinic acid

Methyl 2-(3-fluorophenylamino)nicotinate (639 mg, 2.60 mmol) and potassium hydroxide (437 mg, 7.79 mmol) in methanol (9 ml) and water (2 ml) were stirred at room temperature for 5 h. Methanol was evaporated, the mixture was diluted with water and the pH was adjusted to 2 by addition of 2 M HCl. The aqueous solution was extracted three times with EtOAc. The combined organic phases were dried and concentrated. 538 mg of the title compound was obtained.

$^1$H NMR (400 MHz, DMSO-d$_6$) δ ppm 6.77-6.86 (m, 1 H) 6.94 (dd, 1 H) 7.29-7.37 (m, 2 H) 7.91-7.97 (m, 1 H) 8.28 (dd, 1 H) 8.45 (dd, 1 H) 10.61 (s, 1 H) 13.70 (br. s., 1 H).

Step 3: 2-(3-Fluorophenylamino)-N-(2-methylbut-3-yn-2-yl)nicotinamide 2-(3-Fluorophenylamino)nicotinic acid (538 mg, 2.317 mmol), EDCI (533 mg, 2.78 mmol), HOBt (94 mg, 0.695 mmol), DIPEA (1.211 ml, 6.95 mmol) and 1,1-dimethylpropargylamine (0.293 ml, 2.78 mmol) in DCM (10 ml) were stirred at room temperature overnight. The mixture was washed twice with water, dried and concentrated. The crude product was purified by flash chromatography. 310 mg of the title compound was obtained.

$^1$H NMR (400 MHz, CDCl$_3$) δ ppm 1.77 (s, 6 H) 2.44 (s, 1 H) 6.16 (br. s., 1 H) 6.67-6.75 (m, 2 H) 7.20-7.28 (m, 2 H) 7.67 (dd, 1 H) 7.78 (dt, 1 H) 8.35 (dd, 1 H) 10.50 (br. s., 1 H).

Example 122

2-(2-Fluorophenylamino)-N-(2-methylbut-3-yn-2-yl)nicotinamide

Step 1: Methyl 2-(2-fluorophenylamino)nicotinate

A mixture of 2-fluoronicotinic acid methyl ester (500 mg, 3.22 mmol) and 2-fluoroaniline (716 mg, 6.45 mmol) was heated in a microwave oven at 120° C. for 30 minutes. The reaction mixture was then dissolved in DCM and washed with 2× water. The organic phase was dried and concentrated. Diethyl ether was added and the precipitate was filtered off. 502 mg of the title compound was obtained.

$^1$H NMR (400 MHz, CDCl$_3$) δ ppm 3.95 (s, 3 H) 6.77 (dd, 1 H) 6.95-7.02 (m, 1 H) 7.10-7.17 (m, 2 H) 8.26 (dd, 1 H) 8.40 (dd, 1 H) 8.55 (td, 1 H) 10.37 (br. s., 1 H).

Step 2: 2-(2-Fluorophenylamino)nicotinic acid

A mixture of methyl 2-(2-fluorophenylamino)nicotinate (502 mg, 2.039 mmol) and potassium hydroxide (343 mg, 6.12 mmol) in methanol (8 ml) and water (2 ml) was refluxed for 1 h. Methanol was evaporated, the mixture was diluted with water and the pH was adjusted to 2 by addition of 2 M HCl. The solution was extracted with EtOAc×3. The combined organic phases were dried and concentrated. 419 mg of the title compound was obtained.

¹H NMR (400 MHz, DMSO-d₆) δ ppm 6.94 (dd, 1 H) 7.00-7.07 (m, 1 H) 7.19 (t, 1 H) 7.27 (ddd, 1 H) 8.29 (dd, 1 H) 8.43 (dd, 1 H) 8.58 (td, 1 H) 10.65 (d, 1 H) 13.70 (br. s., 1 H).

Step 3: 2-(2-Fluorophenylamino)-N-(2-methylbut-3-yn-2-yl)nicotinamide 2-(2-Fluorophenylamino)nicotinic acid (0.419 g, 1.804 mmol), EDCI (415 mg, 2.165 mmol), HOBt (73 mg, 0.541 mmol), DIPEA (0.943 ml, 5.41 mmol) and 1,1-dimethyl-propargylamine (0.228 ml, 2.165 mmol) in DCM (10 ml) were stirred at room temperature overnight. The mixture was washed twice with water, dried and concentrated. The crude product was purified by flash chromatography. 201 mg of the title compound was obtained.

¹H NMR (400 MHz, CDCl₃) δ ppm 1.78 (s, 6 H) 2.42 (s, 1 H) 6.17 (br. s., 1 H) 6.72 (dd, 1 H) 6.93-7.01 (m, 1 H) 7.07-7.15 (m, 2 H) 7.68 (dd, 1 H) 8.33 (m, 2 H) 10.33 (br. s., 1 H)

Example 123

2-(4,4-Difluorocyclohexylamino)-N-(2-methylbut-3-yn-2-yl)nicotinamide

Step 1: Methyl 2-(4,4-difluorocyclohexylamino)nicotinate

2-Fluoronicotinic acid methyl ester (0.30 g, 1.934 mmol), 4,4-difluorocyclohexylamine hydrochloride (0.332 g, 1.934 mmol) and triethylamine (0.539 ml, 3.87 mmol) in ACN (3 ml) were heated in a microwave oven at 125° C. for 3 h. The formed precipitate was filtered off and rinsed with ACN. The filtrate was concentrated, some diethyl ether was added, and the precipitate was filtered off. The filtrate was concentrated which yielded 404 mg of the title compound.

Step 2: 2-(4,4-Difluorocyclohexylamino)nicotinic acid

Methyl 2-(4,4-difluorocyclohexylamino)nicotinate (0.404 g, 1.495 mmol) and potassium hydroxide (0.252 g, 4.48 mmol) in water (2 ml) and methanol (8 ml) were stirred at room temperature overnight. Methanol was evaporated, the mixture was diluted with water and the pH was adjusted to 2 by addition of 2 M HCl. The solution was extracted 3 times with EtOAc. The combined organic phases were dried and concentrated. 328 mg of the title compound was obtained.

¹H NMR (400 MHz, DMSO-d₆) δ ppm 1.42-1.67 (m, 2 H) 1.89-2.1.3 (m, 6 H) 4.15 (m, 1 H) 6.63 (dd, 1 H) 8.10 (dd, 1 H) 8.14 (m, 1 H) 8.27 (dd, 1 H) 13.48 (br. s., 1 H).

Step 3: 2-(4,4-Difluorocyclohexylamino)-N-(2-methylbut-3-yn-2-yl)nicotinamide 2-(4,4-Difluorocyclohexylamino)nicotinic acid (0.328 g, 1.280 mmol), EDCI (0.294 g, 1.536 mmol), HOBt (0.052 g, 0.384 mmol), DIPEA (0.669 ml, 3.84 mmol) and 1,1-dimethylpropargylamine (0.162 ml, 1.536 mmol) in DCM (8 ml) were stirred at room temperature over weekend. The mixture was washed twice with water, dried and concentrated. The crude product was purified by flash chromatography. 288 mg of the title compound was obtained.

¹H NMR (400 MHz, CDCl₃) δ ppm 1.73 (m, 8 H) 1.81-2.01 (m, 2 H) 2.02-2.22 (m, 4 H) 2.40 (s, 1 H) 4.03-4.25 (m, 1 H) 6.02 (br. s., 1 H) 6.48 (dd, 1 H) 7.52 (dd, 1 H) 8.12 (d, 1 H) 8.20 (dd, 1H).

Example 124

5-Bromo-NV-(2-methylbut-3-yn-2-yl)-2-(propylamino)benzamide

Step 1: Methyl 5-bromo-2-(propylamino)benzoate

Methyl 2-amino-5-bromobenzoate (0.5 g, 2.173 mmol) was dissolved in dichloroethane (15 ml). The solution was cooled to 0° C. Acetic acid (0.311 ml, 5.43 mmol), propionaldehyde (0.166 ml, 2.282 mmol) and sodium triacetoxy borohydride (0.921 g, 4.35 mmol) were added. The reaction mixture was stirred at room temperature for 3 h. It was cooled to 0° C. followed by addition of water (15 ml). The organic phase was washed with 1 M Na₂CO₃, and brine, and was then dried and concentrated. 527 mg of the title compound was, obtained.

¹H NMR (400 MHz, CDCl₃) δ ppm 0.97-1.05 (m, 3 H) 1.70 (sxt, 2 H) 3.13 (td, 2 H) 3.85 (s, 3 H) 6.56 (d, 1 H) 7.38 (m, 1 H) 7.69 (br. s., 1 H) 7.98 (d, 1 H).

Step 2: 5-Bromo-2-(propylamino)benzoic acid

Methyl 5-bromo-2-(propylamino)benzoate (0.527 g, 1.937 mmol) and potassium hydroxide (0.326 g, 5.81 mmol) in methanol (8 ml) and water (2 ml) were refluxed for 8 h. Methanol was evaporated, the mixture was diluted with water and the pH was adjusted to 2 by addition of 2 M HCl. The solution was extracted three times with EtOAc. The combined organic phases were dried and concentrated. 454 mg of the title compound was obtained.

¹H NMR (400 MHz, DMSO-d₆) δ ppm 0.94 (t, 3 H) 1.59 (sxt, 2 H) 3.13 (t, 2 H) 6.72 (d, 1 H) 7.47 (dd, 1 H) 7.83 (d, 1 H).

Step 3: 5-Bromo-N-(2-methylbut-3-yn-2-yl)-2-(propylamino)benzamide

5-Bromo-2-(propylamino)benzoic acid (450 mg, 1.743 mmol), EDCI (401 mg, 2.092 mmol), HOBt (70.7 mg, 0.523 mmol), DIPEA (1.215 ml, 6.97 mmol) and 1,1-dimethylpropargylamine (0.220 ml, 2.092 mmol) in DCM (8 ml) were stirred at room temperature overnight. The mixture was washed twice with water, dried and concentrated. The crude product was purified by flash chromatography. 318 mg of the title compound was obtained.

¹H NMR (400 MHz, CDCl₃) δ ppm 1.00 (t, 3 H) 1.68 (sxt, 2 H) 1.74 (s, 6 H) 2.40 (s, 1 H) 3.08 (td, 2 H) 5.99 (br. s., 1 H) 6.56 (d, 1 H) 7.34 (dd, 1 H) 7.37 (d, 1 H) 7.50 (br. s., 1 H).

Example 125

N-(2-Methylbut-3-yn-2-yl)-2-(1,1,1-trifluoro-2-methylpropan-2-ylamino)nicotinamide Step 1: Methyl 2-(1,1,1-trifluoro-2-methylpropan-2-ylamino)nicotinate A mixture of 2-fluoronicotinic acid methyl ester (0.4 g, 2.58 mmol) and 2,2,2-trifluoro-1,1-dimethyl-ethylamine (0.888 ml, 7.74 mmol) was heated in a microwave oven at 150° C. for 13 h. The reaction mixture was then dissolved in DCM and washed twice with water. The organic phase was dried and concentrated. The crude product was purified by flash chromatography. 89 mg of the title compound was obtained.

$^1$H NMR (400 MHz, CDCl$_3$) δ ppm 1.74-1.77 (m, 6 H) 3.88 (s, 3 H) 6.59 (dd, 1 H) 8.13 (dd, 1 H) 8.25 (dd, 1 H) 8.50 (br. s., 1 H).

Step 2: 2-(1,1,1-Trifluoro-2-methylpropan-2-ylamino)nicotinic acid

Methyl 2-(1,1,1-trifluoro-2-methylpropan-2-ylamino)nicotinate (89 mg, 0.339 mmol) and potassium hydroxide (57.1 mg, 1.018 mmol) in methanol (2 ml) and water (0.5 ml) were stirred at room temperature overnight. Methanol was evaporated, the mixture was diluted with water and the pH was adjusted to 2 by addition of 2 M HCl. The solution was extracted three times with EtOAc. The combined organic phases were dried and concentrated. 77 mg of the title compound was obtained.

Step 3: N-(2-Methylbut-3-yn-2-yl)-2-(1,1,1-trifluoro-2-methylpropan-2-ylamino)-nicotinamide 2-(1,1,1-Trifluoro-2-methylpropan-2-ylamino)nicotinic acid (77 mg, 0.310 mmol), EDCI (71 mg, 0.372 mmol), HOBt (13 mg, 0.093 mmol), DIPEA (0.162 ml, 0.931 mmol) and 1,1-dimethylpropargylamine (0.039 ml, 0.372 mmol) in DCM (5 ml) were stirred at room temperature overnight. The mixture was washed twice with water, dried and concentrated. The crude product was purified by preparative HPLC. 41 mg of the title compound was obtained.

$^1$H NMR (400 MHz, CDCl$_3$) δ ppm 1.72 (d, 6 H) 1.74 (s, 6 H) 2.40 (s, 1 H) 6.07 (br. s., 1 H) 6.55 (dd, 1 H) 7.54 (dd, 1 H) 8.18 (dd, 1 H) 8.38 (s, 1 H).

Example 126

N-(2-Methylbut-3-yn-2-yl)-4-(propylamino)thiophene-3-carboxamide

Step 1: Methyl 3-((2-methoxy-2-oxoethyl)thio)propanoate

To a solution of methyl 2-mercaptoacetate (50.0 g, 0.47 mol) and methyl acrylate (44.7 mL, 0.49 mmol) in DCM (500 mL) at 0° C. was added piperidine (3 drops) and stirred at rt for 1 h. The reaction mixture was quenched with water and extracted with DCM. The organic layer was washed with water, dried (anhyd. Na$_2$SO$_4$) and concentrated under reduced pressure to give the title compound as colourless oil. Yield: 80.9 g.

$^1$H-NMR (400 MHz, CDCl$_3$): δ 3.75 (s, 3H), 3.70 (s, 3H), 3.26 (s, 2H), 2.91 (t, 2H), 2.66 (t, 2H).

Step 2: Methyl 4-oxotetrahydrothiophene-3-carboxylate

To a suspension of NaOMe (10.16 g, 187.5 mmol) in THF (100 mL) was added a solution of methyl 3-((2-methoxy-2-oxoethyl)thio)propanoate (30.0 g, 156.3 mmol) in THF (50 mL) and refluxed for 2 h. The reaction mixture was poured into ice water and acidified with 1N HCl and extracted with DCM. The organic layer was washed with water, dried (anhyd. Na$_2$SO$_4$) and concentrated under reduced pressure. The crude residue was purified by flash chromatography over silica gel using hexane-EtOAc (10%) as the eluent to give the title compound as a colourless oil. Yield: 10.2 g.

$^1$H-NMR (400 MHz; CDCl$_3$): δ 4.03 (bs, 1H), 3.68 (s, 3H), 3.28-3.36 (m, 1H), 3.02-3.08 (m, 1H), 2.81-2.89 (m, 1H), 2.60-2.70 (m, 1H).

Step 3: Methyl 4-aminothiophene-3-carboxylate

To a solution of methyl 4-oxotetrahydrothiophene-3-carboxylate (10 g, 63.29 mmol) in MeCN (50 mL) was added NH$_2$OH.HCl (8.73 g, 126.6 mmol) and it was refluxed for 2 h. The precipitated solid was filtered and washed with Et$_2$O. The solid was dissolved in water, basified with aq. NaHCO$_3$ solution and extracted with DCM. The organic layer was washed with water and concentrated under reduced pressure to give the title compound as yellow oil. Yield: 7.6 g.

$^1$H-NMR (400 MHz; CDCl$_3$): δ 7.92 (d, 1H), 6.09 (d, 1H), 4.68 (bs, 2H), 3.86 (s, 3H).

Step 4: Methyl 4-propionamidothiophene-3-carboxylate

To a solution of methyl 4-aminothiophene-3-carboxylate (5.7 mL, 71.7 mmol) in DCM (80 mL) were added EDCI (10.9 g, 57.3 mmol), HOBt (7.7 g, 57.3 mmol) and DIPEA (25.6 mL, 143.4 mmol). The reaction mixture was stirred at rt for 30 min. A solution of propionic acid (7.5 g, 47.8 mmol) in DCM (80 mL) was added and stirred for 16 h. The reaction was quenched by water and extracted with EtOAc. The organic layer was washed with water and concentrated under reduced pressure. The crude was purified by flash chromatography over silica gel using hexane-EtOAc (10%) as the eluent to give the title compound as a pale green Crystalline-solid. Yield: 7.6 g.

$^1$H-NMR (400 MHz; CDCl$_3$): δ 10.05 (s, 1H), 8.04 (bs, 2H), 3.93 (s, 3H), 2.46 (q, 2H), 1.27 (t, 3H).

Step 5: Methyl 4-(propylamino)thiophene-3-carboxylate

To a solution of methyl 4-propionamidothiophene-3-carboxylate (5.0 g, 23.4 mmol) in THF (50 mL) was added BH$_3$-DMS (10.4 mL, 117.4 mmol) at 0° C. and stirred at rt for 2 h. The reaction mixture was quenched by MeOH and concentrated under reduced pressure. The crude was purified by flash chromatography over silica gel using hexane-EtOAc (15%) as the eluent to give the title compound as a pale yellow oil. Yield: 1.02 g.

$^1$H-NMR (400 MHz; CDCl$_3$): δ 7.96 (d, 1H), 5.94 (bs, 1H), 5.79 (d, 1H), 3.84 (s, 3H), 3.06 (t, 2H), 1.66-1.72 (m, 2H), 1.01 (t, 3H).

Step 6: 4-(Propylamino)thiophene-3-carboxylic acid

To a solution of methyl 4-(propylamino)thiophene-3-carboxylate (0.4 g, 2.0 mmol) in EtOH (5 mL) was added 10% aqueous NaOH solution (2 mL) and heated at 7° C. for 1 h. The reaction mixture was cooled to 0° C. and neutralised to pH~7 using aq. NaHSO$_3$ solution. The solution was extracted with EtOAc, washed with water, dried (anhyd. Na$_2$SO$_4$) and concentrated under reduced pressure to give the title compound. Yield: 0.33 g.

$^1$H-NMR (400 MHz, DMSO-d$_6$): δ 7.45 (d, 1H), 5.62 (d, 1H), 2.91 (t, 2H), 1.50-1.60 (m, 2H), 0.95 (t, 3H).

Step 7: N-(2-Methylbut-3-yn-2-yl)-4-(propylamino)thiophene-3-carboxamide

To a solution of 4-(propylamino)thiophene-3-carboxylic acid (0.33 g, 1.78 mmol) in DCM (10 mL) were added EDCI (0.513 g, 2.6 mmol), HOBt (0.361 g, 2.6 mmol) and DIPEA (1.0 mL, 5.35 mmol). The reaction mixture was stirred at rt for 30 min. A solution of 2-methylbut-3-yn-2-amine (0.192 g, 2.3 mmol) in DCM (2 mL) was added and stirred for 8 h. The reaction was quenched by water and extracted with EtOAc. The organic layer was washed with water and concentrated under reduced pressure. The crude was purified by flash chromatography over silica gel using hexane-EtOAc (30%) as the eluent to give the title compound as a white solid. Yield: 0.25 g (56%);

$^1$H-NMR (400 MHz; DMSO-d$_6$): δ 8.14 (d, 1H), 7.99 (bs, 1H), 6.42 (bs, 1H), 5.95 (d, 1H), 3.11 (s, 1H), 2.93-3.01 (m, 2H), 1.59 (m, 8H), 0.94 (t, 3H).

Example 127

N-(2-Methylbut-3-yn-2-yl)-2-(phenylamino)nicotinamide

Step 1: Methyl 2-(phenylamino)nicotinate

2-Fluoronicotinic acid methyl ester (0.50 g, 3.22 mmol) and aniline (0.587 ml, 6.45 mmol) were heated in a microwave, reactor at 120° C. for 20 minutes. The reaction mixture was dissolved in DCM (30 ml) and washed with 2× water. The organic phase was dried with Na$_2$SO$_4$ and concentrated. 0.716 g of the title compound was obtained.

Step 2: 2-(Phenylamino)nicotinic acid

Methyl 2-(phenylamino)nicotinate (0.716 g, 3.14 mmol) and potassium hydroxide (0.528 g, 9.41 mmol) in methanol (5 ml) and water (2 ml) were stirred at room temperature for 3 hours. Methanol was evaporated and the reaction mixture was diluted with water. The pH was adjusted to 2 by addition of 1 M HCl. It was extracted with 2×EtOAc, dried with Na$_2$SO$_4$ and concentrated. 0.653 g of the title compound was obtained.

$^1$H NMR (400 MHz, DMSO-d$_6$) δ ppm 6.87 (dd, 1 H) 7.02 (tt, 1 H) 7.33 (m, 2 H) 7.72 (m, 2 H) 8.26 (dd, 1 H) 8.40 (dd, 1 H) 10.44 (s, 1 H) 13.58 (br. s., 1 H).

Step 3: N-(2-Methylbut-3-yn-2-yl)-2-(phenylamino)nicotinamide 2-(Phenylamino)nicotinic acid (0.653 g, 3.05 mmol), 1,1-dimethylpropargylamine (0.353 ml, 3.35 mmol), triethylamine (1.275 ml, 9.14 mmol) and 50% 1-propanephosphonic acid cyclic anhydride (3.63 ml, 6.10 mmol) in DCM (5 ml) were stirred at room temperature overnight. The reaction mixture was dissolved in DCM (10 ml) and washed with 2× water. The organic phase was dried with Na$_2$SO$_4$ and concentrated. The crude product was purified by flash chromatography. 257 mg of the title compound was obtained.

$^1$H NMR (400 MHz, CDCl$_3$) δ ppm 1.78 (s, 6 H) 2.44 (s, 1 H) 6.15 (br. s., 1 H) 6.69 (dd, 1 H) 7.03 (m, 1 H) 7.33 (m, 2 H) 7.64-7.70 (m, 3 H) 8.32 (dd, 1 H) 10.31 (br. s., 1 H).

Example 128

2-(tert-Butylamino)-N-(2-methylbut-3-yn-2-yl)-5-(trifluoromethyl)-nicotinamide

Step 1:
2-(tert-Butylamino)-5-(trifluoromethyl)nicotinic acid

2-Chloro-5-(trifluoromethyl)pyridine-3-carboxylic acid (0.95 g, 4.21 mmol) and tert-butylamine (4.43 ml, 42.1 mmol) were heated in a microwave reactor at 120° C. for 40 minutes. Excess tert-butylamine was evaporated and the reaction mixture was made acidic by addition of 1 M HCl. The mixture was extracted with ethyl acetate, dried with Na$_2$SO$_4$ and concentrated. The crude product was purified by flash chromatography. 0.91 g of the title compound was obtained.

$^1$H NMR (400 MHz, DMSO-d$_6$) δ ppm 1.47 (s, 9 H) 8.23 (dd, 1 H) 8.57-8.60 (m, 1 H) 8.69 (br. s., 1 H) 13.64 (br. s., 1 H).

Step 2: 2-(tert-Butylamino)-N-(2-methylbut-3-yn-2-yl)-5-(trifluoromethyl)nicotinamide 2-(tert-Butylamino)-5-(trifluoromethyl)nicotinic acid (0.1 g, 0.381 mmol), EDCI (88 mg, 0.458 mmol), HOBt (15 mg, 0.114 mmol), DIPEA (0.166 ml, 0.953 mmol) and 1,1-dimethylpropargylamine (0.048 ml, 0.458 mmol) in DCM (5 ml) were stirred at room temperature overnight. The reaction mixture was washed with water and 1 M NaOH. The mixture was dried with Na$_2$SO$_4$ and concentrated. The crude product was purified by preparative HPLC. 80 mg of the title compound was obtained.

$^1$H NMR (400 MHz, CDCl$_3$) δ ppm 1.48 (s, 9 H) 1.75 (s, 6 H) 2.42 (s, 1 H) 6.00 (br. s., 1 H) 7.60 (d, 1 H) 8.41 (dd, 1 H) 8.43 (br. s., 1 H).

Example 129

5-Chloro-N-(2-methylbut-3-yn-2-yl)-2-(phenylamino)nicotinamide

Step 1: 5-Chloro-2-(phenylamino)nicotinic acid

Methyl 2,5-dichloronicotinate (0.309 g, 1.500 mmol) and aniline (0.140 g, 1.500 mmol) were heated in a microwave reactor at 150° C. for 1 hour. The reaction mixture was then dissolved in ethyl acetate and washed with 2× water. The organic phase was dried with Na$_2$SO$_4$ and concentrated. The crude product was purified by flash chromatography. 76 mg of the title compound was obtained.

$^1$H NMR (400 MHz, CDCl$_3$) δ ppm 7.07-7.12 (m, 1 H) 7.36 (m, 2 H) 7.58-7.70 (m, 2 H) 8.26 (d, 1 H) 8.35 (d, 1 H) 9.99 (br. s., 1 H).

Step 2: 5-Chloro-N-(2-methylbut-3-yn-2-yl)-2-(phenylamino)nicotinamide

5-Chloro-2-(phenylamino)nicotinic acid (76 mg, 0.306 mmol), 1,1-dimethylpropargylamine (0.035 ml, 0.336 mmol), EDCI (70 mg, 0.367 mmol), HOBt (12 mg, 0.092 mmol) and DIPEA (0.117 ml, 0.672 mmol) in DCM (5 ml) were stirred at room temperature overnight. The reaction mixture was dissolved in DCM (10 ml) and washed with water and 1 M NaOH. The mixture was dried with Na$_2$SO$_4$ and concentrated. The crude product was purified by preparative HPLC. 31 mg of the title compound was obtained.

¹H NMR (400 MHz, CDCl₃) δ ppm 1.76 (s, 6 H) 2.44 (s, 1 H) 6.13 (br. s., 1 H) 7.03 (t, 1 H) 7.31 (t, 2 H) 7.58-7.63 (m, 3 H) 8.24 (d, 1 H) 10.20 (br. s., 1 H).

Example 130

2-(Butylamino)-N-(2-methylbut-3-yn-2-yl)thiophene-3-carboxamide

Step 1: Methyl 2-(butylamino)thiophene-3-carboxylate

Methyl 2-amino-3-thiophenecarboxylate (1 g, 6.36 mmol), acetic acid, glacial (0.401 ml, 7.00 mmol), butyraldehyde (0.631 ml, 7.00 mmol) and sodium triacetoxy borohydride (1.348 g, 6.36 mmol) in DCM (20 ml) were stirred at room temperature for overnight. The reaction mixture was washed with 1 M NaHCO₃-solution (20 ml), dried with Na₂SO₄ and concentrated. The crude product was purified by flash chromatography. 315 mg of the title compound was obtained.

¹H NMR (400 MHz, CDCl₃) δ ppm 0.96 (t, 3 H) 1.34-1.55 (m, 2 H) 1.63-1.72 (m, 2 H) 3.23 (td, 2 H) 3.79 (s, 3 H) 6.15 (dd, 1 H) 7.01 (d, 1 H) 7.40 (br. s., 1 H).

Step 2: 2-(Butylamino)thiophene-3-carboxylic acid

Methyl 2-(butylamino)thiophene-3-carboxylate (0.315 g, 1.477 mmol) and potassium hydroxide (0.166 g, 2.95 mmol) in methanol (5 ml) and water (1 ml) was refluxed for 9 hours. Methanol was evaporated and the reaction mixture was diluted with water (25 ml) and washed with ethyl acetate. The pH was adjusted to 1 by addition of 1 M HCl. The mixture was extracted with ethyl acetate (2×50 ml). The organic phase was dried with Na₂SO₄ and concentrated. 222 mg of the title compound was obtained.

Step 3: 2-(Butylamino)-N-(2-methylbut-3-yn-2-yl)thiophene-3-carboxamide 2-(Butylamino)thiophene-3-carboxylic acid (222 mg, 1.114 mmol), 1,1-dimethylpropargylamine (0.129 ml, 1.225 mmol), EDCI (256 mg, 1.337 mmol), HOBt (45.2 mg, 0.334 mmol) and DIPEA (0.427 ml, 2.451 mmol) in DCM (5 ml) were stirred at room temperature overnight. The reaction mixture was dissolved in DCM (20 ml), washed with 1 M NaOH, dried with Na₂SO₄ and concentrated. The crude product was purified by preparative HPLC. 26 mg of the title compound was obtained.

¹H NMR (400 MHz, CDCl₃) δ ppm 0.94 (t, 3 H) 1.43 (sxt, 2H) 1.62-1.68 (m, 2 H) 1.71 (s, 6 H) 2.37 (s, 1 H) 3.18 (td, 2 H) 5.55 (br. s., 1 H) 6.16 (dd, 1 H) 6.71 (d, 1 H) 8.04 (br. s., 1 H).

Example 131

2-(4-Fluorophenylamino)-N-(2-methylbut-3-yn-2-yl)nicotinamide

Step 1: Methyl 2-(4-fluorophenylamino)nicotinate

A mixture of 2-fluoronicotinic acid methyl ester (0.5 g, 3.22 mmol) and 4-fluoroaniline (6.45 mmol, 0.62 ml) was mixed and heated in a microwave, reactor at 120° C. for 20 min. The crude product was dissolved in DCM, washed with water, dried and evaporated to dryness. This gave 554 mg of the title compound.

¹H NMR (400 MHz, CDCl₃) δ ppm 3.93 (s, 3 H) 6.71 (dd, 1 H) 7.03 (m, 2 H) 7.59-7.65 (m, 2 H) 8.22 (dd, 1 H) 8.34 (dd, 1 H) 10.07 (br. s., 1 H).

Step 2: 2-(4-Fluorophenylamino)nicotinic acid

To a solution of methyl 2-(4-fluorophenylamino)nicotinate (0.554 g, 2.250 mmol) in methanol/water 4:1 (10 ml) was added potassium hydroxide (0.379 g, 6.75 mmol). The mixture was stirred at r.t. for 2 h and refluxed for 1.5 h. Methanol was evaporated. The remaining aqueous solution was acidified and extracted with EtOAc three times. The organic layers were pooled, dried and evaporated to dryness. Yield: 0.47 g.

¹H NMR (400 MHz, DMSO-d₆) δ ppm 6.86 (dd, 1 H) 7.15 (m, 2 H) 7.68-7.75 (m, 2 H) 8.24 (dd, 1 H) 8.36 (dd, 1 H) 10.38 (s, 1 H) 13.57 (br. s., 1 H).

Step 3: 2-(4-Fluorophenylamino)-N-(2-methylbut-3-yn-2-yl)nicotinamide 2-(4-Fluorophenylamino)nicotinic acid (0.466 g, 2.007 mmol) and DCM (6 ml) were mixed. EDCI (0.462 g, 2.408 mmol), HOBt (0.081 g, 0.602 mmol) and DIPEA (0.769 ml, 4.41 mmol) were added. 1,1-Dimethylpropargylamine (0.211 ml, 2.007 mmol) was added. The mixture was stirred overnight and washed with water. The organic layer was evaporated to dryness. Preparative HPLC gave 165 mg of the title compound.

¹H NMR (400 MHz, CDCl₃) δ ppm 1.77 (s, 6 H) 2.43 (s, 1 H) 6.15 (br. s., 1 H) 6.67 (dd, 1 H) 7.01 (m, 2 H) 7.56-7.62 (m, 2 H) 7.64 (dd, 1 H) 8.28 (dd, 1 H) 10.28 (s, 1 H).

Example 132

N-(2-Methylbut-3-yn-2-yl)-4-(2,2,3,3,3-pentafluoropropylamino)-pyrimidine-5-carboxamide Step 1: Ethyl 2-(methylthio)-4-(2,2,3,3,3-pentafluoropropylamino)pyrimidine-5-carboxylate Ethyl 4-chloro-2-methylthio-5-pyrimidinecarboxylate (0.6 g, 2.58 mmol) and 2,2,3,3,3-pentafluoropropylamine (0.384 g, 2.58 mmol) in ethanol (2 ml) were heated in a microwave reactor at 140° C. for 30 minutes. The reaction mixture was then dissolved in ethyl acetate (20 ml) and washed with 4× water. The organic phase was dried with Na₂SO₄ and concentrated. The crude product was purified by flash chromatography. 243 mg of the title compound was obtained.

¹H NMR (400 MHz, CDCl₃) δ ppm 1.40 (t, 3 H) 2.53 (s, 3 H) 4.29-4.43 (m, 4 H) 8.59 (br. s., 1 H) 8.71 (s, 1 H).

Step 2: Ethyl 4-(2,2,3,3,3-pentafluoropropylamino)pyrimidine-5-carboxylate

Ethyl 2-(methylthio)-4-(2,2,3,3,3-pentafluoropropylamino)pyrimidine-5-carboxylate (0.990 g, 2.87 mmol) in ethanol (57 ml) was hydrogenated using an H-cube with a 10% Pd/C 70 mm CatCart, full H₂, 1 ml/min flow at 60° C. The mixture was concentrated and the crude product was purified by flash chromatography. 187 mg of the title compound was obtained.

¹H NMR (400 MHz, CDCl₃) δ ppm 1.39 (t, 3 H) 4.32-4.46 (m, 4 H) 8.53 (br. s., 1 H) 8.70 (s 1 H) 8.91 (s, 1 H).

Step 3: 4-(2,2,3,3,3-Pentafluoropropylamino)pyrimidine-5-carboxylic acid

Ethyl 4-(2,2,3,3,3-pentafluoropropylamino)pyrimidine-5-carboxylate (0.187 g, 0.625 mmol) and potassium hydroxide (0.105 g, 1.875 mmol) in methanol (3 ml) and water (1 ml) were stirred at room temperature overnight. Methanol was evaporated and the reaction mixture was diluted with water. The pH was adjusted to 2 by addition of 2 M HCl. It was extracted three times with EtOAc, dried with $Na_2SO_4$ and concentrated. 103 mg of the title compound was obtained.

$^1$H NMR (400 MHz, DMSO-$d_6$) δ ppm 4.50 (td, 2 H) 8.72 (s, 1 H) 8.81 (s, 1 H).

Step 4: N-(2-Methylbut-3-yn-2-yl)-4-(2,2,3,3,3-pentafluoropropylamino)pyrimidine-5-carboxamide 4-(2,2,3,3,3-pentafluoropropylamino)pyrimidine-5-carboxylic acid (0.04 g, 0.148 mmol), EDCI (34 mg, 0.177 mmol), HOBt (6 mg, 0.044 mmol), DIPEA (0.051 ml, 0.295 mmol) and 1,1-dimethylpropargylamine (0.020 ml, 0.192 mmol) in DCM (3 ml) were stirred at room temperature overnight. The reaction mixture was washed with water and 1 M NaOH. The mixture was dried with $Na_2SO_4$ and concentrated. The crude product was purified by preparative HPLC. 14 mg of the title compound was obtained.

$^1$H NMR (400 MHz, $CDCl_3$) δ ppm 1.76 (s, 6 H) 2.43 (s, 1 H) 4.33 (m, 2 H) 6.25 (br. s., 1 H) 8.45 (s, 1 H) 8.64 (s, 1 H) 8.88-9.05 (m, 1 H).

Example 133

2-(3,3-Difluorocyclobutylamino)-N-(2-methylbut-3-yn-2-yl)nicotinamide

Step 1: 2-(3,3-Difluorocyclobutylamino)nicotinic acid

To a solution of methyl 2-(3,3-difluorocyclobutylamino) nicotinate (0.376 g, 1.552 mmol) in methanol (8 ml) and water (2 ml) was added potassium hydroxide (0.087 g, 1.552 mmol).

The mixture was refluxed for four hours. Methanol was evaporated and the remaining aqueous phase was acidified with 2 M HCl. Extracted with EtOAc. The organic layers were pooled, dried and evaporated to dryness. 245 mg of title compound was obtained.

$^1$H NMR (400 MHz, DMSO-$d_6$) δ ppm 2.53-2.68 (m, 2 H) 2.96-3.07 (m, 2 H) 4.32-4.43 (m, 1 H) 6.69 (dd, 1 H) 8.10 (d, 1 H) 8.25 (d, 1 H) 8.28 (dd, 1 H) 13.16 (br. s., 1 H).

Step 2: 2-(3,3-Difluorocyclobutylamino)-N-(2-methylbut-3-yn-2-yl)nicotinamide

To a solution of 2-(3,3-difluorocyclobutylamino)nicotinic acid (0.07 g, 0.307 mmol) in DCM (3 ml) was added EDCI (0.071 g, 0.368 mmol), HOBt (0.012 g, 0.092 mmol), DIPEA (0.107 ml, 0.614 mmol) and 1,1-dimethylpropargylamine (0.042 ml, 0.399 mmol). The mixture was stirred overnight, washed with 1 M NaOH and water and evaporated to dryness. Preparative HPLC gave 59 mg of the title compound.

$^1$H NMR (400 MHz, $CDCl_3$) δ ppm 1.74 (s, 6 H) 2.42 (s, 1 H) 2.47-2.60 (m, 2 H) 3.00-3.11 (m, 2 H) 4.33-4.45 (m, 1 H) 6.10 (br. s., 1 H) 6.55 (dd, 1 H) 7.55 (dd, 1 H) 8.22 (dd, 1 H) 8.38 (d, 1 H).

Example 134

3-((4-Chlorophenyl)amino)-N-(2-methylbut-3-yn-2-yl)isonicotinamide

Step 1: 3-((4-Chlorophenyl)amino)isonicotinic acid

3-Fluoroisonicotinic acid (500 mg, 3.54 mmol) and 4-chloroaniline (450 mg, 3.54 mmol) were dissolved in dry THF under argon and the mixture was cooled to −78° C. A solution of LiHMDS (1.0 M, 10.63 mmol, 10.63 mL) was added slowly dropwise using a syringe at −78° C. and the reaction mixture was allowed to warm to ambient temperature, stirred for 16 h at room temperature. After 16 h the reaction was quenched with aqueous $NH_4Cl$ (10 mL), extracted with 10% MeOH: DCM (15 mL×2). The combined organics were washed with brine, dried over anh. $Na_2SO_4$. The crude was subjected to next step without any purification.

$^1$H NMR (300 MHz, DMSO-$d_6$) δ ppm 7.18 (m, 2 H), 7.27 (m, 2 H) 7.70 (m, 1 H) 7.97 (m, 1 H), 8.52 (s, 1 H), 10.1 (br, 1 H).

Step 2: 3-((4-Chlorophenyl)amino)-N-(2-methylbut-3-yn-2-yl)isonicotinamide

To a stirred suspension of 3-((4-chlorophenyl)amino) isonicotinic acid (280 mg, 1.13 mmol) in DCM, were added DIPEA (0.4 mL, 2.251 mmol) and HATU (428 mg, 1.13 mmol) at 0° C. 1,1-dimethylpropargylamine (0.11 mL, 1.13 mmol) was added to the reaction mixture slowly via syringe. The mixture was stirred for 16 h at room temperature. Ice cold water (5.0 mL) was added. The mixture was extracted with EtOAC (10 mL×2). The combined organics were washed with brine, dried over $Na_2SO_4$ and evaporated to dryness. Purification by flash chromatography yielded 100 mg of the title compound.

$^1$H NMR (300 MHz, DMSO-$d_6$) δ ppm 8.86 (s, 1 H), 8.57 (s 1 H) 8.54 (s, 1 H) 8.17 (d, 1 H), 7.51 (d, 1 H), 7.31 (d, 2 H), 7.12 (d, 2 H), 3.1 (s, 1 H), 1.52 (s, 6 H).

Example 135

2-(3,3-Difluoropropylamino)-3,5-difluoro-N-(2-methylbut-3-yn-2-yl)benzamide

Step 1: 2-(3,3-Difluoropropylamino)-3,5-difluorobenzoic acid

2-Bromo-3,5-difluorobenzoic acid (0.2 g, 0.844 mmol), 3,3-difluoropropan-1-amine hydrochloride (0.222 g, 1.688 mmol), copper powder (3.2 mg, 0.051 mmol), copper(I) bromide (6.1 mg, 0.042 mmol), potassium carbonate (0.257 g, 1.857 mmol) and dry DMF (4 ml) were heated by microwave irradiation at 170° C. for 1 h. Some EtOAc was added and the organic phase was washed 2 times with 0.5 M citric acid, dried over $Na_2SO_4$, filtered and evaporated. 0.212 g of the crude compound was obtained and used as such in the following step.

$^1$H NMR (400 MHz, $CDCl_3$) δ ppm 2.06-2.22 (m, 2 H) 3.54-3.62 (m, 2 H) 5.77-6.15 (m, 1 H) 7.00 (ddd, 1 H) 7.54 (ddd, 1 H).

Step 2: 2-(3,3-Difluoropropylamino)-3,5-difluoro-N-(2-methylbut-3-yn-2-yl)benzamide 2-(3,3-Difluoropropylamino)-3,5-difluorobenzoic acid (0.212 g, 0.591 mmol), 1,1-dimethylpropargylamine (0.068 ml, 0.650 mmol), HOBt (0.088 g, 0.650 mmol), EDCI (0.125 g, 0.650 mmol) and DIPEA (0.113 ml, 0.650 mmol) in DCM (5 ml) were stirred at room temperature for 4 h. 0.05 ml (0.475 mmol) of 1,1-dimethylpropargylamine was added and the mixture was stirred at room temperature overnight. Some DCM was added and the organic phase was washed with 1 M HCl and 1 M $Na_2CO_3$, dried over $Na_2SO_4$, filtered and evaporated. The crude product was purified by preparative HPLC. 0.018 g of the title compound was obtained.

$^1$H NMR (400 MHz, $CDCl_3$) δ ppm 1.74 (s, 6 H) 2.06-2.20 (m, 2 H) 2.40 (s, 1 H) 3.31 (td, 2 H) 5.02 (br. s, 1 H) 5.74-6.17 (m, 1 H) 6.93 (ddd, 1 H) 7.24-7.28 (m, 1 H) 7.73 (br. s., 1 H).

Example 136

3-(Isobutylamino)-N-(2-methylbut-3-yn-2-yl)thiophene-2-carboxamide

Step 1: Ethyl 3-(tert-butoxycarbonylamino)thiophene-2-carboxylate

Di-tert-butyl dicarbonate (0.501 g, 2.294 mmol) was added to a stirred solution of ethyl 3-aminothiophene-2-carboxylate (0.357 g, 2.085 mmol) and 4-dimethylaminopyridine (0.255 g, 2.085 mmol) in dry pyridine (10 ml) at 0° C. Resulting mixture was stirred at room temperature for 6 days. After concentration to dryness, the residue was dissolved in EtOAc and washed twice with 1 M $NaHCO_3$ and brine, dried over $Na_2SO_4$, filtered and evaporated. The crude product was purified by flash chromatography. 0.279 g of the title compound was obtained.

$^1$H NMR (400 MHz, $CDCl_3$) δ ppm 1.38 (t, 3 H) 1.52 (s, 9 H) 4.34 (q, 2 H) 7.42 (d, 1 H) 7.88 (d, 1 H) 9.38 (br. s., 1 H).

Step 2: 3-(tert-Butoxycarbonylamino)thiophene-2-carboxylic acid

To a solution of ethyl 3-(tert-butoxycarbonylamino)thiophene-2-carboxylate (0.279 g, 1.028 mmol) in THF (4 ml) and methanol (2 ml) was added sodium hydroxide pellets (0.123 g, 3.08 mmol) dissolved in $H_2O$ (1 ml). The mixture was stirred at 60° C. for 1.5 h. After evaporation of the organic solvents, the pH was adjusted to 5 with 2 M HCl and mixture was extracted 3 times with EtOAc. Combined organic phases were dried over $Na_2SO_4$, filtered and evaporated. 0.230 g of the title compound was obtained.

$^1$H NMR (400 MHz, $CDCl_3$) δ ppm 1.54 (s, 9 H) 7.53 (d, 1 H) 7.92 (d, 1 H) 9.19 (s, 1 H)

Step 3: tert-Butyl 2-(2-methylbut-3-yn-2-ylcarbamoyl)thiophen-3-ylcarbamate 3-(tert-Butoxycarbonylamino)thiophene-2-carboxylic acid (0.230 g, 0.945 mmol), 1,1-dimethylpropargylamine (0.109 ml, 1.040 mmol), HOBt (0.141 g, 1.040 mmol), EDCI (0.199 g, 1.040 mmol) and DIPEA (0.346 ml, 1.985 mmol) in DCM (5 ml) were stirred at room temperature overnight. Some DCM was added and the organic phase was washed with 1 M HCl and 1 M $Na_2CO_3$, dried over $Na_2SO_4$, filtered and evaporated. 0.215 g of the title compound was obtained.

$^1$H NMR (400 MHz, $CDCl_3$) δ ppm 1.52 (s, 9 H) 1.75 (s, 6 H) 2.45 (s, 1 H) 5.63 (s, 1 H) 7.28 (d, 1 H) 7.97 (d, 1 H) 10.04 (s, 1 H).

Step 4: 3-Amino-N-(2-methylbut-3-yn-2-yl)thiophene-2-carboxamide

Thionyl chloride (0.458 ml, 6.27 ml) was added dropwise to a stirred solution of tert-butyl 2-(2-methylbut-3-yn-2-ylcarbamoyl)thiophen-3-ylcarbamate (0.215 g, 0.697 mmol) in dry methanol (10 ml) at 0° C. under $N_2$ atmosphere. Resulting mixture was stirred at room temperature overnight. After concentration to dryness, some 1 M $Na_2CO_3$ was added and the mixture, was extracted 3 times with EtOAc. Combined organic phases were dried over $Na_2SO_4$, filtered and evaporated. The crude product was purified by flash chromatography. 0.040 g of the title compound was obtained.

$^1$H NMR (400 MHz, $CDCl_3$) δ ppm 1.72 (s, 6 H) 2.39 (s, 1 H) 5.44 (br. s., 1 H) 5.63 (br. s., 2 H) 6.54 (d, 1 H) 7.10 (d, 1 H).

Step 5: 3-(Isobutylamino)-N-(2-methylbut-3-yn-2-yl)thiophene-2-carboxamide

Isobutyraldehyde (0.023 ml, 0.250 mmol) and glacial acetic acid (0.033 ml, 0.576 mmol) were added to 3-amino-N-(2-methylbut-3-yn-2-yl)thiophene-2-carboxamide (0.040 g, 0.192 mmol) in DCM (10 ml) at 0° C. Sodium triacetoxy borohydride (0.183 g, 0.864 mmol) was added and the mixture was stirred at room temperature for 3 h. The reaction was quenched with 10 ml of water and resulting layers were separated. The organic phase was washed with 1 M $Na_2CO_3$ and brine, dried over $Na_2SO_4$, filtered and evaporated. Crude compound was purified by preparative HPLC. 0.022 g of the title compound was obtained.

$^1$H NMR (400 MHz, $CDCl_3$) δ ppm 0.96 (d, 6 H) 1.71 (s, 6 H) 1.79-1.90 (m, 1 H) 2.38 (s, 1 H) 3.03 (d, 2 H) 5.30 (s, 1 H) 6.65 (d, 1 H) 7.15 (d, 1 H) 7.43 (br. s, 1 H).

Example 137

5-Fluoro-N-(2-methylbut-3-yn-2-yl)-2-(3-methylisothiazol-5-ylamino)nicotinamide

Step 1: Ethyl 5-fluoro-2-(3-methylisothiazol-5-ylamino)nicotinate

Water (0.022 ml, 1.228 mmol) was added to a mixture of tris(dibenzylideneacetone)-dipalladium(0) (0.056 g, 0.061 mmol), 9,9-dimethyl-4,5-bis(diphenylphosphino)xanthene (0.053 g, 0.092 mmol), 5-amino-3-methylisothiazole hydrochloride (0.222 g, 1.473 mmol), sodium carbonate (0.182 g, 1.719 mmol), sodium tert-butoxide (0.118 g, 1.228 mmol), 2-chloro-5-fluoronicotinic acid ethyl ester (0.188 ml, 1.228 mmol) and dry toluene (7 ml) under argon atmosphere. The mixture was heated at 100° C. overnight. Some THF was added to the cooled reaction mixture. After filtration, the filtrate was evaporated to dryness and purified by flash chromatography. 0.014 g of the title compound was obtained.

$^1$H NMR (400 MHz, $CDCl_3$) δ ppm 1.44 (t, 3 H) 2.42 (s, 3 H) 4.44 (q, 2 H) 6.64 (s, 1 H) 8.05 (dd, 1 H) 8.45 (d, 1 H) 10.88 (s, 1 H).

Step 2: 5-Fluoro-2-(3-methylisothiazol-5-ylamino)nicotinic acid

Lithium hydroxide (9.2 mg, 0.384 mmol) was added to a solution of ethyl 5-fluoro-2-(3-methylisothiazol-5-ylamino)

nicotinate (0.054 g, 0.192 mmol) in THF (4 ml) and H₂O (2 ml) at 0° C. The mixture was stirred at room temperature for 1 h. The mixture was acidified with 1 M HCl and extracted twice with DCM. Combined organic phases were dried over Na₂SO₄, filtered and evaporated. 0.033 g of the title compound was obtained.

¹H NMR (400 MHz, MeOD-d₄) δ ppm 2.30 (s, 3 H) 6.74 (s, 1 H) 8.10 (dd, 1 H) 8.40 (d, 1 H).

Step 3: 5-Fluoro-N-(2-methylbut-3-yn-2-yl)-2-(3-methylisothiazol-5-ylamino)nicotinamide 5-Fluoro-2-(3-methylisothiazol-5-ylamino)nicotinic acid (0.033 g, 0.130 mmol), 1,1-dimethylpropargylamine (0.015 ml, 0.143 mmol), HOBt (0.019 g, 0.143 mmol), EDCI (0.027 g, 0.143 mmol) and DIPEA (0.048 ml, 0.274 mmol) in DCM (5 ml) were stirred at room temperature over weekend. Some DCM was added and the organic phase was washed with 1 M HCl and 1 M Na₂CO₃, dried over Na₂SO₄, filtered and evaporated. The crude product was purified by preparative HPLC. 6.3 mg of the title compound was obtained.

¹H NMR (400 MHz, CDCl₃) δ ppm 1.79 (s, 6 H) 2.42 (s, 3 H) 2.46 (s, 1 H) 6.18 (br. s., 1 H) 6.64 (s, 1 H) 7.50-7.54 (m, 1 H) 8.42 (d, 1 H) 11.29 (s, 1 H).

Example 138

5-Chloro-N-(2-methylbut-3-yn-2-yl)-2-(pyridin-3-ylamino)nicotinamide

Step 1: Methyl 5-chloro-2-(pyridin-3-ylamino)nicotinate

Tris(dibenzylideneacetone)dipalladium(0) (6.67 mg, 7.28 µmol), rac-2,2'-bis(diphenylphosphino)-1,1'-binaphthyl (4.99 mg, 8.01 µmol), 3-aminopyridine (0.137 g, 1.456 mmol), cesium carbonate (0.664 g, 2.039 mmol), methyl 2,5-dichloronicotinate (0.3 g, 1.456 mmol) and 1,4-dioxane (3 ml) were heated at 100° C. overnight under argon atmosphere. Some THF was added to the cooled reaction mixture and the mixture was filtrated. The filtrate was evaporated to dryness and purified by flash chromatography. 0.073 g of the title compound was obtained.

¹H NMR (400 MHz, CDCl₃) δ ppm 3.97 (s, 3 H) 7.25-7.30 (m, 1 H) 8.20-8.25 (m, 2 H) 8.30 (dd, 1 H) 8.33 (d, 1 H) 8.78 (d, 1 H) 10.18 (br. s., 1 H).

Step 2: 5-Chloro-2-(pyridin-3-ylamino)nicotinic acid

Lithium hydroxide (0.013 g, 0.554 mmol) was added to a solution of methyl 5-chloro-2-(pyridin-3-ylamino)nicotinate (0.073 g, 0.277 mmol) in THF (3 ml) and H₂O (1 ml) at 0° C. The mixture was stirred at room temperature for 2 h. THF was evaporated, some water was added and the mixture was extracted once with DCM. pH of the water phase was adjusted to 4 with 2 M HCl and it was extracted 3 times with EtOAc. Combined organic phases were dried over Na₂SO₄, filtered and evaporated. 0.025 g of the title compound was obtained.

¹H NMR (400 MHz, DMSO-d₆) δ ppm 7.38 (dd, 1 H) 8.18 (d, 1 H) 8.21-8.32 (m, 2 H) 8.44 (d, 1 H) 8.82 (d, 1 H) 10.43 (br. s., 1 H).

Step 3: 5-Chloro-N-(2-methylbut-3-yn-2-yl)-2-(pyridin-3-ylamino)nicotinamide

5-Chloro-2-(pyridin-3-ylamino)nicotinic acid (0.025 g, 0.100 mmol), 1,1-dimethylpropargylamine (0.012 ml, 0.110 mmol), HOBt (0.015 g, 0.110 mmol), EDCI (0.021 g, 0.110 mmol) and DIPEA (0.019 ml, 0.110 mmol) in DCM (5 ml) were stirred at room temperature overnight. Some DCM was added and the organic phase was washed with 1 M HCl and 1 M Na₂CO₃, dried over Na₂SO₄, filtered and evaporated. The crude product was purified by preparative HPLC. 4.4 mg of the title compound was obtained.

¹H NMR (400 MHz, CDCl₃) δ ppm 1.79 (s, 6 H) 2.46 (s, 1 H) 6.26 (br. s., 1 H) 7.19-7.28 (m, 1 H) 7.66 (d, 1 H) 8.14 (ddd, 1 H) 8.23-8.32 (m, 2 H) 8.81 (d, 1 H) 10.42 (s, 1 H).

Example 139

5-Chloro-2-(3,3-difluorocyclobutylamino)-N-(2-methylbut-3-yn-2-yl)nicotinamide

Step 1: Methyl 2-(3,3-difluorocyclobutylamino)nicotinate

2-Fluoronicotinic acid methyl ester, (0.3 g, 1.934 mmol), 3,3-difluorocyclobutanamine hydrochloride (0.278 g, 1.934 mmol), triethylamine (0.539 ml, 3.87 mmol) and DMF (3 ml) were heated by microwave irradiation at 140° C. for 2 h. Some EtOAc was added and the organic phase was washed 3 times with H₂O, dried over Na₂SO₄, filtered and evaporated. Crude product was purified by flash chromatography. 0.166 g of the title compound was obtained.

¹H NMR (400 MHz, CDCl₃) δ ppm 2.42-2.66 (m, 2 H) 2.98-3.22 (m, 2 H) 3.89 (s, 3 H) 4.34-4.61 (m, 1 H) 6.60 (dd, 1 H) 8.07-8.19 (m, 2 H) 8.29 (dd, 1 H).

Step 2: Methyl 5-chloro-2-(3,3-difluorocyclobutylamino)nicotinate

Methyl 2-(3,3-difluorocyclobutylamino)nicotinate (0.166 g, 0.685 mmol), N-chlorosuccinimide (0.092 g, 0.685 mmol) and DMF (5 ml) were stirred at 65° C. for 7 h. 0.025 g (0.187 mmol) N-chlorosuccinimide was added and the reaction mixture was stirred an additional 1 h at 65° C. Some water was added and mixture was acidified with 1M HCl and extracted 3 times with EtOAc. Combined organic phases were dried over Na₂SO₄, filtered and evaporated. 0.185 g of the title compound was obtained.

¹H NMR (400 MHz, MeOD-d₄) δ ppm 2.45-2.64 (m, 2 H) 2.94-3.11 (m, 2 H) 3.90 (s, 3 H) 4.32-4.42 (m, 1 H) 8.13 (d, 1 H) 8.23 (d, 1 H).

Step 3: 5-Chloro-2-(3,3-difluorocyclobutylamino)nicotinic acid

Lithium hydroxide (0.032 g, 1.337 mmol) was added to a solution of methyl 5-chloro-2-(3,3-difluorocyclobutylamino)nicotinate (0.185 g, 0.669 mmol) in THF (4 ml) and H₂O (2 ml) at 0° C. The mixture was stirred at room temperature for 3.5 h. THF was evaporated, some water was added and mixture was extracted once with DCM. pH of the water phase was adjusted to 4 with 2 M HCl and it was extracted 3 times with EtOAc. Combined organic phases were dried over Na₂SO₄, filtered and evaporated. 0.159 g of the title compound was obtained.

¹H NMR (400 MHz, DMSO-d₆) δ ppm 2.55-2.73 (m, 2 H) 2.88-3.12 (m, 2 H) 4.33 (m., 1 H) 8.06 (d, 1 H) 8.28 (d, 1 H) 8.32 (d, 1 H).

Step 4: 5-Chloro-2-(3,3-difluorocyclobutylamino)-N-(2-methylbut-3-yn-2-yl)nicotinamide 5-Chloro-2-(3,3-difluorocyclobutylamino)nicotinic acid (0.159 g, 0.605 mmol), 1,1-dimethylpropargylamine (0.070 ml, 0.666 mmol), HOBt (0.090 g, 0.666 mmol), EDCI (0.128 g, 0.666 mmol) and DIPEA (0.116 ml, 0.666 mmol) in DCM (5 ml) were stirred at room temperature overnight. Some DCM was added and the organic phase was washed with 1 M HCl and 1 M $Na_2CO_3$, dried over $Na_2SO_4$; filtered and evaporated. The crude product was purified by flash chromatography. 0.147 g of the title compound was obtained.

$^1$H NMR (400 MHz, $CDCl_3$) δ ppm 1.75 (s, 6 H) 2.43 (s, 1 H) 2.45-2.66 (m, 2 H) 2.92-3.16 (m, 2 H) 4.24-4.46 (m, 1 H) 6.03 (br. s., 1 H) 7.51 (d, 1 H) 8.17 (d, 1 H) 8.30 (d, 1 H).

Example 140

2-(6-Cyclopentylpyridin-3-ylamino)-5-fluoro-N-(2-methylbut-3-yn-2-yl)nicotinamide Step 1: Ethyl 2-(6-cyclopentylpyridin-3-ylamino)-5-fluoronicotinate Tris(dibenzylideneacetone)dipalladium(0) (4.50 mg, 4.91 µmol), rac-2,2'-bis(diphenylphosphino)-1,1'-binaphthyl (3.36 mg, 5.40 µmol), 6-cyclopentylpyridin-3-amine (0.159 g, 0.982 mmol), cesium carbonate (0.448 g, 1.375 mmol), 2-chloro-5-fluoronicotinic acid ethyl ester (0.150 ml, 0.982 mmol) and 1,4-dioxane (3 ml) were heated at 100° C. for 4 h under argon atmosphere. Some THF was added to the cooled reaction mixture and the mixture was filtrated through a celite pad. The filtrate was evaporated to dryness. 0.324 g of the title compound was obtained.

$^1$H NMR (400 MHz, $CDCl_3$) δ ppm 1.44 (t, 4 H) 1.68-1.87 (m, 6 H) 2.02-2.14 (m, 2 H) 3.17 (quin, 1 H) 4.42 (q, 2 H) 7.16 (d, 1 H) 8.01 (dd, 1 H) 8.05 (dd, 1 H) 8.25 (d, 1 H) 8.70 (d, 1 H) 9.99 (s, 1 H).

Step 2: 2-(6-Cyclopentylpyridin-3-ylamino)-5-fluoronicotinic acid

Lithium hydroxide (0.047 g, 1.967 mmol) was added to a solution of ethyl 2-(6-cyclopentylpyridin-3-ylamino)-5-fluoronicotinate (0.324 g, 0.984 mmol) in THF (4 nil) and $H_2O$ (2 ml) at 0° C. The mixture was stirred at room temperature for 1 h. THF was evaporated, some water and DCM were added. Formed precipitate was filtrated, washed with small amount of DCM and dried in the vacuum oven at 40° C. 0.190 g of the title compound was obtained.

$^1$H NMR (400 MHz, $DMSO-d_6$) δ ppm 1.53-1.83 (m, 6 H) 1.87-2.07 (m, 2 H) 3.07 (quin, 1 H) 7.14 (d, 1 H) 7.94 (dd, 1 H) 8.07 (d, 1 H) 8.12 (dd, 1 H) 8.61 (d, 1 H) 12.98 (s, 1 H)

Step 3: 2-(6-Cyclopentylpyridin-3-ylamino)-5-fluoro-N-(2-methylbut-3-yn-2-yl)nicotinamide 2-(6-Cyclopentylpyridin-3-ylamino)-5-fluoronicotinic acid (0.100 g, 0.332 mmol), 1,1-dimethylpropargylamine (0.038 ml, 0.365 mmol), HOBt (0.049 g, 0.365 mmol), EDCI (0.070 g, 0.365 mmol) and DIPEA (0.064 ml, 0.365 mmol) in DCM (5 ml) were stirred at room temperature overnight. Some DCM vas added and the organic phase was washed with 1 M HCl and 1 M $Na_2CO_3$, dried over $Na_2SO_4$, filtered and evaporated. The crude product was purified by flash chromatography. 0.092 g of the title compound was obtained.

$^1$H NMR (400 MHz, $CDCl_3$) δ ppm 1.74-1.98 (m, 12 H) 2.32-2.43 (m, 2 H) 2.45 (s, 1 H) 3.75 (quin, 1 H) 7.55 (d, 1 H) 7.86 (d, 1 H) 1.95 (dd, 1 H) 8.24 (dd, 1 H) 8.47 (br. s., 1 H) 9.35 (br. s., 1 H) 11.39 (br. s., 1 H).

Example 141

2-(3,3-Difluorocyclobutylamino)-N-(2-methylbut-3-yn-2-yl)-5-(trifluoromethyl)nicotinamide Step 1: Methyl 2-(3,3-difluorocyclobutylamino)-5-(trifluoromethyl)nicotinate Methyl 2-chloro-5-(trifluoromethyl)nicotinate (0.156 g, 0.651 mmol), 3,3-difluorocyclobutanamine hydrochloride (0.093 g 0.651 mmol), triethylamine (0.182 ml, 1.302 mmol) and DMF (3 ml) were heated by microwave irradiation at 140° C. for 2 h. Some EtOAc was added and the organic phase was washed 3 times with $H_2O$, dried over $Na_2SO_4$, filtered and evaporated. Crude product was purified by flash chromatography. 0.018 g of the title compound was obtained.

$^1$H NMR (400 MHz, $CDCl_3$) δ ppm 2.48-2.65 (m, 2 H) 3.05-3.19 (m, 2 H) 3.94 (s, 3 H) 4.44-4.57 (m, 1 H) 8.34 (dd, 1 H) 8.45-8.55 (m, 2 H).

Step 2: 2-(3,3-Difluorocyclobutylamino)-5-(trifluoromethyl)nicotinic acid

Lithium hydroxide (2.78 mg, 0.116 mmol) was added to a solution of methyl 2-(3,3-difluorocyclobutylamino)-5-(trifluoromethyl)nicotinate (0.018 g, 0.058 mmol) in THF (4 ml) and $H_2O$ (2 ml) at 0° C. The mixture was stirred at room temperature for 2 h. THF was evaporated, some water was added and mixture was extracted once with DCM. pH of the water phase was adjusted to 4 with 2 M HCl and it was extracted 3 times with EtOAc. Combined organic phases were dried over $Na_2SO_4$, filtered and evaporated. 0.013 g of the title compound was obtained.

$^1$H NMR (400 MHz, $MeOD-d_4$) δ ppm 2.49-2.68 (m, 2 H) 2.99-3.16 (m, 2 H) 4.39-4.55 (m, 1 H) 8.35 (dd, 1 H) 8.50 (dd, 1 H).

Step 3: 2-(3,3-Difluorocyclobutylamino)-N-(2-methylbut-3-yn-2-yl)-5-(trifluoromethyl) nicotinamide 2-(3,3-Difluorocyclobutylamino)-5-(trifluoromethyl) nicotinic acid (0.013 g, 0.044 mmol), 1,1-dimethylpropargylamine (5.1 µl, 0.048 mmol), HOBt (6.52 mg, 0.048 mmol), EDCI (9.26 mg, 0.048 mmol) and DIPEA (8.4 µl 0.048 mmol) in DCM (5 ml) were stirred at room temperature overnight. Some DCM was added and the organic phase was washed with 1 M HCl and 1 M $Na_2CO_3$, dried over $Na_2SO_4$, filtered and evaporated. The crude product was purified by preparative HPLC. 5.4 mg of the title compound was obtained.

$^1$H NMR (400 MHz, $CDCl_3$) δ ppm 1.77 (s, 6 H) 2.45 (s, 1 H) 2.48-2.67 (m, 2 H) 2.97-3.18 (m, 2 H) 4.35-4.51 (m, 1 H) 6.09 (br. s., 1 H) 7.69 (d, 1 H) 8.46 (dd, 1 H) 8.77 (d, 1 H).

Example 142

N-(2-Methylbut-3-yn-2-yl)-2-(phenethylamino)nicotinamide

Step 1: Ethyl 2-(phenethylamino)nicotinate

Ethyl 2-chloronicotinate (0.161 ml, 1.078 mmol), phenethylamine (0.406 ml, 3.23 mmol) and dry ethanol (2 ml)

were heated by microwave irradiation at 160° C. for 1 h. Some H₂O was added and mixture was extracted 2 times with EtOAc. Combined organic phases were dried over Na₂SO₄, filtered and evaporated. The crude product was purified by flash chromatography. 0.250 g of the title compound was obtained.

¹H NMR (400 MHz, CDCl₃) δ ppm 1.35 (t, 3 H) 2.96 (t, 2 H) 3.73-3.82 (m, 2 H) 4.30 (q, 2 H) 6.51 (dd, 1 H) 7.17-7.35 (m, 5 H) 8.01 (br. s., 1 H) 8.11 (dd, 1 H) 8.29 (dd, 1 H).

Step 2: 2-(Phenethylamino)nicotinic acid

Lithium hydroxide (0.044 g, 1.850 mmol) was added to a solution of ethyl 2-(phenethylamino)nicotinate (0.250 g, 0.925 mmol) in THF (4 ml) and H₂O (2 ml) at 0° C. The mixture was stirred for 2 h at 60° C. and further refluxed for 2 h. THF was evaporated, some water was added and mixture was extracted once with DCM. pH of the water phase was adjusted to 3 with 1 M HCl and it was extracted 3 times with EtOAc. Combined organic phases were dried over Na₂SO₄, filtered and evaporated. 0.173 g of the title compound was obtained.

¹H NMR (400 MHz, DMSO-d₆) δ ppm 2.87 (t, 2 H) 3.61-3.75 (m, 2 H) 6.59 (dd, 1 H) 7.14-7.35 (m, 5 H) 8.05 (dd, 1 H) 8.14 (br. s., 1 H) 8.28 (dd, 1 H) 12.99 (br. s., 1 H).

Step 3: N-(2-Methylbut-3-yn-2-yl)-2-(phenethylamino)nicotinamide 2-(Phenethylamino)nicotinic acid (0.100 g, 0.413 mmol), 1,1-dimethylpropargylamine (0.048 ml, 0.454 mmol), HOBt (0.061 g, 0.454 mmol), EDCI (0.087 g, 0.454 mmol) and DIPEA (0.079 ml, 0.454 mmol) in DCM (5 ml) were stirred at room temperature for 3 h. 0.025 ml (0.238 mmol) of 1,1-dimethylpropargylamine was added and mixture was stirred at room temperature overnight. Some DCM was added and the organic phase was washed with 1 M HCl and 1 M Na₂CO₃, dried over Na₂SO₄, filtered and evaporated. The crude product was purified by preparative HPLC. 0.025 g of the title compound was obtained.

¹H NMR (400 MHz, CDCl₃) δ ppm 1.72 (s, 6 H) 2.39 (s, 1 H) 2.89-2.99 (m, 2 H) 3.67-3.78 (m, 2 -H) 6.02 (br. s., 1 H) 6.46 (dd, 1 H) 7.14-7.22 (m, 1H) 7.22-7.34 (m, 4H) 7.50 (dd, 1 H) 8.14 (t, 1 H) 8.22 (dd, 1 H).

Example 143

N-(2-Methylbut-3-yn-2-yl)-2-(3-phenylpropylamino)nicotinamide

Step 1: Ethyl 2-(3-phenylpropylamino)nicotinate

Ethyl 2-chloronicotinate (0.161 ml, 1.078 mmol), 3-phenylpropylamine (0.460 ml, 3.23 mmol) and dry ethanol (2 ml) were heated by microwave irradiation at 160° C. for 1 h. Some H₂O was added and mixture was extracted 2 times with EtOAc. Combined organic phases were dried over Na₂SO₄, filtered and evaporated. The crude product was purified by flash chromatography. 0.285 g of the title compound was obtained.

¹H NMR (400 MHz, CDCl₃) δ ppm 1.38 (t, 3 H) 1.93-2.07 (m, 2 H) 2.68-2.80 (m, 2 H) 3.55 (td, 2 H) 4.32 (q, 2 H) 6.50 (dd, 1 H) 7.12-7.24 (m, 3 H) 7.24-7.32 (m, 2H) 8.05 (br. s., 1 H) 8.11 (dd, 1 H) 8.27 (dd, 1 H).

Step 2: 2-(3-Phenylpropylamino)nicotinic acid

Lithium hydroxide (0.048 g, 2.005 mmol) was added to a solution of ethyl 2-(3-phenylpropylamino)nicotinate (0.285 g, 1.002 mmol) in THF (4 ml) and H₂O (2 ml) at 0° C. The mixture was stirred for 2 h at 60° C. and further refluxed for 2 h. THF was evaporated, some water was added and mixture was extracted once with DCM. pH of the water phase was adjusted to 3 with 1 M HCl and it was extracted 3 times with EtOAc. Combined organic phases were dried over Na₂SO₄, filtered and evaporated. 0.236 g of the title compound was obtained.

¹H NMR (400 MHz, DMSO-d₆) δ ppm 1.88 (dt, 2 H) 2.60-2.71 (m, 2 H) 3.44 (t, 2 H) 6.57 (dd, 1H) 7.11-7.24 (m, 3 H) 7.24-7.33 (m, 2 H) 8.05 (dd, 1 H) 8.15 (br. s., 1H) 8.24 (dd, 1 H) 13.01 (br. s., 1 H).

Step 3: N-(2-Methylbut-3-yn-2-yl)-2-(3-phenylpropylamino)nicotinamide 2-(3-Phenylpropylamino)nicotinic acid (0.160 g, 0.390 mmol), 1,1-dimethylpropargylamine (0.045 ml, 0.429 mmol), HOBt (0.058 g, 0.429 mmol), EDCI (0.082 g, 0.429 mmol) and DIPEA (0.075 ml, 0.429 mmol) in DCM (5 ml) were stirred at room temperature for 3 h. 0.025 ml (0.238 mmol) of 1,1-dimethylpropargylamine was added and mixture was stirred at room temperature overnight. Some DCM was added and the organic phase was washed with 1 M HCl and 1 M Na₂CO₃, dried over Na₂SO₄, filtered and evaporated. The crude product was purified by flash chromatography. 0.063 g of the title compound was obtained.

¹H NMR (400 MHz, CDCl₃) δ ppm 1.73 (s, 6 H) 1.92-2.03 (m, 2 H) 2.39 (s, 1 H) 2.68-2.77 (m, 2 H) 3.50 (td, 2 H) 6.05 (br. s., 1 H) 6.44 (dd, 1 H) 7.11-7.23 (m, 3 H) 7.23-7.31 (m, 2 H) 7.50 (dd, 1 H) 8.10-8.23 (m, 2 H).

Example 144

5-Fluoro-2-(3-(4-fluorophenoxy)propylamino)-N-(2-methylbut-3-yn-2-yl)nicotinamide Step 1: Ethyl 5-fluoro-2-(3-(4-fluorophenoxy)propylamino)nicotinate 2-Chloro-5-fluoronicotinic acid ethyl ester (0.150 ml, 0.982 mmol), 3-(4-fluorophenoxy)-propan-1-amine hydrochloride (0.606 g, 2.95 mmol), triethylamine (0.411 ml, 2.95 mmol) and dry ethanol (2 ml) were heated by microwave irradiation at 160° C. for 1 h. Some H₂O was added and mixture was extracted 2 times with EtOAc. Combined organic phases were dried over Na₂SO₄, filtered and evaporated. The crude product was purified by flash chromatography. 0.197 g of the title compound was obtained.

¹H NMR (400 MHz, CDCl₃) δ ppm 1.38 (t, 3 H) 2.12 (quin, 2H) 3.68 (td, 2 H) 4.04 (t, 2 H) 4.33 (q, 2 H) 6.82-6.90 (m, 2 H) 6.91-7.01 (m, 2 H) 7.87 (dd, 1 H) 7.99 (br. s., 1 H) 8.17 (d, 1 H).

Step 2: 5-Fluoro-2-(3-(4-fluorophenoxy)propylamino)nicotinic acid

Lithium hydroxide (0.028 g, 1.171 mmol) was added to a solution of ethyl 5-fluoro-2-(3-(4-fluorophenoxy)propylamino)nicotinate (0.197 g, 0.586 mmol) in THF (4 ml) and H₂O (2 ml) at 0° C. The mixture was stirred for 1.5 h at 60° C. THF was evaporated, some water was added and mixture was extracted once with DCM. pH of the water phase was adjusted to 3 with 1 M HCl and it was extracted 3 times with EtOAc. Combined organic phases were dried over Na₂SO₄, filtered and evaporated. 0.173 g of the title compound was obtained.

¹H NMR (400 MHz, DMSO-d₆) δ ppm 1.96-2.06 (m, 2 H) 3.59 (t, 2 H) 4.02 (t, 2 H) 6.90-7.01 (m, 2 H) 7.04-7.17 (m, 2 H) 7.89 (dd, 1 H) 8.12 (br. s., 1 H) 8.30 (d, 1 H) 12.64-14.02 (m, 1 H).

Step 3: 5-Fluoro-2-(3-(4-fluorophenoxy)propylamino)-N-(2-methylbut-3-yn-2-yl)nicotinamide 5-Fluoro-2-(3-(4-fluorophenoxy)propylamino)nicotinic acid (0.100 g, 0.324 mmol), 1,1-dimethylpropargylamine (0.038 ml, 0.357 mmol), HOBt (0.048 g, 0.357 mmol), EDC (0.068 g, 0.357 mmol) and DIPEA (0.062 ml, 0.357 mmol) in DCM (5 ml) were stirred at room temperature for 3 h. 0.025 ml (0.238 mmol) of 1,1-dimethylpropargylamine was added and mixture was stirred at room temperature overnight. Some DCM was added and the organic phase was washed with 1 M HCl and 1 M Na₂CO₃, dried over Na₂SO₄, filtered and evaporated. The crude product was purified by preparative HPLC. 0.073 g of the title compound was obtained.

¹H NMR (400 MHz, CDCl₃) δ ppm 1.73 (s, 6 H) 2.11 (quin, 2 H) 2.39 (s, 1 H) 3.58-3.68 (m, 2 H) 4.02 (t, 2 H) 5.96 (br. s., 1 H) 6.82-6.90 (m, 2 H) 6.90-6.99 (m, 2 H) 7.30 (dd, 1 H) 7.97-8.05 (m, 1 H) 8.11 (d, 1 H).

Example 145

5-Fluoro-2-(2-(4-fluorophenoxy)ethylamino)-N-(2-methylbut-3-yn-2-yl)nicotinamide Step 1: Ethyl 5-fluoro-2-(2-(4-fluorophenoxy)ethylamino)nicotinate 2-Chloro-5-fluoronicotinic acid ethyl ester (0.150 ml, 0.982 mmol), 2-(4-fluorophenoxy)ethanamine (0.152 g, 0.982 mmol), triethylamine (0.411 ml, 2.95 mmol) and dry ethanol (2 ml) were heated by microwave irradiation at 160° C. for 2 h. Some H₂O was added and mixture was extracted 2 times with EtOAc. Combined organic phases were dried over Na₂SO₄, filtered and evaporated. The crude product was purified by reverse phase flash chromatography. 0.056 g of the title compound was obtained.

¹H NMR (400 MHz, CDCl₃) δ ppm 1.38 (t, 3 H) 3.89 (q, 2 H) 4.09-4.15 (m, 2 H) 4.33 (q, 2 H) 6.83-6.91 (m, 2 H) 6.91-7.01 (m, 2 H) 7.88 (dd, 1 H) 8.06-8.15 (m, 1H) 8.18 (d, 1H).

Step 2: 5-Fluoro-2-(2-(4-fluorophenoxy)ethylamino)nicotinic acid

Lithium hydroxide (8.32 mg, 0.347 mmol) was added to a solution of ethyl 5-fluoro-2-(2-(4-fluorophenoxy)ethylamino)nicotinate (0.056 g, 0.174 mmol) in THF (3 ml) and H₂O (2 ml) at 0° C. The mixture was stirred at room temperature for 3.5 h. THF was evaporated, some water was added and mixture was extracted once with DCM. pH of the water phase was adjusted to 3 with 1 M HCl and it was extracted 3 times with EtOAc. Combined organic phases were dried over Na₂SO₄, filtered and evaporated. 0.045 g of the title compound was obtained.

¹H NMR (400 MHz, DMSO-d₆) δ ppm 3.71-3.87 (m, 2 H) 4.12 (t, 2 H) 6.93-7.03 (m, 2 H) 7.06-7.18 (m, 2 H) 7.92 (dd, 1 H) 8.20 (br. s., 1 H) 8.34 (d, 1 H) 13.42 (br. s., 1 H).

Step 3: 5-Fluoro-2-(2-(4-fluorophenoxy)ethylamino)-N-(2-methylbut-3-yn-2-yl)nicotinamide 5-Fluoro-2-(2-(4-fluorophenoxy)ethylamino)nicotinic acid (0.050 g, 0.170 mmol), 1,1-dimethylpropargylamine (0.020 ml, 0.187 mmol), HOBt (0.025 g, 0.187 mmol), EDCI (0.036 g, 0.187 mmol) and DIPEA (0.033 ml, 0.187 mmol) in DCM (5 ml) were stirred at room temperature for 4.5 h. Some DCM was added and the organic phase was washed with 1 M HCl and 1 M Na₂CO₃, dried over Na₂SO₄, filtered and evaporated. The crude product was purified by flash chromatography. 0.046 g of the title compound was obtained.

¹H NMR (400 MHz, CDCl₃) δ ppm 1.73 (s, 6 H) 2.40 (s, 1 H) 3.83 (q, 2 H) 4.10 (t, 2 H) 6.01 (br. s., 1 H) 6.81-6.90 (m, 2 H) 6.90-6.99 (m, 2 H) 7.32 (dd, 1 H) 7.99-8.19 (m, 2 H).

Example 146

5-Chloro-2-(3-ethoxypropylamino)-N-(2-methylbut-3-yn-2-yl)nicotinamide

Step 1: 5-Chloro-2-(3-ethoxypropylamino)nicotinic acid

Propylene glycol, monoethyl ether (0.240 ml, 2.086 mmol), Dess-Martin periodinane (15% in DCM, 5.41 ml, 2.61 mmol) and dry DCE (10 ml) were stirred at room temperature for 2 h. 2-Amino-5-chloro nicotinic acid (0.3 g, 1.738 mmol) dissolved in dry DCE (2 ml) and glacial acetic acid (0.249 ml, 4.35 mmol) were added slowly. Sodium triacetoxy borohydride (0.737 g, 3.48 mmol) was added and the mixture was stirred at room temperature overnight. The reaction was quenched with 10 ml of water. Formed precipitate was filtered, washed with small amount of DCE and dried in the vacuum oven at 40° C. 0.171 g of the title compound was obtained.

¹H NMR (400 MHz, DMSO-d₆) δ ppm 1.11 (t, 3 H) 1.78 (quin, 2 H) 3.37-3.45 (m, 4 H) 3.48 (t, 2 H) 8.00 (d, 1 H) 8.17-8.31 (m, 2 H) 13.22 (br. s., 1 H).

Step 2: 5-Chloro-2-(3-ethoxypropylamino)-N-(2-methylbut-3-yn-2-yl)nicotinamide

5-Chloro-2-(3-ethoxypropylamino)nicotinic acid (0.100 g, 0.387 mmol), 1,1-dimethylpropargylamine (0.045 ml, 0.425 mmol), HOBt (0.057 g, 0.425 mmol), EDCI (0.082 g, 0.425 mmol) and DIPEA (0.074 ml, 0.425 mmol) in DCM (5 ml) were stirred at room temperature overnight. Some DCM was added and the organic phase was washed with 1 M HCl and 1 M Na₂CO₃, dried over Na₂SO₄, filtered and evaporated. The crude product was purified by preparative HPLC. 0.061 g of the title compound was obtained.

¹H NMR (400 MHz, CDCl₃) δ ppm 1.20 (t, 3 H) 1.73 (s, 6 H) 1.90 (quin, 2 H) 2.41 (s, 1 H) 3.38-3.61 (m, 6 H) 6.06 (s, 1 H) 7.47 (d, 1 H) 8.06 (t, 1 H) 8.13 (d, 1 H).

Example 147

2-(2-tert-Butoxyethylamino)-5-chloro-N-(2-methylbut-3-yn-2-yl)nicotinamide

Step 1: 2-(2-tert-Butoxyethylamino)-5-chloronicotinic acid 2-(tert-Butoxy)ethanol (0.183 ml, 1.391 mmol), Dess-Martin periodinane (15% in DCM, 3.62 ml, 1.738 mmol) and dry DCE (10 ml) were stirred at room temperature for 2 h. 2-Amino-5-chloro nicotinic acid (0.2 g, 1.159 mmol) dissolved in DCE (2 ml) and glacial acetic acid (0.166 ml, 2.90 mmol) were added slowly. Sodium triacetoxy borohydride (0.491 g, 2.318 mmol) was added and the mixture was stirred at room temperature overnight. The reaction was quenched with 10 ml of water. pH was adjusted to 5 with 2 M HCl and mixture was extracted 2 times with DCM. Combined organic phases were dried over $Na_2SO_4$, filtered and evaporated. Impure product mixture (0.42 g, purity max 50%) was used as such in the next step.

$^1$H NMR (400 MHz, $CDCl_3$) δ ppm 1.24 (s, 9 H) 3.56-3.62 (m, 2 H) 3.63-3.70 (m, 2 H) 8.16 (d, 1 H) 8.27 (d, 1 H).

Step 2: 2-(2-tert-Butoxyethylamino)-5-chloro-N-(2-methylbut-3-yn-2-yl)nicotinamide 2-(2-tert-Butoxyethylamino)-5-chloronicotinic acid (0.100 g, 0.367 mmol), 1,1-dimethylpropargylamine (0.042 ml, 0.403 mmol), HOBt (0.054 g, 0.403 mmol), EDCI (0.077 g, 0.403 mmol) and DIPEA (0.070 ml, 0.403 mmol) in DCM (5 ml) were stirred at room temperature over weekend. Some DCM was added and the organic phase was washed with 1 M HCl and 1 M $Na_2CO_3$, dried over $Na_2SO_4$, filtered and evaporated. The rude product was purified by flash chromatography. 0.043 g of the title compound was obtained.

$^1$H NMR (400 MHz, $CDCl_3$) δ ppm 1.20 (s, 9 H) 1.73 (s, 6 H) 2.39 (s, 1 H) 3.49-3.66 (m, 4 H) 5.96 (br. s., 1 H) 7.46 (d, 1 H) 8.02 (br. s., 1 H) 8.13 (d, 1 H).

Example 148

5-Chloro-2-(2-ethoxyethylamino)-N-(2-methylbut-3-yn-2-yl)nicotinamide

Step 1: 5-Chloro-2-(2-ethoxyethylamino)nicotinic acid

2-Ethoxyethanol (0.137 ml, 1.391 mmol), Dess-Martin periodinane (15% in DCM, 3.59 ml, 1.738 mmol) and dry DCE (10 ml) were, stirred at room temperature for 2 h. 2-Amino-5-chloro nicotinic acid (0.2 g, 1.159 mmol) dissolved in DCE (2 ml) and glacial acetic acid (0.166 ml, 2.90 mmol) were added slowly. Sodium triacetoxy borohydride (0.491 g, 2.318 mmol) was added and the mixture was stirred at room temperature overnight. The reaction was quenched with 10 ml of water. pH was adjusted to 5 with 2 M HCl and mixture was, extracted 2 times with DCM. Combined organic phases were dried over $Na_2SO_4$, filtered and evaporated. The crude product was purified by flash chromatography. 0.039 g of the title compound was obtained.

$^1$H NMR (400 MHz, $CDCl_3$) δ ppm 1.24 (t, 3 H) 3.57 (q, 2 H) 3.62-3.69 (m, 2 H) 3.71 (d, 2 H) 8.02-8.14 (m, 2 H) 8.25 (d, 1 H).

Step 2: 5-Chloro-2-(2-ethoxyethylamino)-N-(2-methylbut-3-yn-2-yl)nicotinamide

5-Chloro-2-(2-ethoxyethylamino)nicotinic acid (0.039 g, 0.159 mmol), 1,1-dimethylpropargylamine (0.018 ml, 0.175 mmol), HOBt (0.024 g, 0.175 mmol), EDCI (0.034 g, 0.175 mmol) and DIPEA (0.031 ml, 0.175 mmol) in DCM (5 ml) were stirred at room temperature overnight. Some DCM was added and the organic phase was washed with 1 M HCl and 1 M $Na_2CO_3$, dried over $Na_2SO_4$, filtered and evaporated. The crude product was purified by preparative HPLC. 0.025 g of the title compound was obtained.

$^1$H NMR (400 MHz, $CDCl_3$) δ ppm 1.21 (t, 3 H) 1.73 (s, 6 H) 2.40 (s, 1 H) 3.53 (q, 2 H) 3.58-3.69 (m, 4 H) 6.04 (br. s., 1 H) 7.48 (d, 1 H) 8.07 (br. s., 1 H) 8.12 (d, 1 H).

Example 149

2-(3-Fluoro-4-methylphenylamino)-N-(2-methylbut-3-yn-2-yl)nicotinamide

Step 1: Methyl 2-(3-fluoro-4-methylphenylamino)nicotinate

2-Fluoronicotinic acid methyl ester (0.3 g, 1.934 mmol) and 3-fluoro-4-methylaniline (0.217 ml, 1.934 mmol) were heated by microwave irradiation at 120° C. for 20 min. Some DCM was added and mixture was washed twice with $H_2O$. Organic phase was dried over $Na_2SO_4$, filtered and evaporated. 0.419 g of the title compound was obtained.

$^1$H NMR (400 MHz, $CDCl_3$) δ ppm 2.24 (d, 3 H) 3.93 (s, 3 H) 6.72 (dd, 1 H) 7.07-7.13 (m, 1 H) 7.14-7.18 (m, 1 H) 7.70 (dd, 1 H) 8.22 (dd, 1 H) 8.38 (dd, 1 H) 10.16 (br. s., 1 H).

Step 2: 2-(3-Fluoro-4-methylphenylamino)nicotinic acid

Lithium hydroxide (0.077 g, 3.22 mmol) was added to a solution of methyl 2-(3-fluoro-4-methylphenylamino)nicotinate (0.419 g, 1.610 mmol) in THF (6 ml) and $H_2O$ (3 ml) at 0° C. The mixture was stirred at room temperature for 4.5 h. THF was evaporated, some water was added and mixture was extracted once with DCM. pH of the water phase was adjusted to 3 with 1 M HCl. Formed precipitate was filtrated, washed with small amount of DCM and dried in the vacuum oven at 40° C. 0.318 g of the title compound was obtained.

$^1$H NMR (400 MHz, DMSO-$d_6$) δ ppm 2.19 (d, 3 H) 6.89 (dd, 1 H) 7.13-7.25 (m, 2 H) 7.81-7.92 (m, 1 H) 8.25 (dd, 1 H) 8.41 (dd, 1 H) 10.60 (br. s., 1 H).

Step 3: 2-(3-Fluoro-4-methylphenylamino)-N-(2-methylbut-3-yn-2-yl)nicotinamide 2-(3-Fluoro-4-methylphenylamino)nicotinic acid (0.100 g, 0.406 mmol), 1,1-dimethylpropargylamine (0.047 ml, 0.447 mmol), HOBt (0.060 g, 0.447 mmol), EDCI (0.086 g, 0.447 mmol) and DIPEA (0.078 ml, 0.447 mmol) in DCM (5 ml) were stirred at room temperature overnight. Some DCM was added and the organic phase was washed with 1 M HCl and 1 M $Na_2CO_3$, dried over $Na_2SO_4$, filtered and evaporated. The crude product was purified by flash chromatography. 0.060 g of the title compound was obtained.

$^1$H NMR (400 MHz, $CDCl_3$) δ ppm 1.77 (s, 6 H) 2.22 (d, 3 H) 2.43 (s, 1 H) 6.15 (br. s., 1 H) 6.69 (dd, 1 H) 7.04-7.11 (m, 1 H) 7.12-7.17 (m, 1 H) 7.58-7.73 (m, 2 H) 8.32 (dd, 1 H) 10.35 (s, 1 H).

Example 150

2-(3-Chloro-4-methoxyphenylamino)-N-(2-methylbut-3-yn-2-yl)nicotinamide

Step 1: Methyl 2-(3-chloro-4-methoxyphenylamino)nicotinate

2-Fluoronicotinic acid methyl ester (0.3 g, 1.934 mmol) and 3-chloro-p-anisidine (0.494 ml, 3.87 mmol) were heated by microwave irradiation at 120° C. for 20 min. Some DCM was added and mixture was washed twice with H₂O and twice with 2 M HCl. Organic phase was dried over $Na_2SO_4$, filtered and evaporated. 0.150 g of the title compound was obtained.

$^1$H NMR (400 MHz, CDCl₃) δ ppm 3.89 (s, 3 H) 3.93 (s, 3 H) 6.71 (dd, 1 H) 6.91 (d, 1 H) 7.45 (dd, 1 H) 7.81 (d, 1 H) 8.22 (dd, 1 H) 8.35 (dd, 1 H) 10.00 (s, 1 H).

Step 2:
2-(3-Chloro-4-methoxyphenylamino)nicotinic acid

Lithium hydroxide (0.025 g, 1.025 mmol) was added to a solution of methyl 2-(3-chloro-4-methoxyphenylamino)nicotinate (0.150 g, 0.512 mmol) in THF (6 ml) and H₂O (3 ml) at 0° C. The mixture was stirred at room temperature for 2.5 h. THF was evaporated, some water was added and mixture was extracted once with DCM. pH of the water phase was adjusted to 4 with 2 M HCl and it was extracted 3 times with EtOAc. Combined organic phases were dried over $Na_2SO_4$, filtered and evaporated. 0.092 g of the title compound was obtained.

$^1$H NMR (400 MHz, DMSO-d₆) δ ppm 3.83 (s, 3 H) 6.85 (dd, 1 H) 7.11 (d, 1 H) 7.46 (dd, 1 H) 7.98 (d, 1H) 8.23 (dd, 1 H) 8.38 (dd, 1 H) 10.31 (s, 1 H) 13.61 (br. s., 1 H).

Step 3: 2-(3-Chloro-4-methoxyphenylamino)-N-(2-methylbut-3-yn-2-yl)nicotinamide 2-(3-Chloro-4-methoxyphenylamino)nicotinic acid (0.092 g, 0.330 mmol), 1,1-dimethylpropargylamine (0.038 ml, 0.363 mmol), HOBt (0.049 g, 0.363 mmol), EDCI (0.070 g, 0.363 mmol) and DIPEA (0.063 ml, 0.363 mmol) in DCM (5 ml) were stirred at room temperature for 3 h. Some DCM was added and the organic phase was washed with 1 M HCl and 1 M $Na_2CO_3$, dried over $Na_2SO_4$, filtered and evaporated. The crude product was purified by flash chromatography. 0.051 g of the title compound was obtained.

$^1$H NMR (400 MHz, CDCl₃) δ ppm 1.77 (s, 6 H) 2.43 (s, 1 H) 3.88 (s, 3 H) 6.15 (br. s., 1 H) 6.67 (dd, 1 H) 6.89 (d, 1 H) 7.42 (dd, 1 H) 7.64 (dd, 1 H) 7.81 (d, 1 H) 8.29 (dd, 1 H) 10.25 (s, 1 H).

Example 151

2-(3,5-Difluorophenylamino)-N-(2-methylbut-3-yn-2-yl)nicotinamide

Step 1: Methyl 2-(3,5-difluorophenylamino)nicotinate

2-Fluoronicotinic acid methyl ester (0.3 g, 1.934 mmol) and 3,5-difluoroaniline (0.387 ml, 3.87 mmol) were heated by microwave irradiation at 120° C. for 20 min. Some DCM was added and mixture was washed twice with H₂O. Organic phase was dried over $Na_2SO_4$, filtered and evaporated. 0.450 g of the title compound was obtained.

$^1$H NMR (400 MHz, CDCl₃) δ ppm 3.94 (s, 3 H) 6.47 (tt, 1 H) 6.82 (dd, 1 H) 7.30-7.49 (m, 2 H) 8.27 (dd, 1 H) 8.43 (dd, 1 H) 10.40 (br. s., 1 H).

Step 2: 2-(3,5-Difluorophenylamino)nicotinic acid

Lithium hydroxide (0.082 g, 3.41 mmol) was added to a solution of methyl 2-(3,5-difluorophenylamino)nicotinate (0.450 g, 1.703 mmol) in THF (6 ml) and H₂O (3 ml) at 0° C. The mixture was stirred at room temperature for 2.5 h. THF was evaporated, some water was added and mixture was extracted once with DCM. pH of the water phase was adjusted to 4 with, 2 M HCl. Formed precipitate was filtrated, washed with small amount of DCM and dried in the vacuum oven at 40° C. 0.399 g of the title compound was obtained.

$^1$H NMR (400 MHz, DMSO-d₆) δ ppm 6.80 (tt, 1 H) 6.99 (dd, 1 H) 7.43-7.63 (m, 2 H) 8.30 (dd, 1 H) 8.47 (dd, 1 H) 10.69 (s, 1 H).

Step 3: 2-(3,5-Difluorophenylamino)-N-(2-methylbut-3-yn-2-yl)nicotinamide 2-(3,5-Difluorophenylamino)nicotinic acid (0.100 g, 0.400 mmol), 1,1-dimethylpropargylamine (0.046 ml, 0.440 mmol), HOBt (0.059 g, 0.440 mmol), EDCI (0.084 g, 0.440 mmol) and DIPEA (0.077 ml, 0.440 mmol) in DCM (5 ml) were stirred at room temperature overnight. Some DCM was added and the organic phase was washed with 1 M HCl and 1 M $Na_2CO_3$, dried over $Na_2SO_4$, filtered and evaporated. The crude product was purified by flash chromatography. 0.083 g of the title compound was obtained.

$^1$H NMR (400 MHz, CDCl₃) δ ppm 1.77 (s, 6 H) 2.44 (s, 1 H) 6.19 (br. s., 1 H) 6.43 (tt, 1 H) 6.78 (dd, 1 H) 7.31-7.42 (m, 2 H) 7.69 (dd, 1 H) 8.37 (dd, 1 H) 10.65 (s, 1 H).

Example 152

2-(3,3-Difluorocyclobutylamino)-5-(difluoromethyl)-N-(2-methylbut-3-yn-2-yl)nicotinamide Step 1: Methyl 2-chloro-5-(dibromomethyl)nicotinate N-Bromosuccinimide (0.449 g, 2.52 mmol) and benzoyl peroxide (0.027 g, 0.084 mmol) were added to a stirred solution of methyl 2-chloro-5-methylnicotinate (0.156 g, 0.840 mmol) in carbon tetrachloride (5 ml). The mixture was refluxed for 10 h. Cooled reaction mixture was filtered and filtrate was evaporated to dryness. The crude product was purified by flash chromatography. 0.140 g of title compound was obtained.

$^1$H NMR (400 MHz, CDCl₃) δ ppm 4.00 (s, 3 H) 6.65 (d, 1 H) 8.43 (d, 1 H) 8.63 (d, 1 H).

Step 2: Methyl 2-chloro-5-formylnicotinate

Silver nitrate (0.139 g, 0.815 mmol) in H₂O (1 ml) was added to a solution of methyl 2-chloro-5-(dibromomethyl)nicotinate (0.140 g, 0.408 mmol) in 2-propanol (5 ml) and the mixture was stirred under N₂ atmosphere at room temperature overnight. The inorganic precipitate was filtrated and washed with small, amount of DCM. The layers of the filtrate were separated and aqueous phase was washed once with DCM. Combined organic phases were dried over $Na_2SO_4$, filtered and evaporated. 0.076 g of the title compound was obtained.

$^1$H NMR (400 MHz, CDCl₃) δ ppm 4.01 (s, 3 H) 8.62 (d, 1 H) 8.97 (d, 1 H) 10.14 (s, 1 H).

Step 3: Methyl 2-chloro-5-(difluoromethyl)nicotinate

To a stirred solution of methyl 2-chloro-5-formylnicotinate (0.076 g, 0.381 mmol) in DCM (5 ml) was added diethylaminosulfur trifluoride (0.200 ml, 1.523 mmol). Reaction mixture was stirred at room temperature for 2 hours under N₂ atmosphere. After completion of the reaction, the mixture was quenched with aqueous saturated NaHCO₃. Layers were separated and aqueous phase was washed 3 times with DCM. Combined organic phases were dried over Na₂SO₄, filtered and evaporated. 0.078 g of the title compound was obtained.

$^1$H NMR (400 MHz, CDCl₃) δ ppm 3.99 (s, 3 H) 6.76 (t, 1 H) 8.32 (dt, 1 H) 8.66 (dt, 1 H).

Step 4: 2-(3,3-Difluorocyclobutylamino)-5-(difluoromethyl)nicotinic acid

Methyl 2-chloro-5-(difluoromethyl)nicotinate (0.105 g, 0.474 mmol), 3,3-difluorocyclobutanamine hydrochloride (0.068 g, 0.474 mmol), triethylamine (0.132 ml, 0.948 mmol) and ACN (0.5 ml) were heated by microwave irradiation at 140° C. for 70 min. Formed precipitate was filtrated and washed with small amount of ACN. The filtrate was evaporated and redissolved in THF (4 ml) and H₂O (2 ml). Lithium hydroxide (0.023 g, 0.948 mmol) was added at 0° C. and the mixture was stirred at room temperature for, 1.5 h. THF was evaporated, some water was added and mixture was extracted once with DCM. pH of the water phase was adjusted to 3 with 2 M HCl. Formed precipitate was filtrated, washed with small amount of DCM and dried in the vacuum oven at 40° C. 0.027 g of the title compound was obtained.

$^1$H NMR (400 MHz, MeOD-d₄) δ ppm 2.48-2.66 (m, 2 H), 3.00-3.14 (m, 2 H) 4.38-4.49 (m, 1 H) 6.74 (t, 1 H) 8.29-8.33 (m, 1 H) 8.38 (dt, 1 H).

Step 5: 2-(3,3-Difluorocyclobutylamino)-5-(difluoromethyl)-N-(2-methylbut-3-yn-2-yl)nicotinamide 2-(3,3-Difluorocyclobutylamino)-5-(difluoromethyl) nicotinic acid (0.030 g, 0.108 mmol), 1,1-dimethylpropargylamine (0.012 ml, 0.119 mmol), HOBt (0.016 g, 0.119 mmol), EDCI (0.023 g, 0.119 mmol) and DIPEA (0.021 ml, 0.119 mmol) in DCM (5 ml) were stirred at room temperature overnight. Some DCM was added and the organic phase was washed with 1 M HCl and 1 M Na₂CO₃; dried over Na₂SO₄, filtered and evaporated. The crude product was purified by preparative chromatography. 3.92 mg of the title compound was obtained.

$^1$H NMR (400 MHz, CDCl₃) δ ppm 1.76 (s, 6 H) 2.43 (s, 1 H) 2.46-2.63 (m, 2 H) 2.98-3.17 (m, 2 H) 4.33-4.48 (m, 1 H) 6.13 (br. s., 1 H) 6.60 (t, 1 H) 7.65-7.72 (m, 1 H) 8.29 (q, 1 H) 8.66 (d, 1 H).

Example 153

5-Bromo-2-(ethylamino)-N-(2-methylbut-3-yn-2-yl) nicotinanilide

Step 1: Ethyl 5-bromo-2-(ethylamino)nicotinate

Ethyl-2-amino-5-bromonicotinate (1.5 g, 6.12 mmol), acetaldehyde (0.359 ml, 6.43 mmol) and acetic acid, glacial (0.876 ml, 15.30 mmol) in 1,2-dichloroethane (45 ml) were cooled to 0° C. Sodium triacetoxy borohydride (2.59 g, 12.24 mmol) was added and the reaction mixture was stirred at room temperature overnight. It was cooled to 0° C. and water (15 ml) was added. The organic layer was separated, washed with 1M Na₂CO₃ and brine, dried with Na₂SO₄ and concentrated. The crude product was purified by flash chromatography. 1.07 g of the title compound was obtained.

$^1$H NMR (400 MHz, CDCl₃) δ ppm 1.26 (t, 3 H) 1.38 (t, 3 H) 3.50 (qd, 2 H) 4.32 (q, 2 H) 7.91 (br. s., 1 H) 8.18 (d, 1 H) 8.28 (d, 1 H).

Step 2: 5-Bromo-2-(ethylamino)nicotinic acid

Ethyl 5-bromo-2-(ethylamino)nicotinate (1.07 g, 3.92 mmol) and potassium hydroxide (0.659 g, 11.75 mmol) in methanol (10 ml) and water (2.5 ml) were stirred at room temperature for 3 hours. Methanol was evaporated and the reaction mixture was diluted with water. The pH was adjusted to 2 by addition of 1 M HCl. The title compound precipitated and was filtered off. 0.81 g of the title compound was obtained.

$^1$H NMR (400 MHz, DMSO-d₆) δ ppm 1.15 (t, 3 H) 3.43 (q, 2 H) 8.02 (br. s., 1 H) 8.10 (d, 1 H) 8.33 (d, 1 H).

Step 3: 5-Bromo-2-(ethylamino)-N-(2-methylbut-3-yn-2-yl)nicotinamide

5-Bromo-2-(ethylamino)nicotinic acid (0.81 g, 3.31 mmol), EDCI (0.760 g, 3.97 mmol), HOBt (0.134 g, 0.992 mmol), DIPEA (1.727 ml, 9.92 mmol) and 1,1-dimethylpropargylamine (0.417 ml, 3.97 mmol) in DCM (10 ml) were stirred at room temperature overnight. The reaction mixture was washed twice with Water, dried with Na₂SO₄ and concentrated. The crude product was purified by flash chromatography. 0.617 g of the title compound was obtained.

$^1$H NMR (400 MHz, CDCl₃) δ ppm 1.23 (t, 3 H) 1.73 (s, 6 H) 2.41 (s, 1 H) 3.44 (qd, 2 H) 6.05 (br. s., 1 H) 7.57 (d, 1 H) 7.98 (br. s., 1 H) 8.20 (d, 1 H).

Example 154

5-Ethoxy-N-(2-methylbut-3-yn-2-yl)-2-(propylamino)benzamide

Step 1: Ethyl 2-amino-5-hydroxybenzoate

2-Amino-5-hydroxybenzoic acid, 97% (1.0 g, 6.53 mmol) and concentrated sulphuric acid (1.6 ml, 11.60 mmol) in ethanol (15 ml) was heated in a microwave reactor at 100° C. for 13 hours. The solvent was evaporated, the mixture was diluted with water and mixture was neutralized by addition of 1M NaOH. The formed precipitate was filtered of to give 1.057 g of the title compound.

$^1$H NMR (400 MHz, DMSO-d₆) δ ppm 1.29 (t, 3 H) 4.22 (q, 2 H) 6.06 (s, 2 H) 6.63 (d, 1 H) 6.80 (dd, 1 H) 7.12 (d, 1 H) 8.65 (s, 1 H).

Step 2: Ethyl 2-acetamido-5-hydroxybenzoate

Ethyl 2-amino-5-hydroxybenzoate (1.05 g, 5.80 mmol) and acetic anhydride (0.547 ml, 5.80 mmol) in ethanol (10 ml) was stirred at 50° C. for 2 hours. Water was added and the formed precipitate was filtered off to give 0.927 g of the title compound.

$^1$H NMR (400 MHz, CDCl₃) δ ppm 1.40 (t, 3 H) 2.23 (s, 3 H) 4.36 (q, 2 H) 6.28 (br. s., 1 H) 7.09 (dd, 1 H) 7.52 (d, 1 H) 8.53 (d, 1 H) 10.85 (br. s., 1 H).

Step 3: Ethyl 2-acetamido-5-ethoxybenzoate

Ethyl 2-acetamido-5-hydroxybenzoate (0.927 g, 4.15 mmol), potassium carbonate (2.87 g, 20.76 mmol) and iodoethane (1.328 ml, 16.62 mmol) in dry acetone (10 ml)

was refluxed for 7 hours. The reaction mixture was evaporated, diluted with DCM, washed with 2× water, dried with $Na_2SO_4$ and concentrated. 0.973 g of the title compound was obtained.

$^1$H NMR (400 MHz, $CDCl_3$) δ ppm 1.39-1.45 (dt, 6 H) 2.21 (s, 3 H) 4.04 (q, 2 H) 4.37 (q, 2 H) 7.10 (dd, 1 H) 7.53 (d, 1 H) 8.60 (d, 1 H) 10.80 (br. s., 1 H).

Step 4: Ethyl 2-amino-5-ethoxybenzoate

Ethyl 2-acetamido-5-ethoxybenzoate, (1.038 g, 4.13 mmol) and 10% HCl/EtOH (10 ml) was refluxed for 3 hours. The reaction mixture was evaporated, diluted with EtOAc, washed with 2× saturated $NaHCO_3$ and brine, dried with $Na_2SO_4$ and concentrated. 0.695 g of the title compound was obtained.

$^1$H NMR (400 MHz, $CDCl_3$) δ ppm 1.38 (t, 6 H) 3.98 (q, 2 H) 4.33 (q, 2 H) 6.63 (d, 1 H) 6.95 (dd, 1 H) 7.38 (d, 1 H).

Step 5: Ethyl 5-ethoxy-2-(propylamino)benzoate

Ethyl 2-amino-5-ethoxybenzoate (0.695 g, 3.32 mmol), propionaldehyde (0.254 ml, 3.49 mmol), acetic acid, glacial (0.475 ml, 8.30 mmol) and sodium triacetoxy borohydride (1.408 g, 6.64 mmol) in 1,2-dichloroethane (10 ml) were stirred at room temperature overnight. This mixture was dissolved in 1,2-dichloroethane (10 ml). Water (10 ml) was added. The organic phase was separated, washed with 1 M $NaHCO_3$ and water, dried with $Na_2SO_4$ and concentrated. The crude product was purified by flash chromatography. 0.369 g of the title compound was obtained.

$^1$H NMR (400 MHz, $CDCl_3$) δ ppm 1.02 (t, 3 H) 1.37 (m, 6 H) 1.62-1.77 (m, 2 H) 3.13 (m, 2 H) 3.97 (q, 2 H) 4.31 (q, 2 H) 6.64 (d, 1 H) 6.98-7.08 (m, 1H) 7.26 (s, 1 H) 7.35 (br. s., 1 H) 7.46 (d, 1 H).

Step 6: 5-Ethoxy-2-(propylamino)benzoic acid

Ethyl 5-ethoxy-2-(propylamino)benzoate (0.369 g, 1.468 mmol) and potassium hydroxide (0.247 g, 4.40 mmol) in methanol (5 ml) and water (3 ml) were stirred at room temperature for 2 days. Methanol was evaporated and the reaction mixture was dissolved in water. The pH adjusted to 2 by addition of 1 M HCl and it was extracted three times with EtOAc. The organic phase was dried with $Na_2SO_4$ and concentrated. The crude product was purified by flash chromatography. 0.191 g of the title compound was obtained.

$^1$H NMR (400 MHz, $CDCl_3$) δ ppm 1.03 (t, 3 H) 1.38 (t, 3 H) 1.70 (sxt, 2 H) 3.16 (t, 2 H) 3.99 (q, 2 H) 6.68 (d, 1 H) 7.09 (dd, 1 H) 7.49 (d, 1 H).

Step 7: 5-Ethoxy-N-(2-methylbut-3-yn-2-yl)-2-(propylamino)benzamide

5-Ethoxy-2-(propylamino)benzoic acid (0.191 g, 0.855 mmol), 1,1-dimethylpropargylamine (0.108 ml, 1.027 mmol), EDCI (0.197 g, 1.027 mmol), HOBt (35 nig, 0.257 mmol) and DIPEA (0.447 ml, 2.57 mmol) in DCM (5 ml) were stirred at room temperature overnight. The reaction mixture was washed twice with water, dried with $Na_2SO_4$ and concentrated. The crude product was purified by flash chromatography. 80 mg of the title, compound was obtained.

$^1$H NMR (400 MHz, $CDCl_3$) δ ppm 0.99 (t, 3 H) 1.38 (t, 3 H) 1.67 (q, 2 H) 1.72 (s, 6 H) 2.38 (s, 1 H) 3.06 (t, 2 H) 3.98 (q, 2 H) 6.27 (br. s., 1 H) 6.70 (br. s., 1 H) 6.92-6.97 (m, 2 H).

Example 155

2-(tert-Butylamino)-5-chloro-N-(2-methylbut-3-yn-2-yl)nicotinamide

Step 1: 2-(tert-Butylamino)-5-chloronicotinic acid 2,5-Dichloronicotinic acid (1.00 g, 5.21 mmol) and tert-butylamine (1.905 g, 26.0 mmol) were heated a microwave reactor at 140° C. for 4 hours. The mixture was diluted in water and the pH was adjusted to 4 by addition of 2 M HCl. It was extracted with 2×EtOAc, dried with $Na_2SO_4$ and concentrated. The crude product was purified by flash chromatography. 0.474 g of the title compound was obtained.

$^1$H NMR (400 MHz, DMSO-$d_6$) δ ppm 1.43 (s, 9 H) 8.01 (d, 1 H) 8.25 (br. s., 1 H) 8.28 (d, 1 H) 13.43 (br. s., 1 H).

Step 2: 2-(tert-Butylamino)-5-chloro-N-(2-methylbut-3-yn-2-yl)nicotinamide 2-(tert-Butylamino)-5-chloronicotinic acid (114 mg, 0.5 mmol), 1,1-dimethyl-propargylamine (0.053 ml, 0.500 mmol), EDCI (0.115 g, 0.600 mmol), HOBt (20.27 mg, 0.150 mmol) and DIPEA (0.175 ml, 1.000 mmol) in DCM (5 ml) were stirred at room temperature overnight. The reaction mixture was washed with 1 M NaOH-solution and water, dried with $Na_2SO_4$ and concentrated. The crude product was purified by preparative HPLC. 77 mg of the title compound was obtained.

$^1$H NMR (400 MHz, $CDCl_3$) δ ppm 1.45 (s, 9 H) 1.73 (s, 6 H) 2.40 (s, 1 H) 5.95 (br. s., 1 H) 7.43 (d, 1 H) 7.96 (br. s., 1 H) 8.12 (d, 1 H).

Example 156

2-(3,3-Difluorocyclobutylamino)-5-fluoro-N-(2-methylbut-3-yn-2-yl)nicotinamide

Step 1: 2-(3,3-Difluorocyclobutylamino)-5-fluoronicotinic acid

2-Chloro-5-fluoropyridine-3-carboxylic acid (0.3 g, 1.709 mmol), 3,3-difluorocyclo-butanamine hydrochloride (0.245 g, 1.709 mmol), copper (10.86 mg, 0.171 mmol), copper(I) bromide (0.025 g, 0.171 mmol) and potassium carbonate (0.472 g, 3.42 mmol) in DMF (3 ml) were heated in a microwave reactor at 140° C. for 1 hour. The mixture was diluted with water, (5 ml) and the pH was adjusted to 3 by addition of 0.5 M HCl. It was extracted three times with EtOAc, dried with $Na_2SO_4$ and concentrated. 0.320 g of the title compound was obtained.

$^1$H NMR (400 MHz, DMSO-$d_6$) δ ppm 2.82-2.94 (m, 2 H) 2.95-3.09 (m, 2 H) 3.99-4.17 (m, 1 H) 7.94 (dd, 1 H) 8.11 (br. s., 1 H) 8.34 (d, 1 H) 13.53 (br. s., 1 H).

Step 2: 2-(3,3-Difluorocyclobutylamino)-5-fluoro-N-(2-methylbut-3-yn-2-yl)nicotinamide 2-(3,3-Difluorocyclobutylamino)-5-fluoronicotinic acid (0.320 g, 1.300 mmol), 1,1-dimethylpropargylamine (0.137 ml, 1.300 mmol), EDCI (0.299 g, 1.560 mmol), HOBt (53 nig 0.390 mmol) and DIPEA (0.679 ml, 3.90 mmol) in DCM (5 ml) were stirred at room temperature overnight. The reaction mixture washed with 1 M NaOH and water, dried with Na$_2$SO$_4$ and concentrated. The crude product was purified by flash chromatography. 44 mg of the title compound was obtained.

$^1$H NMR (400 MHz, CDCl$_3$) δ ppm 1.74 (s, 6 H) 2.42 (s, 1 H) 2.44-2.62 (m, 2 H) 2.93-3.15 (m, 2 H) 4.21-4.44 (m, 1 H) 5.99 (br. s., 1 H) 7.33 (dd, 1 H) 8.09 (br. s., 1 H) 8.12 (d, 1 H).

Example 157

5-Fluoro-2-(4-fluorophenylamino)-N-(2-methylbut-3-yn-2-yl)nicotinamide

Step 1: Ethyl 5-fluoro-2-(4-fluorophenylamino)nicotinate

2-Chloro-5-fluoronicotinic acid ethyl ester (1.00 g, 4.91 mmol) and 4-fluoroaniline (1.092 g, 9.82 mmol) were heated in a microwave reactor at 150° C. for 2 hours. The reaction mixture was then diluted with DCM, washed twice with water, dried with Na$_2$SO$_4$ and concentrated. The crude product was purified by flash chromatography. 0.589 g of the title compound was obtained.

$^1$H NMR (400 MHz, CDCl$_3$) δ ppm 1.42 (t, 3 H) 4.40 (q, 2 H) 6.98-7.08 (m, 2 H) 7.53-7.64 (m, 2 H) 7.98 (dd, 1 H) 8.24 (d, 1 H) 9.96 (br. s., 1 H).

Step 2: 5-Fluoro-2-(4-fluorophenylamino)nicotinic acid

Ethyl 5-fluoro-2-(4-fluorophenylamino)nicotinate (0.589 g, 2.117 mmol) and potassium hydroxide (375 mg, 6.69 mmol) in methanol (8 ml) and water (2 ml) were stirred at room temperature for 2 hours. Methanol was evaporated, the mixture was diluted in water and the pH value was adjusted to 2 by addition of 2 M HCl. The solution was extracted three times with EtOAc. The combined organic phases were dried with Na$_2$SO$_4$ and concentrated. 523 mg of the title compound was obtained.

$^1$H NMR (400 MHz, DMSO-d$_6$) δ ppm 7.10-7.21 (m, 2 H) 7.63-7.72 (m, 2 H) 8.08 (dd, 1 H) 8.42 (d, 1 H) 10.21 (br. s., 1 H).

Step 3: 5-Fluoro-2-(4-fluorophenylamino)-N-(2-methylbut-3-yn-2-yl)nicotinamide 5-Fluoro-2-(4-fluorophenylamino)nicotinic acid (0.523 g, 2.090 mmol), EDCI (0.481 g, 2,508 mmol), HOBt (85 mg, 0.627 mmol), DIPEA (1.092 ml, 6.27 mmol) and 1,1-dimethylpropargylamine (0.264 ml, 2.508 mmol) in DCM (10 ml) were stirred at room temperature overnight. The mixture was washed twice with water, dried with Na$_2$SO$_4$ and concentrated. The crude product was purified by flash chromatography. 0.310 g of the title compound was obtained.

$^1$H NMR (400 MHz, CDCl$_3$) δ ppm 1.77 (s, 6 H) 2.44 (s, 1 H) 6.09 (br. s., 1 H) 6.94-7.07 (m, 2 H) 7.42 (dd, 1 H) 7.50-7.60 (m, 2 H) 8.18 (d, 1 H) 10.03 (br. s., 1 H).

Example 158

5-Fluoro-N-(2-methylbut-3-yn-2-yl)-2-(1,1,1-trifluoropropan-2-ylamino)nicotinamide

Step 1: 5-Fluoro-2-(1,1,1-trifluoropropan-2-ylamino)nicotinic acid

2-Chloro-5-fluoropyridine-3-carboxylic acid (0.199 ml, 1.709 mmol), 1,1,1-trifluoro-isopropylamine (0.193 g, 1.709 mmol), copper (10.86 mg, 0.171 mmol), copper(I) bromide (0.025 g, 0.171 mmol) and potassium carbonate (0.472 g, 3.42 mmol) in DMF (2 ml) were heated in a microwave reactor at 140° C. for 1 hour. The mixture was concentrated and diluted with water (5 ml), and the pH was adjusted to 3 by addition of 0.1 M HCl-solution. The solution was extracted three times with EtOAc. The combined organic phase was dried with Na$_2$SO$_4$ and concentrated. The crude product was purified by preparative HPLC. 7 mg of the title compound was obtained.

$^1$H NMR (400 MHz, MeOD-d$_4$) δ ppm 1.40 (d, 3 H) 5.20 (spt, 1 H) 8.00 (dd, 1 H) 8.22 (d, 1 H).

Step 2: 5-Fluoro-N-(2-methylbut-3-yn-2-yl)-2-(1,1,1-trifluoropropan-2-ylamino)nicotinamide 5-Fluoro-2-(1,1,1-trifluoropropan-2-ylamino)nicotinic acid (7 mg, 0.028 mmol), EDCI (7.98 mg 0.042 mmol), HOBt (1.875 mg, 0.014 mmol), DIPEA (0.015 ml, 0.083 mmol) and 1,1-dimethylpropargylamine (5.84 µl, 0.056 mmol) in DCM (1 ml) were stirred at room temperature overnight. The mixture was washed once with water and twice with 1 M NaOH, dried with Na$_2$SO$_4$ and concentrated. The crude product was purified by flash chromatography. 6 mg of the title compound was obtained.

$^1$H NMR (400 MHz, CDCl$_3$) δ ppm 1.40 (d, 3 H) 1.75 (d, 6 H) 2.42 (s, 1 H) 5.04-5.22 (m, 1H) 5.99 (br. s., 1 H) 7.35 (dd, 1 H) 8.01 (d, 1 H) 8.11 (d, 1 H).

Example 159

4-(4-Chlorophenylamino)-N-(2-methylbut-3-yn-2-yl)nicotinamide

Step 1: 4-(4-Chlorophenylamino)nicotinic acid

4-Chloronicotinic acid (2.00 g, 12.69 mmol) and 4-chloroaniline (1.619 g, 12.69 mmol) in acetonitrile (5 ml) were heated in a microwave reactor at 140° C. for 20 minutes. The reaction mixture was then concentrated and diluted with water. The pH was adjusted to 2 by addition of 1 M HCl. The title compound precipitated and was filtered off and dried in vacuum. 2.73 g of the title compound was obtained.

$^1$H NMR (400 MHz, DMSO-d$_6$) δ ppm 7.05 (d, 1 H) 7.44 (d, 2 H) 7.59 (d, 2 H) 8.27 (d, 1 H) 8.88 (s, 1 H) 11.37 (br. s., 1 H).

Step 2: 4-(4-Chlorophenylamino)-N-(2-methylbut-3-yn-2-yl)nicotinamide 4-(4-Chlorophenylamino)nicotinic acid (249 mg, 1.00 mmol), EDCI (0.230 g, 1.200 mmol), HOBt (40.5 mg, 0.300 mmol), DIPEA (0.348 ml, 2.00 mmol) and 1,1-dimethylpropargylamine (0.126 ml, 1.200 mmol) in DCM (10 ml) were stirred at room temperature overnight. The mixture was washed twice with water, dried with Na$_2$SO$_4$ and concentrated. The crude product was purified by preparative HPLC. 53 mg of the title compound was obtained.

$^1$H NMR (400 MHz, CDCl$_3$) δ ppm 1.77 (s, 6 H) 2.43 (s, 1 H) 6.94 (d, 1 H) 7.15-7.24 (m, 2 H) 7.37-7.48 (m, 2 H) 7.75 (br. s., 1 H) 8.08 (d, 1 H) 9.00 (s, 1 H) 10.93 (br. s., 1 H).

Example 160

5-Fluoro-N-(2-methylbut-3-yn-2-yl)-2-(phenylamino)nicotinamide

Step 1: 5-Fluoro-2-(phenylamino)nicotinic acid

2-Chloro-5-fluoropyridine-3-carboxylic acid (0.331 ml, 2.85 mmol), aniline (0.260 ml, 2.85 mmol), copper (0.018 g, 0.285 mmol), copper(I) bromide (0.041 g, 0.171 mmol) and potassium carbonate (0.787 g, 5.70 mmol) in DMF (5 ml) were heated, in a microwave reactor, to 140° C. over 1 hour. The mixture was concentrated and diluted with water (5 ml), and the pH was adjusted to 3 by addition of 0.1 M HCl. The solution was extracted three times with EtOAc. The combined organic phase was dried with $Na_2SO_4$ and concentrated. The crude product was purified by flash chromatography. 48 mg of the title compound was obtained.

$^1$H NMR (400 MHz, $CDCl_3$) δ ppm 6.96 (t, 1 H) 7.23-7.30 (m, 2 H) 7.36 (d, 1 H) 7.64 (d, 2 H) 7.93-8.07 (m, 1 H) 8.14 (s, 1 H) 10.88 (br. s., 1 H).

Step 2: 5-Fluoro-N-(2-methylbut-3-yn-2-yl)-2-(phenylamino)nicotinamide

5-Fluoro-2-(phenylamino)nicotinic acid (0.048 g, 0.207 mmol), EDCI (0.048 g, 0.248 mmol), HOBt (14 mg, 0.103 mmol), DIPEA (0.072 ml, 0.413 mmol) and 1,1-dimethyl-propargylamine (0.026 ml, 0.248 mmol) in DCM (5 ml) were, stirred at room-temperature overnight. The mixture was washed with water and 1 M NaOH, dried with $Na_2SO_4$ and concentrated. The crude product was purified by flash chromatography. 4.7 mg of the title compound was obtained.

$^1$H NMR (400 MHz, $CDCl_3$) δ ppm 1.77 (s, 6 H) 2.44 (s, 1 H) 6.09 (br. s., 1 H) 7.02 (tt, 1 H) 7.28-7.35 (m, 2 H) 7.43 (dd, 1 H) 7.57-7.67 (m, 2 H) 8.21 (d, 1 H) 10.03 (br. s., 1 H).

Example 161

N-(2-Methylbut-3-yn-2-yl)-4-(4-(trifluoromethyl)phenylamino)-pyrimidine-5-carboxamide

Step 1: 4-(4-(Trifluoromethyl)phenylamino)pyrimidine-5-carboxylic acid

Ethyl 4-(4-(trifluoromethyl)phenylamino)pyrimidine-5-carboxylate (0.133 g, 0.427 mmol) and potassium hydroxide (0.072 g, 1.282 mmol) in methanol (5 ml) and water (1 ml) were stirred at room temperature for 2 hours. Methanol was evaporated and the mixture was diluted with water. The pH was adjusted to 3 by addition of 0.1 M HCl and the solution was extracted three times with EtOAc. The combined organic phase was dried with $Na_2SO_4$ and concentrated. 119 mg of the title compound was obtained.

$^1$H NMR (400 MHz, DMSO-$d_6$) δ ppm 7.74 (d, 2 H) 7.98 (d, 2 H) 8.85 (s, 1 H) 8.97 (s, 1 H) 10.78 (br. s., 1 H).

Step 2: N-(2-Methylbut-3-yn-2-yl)-4-(4-(trifluoromethyl)phenylamino)pyrimidine-5-carboxamide 4-(4-(Trifluoromethyl)phenylamino)pyrimidine-5-carboxylic acid (0.050 g, 0.177 mmol), EDCI (0.041 g, 0.212 mmol), HOBt (0.012 g, 0.088 mmol), DIPEA (0.062 ml, 0.353 mmol) and 1,1-dimethylpropargylamine (0.022 ml, 0.212 mmol) in DCM (5 ml) were stirred at room temperature overnight. The mixture was washed with water and 1 M NaOH, dried with $Na_2SO_4$ and concentrated. The crude product was purified by flash chromatography. 33 mg of the title compound was obtained.

$^1$H NMR (400 MHz, $CDCl_3$) δ ppm 1.79 (s, 6 H) 2.46 (s, 1 H) 6.29 (br. s., 1 H) 7.61 (d, 2 H) 7.85 (d, 2 H) 8.57 (s, 1 H) 8.76 (s, 1 H) 10.97 (br. s., 1 H).

Example 162

2-(tert-Butylamino)-5-fluoro-N-(2-methylbut-3-yn-2-yl)nicotinamide

Step 1: 2-(tert-Butylamino)-5-fluoronicotinic acid 2,5-Difluoronicotinic acid (1 g, 6.29 mmol) and tert-butylamine (6.61 ml, 62.9 mmol) were heated in a microwave reactor at 140° C. for 3 hours. The excess amine was evaporated and water was added. The mixture was made acidic by adding 1 M HCl and it was extracted with 3× ethyl acetate. The organic layer was dried with $Na_2SO_4$ and concentrated. The crude product was purified by flash chromatography. 0.801 g of the title compound was obtained.

$^1$H NMR (400 MHz, DMSO-$d_6$) δ ppm 1.42 (s, 9 H) 7.89 (dd, 1 H) 8.10 (br. s., 1 H) 8.30 (d, 1 H) 13.36 (br. s., 1 H).

Step 2: 2-(tert-Butylamino)-5-fluoro-N-(2-methylbut-3-yn-2-yl)nicotinamide 2-(tert-Butylamino)-5-fluoronicotinic acid (106 mg, 0.500 mmol), 1,1-dimethyl-propargylamine (0.053 ml, 0.500 mmol), EDCI (0.115 g, 0.600 mmol), HOBt (20.27 mg, 0.150 mmol) and DIPEA (0.174 ml, 1.00 mmol) in DCM (5 ml) were stirred at room temperature overnight. The reaction mixture was washed with water and 1 M NaOH, dried with $Na_2SO_4$ and concentrated. The crude product was purified by preparative HPLC. 80 mg of the title compound was obtained.

$^1$H NMR (400 MHz, $CDCl_3$) δ ppm 1.45 (s, 9 H) 1.73 (s, 6 H) 2.40 (s, 1 H) 5.96 (br. s., 1 H) 7.26 (dd, 1 H) 7.71 (br. s., 1 H) 8.09 (d, 1 H).

Example 163

2-(3,3-Difluorocyclobutylamino)-N-(3-ethylpent-1-yn-3-yl)-5-fluoronicotinamide

Step 1: Methyl 2,5-difluoronicotinate 2,5-Difluoronicotinic acid (5 g, 31.4 mmol), potassium carbonate (4.34 g, 31.4 mmol) and iodomethane (2.349 ml, 37.7 mmol) in DMF (30 ml) were stirred at 40° C. overnight. The mixture was diluted with water and extracted with 3× ethyl acetate. The combined organic phases were washed with 5× water, dried with $Na_2SO_4$ and concentrated. 4.4 g of the title compound was obtained.

$^1$H NMR (400 MHz, $CDCl_3$) δ ppm 3.98 (s, 3 H) 8.12 (td, 1 H) 8.24 (dd, 1 H).

Step 2: 2-(3,3-Difluorocyclobutylamino)-5-fluoronicotinic acid

Methyl 2,5-difluoronicotinate (0.15 g, 0.866 mmol), 3,3-difluorocyclobutanamine hydrochloride (0.124 g, 0.866 mmol) and triethylamine (0.242 ml, 1.733 mmol) in acetonitrile (3 ml) were heated in a microwave reactor at 125° C. for 1 hour. The mixture was concentrated and diluted with THF (6 ml) and water (3 ml). Lithium hydroxide (0.062 g, 2.60 mmol) was added at 0° C. and the reaction mixture was stirred at room temperature for 2 hours. It was concentrated, diluted with water and washed with DCM. The pH of the water phase was then adjusted to 1 by addition of 2 M HCl.

The title compound precipitated and was filtered off, washed with water and dried in a vacuum oven. 47 mg of the title compound was obtained.
$^1$H NMR (400 MHz, DMSO-$d_6$) δ ppm 2.54-2.65 (m, 2 H) 2.93-3.07 (m, 2 H) 4.31 (br. s., 1 H) 7.94 (dd, 1 H) 8.17 (br. s., 1 H) 8.33 (d, 1 H)

Step 3: 2-(3,3-Difluorocyclobutylamino)-N-(3-ethylpent-1-yn-3-yl)-5-fluoro-nicotinamide 2-(3,3-Difluorocyclobutylamino)-5-fluoronicotinic acid (47 mg, 0.191 mmol), EDCI (43.9 rig, 0,229 mmol), HOBt (7.74 mg, 0.057 mmol), DIPEA (0.133 ml, 0.764 mmol) and 3-ethylpent-1-yn-3-amine hydrochloride (42.3 mg, 0.286 mmol) in DCM (6 ml) were stirred at room temperature overnight. The reaction mixture was washed twice with water, dried with Na$_2$SO$_4$ and concentrated. The crude product was purified by preparative HPLC. 10.9 mg of the title compound was obtained.
$^1$H NMR (400 MHz, CDCl$_3$) δ ppm 1.04 (t, 6 H) 1.77-1.99 (m, 2 H) 2.17-2.33 (m, 2 H) 2.38-2.61 (m, 3 H) 2.93-3.22 (m, 2 H) 4.14-4.45 (m, 1 H) 5.89 (br. s., 1 H) 7.34 (dd, 1 H) 7.95 (d, 1 H) 8.12 (d, 1 H).

Example 164

2-(3,3-Difluorocyclobutylamino)-5-fluoro-N-(3-methylpent-1-yn-3-yl)nicotinamide 2-(3,3-Difluorocyclobutylamino)-5-fluoronicotinic acid (0.06 g, 0.244 mmol), EDCI (0.056 g, 0.292 mmol), HOBt (9.88 mg, 0.073 mmol), DIPEA (0.170 ml, 0.975 mmol) and 3-amino-3-methyl-1-pentyne hydrochloride (0.039 g, 0.292 mmol) in DCM (5 ml) were stirred at room temperature overnight. The reaction mixture was washed twice with water, dried with. Na$_2$SO$_4$ and concentrated. The crude product was purified by flash chromatography. 46 mg of the title compound was obtained.
$^1$H NMR (400 MHz, CDCl$_3$) δ ppm 1.07 (t, 3 H) 1.72 (s, 3 H) 1.84-1.98 (m, 1 H) 2.10-2.21 (m, 1 H) 2.44 (s, 1 H) 2.45-2.59 (m, 2 H) 2.96-3.12 (m, 2 H) 4.23-4.41 (m, 1 H) 5.94 (br. s., 1 H) 7.32 (dd, 1 H) 8.04 (d, 1 H) 8.12 (d, 1 H).

Example 165

2-(3-Fluoro-5-methoxyphenylamino)-N-(2-methylbut-3-yn-2-yl)nicotinamide

Step 1: Methyl 2-(3-fluoro-5-methoxyphenylamino)nicotinate

2-Fluoronicotinic acid methyl ester (0.4 g, 2.58 mmol) and 3-fluoro-5-methoxyaniline (0.354 ml, 3.09 mmol) were heated by microwave irradiation at 120° C. for 50 min. 0.1 ml (0.873 mmol) of 3-fluoro-5-methoxyaniline was added and mixture was irradiated for 30 min at 120° C. Some DCM was added and mixture was washed twice with H$_2$O. Organic phase was dried over Na$_2$SO$_4$, filtered and evaporated. Crude product was purified by trituration with diethyl ether. 0.293 g of the title compound was obtained.
$^1$H NMR (400 MHz, DMSO-$d_6$) δ ppm 3.78 (s, 3 H) 3.91 (s, 3 H) 6.48 (dt, 1 H) 6.96 (dd, 1 H) 7.03-7.11 (m, 1 H) 7.42 (dt, 1 H) 8.29 (dd, 1 H) 8.48 (dd, 1 H) 10.20 (s, 1 H).

Step 2: 2-(3-Fluoro-5-methoxyphenylamino)nicotinic acid

Lithium hydroxide (0.051 g, 2.121 mmol) was slowly added to a solution of methyl 2-(3-fluoro-5-methoxyphenylamino)nicotinate (0.293 g, 1.061 mmol) in THF (4 ml) and H$_2$O (2 ml) at 0° C. The mixture was stirred at room temperature for 2 h. THF was evaporated, some water was added and mixture was extracted once with DCM. pH of the water phase was adjusted to 4 with 2 M HCl and it was extracted 3 times with EtOAc. Combined organic phases were dried over Na$_2$SO$_4$, filtered and evaporated. 0.273 g of the title compound was obtained.
$^1$H NMR (400 MHz, DMSO-$d_6$) δ ppm 3.77 (s, 3 H) 6.46 (dt, 1 H) 6.93 (dd, 1 H) 7.04-7.12 (m, 1 H) 7.41 (dt, 1 H) 8.27 (dd, 1 H) 8.44 (dd, 1 H) 10.59 (br. s., 1 H) 13.66 (s, 1 H).

Step 3: 2-(3-Fluoro-5-methoxyphenylamino)-N-(2-methylbut-3-yn-2-yl)nicotinamide 2-(3-Fluoro-5-methoxyphenylamino)nicotinic acid (0.050 g, 0.191 mmol), 1,1-dimethylpropargylamine (0.020 ml, 0.191 mmol), HOBt (0.028 g, 0.210 mmol), EDCI (0.040 g, 0.210 mmol) and DIPEA (0.037 ml, 0.210 mmol) in DCM (5 ml) were stirred at room temperature for 3 h. 0.010 ml (0.096 mmol) 1,1-dimethylpropargylamine was added and the mixture was stirred at room temperature overnight. Some DCM was added and the organic phase was washed with 1 M HCl and 1 M Na$_2$CO$_3$, dried over Na$_2$SO$_4$, filtered and evaporated. The crude product was purified by preparative HPLC. 0.027 g of the title compound was obtained.
$^1$H NMR (400 MHz, CDCl$_3$) δ ppm 1.77 (s, 6 H) 2.44 (s, 1 H) 3.80 (s, 3 H) 6.17 (br. s., 1 H) 6.29 (dt, 1 H) 6.73 (dd, 1 H) 6.95-7.00 (m, 1 H) 7.31 (dt, 1 H) 7.66 (dd, 1 H) 8.34 (dd, 1 H) 10.48 (s, 1 H).

Example 166

2-(3-Fluoro-5-methoxyphenylamino)-N-(3-methylpent-1-yn-3-yl)nicotinamide 2-(3-Fluoro-5-methoxyphenylamino)nicotinic acid (0.050 g, 0.191 mmol), 3-amino-3-methyl-1-pentyne hydrochloride (0.025 g, 0.191 mmol), HOBt (0.028 g, 0.210 mmol), EDCI (0.040 g, 0.210 mmol) and DIPEA (0.070 ml, 0.400 mmol) in DCM (5 ml) were stirred at room temperature for 3 h. 0.012 g (0.096 mmol) 3-amino-3-methyl-1-pentyne hydrochloride was added and the mixture was stirred at room temperature overnight. Some DCM was added and the organic phase was washed with 1 M HCl and 1 M Na$_2$CO$_3$, dried over Na$_2$SO$_4$, filtered and evaporated. The crude product was purified by preparative HPLC. 0.030 g of the title compound was obtained.
$^1$H NMR (400 MHz, CDCl$_3$) δ ppm 1.09 (t, 3 H) 1.75 (s, 3 H) 1.85-1.99 (m, 1 H) 2.12-2.26 (m, 1 H) 2.45 (s, 1 H) 3.80 (s, 3 H) 6.11 (br. s., 1 H) 6.29 (dt, 1 H) 6.74 (dd, 1 H) 6.93-7.02 (m, 1 H) 7.30 (dt, 1 H) 7.67 (dd, 1 H) 8.35 (dd, 1 H) 10.44 (s, 1 H).

Example 167

2-(3-Chloro-5-methoxyphenylamino)-N-(2-methylbut-3-yn-2-yl)nicotinamide

Step 1: Methyl 2-(3-chloro-5-methoxyphenylamino)nicotinate

2-Fluoronicotinic acid methyl ester (0.4 g, 2.58 mmol) and 3-chloro-5-methoxyaniline (0.488 g, 3.09 mmol) were heated by microwave irradiation at 120° C. for 50 min. Some DCM was added and mixture was washed twice with H$_2$O.

Organic phase was dried over Na₂SO₄, filtered and evaporated. Crude product was purified by trituration with diethyl ether. 0.451 g of the title compound was obtained.

$^1$H NMR (400 MHz, DMSO-d$_6$) δ ppm 3.78 (s, 3 H) 3.91 (s, 3 H) 6.68 (t, 1 H) 6.97 (dd, 1 H) 7.24 (t, 1 H) 7.59 (t, 1 H) 8.29 (dd, 1 H) 8.48 (dd, 1 H) 10.16 (s, 1 H).

Step 2:
2-(3-Chloro-5-methoxyphenylamino)nicotinic acid

Lithium hydroxide (0.074 g, 3.08 mmol) was slowly added to a solution of methyl 2-(3-chloro-5-methoxyphenylamino)nicotinate (0.451 g, 1.541 mmol) in THF (6 ml) and H₂O (3 ml) at 0° C. The mixture was stirred at room temperature for 2 h. THF was evaporated, some water was added and mixture was extracted once with DCM. pH of the water phase was adjusted to 4 with 2 M HCl and it was extracted 3 times with EtOAc. Combined organic phases were dried over Na₂SO₄, filtered and evaporated. 0.421 g of the title compound was obtained.

$^1$H NMR (400 MHz, DMSO-d$_6$) δ ppm 3.78 (s, 3 H) 6.67 (t, 1 H) 6.94 (dd, 1 H) 7.25 (t, 1 H) 7.56 (t, 1 H) 8.27 (dd, 1 H) 8.45 (dd, 1 H) 10.56 (s, 1 H).

Step 3: 2-(3-Chloro-5-methoxyphenylamino)-N-(2-methylbut-3-yn-2-yl)nicotinamide 2-(3-Chloro-5-methoxyphenylamino)nicotinic acid (0.050 g, 0.179 mmol), 1,1-dimethylpropargylamine (0.019 ml, 0.179 mmol), HOBt (0.027 g, 0.197 mmol), EDCI (0.038 g, 0.197 mmol) and DIPEA (0.066 ml, 0.377 mmol) in DCM (5 ml) were stirred at room temperature for 3 h. 0.010 ml (0.096 mmol) 1,1-dimethylpropargylamine was added and the mixture was stirred at room temperature overnight. Some DCM was added and the organic phase was washed with 1 M HCl and 1 M Na₂CO₃, dried over Na₂SO₄, filtered and evaporated. The crude product was purified by preparative HPLC. 0.025 g of the title compound was obtained.

$^1$H NMR (400 MHz, CDCl₃) δ ppm 1.77 (s, 6 H) 2.44 (s, 1 H) 3.80 (s, 3 H) 6.17 (br. s., 1 H) 6.50-6.59 (m, 1 H) 6.73 (dd, 1 H) 7.21 (t, 1 H) 7.45 (t, 1 H) 7.66 (dd, 1 H) 8.35 (dd, 1 H) 10.47 (s, 1 H).

Example 168

2-(3-Chloro-5-methoxyphenylamino)-N-(3-methylpent-1-yn-3-yl)nicotinamide 2-(3-Chloro-5-methoxyphenylamino)nicotinic acid (0.050 g, 0.179 mmol), 3-amino-3-methyl-1-pentyne hydrochloride (0.024 g, 0.179 mmol), HOBt (0.027 g, 0.197 mmol), EDCI (0.038 g, 0.197 mmol) and DIPEA (0.066 ml, 0.377 mmol) in DCM (5 ml) were stirred at room temperature for 3 h. 0.012 g (0.090 mmol) 3-amino-3-methyl-1-pentyne hydrochloride was added and the mixture was stirred at room temperature overnight. Some DCM was added and, the organic phase was washed with 1 M HCl and 1 M Na₂CO₃, dried over Na₂SO₄, filtered and evaporated. The crude product was purified by preparative HPLC. 0.037 g of the title compound was obtained.

$^1$H NMR (400 MHz, CDCl₃) δ ppm 1.09 (t, 3 H) 1.75 (s, 3 H) 1.85-2.00 (m, 1 H) 2.12-2.25 (m, 1 H) 2.45 (s, 1 H) 3.80 (s, 3 H) 6.11 (s, 1 H) 6.48-6.59 (m, 1 H) 6.74 (dd, 1 H) 7.21 (t, 1 H) 7.44 (t, 1 H) 7.67 (dd, 1 H) 8.35 (dd, 1 H) 10.43 (s, 1 H).

Example 169

2-(2-Fluoro-3-methoxyphenylamino)-N-(2-methylbut-3-yn-2-yl)nicotinamide

Step 1: Methyl 2-(2-fluoro-3-methoxyphenylamino)nicotinate

2-Fluoronicotinic acid methyl ester (0.4 g, 2.58 mmol) and 2-fluoro-3-methoxyaniline (0.340 ml, 2.84 mmol) were heated by microwave irradiation at 120° C. for 45 min. Some DCM was added, and mixture was washed twice with H₂O. Organic phase was dried over Na₂SO₄, filtered and evaporated. 0.633 g of the title compound was obtained.

$^1$H NMR (400 MHz, CDCl₃) δ ppm 3.91 (s, 3 H) 3.95 (s, 3 H) 6.68 (td, 1 H) 6.76 (dd, 1 H) 7.05 (td, 1 H) 8.08 (ddd, 1 H) 8.26 (dd, 1 H) 8.39 (dd, 1 H) 10.30 (br. s., 1 H).

Step 2:
2-(2-Fluoro-3-methoxyphenylamino)nicotinic acid

Lithium hydroxide (0.110 g, 4.58 mmol) was slowly added to a solution of methyl 2-(2-fluoro-3-methoxyphenylamino)nicotinate (0.633 g, 2.291 mmol) in THF (6 ml) and H₂O (3 ml) at 0° C. The mixture was first stirred at room temperature for 2 h and then at 40° C. for 2 h. THF was evaporated, some water was added and mixture was extracted once with DCM. pH of the water phase was adjusted to 4 with 2 M HCl and it was extracted 3 times with EtOAc. Combined organic phases were dried over Na₂SO₄, filtered and evaporated. 0.495 g of the title compound was obtained.

$^1$H NMR (400 MHz, DMSO-d$_6$) δ ppm 3.85 (s, 3 H) 6.84 (td, 1 H) 6.93 (dd, 1 H) 7.09 (td, 1 H) 8.13 (ddd, 1H) 8.28 (dd, 1 H) 8.42 (dd, 1 H) 10.62 (br. s., 1 H) 12.48-15.12 (m, 1 H).

Step 3: 2-(2-Fluoro-3-methoxyphenylamino)-N-(2-methylbut-3-yn-2-yl)nicotinamide 2-(2-Fluoro-3-methoxyphenylamino)nicotinic acid (0.050 g, 0.191 mmol), 1,1-dimethylpropargylamine (0.020 ml, 0.191 mmol), HOBt (0.028 g, 0.210 mmol), EDCI (0.040 g, 0.210 mmol) and DIPEA (0.037 ml, 0.210 mmol) in DCM (5 ml) were stirred at room temperature overnight. In the morning, 0.010 ml (0.096 mmol) 1,1-dimethylpropargylamine was added and the mixture was stirred for 5 h. Some DCM was added and the organic phase was washed with 1 M HCl and 1 M Na₂CO₃, dried over Na₂SO₄, filtered and evaporated. The crude product was purified by preparative HPLC. 0.023 g of the title compound was obtained.

$^1$H NMR (400 MHz, CDCl₃) ppm 1.78 (s, 6 H) 2.42 (s, 1 H) 3.89 (s, 3 H) 6.16 (br. s., 1 H) 6.67 (td, 1 H) 6.72 (dd, 1 H) 7.02 (td, 1 H) 7.67 (dd, 1 H) 7.86 (ddd, 1 H) 8.31 (dd, 1 H) 10.23 (br. s., 1 H).

Example 170

2-(2-Fluoro-3-methoxyphenylamino)-N-(3-methylpent-1-yn-3-yl)nicotinamide 2-(2-Fluoro-3-methoxyphenylamino)nicotinic acid (0.050 g, 0.191 mmol), 3-amino-3-methyl-1-pentyne hydrochloride (0.025 g, 0.191 mmol), HOBt (0.028 g, 0.210 mmol), EDCI (0.040 g, 0.210 mmol) and DIPEA (0.070 ml, 0.400 mmol) in DCM (5 ml) were stirred at room temperature overnight. In the morning, 0.013 g (0.096 mmol)

3-amino-3-methyl-1-pentyne hydrochloride and 0.035 ml (0.200 mmol) DIPEA were added and the mixture was stirred for 5 h. Some DCM was added and the organic phase was washed with 1 M HCl and 1 M $Na_2CO_3$, dried over $Na_2SO_4$, filtered and evaporated. The crude product was purified by preparative HPLC. 0.033 g of the title compound was obtained.

$^1$H NMR (400 MHz, $CDCl_3$) δ ppm 1.07 (t, 3 H) 1.77 (s, 3 H) 1.93 (dq, 1 H) 2.15-2.32 (m, 1 H) 2.43 (s, 1 H) 3.89 (s, 3 H) 6.11 (br. s., 1 H) 6.66 (td, 1 H) 6.73 (dd, 1 H) 7.02 (td, 1 H) 7.67 (dd, 1 H) 7.88 (ddd, 1 H) 8.31 (dd, 1 H) 10.21 (br. s., 1 H).

Example 171

5-Fluoro-2-(4-fluorophenylamino)-N-(3-methylpent-1-yn-3-yl)nicotinamide

5-Fluoro-2-(4-fluorophenylamino)nicotinic acid (0.050 g, 0.200 mmol), 3-amino-3-methyl-1-pentyne hydrochloride (0.029 g, 0.220 mmol), HOBt (0.030 g, 0.220 mmol), EDCI (0.042 g, 0.220 mmol) and DIPEA (0.073 ml, 0.420 mmol) in DCM (5 ml) were stirred at room temperature for 5 h. Some DCM was added and the organic phase was washed with 1 M HCl and 1 M $Na_2CO_3$, dried over $Na_2SO_4$, filtered and evaporated. The crude product was purified by preparative HPLC. 0.034 g of the title compound was obtained.

$^1$H NMR (400 MHz, $CDCl_3$) δ ppm 1.09 (t, 3 H) 1.75 (s, 3 H) 1.88-2.01 (m, 1 H) 2.12-2.26 (m, 1 H) 2.46 (s, 1 H) 6.04 (br. s., 1 H) 6.92-7.09 (m, 2 H) 7.42 (dd, 1 H) 7.50-7.59 (m, 2 H) 8.18 (d, 1 H) 9.99 (s, 1 H).

Example 172

5-Fluoro-N-(3-methylpent-1-yn-3-yl)-2-(phenylamino)nicotinamide

5-Fluoro-2-(phenylamino)nicotinic acid (0.050 g, 0.215 mmol), 3-amino-3-methyl-1-pentyne hydrochloride (0.032 g, 0.237 mmol), HOBt (0.032 g, 0.237 mmol), EDCI (0.045 g, 0.237 mmol) and DIPEA (0.079 ml, 0.452 mmol) in DCM (5 ml) were stirred at room temperature for 3 h. Some DCM was added and the organic phase was washed with 1 M HCl and 1 M $Na_2CO_3$, dried over $Na_2SO_4$, filtered and evaporated. The crude product was purified by preparative HPLC. 0.034 g of the title compound was obtained.

$^1$H NMR (400 MHz, $CDCl_3$) δ ppm 1.08 (t, 3 H) 1.74 (s, 3 H) 1.85-1.98 (m, 1 H) 2.12-2.27 (m, 1 H) 2.46 (s, 1 H) 6.05 (br. s., 1 H) 7.02 (tt, 1 H) 7.28-7.35 (m, 2 H) 7.42 (dd, 1 H) 7.60 (dd, 2 H) 8.21 (d, 1 H) 9.99 (s, 1 H).

Example 173

2-(2,4-Difluorophenylamino)-N-(2-methylbut-3-yn-2-yl)nicotinamide

Step 1: Methyl 2-(2,4-difluorophenylamino)nicotinate

2-Fluoronicotinic acid methyl ester (0.4 g, 2.58 mmol) and 2,4-difluoroaniline (0.310 ml, 3.09 mmol) were heated by microwave irradiation at 130° C. for 20 min. Some DCM was added and mixture was washed twice with $H_2O$. Organic phase was dried over $Na_2SO_4$, filtered and evaporated. 0.554 g of the title compound was obtained.

$^1$H NMR (400 MHz, $CDCl_3$) δ ppm 3.95 (s, 3 H) 6.76 (dd, 1 H) 6.84-6.95 (m, 2 H) 8.26 (dd, 1 H) 8.34-8.46 (m, 2 H) 10.19 (br. s., 1 H).

Step 2: 2-(2,4-Difluorophenylamino)nicotinic acid

Lithium hydroxide (0.100 g, 4.19 mmol) was slowly added to a solution of methyl 2-(2,4-difluorophenylamino) nicotinate (0.554 g, 2.097 mmol) in THF (6 ml) and $H_2O$ (3 ml) at 0° C. The mixture was stirred at room temperature overnight. THF was evaporated, some water was added and mixture was extracted once with DCM. pH of the Water phase as adjusted to 4 with 2 M HCl and it was extracted 3 times with EtOAc. Combined organic phases were dried over $Na_2SO_4$, filtered and evaporated. 0.455 g of the title compound was obtained.

$^1$H NMR (400 MHz, DMSO-$d_6$) δ ppm 6.92 (dd, 1 H) 7.04-7.14 (m, 1 H) 7.34 (ddd, 1 H) 8.27 (dd, 1 H) 8.39 (dd, 1H) 8.46 (td, 1 H) 10.47 (s, 1H) 13.69 (br. s, 1 H).

Step 3: 2-(2,4-Difluorophenylamino)-N-(2-methylbut-3-yn-2-yl)nicotinamide 2-(2,4-Difluorophenylamino)nicotinic acid (0.050 g, 0.200 mmol), 1,1-dimethylpropargylamine (0.023 ml, 0.220 mmol), HOBt (0.030 g, 0.220 mmol), EDCI (0.042 g, 0.220 mmol) and DIPEA (0.038 ml, 0.220 mmol) in DCM (5 ml) were stirred at room temperature overnight. Some DCM was added and the organic phase was washed with 1 M HCl and M $Na_2CO_3$, dried over $Na_2SO_4$, filtered and evaporated. The crude product was purified by preparative HPLC. 0.017 g of the title compound was obtained.

$^1$H NMR (400 MHz, $CDCl_3$) δ ppm 1.78 (s, 6 H) 2.43 (s, 1 H) 6.16 (br. s., 1 H) 6.72 (dd, 1 H) 6.80-6.94 (m, 2 H) 7.67 (dd, 1 H) 8.13-8.23 (m, 1 H) 8.29 (dd, 1 H) 10.23 (br. s., 1 H).

Example 174

2-(2,4-Difluorophenylamino)-N-(3-methylpent-1-yn-3-yl)nicotinamide 2-(2,4-Difluorophenylamino)nicotinic acid (0.050 g, 0.200 mmol), 3-amino-3-methyl-1-pentyne hydrochloride (0.029 g, 0.220 mmol), HOBt (0.030 g, 0.220 mmol), EDCI (0.042 g, 0.220 mmol) and DIPEA (0.073 ml, 0.420 mmol) in DCM (5 ml) were stirred at room temperature overnight. Some DCM was added and the organic phase was washed with 1 M HCl and 1 M $Na_2CO_3$, dried over $Na_2SO_4$, filtered and evaporated. The crude product was purified by preparative HPLC. 0.025 g of the title compound was obtained.

$^1$H NMR (400 MHz, $CDCl_3$) δ ppm 1.08 (t, 3 H) 1.77 (s, 3 H) 1.94 (dq, 1 H) 2.17-2.31 (m, 1 H) 2.44 (s, 1 H) 6.12 (br. s., 1 H) 6.72 (dd, 1 H) 6.81-6.93 (m, 2 H) 7.67 (dd, 1 H) 8.15-8.25 (m, 1 H) 8.29 (dd, 1 H) 10.20 (br. s., 1 H).

Example 175

5-Fluoro-2-(3-fluorophenylamino)-N-(2-methylbut-3-yn-2-yl)nicotinamide

Step 1: Methyl 5-fluoro-2-(3-fluorophenylamino)nicotinate

Methyl 2,5-difluoronicotinate (1.0 g, 5.78 mmol) and 3-fluoroaniline (0.555 ml, 5.78 mmol) were heated by microwave irradiation at 150° C. for 1 h. Some DCM was added and mixture was washed twice with H₂O. Organic phase was dried over Na₂SO₄, filtered and evaporated. The crude product was purified by flash chromatography. 0.180 g of the title compound was obtained.

¹H NMR (400 MHz, CDCl₃) δ ppm 3.96 (s, 3 H) 6.67-6.81 (m, 1 H) 7.18-7.30 (m, 2 H) 7.64-7.81 (m, 1 H) 8.00 (dd, 1 H) 8.31 (d, 1 H) 10.16 (br. s., 1 H).

Step 2: 5-Fluoro-2-(3-fluorophenylamino)nicotinic acid

Lithium hydroxide (0.033 g, 1.362 mmol) was slowly added to a solution of methyl 5-fluoro-2-(3-fluorophenylamino)nicotinate (0.18 g, 0.681 mmol) in THF (4 ml) and H₂O (2 ml) at 0° C. The mixture was stirred at room temperature for 4 h. THF was evaporated, some water was added and, mixture was extracted once with DCM. pH of the water phase was adjusted to 4 with 2 M HCl and it was extracted 3 times with EtOAc. Combined organic phases were dried over Na₂SO₄, filtered and evaporated. 0.159 g of the title compound was obtained.

¹H NMR (400 MHz, DMSO-d₆) δ ppm 6.82 (dddd, 1 H) 7.23-7.39 (m, 2 H) 7.86 (dt, 1 H) 8.12 (dd, 1 H) 8.50 (d, 1 H) 10.47 (s, 1 H).

Step 3: 5-Fluoro-2-(3-fluorophenylamino)-N-(2-methylbut-3-yn-2-yl)nicotinamide

5-Fluoro-2-(3-fluorophenylamino)nicotinic acid (0.040 g, 0.160 mmol), 1,1-dimethylpropargylamine (0.019 ml, 0.176 mmol), HOBt (0.024 g, 0.176 mmol), EDCI (0.034 g, 0.176 mmol) and DIPEA (0.031 ml, 0.176 mmol) in DCM (5 ml) were stirred at room temperature for 5 h. Some DCM was added and the organic phase was washed with 1 M HCl and 1 M Na₂CO₃, dried over Na₂SO₄, filtered and evaporated. The crude product was purified by preparative HPLC. 0.018 g of the title compound was obtained.

¹H NMR (400 MHz, CDCl₃) δ ppm 1.77 (s, 6 H) 2.44 (s, 1 H) 6.11 (br. s., 1 H) 6.65-6.74 (m, 1 H) 7.18-7.25 (m, 2 H) 7.45 (dd, 1 H) 7.66-7.74 (m, 1 H) 8.24 (d, 1 H) 10.26 (s, 1 H).

Example 176

5-Fluoro-2-(3-fluorophenylamino)-N-(3-methylpent-1-yn-3-yl)nicotinamide

5-Fluoro-2-(3-fluorophenylamino)nicotinic acid (0.050 g, 0.200 mmol), 3-amino-3-methyl-1-pentyne hydrochloride (0.029 g, 0.220 mmol), HOBt (0.030 g, 0.220 mmol), EDCI (0.042 g, 0.220 mmol) and DIPEA (0.073 ml, 0.420 mmol) in DCM (5 ml) were stirred at room temperature for 5 h. Some DCM was added and the organic phase was washed with 1 M HCl and 1 M Na₂CO₃, dried over Na₂SO₄, filtered and evaporated. The crude product was purified by preparative HPLC. 0.027 g of the title compound was obtained.

¹H NMR (400 MHz, CDCl₃) δ ppm 1.09 (t, 3 H) 1.75 (s, 3 H) 1.93 (dq, 1 H) 2.11-2.26 (m, 1 H) 2.46 (s, 1 H) 6.06 (br. s., 1 H) 6.64-6.74 (m, 1 H) 7.18-7.25 (m, 2 H) 7.44 (dd, 1 H) 7.65-774 (m, 1 H) 8.24 (d, 1 H) 10.22 (s, 1 H).

Example 177

5-Chloro-2-(3,3-difluorocyclobutylamino)-N-(3-methylpent-1-yn-3-yl)nicotinamide

5-Chloro-2-(3,3-difluorocyclobutylamino)nicotinic acid (0.05 g, 0,190 mmol), 3-mino-3-methyl-1 pentyne HCl (0.031 g, 0.228 mmol), HOBt (0.008 g, 0.06 mmol), EDCI (0.044 g, 0.228 mmol) and DIPEA (0.066 ml, 0.381 mmol) in DCM (5 ml) were stirred at room temperature overnight. The mixture was washed with 1 M NaOH and water, dried over Na₂SO₄, filtered and evaporated. The crude product was purified by preparative HPLC. 0.055 g of the title compound was obtained.

¹H NMR (400 MHz, CDCl₃) δ ppm 1.07 (t, 3 H) 1.72 (s, 3 H) 1.91 (m, 1 H) 2.08-2.23 (m, 1 H) 2.45 (s, 1 H) 2.46-2.61 (m, 2 H) 2.91-3.15 (m, 2 H) 4.24-4.44 (m, 1 H) 5.97 (br. s., 1 H) 7.50 (d, 1 H) 8.16 (d, 1 H) 8.24 (d, 1 H).

Example 178

2-(3-Cyanophenylamino)-5-fluoro-N-(3-methylpent-1-yn-3-yl)nicotinamide 2-(3-Cyanophenylamino)-5-fluoronicotinic acid (0.025 g, 0.097 mmol), 3-amino-3-methyl-1-pentyne hydrochloride (0.014 g, 0.107 mmol), HOBt (0.014 g, 0.107 mmol), EDCI (0.020 g, 0.107 mmol) and DIPEA (0.036 ml, 0.204 mmol) in DCM (5 ml) were stirred at room temperature for 5 h. Some DCM was added and the organic phase was washed with 1 M HCl and 1 M Na₂CO₃, dried over Na₂SO₄, filtered and evaporated. The crude product was purified by preparative HPLC. 0.009 g of the title compound was obtained.

¹H NMR (400 MHz, CDCl₃) δ ppm 1.09 (t, 3 H) 1.76 (s, 3 H) 1.89-1.99 (m, 1 H) 2.14-2.26 (m, 1 H) 2.47 (s, 1 H) 6.09 (br. s., 1 H) 7.21-7.29 (m, 1 H) 7.37 (t, 1 H) 7.47 (dd, 1 H) 7.67 (ddd, 1 H) 8.20-8.31 (m, 2 H) 10.42 (s, 1 H).

Example 179

2-(2-Fluoro-5-methoxyphenylamino)-N-(2-methylbut-3-yn-2-yl)nicotinamide

Step 1: Methyl 2-(2-fluoro-5-methoxyphenylamino)nicotinate

2-Fluoronicotinic acid methyl ester (0.3 g, 1.934 mmol) and 2-fluoro-5-methoxyaniline (0.278 ml, 2.321 mmol) were heated by microwave irradiation at 130° C. for 20 min. Some DCM was added and mixture was washed twice with H₂O. Organic phase was dried over Na₂SO₄, filtered and evaporated. Crude product was purified by trituration with diethyl ether. 0.324 g of the title compound was obtained.

¹H NMR (400 MHz, CDCl₃) δ ppm 3.82 (s, 3 H) 3.95 (s, 3 H) 6.49 (dt, 1 H) 6.78 (dd, 1 H) 7.03 (dd, 1 H) 8.27 (dd, 1 H) 8.33 (dd, 1 H) 8.42 (dd, 1 H) 10.42 (br. s., 1 H).

Step 2: 2-(2-Fluoro-5-methoxyphenylamino)nicotinic acid

Lithium hydroxide (0.056 g, 2.346 mmol) was slowly added to a solution of methyl 2-(2-fluoro-5-methoxyphenylamino)nicotinate (0.324 g, 1.173 mmol) in THF (4 ml) and H₂O (2 ml) at 0° C. The mixture was first stirred at room temperature for 2 h and then at 40° C. for 1.5 h. THF was evaporated, some water was added and mixture was extracted once with DCM. pH of the water phase was adjusted to 4 with 2 M HCl and it was extracted 3 times with EtOAc. Combined organic phases were dried over Na₂SO₄, filtered and evaporated. 0.290 g of the title compound was obtained.

¹H NMR (400 MHz, DMSO-d₆) δ ppm 3.75 (s, 3 H) 6.56 (dt, 1 H) 6.95 (dd, 1 H) 7.18 (dd, 1 H) 8.25-8.35 (m, 2 H) 8.46 (dd, 1 H) 10.76 (br. s., 1 H).

Step 3: 2-(2-Fluoro-5-methoxyphenylamino)-N-(2-methylbut-3-yn-2-yl)nicotinamide 2-(2-Fluoro-5-methoxyphenylamino)nicotinic acid (0.050 g, 0.191 mmol), 1,1-dimethylpropargylamine (0.022 ml, 0.210 mmol), HOBt (0.028 g, 0.210 mmol), EDCI (0.040 g, 0.210 mmol) and DIPEA (0.037 ml, 0.210 mmol) in DCM (5 ml) were stirred at room temperature for 5 h. Some DCM was added and the organic phase was washed with 1 M HCl and 1 M $Na_2CO_3$, dried over $Na_2SO_4$, filtered and evaporated. The crude product was purified by preparative HPLC. 0.020 g of the title compound was obtained.

$^1$H NMR (400 MHz, $CDCl_3$) δ ppm 1.78 (s, 6 H) 2.42 (s, 1 H) 3.80 (s, 3 H) 6.16 (br. s., 1 H) 6.47 (dt, 1 H) 6.74 (dd, 1 H) 7.00 (dd, 1 H) 7.68 (dd, 1 H) 8.11 (dd, 1 H) 8.34 (dd, 1 H) 10.39 (br. s., 1 H).

Example 180

2-(2-Fluoro-5-methoxyphenylamino)-N-(3-methylpent-1-yn-3-yl)nicotinamide 2-(2-Fluoro-5-methoxyphenylamino)nicotinic acid (0.050 g, 0.191 mmol), 3-amino-3-methyl-1-pentyne hydrochloride (0.028 g, 0.210 mmol), HOBt (0.028 g, 0.210 mmol), EDCI (0.040 g, 0.210 mmol) and DIPEA (0.070 ml, 0.400 mmol) in DCM (5 ml) were stirred at room temperature for 5 h. Some DCM was added and the organic phase was washed with 1 M HCl and 1 M $Na_2CO_3$, dried over $Na_2SO_4$, filtered and evaporated. The crude product was purified by preparative HPLC. 0.021 g of the title compound was obtained.

$^1$H NMR (400 MHz, $CDCl_3$) δ ppm 1.07 (t, 3 H) 1.77 (s, 3 H) 1.83-1.99 (m, 1 H) 2.14-2.33 (m, 1 H) 2.43 (s, 1 H) 3.80 (s, 3 H) 6.12 (br. s., 1 H) 6.47 (dt, 1 H) 6.74 (dd, 1 H) 7.00 (dd, 1 H) 7.68 (dd, 1 H) 8.12 (dd, 1 H) 8.34 (dd, 1 H) 10.36 (br. s., 1 H).

Example 181

2-(3-Cyano-4-fluorophenylamino)-N-(2-methylbut-3-yn-2-yl)nicotinamide

Step 1: Methyl 2-(3-cyano-4-fluorophenylamino)nicotinate

2-Fluoronicotinic acid methyl ester (0.3 g, 1.934 mmol) and 3-cyano-4-fluoroaniline (0.253 ml, 2.321 mmol) were heated by microwave irradiation at 120° C. for 80 min. Some DCM was added and mixture was washed twice with $H_2O$. Organic phase was dried over $Na_2SO_4$, filtered and evaporated. 0.461 g of the title compound was obtained.

$^1$H NMR (400 MHz, $CDCl_3$) δ ppm 3.96 (s, 3 H) 6.84 (dd, 1 H) 7.12-7.20 (m, 1 H) 7.73 (ddd, 1 H) 8.28 (dd, 1 H) 8.33 (dd, 1 H) 8.41 (dd, 1 H) 10.34 (s, 1 H).

Step 2: 2-(3-Cyano-4-fluorophenylamino)nicotinic acid

Lithium hydroxide (0.081 g, 3.40 mmol) was slowly added to a solution of methyl 2-(3-cyano-4-fluorophenylamino)nicotinate (0.461 g, 1.700 mmol) in THF (6 ml) and $H_2O$ (3 ml) at 0° C. The mixture was stirred at room temperature for 3.5 h. THF was evaporated, some water was added and mixture was extracted once with DCM. pH of the water phase was adjusted to 4 with 2 M HCl. Formed precipitate was filtrated, washed with small amount of $H_2O$ and dried in the vacuum oven at 40° C. 0.365 g of the title compound was obtained.

$^1$H NMR (400 MHz, DMSO-$d_6$) δ ppm 6.96 (dd, 1 H) 7.48 (t, 1 H) 7.99 (ddd, 1 H) 8.28 (dd, 1 H) 8.38 (dd, 1 H) 8.43 (dd, 1 H) 10.52 (s, 1 H) 13.80 (br. s, 1 H).

Step 3: 2-(3-Cyano-4-fluorophenylamino)-N-(2-methylbut-3-yn-2-yl)nicotinamide 2-(3-Cyano-4-fluorophenylamino)nicotinic acid (0.100 g, 0.389 mmol), 1,1-dimethylpropargylamine (0.045 ml, 0.428 mmol), HOBt (0.058 g, 0.428 mmol), EDCI (0.082 g, 0.428 mmol) and DIPEA (0.074 ml, 0.428 mmol) in DCM (5 ml) were stirred at room temperature for 5 h. Some DCM was added and the organic phase was washed with 1 M HCl and 1 M $Na_2CO_3$, dried over $Na_2SO_4$, filtered and evaporated. The crude product was purified by flash chromatography. 0.068 g of the title compound was obtained.

$^1$H NMR (400 MHz, $CDCl_3$) δ ppm 1.78 (s, 6 H) 2.45 (s, 1 H) 6.21 (br. s., 1 H) 6.80 (dd, 1 H) 7.10-7.17 (m, 1 H) 7.67-7.73 (m, 2 H) 8.32 (dd, 1 H) 8.35 (dd, 1 H) 10.68 (s, 1 H).

Example 182

2-(3-Cyano-4-fluorophenylamino)-N-(3-methylpent-1-yn-3-yl)nicotinamide 2-(3-Cyano-4-fluorophenylamino)nicotinic acid (0.100 g, 0.389 mmol), 3-amino-3-methyl-1-pentyne hydrochloride (0.052 g, 0.389 mmol), HOBt (0.058 g, 0.428 mmol), EDCI (0.082 g, 0.428 mmol) and DIPEA (0,142 ml, 0.816 mmol) in DCM (5 ml) were stirred at room temperature overnight. Some DCM was added and the organic phase was washed with 1 M HCl and 1 M $Na_2CO_3$, dried over $Na_2SO_4$, filtered and evaporated. The crude product was purified by preparative HPLC. 0.069 g of the title compound was obtained.

$^1$H NMR (400 MHz, $CDCl_3$) δ ppm 1.11 (t, 3 H) 1.77 (s, 3 H) 1.90-2.01 (m, 1 H) 2.15-2.27 (m, 1 H) 2.47 (s, 1 H) 6.17 (s, 1 H) 6.81 (dd, 1 H) 7.11-7.18 (m, 1 H) 7.66-7.74 (m, 2 H) 8.32 (dd, 1 H) 8.35 (dd, 1 H) 10.64 (s, 1 H).

Example 183

2-(3-Cyano-5-fluorophenylamino)-N-(2-methylbut-3-yn-2-yl)nicotinamide

Step 1: Methyl 2-(3-cyano-5-fluorophenylamino)nicotinate

2-Fluoronicotinic acid methyl ester (0.3 g, 1.934 mmol) and 3-amino-5-fluorobenzonitrile (0.316 g, 2.321 mmol) were heated by microwave irradiation at 140° C. for 60 min. Some DCM was added and mixture was washed twice with $H_2O$. Organic phase was dried over $Na_2SO_4$, filtered and evaporated. Crude product was purified by flash chromatography. 0.155 g of the title compound was obtained.

$^1$H NMR (400 MHz, $CDCl_3$) δ ppm 3.96 (s, 3 H) 6.88 (dd, 1 H) 6.99 (ddd, 1 H) 7.86-7.98 (m, 2 H) 8.30 (dd, 1 H) 8.45 (dd, 1 H) 10.55 (s, 1 H)

Step 2: 2-(3-Cyano-5-fluorophenylamino)nicotinic acid

Lithium hydroxide (0.027 g, 1.143 mmol) was slowly added to a solution of methyl 2-(3-cyano-5-fluorophenylamino)nicotinate (0.155 g, 0.571 mmol) in THF (6 ml) and H₂O (3 ml) at 0° C. The mixture was stirred at room temperature for 2 h. THF was evaporated, some water was added and mixture was extracted once with DCM. pH of the water phase was adjusted to 4 with 2 M HCl and it was extracted 3 times with EtOAc. Combined organic phases were dried over Na₂SO₄, filtered and evaporated. 0.137 g of the title compound was obtained.

¹H NMR (400 MHz, DMSO-d₆) δ ppm 7.02 (dd, 1 H) 7.38-7.44 (m, 1 H) 8.07 (t, 1 H) 8.15 (dt, 1 H) 8.31 (dd, 1 H) 8.49 (dd, 1 H) 10.77 (s, 1 H).

Step 3: 2-(3-Cyano-5-fluorophenylamino)-N-(2-methylbut-3-yn-2-yl)nicotinamide 2-(3-Cyano-5-fluorophenylamino)nicotinic acid (0.137 g, 0.533 mmol), 1,1-dimethylpropargylamine (0.062 ml, 0.586 mmol), HOBt (0.079 g, 0.586 mmol), EDCI (0.112 g, 0.586 mmol) and DIPEA (0.102 ml, 0.586 mmol) in DCM (5 ml) were stirred at room temperature overnight. Some DCM was added and the organic phase was washed with 1 M HCl and 1 M Na₂CO₃, dried over Na₂SO₄, filtered and evaporated. The crude product was purified by flash chromatography. 0.115 g of the title compound was obtained.

¹H NMR (400 MHz, CDCl₃) δ ppm 1.78 (s, 6 H) 2.45 (s, 1 H) 6.22 (br. s., 1 H) 6.84 (dd, 1 H) 6.95 (ddd, 1 H) 7.72 (dd, 1 H) 7.85 (dt, 1 H) 7.92 (t, 1 H) 8.39 (dd, 1 H) 10.89 (s, 1 H).

Example 184

2-(3-Fluorophenylamino)-N-(3-methylpent-1-yn-3-yl)nicotinamide 2-(3-Fluorophenylamino)nicotinic acid (0.200 g, 0.861 mmol), 3-amino-3-methyl-1-pentyne hydrochloride (0.127 g, 0.947 mmol), HOBt (0.128 g, 0.947 mmol), EDCI (0.182 g, 0.947 mmol) and DIPEA (0.315 ml, 1.809 mmol) in DCM (5 ml) were stirred at room temperature for 6 h. Some DCM was added and the organic phase was washed with 1 M HCl and 1 M Na₂CO₃, dried over Na₂SO₄, filtered and evaporated. The crude product was purified by preparative HPLC. 0.165 g of the title compound was obtained.

¹H NMR (400 MHz, CDCl₃) δ ppm 1.09 (t, 3 H) 1.75 (s, 3 H) 1.93 (dq, 1 H) 2.14-2.26 (m, 1 H) 2.45 (s, 1 H) 6.11 (br. s., 1 H) 6.64-6.79 (m, 2 H) 7.18-7.29 (m, 2 H) 7.67 (dd, 1 H) 7.73-7.81 (m, 1 H) 8.35 (dd, 1 H) 10.46 (s, 1 H).

Example 185

2-(2-Fluorophenylamino)-N-(3-methylpent-1-yn-3-yl)nicotinamide 2-(2-Fluorophenylamino)nicotinic acid, (0.200 g, 0.861 mmol), 3-amino-3-methyl-1-pentyne hydrochloride (0.127 g, 0.947 mmol), HOBt (0.128 g, 0.947 mmol), EDCI (0.182 g, 0.947 mmol) and DIPEA (0.315 ml, 1.809 mmol) in DCM (5 ml) were stirred at room temperature for 6 h. Some DCM was added and the organic phase was washed with 1 M HCl and 1 M Na₂CO₃, dried over Na₂SO₄, filtered and evaporated. The crude product was purified by preparative HPLC. 0.140 g of the title compound was obtained.

¹H NMR (400 MHz, CDCl₃) δ ppm 1.08 (t, 3 H) 1.77 (s, 3 H) 1.94 (dq, 1 H) 2.18-2.31 (m, 1 H) 2.44 (s, 1 H) 6.11 (br. s., 1 H) 6.73 (dd, 1 H) 6.89-7.02 (m, 1 H) 7.05-7.17 (m, 2 H) 7.68 (dd, 1 H) 8.28-8.41 (m, 2 H) 10.30 (br. s., 1 H).

Example 186

2-(3,5-Difluorophenylamino)-N-(3-methylpent-1-yn-3-yl)nicotinamide 2-(3,5-Difluorophenylamino)nicotinic acid (0.100 g, 0.400 mmol), 3-amino-3-methyl-1-pentyne hydrochloride (0.053 g, 0.400 mmol), HOBt (0.059 g, 0.440 mmol), EDCI (0.084 g, 0.440 mmol) and DIPEA (0.146 ml, 0.839 mmol) in DCM (5 ml) were stirred at room temperature for 6 h. Some DCM was added and the organic phase was washed with 1 M HCl and 1 M Na₂CO₃, dried over Na₂SO₄, filtered and evaporated. The crude product was purified by preparative HPLC. 0.064 g of the title compound was obtained.

¹H NMR (400 MHz, CDCl₃) δ ppm 1.09 (t, 3 H) 1.75 (s, 3 H) 1.93 (dq, 1 H) 2.14-2.26 (m, 1 H) 2.46 (s, 1 H) 6.13 (br. s., 1 H) 6.43 (tt, 1 H) 6.79 (dd, 1 H) 7.30-7.41 (m, 2 H) 7.69 (dd, 1 H) 8.37 (dd, 1 H) 10.62 (s, 1 H).

Example 187

2-(3-Cyano-5-fluorophenylamino)-N-(3-methylpent-1-yn-3-yl)nicotinamide 2-(3-Cyano-5-fluorophenylamino)nicotinic acid (0.050 g, 0.194 mmol), 3-amino-3-methyl-1-pentyne hydrochloride (0.026 g, 0.194 mmol), HOBt (0.029 g, 0.214 mmol), EDCI (0.041 g, 0.214 mmol) and DIPEA (0.071 ml, 0.408 mmol) in DCM (5 ml) were stirred at room temperature overnight. Some DCM was added and the organic phase was washed with 1 M HCl and 1 M Na₂CO₃, dried over Na₂SO₄, filtered and evaporated. The crude product was purified by preparative HPLC. 0.032 g of the title compound was obtained.

¹H NMR (400 MHz, CDCl₃) δ ppm 1.09 (t, 3 H) 1.76 (s, 3 H) 1.88-2.02 (m, 1 H) 2.14-2.26 (m, 1 H) 2.46 (s, 1 H) 6.17 (s, 1 H) 6.85 (dd, 1 H) 6.91-6.99 (m, 1 H) 7.72 (dd, 1 H) 7.85 (dt, 1 H) 7.92 (t, 1 H) 8.39 (dd, 1 H) 10.86 (s, 1 H).

Example 188

2-(2-Chloro-5-methoxyphenylamino)-N-(2-methylbut-3-yn-2-yl)nicotinamide

Step 1:
2-(2-Chloro-5-methoxyphenylamino)nicotinic acid

2-Fluoronicotinic acid methyl ester (0.3 g, 1.934 mmol), 6-chloro-m-anisidine hydrochloride (0.610 g, 3.87 mmol) and triethylamine (0.539 ml, 3.87 mmol) were heated by microwave irradiation at 130° C. for 80 min. 0.539 ml (3.87 mmol) triethylamine was added and mixture was irradiated additional 60 min at 130° C. Some DCM was added and mixture was washed twice with H₂O. Organic phase was dried over Na₂SO₄, filtered and evaporated. Crude mixture was purified with flash chromatography to give a mixture of desired product and its methyl ester (97 mg). Lithium hydroxide (0.013 g, 0.553 mmol) was added to this mixture in THF (4 ml) and H₂O (2 ml) at 0° C. After stirring for 3 hours at room temperature, THF was evaporated. Some water was added and mixture was extracted once with DCM. pH of the water phase was adjusted to 4 with 2 M HCl and it was extracted 3 times with EtOAc. Combined organic phases were dried over Na₂SO₄, filtered and evaporated. 0.067 g of the title compound was obtained.

¹H NMR (400 MHz, DMSO-d₆) δ ppm 3.77 (s, 3 H) 6.64 (dd, 1 H) 6.98 (dd, 1 H) 7.40 (d, 1 H) 8.31 (dd, 1 H) 8.41-8.54 (m, 2 H) 10.87 (s, 1 H).

Step 2: 2-(2-Chloro-5-methoxyphenylamino)-N-(2-methylbut-3-yn-2-yl)nicotinamide 2-(2-Chloro-5-methoxyphenylamino)nicotinic acid (0.034 g, 0.122 mmol), 1,1-dimethylpropargylamine (0.013 ml, 0.122 mmol), HOBt (0.018 g, 0.134 mmol), EDCI (0.026 g, 0.134 mmol) and DIPEA (0.045 ml, 0.256 mmol) in DCM (5 ml) were stirred at room temperature for 3 h. 0.013 ml (0.122 mmol) 1,1-dimethylpropargylamine and 0.022 ml (0.128 mmol) DIPEA was added and mixture was stirred at room temperature overnight. Some DCM was added and the organic phase was washed with 1 M HCl and 1 M $Na_2CO_3$, dried over $Na_2SO_4$, filtered and evaporated. The crude product was purified by preparative HPLC. 0.009 g of the title compound was obtained.

$^1$H NMR (400 MHz, $CDCl_3$) δ ppm 1.79 (s, 6 H) 2.42 (s, 1 H) 3.82 (s, 3 H) 6.15 (br. s., 1 H) 6.52 (dd, 1 H) 6.77 (dd, 1 H) 7.29 (m, 1 H) 7.70 (dd, 1 H) 8.24 (d, 1 H) 8.35 (dd, 1 H) 10.34 (s, 1 H).

Example 189

2-(2-Chloro-5-methoxyphenylamino)-N-(3-methyl-pent-1-yn-3-yl)nicotinamide 2-(2-Chloro-5-methoxyphenylamino)nicotinic acid (0.034 g, 0.122 mmol), 3-amino-3-methyl 1-pentyne hydrochloride (0.016 g, 0.122 mmol), HOBt (0.018 g, 0.134 mmol), EDCI (0.026 g, 0.134 mmol) and DIPEA (0.045 ml, 0.256 mmol) in DCM (5 ml) were stirred at room temperature overnight. Some DCM was added and the organic phase was washed with 1M HCl and 0.1 M $Na_2CO_3$, dried over $Na_2SO_4$, filtered and evaporated. The crude product was purified by preparative HPLC. 0.018 g of the title compound was obtained.

$^1$H NMR (400 MHz, $CDCl_3$) δ ppm 1.07 (t, 3 H) 1.78 (s, 3 H) 1.93 (dq, 1 H) 2.21-2.34 (m, 1 H) 2.43 (s, 1 H) 3.81 (s, 3 H) 6.10 (br. s., 1 H) 6.51 (dd, 1 H) 6.77 (dd, 1 H) 7.24-7.30 (m, 1 H) 7.70 (dd, 1 H) 8.24 (d, 1 H) 8.34 (dd, 1 H) 10.31 (s, 1 H).

Example 190

N-(3-Methylpent-1-yn-3-yl)-2-(phenylamino)nicotinamide 2-(Phenylamino)nicotinic acid (0.100 g, 0.467 mmol), 3-amino-3-methyl-1-pentyne hydrochloride (0.062 g, 0.467 mmol), HOBt (0.069 g, 0.513 mmol), EDCI (0.098 g, 0.513 mmol) and DIPEA (0.171 ml, 0.980 mmol) in DCM (5 ml) were stirred at room temperature for 5 h. Some DCM was added and the organic phase was washed with 1 M HCl and 1 M $Na_2CO_3$, dried over $Na_2SO_4$, filtered and evaporated. The crude product was purified by preparative HPLC. 0.051 g of the title compound was obtained.

$^1$H NMR (400 MHz, $CDCl_3$) δ ppm 1.09 (t, 3 H) 1.75 (s, 3 H) 1.93 (dq, 1 H) 2.13-2.27 (m, 1 H) 2.44 (s, 1 H) 6.09 (br. s., 1 H) 6.68 (dd, 1 H) 7.02 (tt, 1 H) 7.28-7.35 (m, 2 H) 7.57-7.71 (m, 3 H) 8.31 (dd, 1 H) 10.25 (s, 1 H).

Example 191

2-(4,4-Difluorocyclohexylamino)-N-(3-methylpent-1-yn-3-yl)nicotinamide 2-(4,4-Difluorocyclohexylamino)nicotinic acid (0.100 g, 0.390 mmol), 3-amino-3-methyl-1-pentyne hydrochloride (0.057 g, 0.429 mmol), HOBt (0.058 g, 0.429 mmol), EDCI (0.082 g, 0.429 mmol) and DIPEA (0.143 ml, 0.820 mmol) in DCM (5 ml) were stirred at room temperature overnight. Some DCM was added and the organic phase was washed with 1 M HCl and 1 M $Na_2CO_3$, dried over $Na_2SO_4$, filtered and evaporated. The crude product was purified by flash chromatography. 0.082 g of the title compound was obtained.

$^1$H NMR (400 MHz, $CDCl_3$) δ ppm 1.06 (t, 3 H) 1.60-1.79 (m, 5 H) 1.79-2.03 (m, 3 H) 2.03-2.27 (m, 5 H) 2.42 (s, 1 H) 4.05-4.24 (m, 1 H) 5.98 (br. s., 1 H) 6.48 (dd, 1 H) 7.45-7.61 (m, 1 H) 8.06 (d, 1 H) 8.20 (dd, 1 H).

Example 192

2-(3-Chloro-4-methoxyphenylamino)-N-(3-methyl-pent-1-yn-3-yl)nicotinamide 2-(3-Chloro-4-methoxyphenylamino)nicotinic acid (0.150 g, 0.538 mmol), 3-amino-3-methyl-1-pentyne hydrochloride (0.072 g, 0.538 mmol), HOBt (0.080 g, 0.592 mmol), EDCI (0.113 g, 0.592 mmol) and DIPEA (0.197 ml, 1.130 mmol) in DCM (5 ml) were stirred at room temperature for 6 h. Some DCM was added and the organic phase was washed with 1 M HCl and 1 M $Na_2CO_3$, dried over $Na_2SO_4$, filtered and evaporated. The crude product was purified by flash chromatography. 0.084 g of the title compound was obtained.

$^1$H NMR (400 MHz, $CDCl_3$) δ ppm 1.09 (t, 3 H) 1.75 (s, 3 H) 1.87-1.99 (m, 1 H) 2.13-2.25 (m, 1 H) 2.45 (s, 1 H) 3.88 (s, 3 H) 6.10 (br. s., 1 H) 6.67 (dd, 1 H) 6.89 (d, 1 H) 7.43 (dd, 1 H) 7.64 (dd, 1 H) 7.80 (d, 1 H) 8.29 (dd, 1 H) 10.21 (s, 1 H).

Example 193

2-(4-Fluoro-3-methoxyphenylamino)-N-(2-methyl-but-3-yn-2-yl)nicotinamide

Step 1: Methyl 2-(4-fluoro-3-methoxyphenylamino)nicotinate

2-Fluoronicotinic acid methyl ester (0.3 g, 1.934 mmol) and 4-fluoro-3-methoxyaniline (0.273 g, 1.934 mmol) were heated by microwave irradiation at 120° C. for 30 min. Some DCM was added and mixture was washed twice with $H_2O$. Organic phase was dried over $Na_2SO_4$, filtered and evaporated. 0.442 g of the title compound was obtained.

$^1$H NMR (400 MHz, $CDCl_3$) δ ppm 3.91 (s, 3 H) 3.94 (s, 3 H) 6.72 (dd, 1 H) 7.03 (dd, 1 H) 7.14 (ddd, 1 H) 7.46 (dd, 1 H) 8.24 (dd, 1 H) 8.36 (dd, 1 H) 10.10 (br. s., 1 H).

Step 2: 2-(4-Fluoro-3-methoxyphenylamino)nicotinic acid

Lithium hydroxide (0.073 g, 3.06 mmol) was slowly added to a solution of methyl 2-(4-fluoro-3-methoxyphenylamino)nicotinate (0.422 g, 1.528 mmol) in THF (6 ml) and $H_2O$ (3 ml) at 0° C. The mixture was stirred at room temperature for 4 h. THF was evaporated, some water was added and mixture was extracted once with DCM. pH of the water phase was adjusted to 4 with 2 M HCl and it was extracted 3 times with EtOAc. Combined organic phases were dried over $Na_2SO_4$, filtered and evaporated. 0.312 g of the title compound was obtained.

¹H NMR (400 MHz, DMSO-d₆) δ ppm 3.85 (s, 3 H) 6.86 (dd, 1 H) 7.13 (dd, 1 H) 7.27 (ddd, 1 H) 7.54 (dd, 1 H) 8.24 (dd, 1 H) 8.37 (dd, 1 H) 10.52 (br. s., 1 H).

Step 3: 2-(4-Fluoro-3-methoxyphenylamino)-N-(2-methylbut-3-yn-2-yl)nicotinamide 2-(4-Fluoro-3-methoxyphenylamino)nicotinic acid (0.100 g, 0.381 mmol), 1,1-dimethylpropargylamine (0.040 ml, 0.381 mmol), HOBt (0.057 g, 0.419 mmol), EDCI (0.080 g, 0.419 mmol) and DIPEA (0.073 ml, 0.419 mmol) in DCM (5 ml) were stirred at room temperature overnight. Some DCM was added and the organic phase was washed with 1 M HCl and 1 M Na₂CO₃, dried over Na₂SO₄, filtered and evaporated. The crude product was purified by preparative HPLC. 0.062 g of the title compound was obtained.

¹H NMR (400 MHz, CDCl₃) δ ppm 1.77 (s, 6 H) 2.44 (s, 1 H) 3.90 (s, 3 H) 6.15 (br. s., 1 H) 6.69 (dd, 1 H) 6.94-7.08 (m, 1 H) 7.19 (ddd, 1 H) 7.35 (dd, 1 H) 7.65 (dd, 1 H) 8.30 (dd, 1 H) 10.32 (s, 1 H).

Example 194

2-(4-Fluoro-3-methoxyphenylamino)-N-(3-methylpent-1-yn-3-yl)nicotinamide 2-(4-Fluoro-3-methoxyphenylamino)nicotinic acid (0.100 g, 0.381 mmol), 3-amino-3-methyl-1-pentyne hydrochloride (0.051 g, 0.381 mmol), HOBt (0.057 g, 0.419 mmol), EDCI (0.080 g, 0.419 mmol) and DIPEA (0.139 ml, 0.801 mmol) in DCM (5 ml) were stirred at room temperature overnight. Some DCM was added and the organic phase was washed with 1 M HCl and 1 M Na₂CO₃, dried over Na₂SO₄, filtered and evaporated. The crude product was purified by flash chromatography. 0.080 g of the title compound was obtained.

¹H NMR (400 MHz, CDCl₃) δ ppm 1.09 (t, 3 H) 1.75 (s, 3 H) 1.86-2.02 (m, 1 H) 2.11-2.26 (m, 1 H) 2.45 (s, 1 H) 3.90 (s, 3 H) 6.11 (br. s., 1 H) 6.69 (dd, 1 H) 7.01 (dd, 1 H) 7.18 (ddd, 1 H) 7.36 (dd, 1 H) 7.66 (dd, 1 H) 8.30 (dd, 1 H) 10.28 (s, 1 H).

Example 195

2-(3,4-Difluorophenylamino)-N-(3-methylpent-1-yn-3-yl)nicotinamide 2-(3,4-Difluorophenylamino)nicotinic acid (0.100 g, 0.400 mmol), 3-amino-3-methyl-1-pentyne hydrochloride (0.053 g, 0.400 mmol), HOBt (0.059 g, 0.440 mmol), EDCI (0.084 g, 0.440 mmol) and DIPEA (0.146 ml, 0.839 mmol) in DCM (5 ml) were stirred at room temperature overnight. Some DCM was added and the organic phase was washed with 1 M HCl and 1 M Na₂CO₃, dried over Na₂SO₄, filtered and evaporated. The crude product was purified by preparative HPLC. 0.083 g of the title compound was obtained.

¹H NMR (400 MHz, CDCl₃) δ ppm 1.09 (t, 3 H) 1.75 (s, 3 H) 1.93 (dq, 1 H) 2.12-2.26 (m, 1 H) 2.45 (s, 1 H) 6.12 (br. s., 1 H) 6.73 (dd, 1 H) 7.07 (dt, 1 H) 7.18 (dddd, 1 H) 7.67 (dd, 1 H) 7.86 (ddd, 1 H) 8.32 (dd, 1 H) 10.42 (s, 1 H).

Example 196

2-(4-Chloro-3-methoxyphenylamino)-N-(2-methylbut-3-yn-2-yl)nicotinamide

Step 1: Methyl 2-(4-chloro-3-methoxyphenylamino)nicotinate

2-Fluoronicotinic acid methyl ester (0.3 g, 1.934 mmol) and 4-chloro-3-methoxyaniline (0.305 g, 1.934 mmol) were heated by microwave irradiation at 120° C. for 20 min. Some DCM was added and mixture was washed twice with H₂O. Organic phase was dried over Na₂SO₄, filtered and evaporated. 0.464 g of the title compound was obtained.

¹H NMR (400 MHz, CDCl₃) δ ppm 3.93 (s, 3 H) 3.94 (s, 3 H) 6.75 (dd, 1 H) 7.18-7.24 (m, 1 H) 7.27-7.30 (m, 1 H) 7.53 (d, 1 H) 8.25 (dd, 1 H) 8.39 (dd, 1 H) 10.24 (s, 1 H).

Step 2: 2-(4-Chloro-3-methoxyphenylamino)nicotinic acid

Lithium hydroxide (0.076 g, 3.17 mmol) was slowly added to a solution of methyl 2-(4-chloro-3-methoxyphenylamino)nicotinate (0.464 g, 1.585 mmol) in THF (6 ml) and H₂O (3 ml) at 0° C. The mixture was stirred at room temperature over weekend. THF was evaporated, some water was added and mixture was extracted once with DCM. pH of the water phase was adjusted to 4 with 2 M HCl and it was extracted 3 times with EtOAc. Combined organic phases were dried over Na₂SO₄, filtered and evaporated. 0.390 g of the title compound was obtained.

¹H NMR (400 MHz, DMSO-d₆) δ ppm 3.87 (s, 3 H) 6.91 (dd, 1 H) 7.30-7.34 (m, 1 H) 7.35-7.41 (m, 1 H) 7.59 (d, 1 H) 8.27 (dd, 1 H) 8.42 (dd, 1 H) 10.51 (s, 1 H) 13.65 (br. s., 1 H).

Step 3: 2-(4-Chloro-3-methoxyphenylamino)-N-(2-methylbut-3-yn-2-yl)nicotinamide 2-(4-Chloro-3-methoxyphenylamino)nicotinic acid (0.070 g, 0.251 mmol), 1,1-dimethylpropargylamine (0.026 ml, 0.251 mmol), HOBt (0.037 g, 0.276 mmol), EDCI (0.053 g, 0.276 mmol) and DIPEA (0.092 ml, 0.527 mmol) in DCM (5 ml) were stirred at room temperature overnight. Some DCM was added and the organic phase was washed with 1 M HCl and 1 M Na₂CO₃, dried over Na₂SO₄, filtered and evaporated. The crude product was purified by flash chromatography. 0.049 g of the title compound was obtained.

¹H NMR (400 MHz, CDCl₃) δ ppm 1.77 (s, 6 H) 2.44 (s, 1 H) 3.92 (s, 3 H) 6.16 (br. s., 1 H) 6.72 (dd, 1 H) 7.26-7.28 (m, 2 H) 7.41 (d, 1 H) 7.67 (dd, 1 H) 8.33 (dd, 1 H) 10.46 (s, 1 H).

Example 197

2-(4-Chloro-3-methoxyphenylamino)-N-(3-methylpent-1-yn-3-yl)nicotinamide 2-(4-Chloro-3-methoxyphenylamino)nicotinic acid (0.070 g, 0.251 mmol), 3-amino-3-methyl-1-pentyne hydrochloride (0.034 g, 0.251 mmol), HOBt (0.037 g, 0.276 mmol), EDCI (0.053 g, 0.276 mmol) and DIPEA (0.092 ml, 0.527 mmol) in DCM (5 ml) were stirred at room temperature overnight. Some DCM was added and the organic phase was washed with 1. M HCl and 1 M Na₂CO₃, dried over Na₂SO₄, filtered and evaporated. The crude product was purified by flash chromatography. 0.080 g of the title compound was obtained.

¹H NMR (400 MHz, CDCl₃) δ ppm 1.09 (t, 3 H) 1.75 (s, 3 H) 1.86-2.00 (m, 1 H) 2.13-2.26 (m, 1 H) 2.46 (s, 1 H) 3.92 (s, 3 H) 6.11 (s, 1 H) 6.72 (dd, 1 H) 7.22-7.29 (m, 2 H) 7.41 (t, 1 H) 7.67 (dd, 1 H) 8.33 (dd, 1 H) 10.42 (s, 1 H)

Example 198

2-(4-Fluorophenylamino)-N-(3-methylpent-1-yn-3-yl)nicotinamide 2-(4-Fluorophenylamino)nicotinic acid (400 mg, 1.723 mmol) was dissolved in DCM (15 ml). EDCI (396 mg, 2.067 mmol), HOBt (69.8 mg, 0.517 mmol), DIPEA (1.200 ml, 6.89 mmol) and 3-amino-3-methyl-1-pentyne HCL (276 mg, 2.067 mmol) were added. The mixture was stirred overnight and washed with water. The organic layer was dried and evaporated to dryness. Flash chromatography gave 255 mg of the title compound.

$^1$H NMR (400 MHz, CDCl$_3$) δ ppm 1.09 (t, 3 H) 1.75 (s, 3 H) 1.93 (m, 1 H) 2.10-2.27 (m, 1 H), 2.45 (s, 1 H) 6.10 (br. s., 1 H) 6.68 (dd, 1 H) 6.96-7.05 (m, 2 H) 7.59 (dd, 2 H) 7.65 (dd, 1 H) 8.28 (dd, 1 H) 10.24 (s, 1 H).

As already mentioned hereinbefore, the compounds of formula I show interesting pharmacological properties, namely they exhibit TRPA1 activity. The said activity is demonstrated with the pharmacological test presented below.

Experiment 1

Determination of TRPA1 Activity In Vitro

The illustrative examples of the present disclosure were screened for TRPA1 activity according to a procedure described in Wei et al., *Anesthesiology* 111 (2009) 147-154. The results are shown in Table 1.

TABLE 1

TRPA1 antagonism in vitro.

| Compound of example | IC50 (µM) |
|---|---|
| 1 | 1.9 |
| 2 | 0.3 |
| 3 | 1.1 |
| 4 | 4.7 |
| 5 | 5.1 |
| 6 | 11.8 |
| 7 | 2.9 |
| 8 | 13.0 |
| 9 | 11.2 |
| 10 | 1.5 |
| 11 | 3.7 |
| 12 | 0.5 |
| 13 | 0.8 |
| 14 | 1.2 |
| 15 | 3.0 |
| 16 | 10.8 |
| 17 | 1.2 |
| 18 | 0.3 |
| 19 | 0.5 |
| 20 | 1.4 |
| 21 | 5.2 |
| 22 | 7.2 |
| 23 | 0.1 |
| 24 | 1.3 |
| 25 | 3.0 |
| 26 | 3.3 |
| 27 | 0.7 |
| 28 | 1.2 |
| 29 | 0.4 |
| 30 | 0.3 |
| 31 | 2.6 |
| 32 | 3.8 |
| 33 | 3.0 |
| 34 | 0.5 |
| 35 | 0.5 |
| 36 | 4.2 |
| 37 | 3.2 |
| 38 | 2.5 |
| 39 | 0.6 |
| 40 | 2.9 |
| 41 | 0.5 |
| 42 | 0.5 |
| 43 | 1.0 |
| 44 | 1.3 |
| 45 | 2.0 |
| 46 | 0.5 |
| 47 | 0.5 |
| 48 | 5.7 |
| 49 | 1.1 |
| 50 | 5.8 |
| 51 | 2.2 |
| 52 | 1.2 |
| 53 | 1.9 |
| 54 | 1.2 |
| 55 | 1.7 |
| 56 | 1.6 |
| 57 | 4.7 |
| 58 | 1.1 |
| 59 | 2.3 |
| 60 | 1.8 |
| 61 | 0.8 |
| 62 | 0.4 |
| 63 | 3.1 |
| 64 | 1.5 |
| 65 | 4.9 |
| 66 | 0.9 |
| 67 | 5.5 |
| 68 | 1.1 |
| 69 | 0.3 |
| 70 | 0.7 |
| 71 | 0.7 |
| 72 | 0.5 |
| 73 | 2.2 |
| 74 | 7.0 |
| 75 | 0.7 |
| 76 | 4.7 |
| 77 | 0.9 |
| 78 | 0.8 |
| 79 | 1.8 |
| 80 | 1.3 |
| 81 | 1.3 |
| 82 | 5.4 |
| 83 | 2.9 |
| 84 | 7.5 |
| 85 | 13.2 |
| 86 | 2.2 |
| 87 | 0.6 |
| 88 | 14.2 |
| 89 | 8.6 |
| 90 | 4.8 |
| 91 | 7.0 |
| 92 | 12.3 |
| 93 | 11.4 |
| 94 | 1.8 |
| 95 | 5.6 |
| 96 | 3.7 |
| 97 | 14.0 |
| 98 | 5.3 |
| 99 | 0.8 |
| 100 | 6.6 |
| 101 | 11.9 |
| 102 | 0.3 |
| 103 | 1.8 |
| 104 | 1.7 |
| 105 | 0.7 |
| 106 | 1.3 |
| 107 | 3.7 |
| 108 | 5.0 |
| 109 | 5.1 |
| 110 | 12.0 |

TABLE 1-continued

TRPA1 antagonism in vitro.

| Compound of example | IC50 (μM) |
|---|---|
| 111 | 2.4 |
| 112 | 3.4 |
| 113 | 7.2 |
| 114 | 4.3 |
| 115 | 4.8 |
| 116 | 1.6 |
| 117 | 2.3 |
| 118 | 12.9 |
| 119 | 18.7 |
| 120 | 8.3 |
| 121 | 1.1 |
| 122 | 4.8 |
| 123 | 3.8 |
| 124 | 0.5 |
| 125 | 4.6 |
| 126 | 8.0 |
| 127 | 4.4 |
| 128 | 1.1 |
| 129 | 0.7 |
| 130 | 2.1 |
| 131 | 1.4 |
| 132 | 13.8 |
| 133 | 5.9 |
| 134 | 4.3 |
| 135 | 5.0 |
| 136 | 8.7 |
| 137 | 9.9 |
| 138 | 12.0 |
| 139 | 0.3 |
| 140 | 5.5 |
| 141 | 0.3 |
| 142 | 5.8 |
| 143 | 3.8 |
| 144 | 2.6 |
| 145 | 3.3 |
| 146 | 5.9 |
| 147 | 5.2 |
| 148 | 14.9 |
| 149 | 0.5 |
| 150 | 1.9 |
| 151 | 0.5 |
| 152 | 2.4 |
| 153 | 10.4 |
| 154 | 7.1 |
| 155 | 0.8 |
| 156 | 1.6 |
| 157 | 0.7 |
| 158 | 4.0 |
| 159 | 11.4 |
| 160 | 1.4 |
| 161 | 1.3 |
| 162 | 3.7 |
| 163 | 0.1 |
| 164 | 0.1 |
| 165 | 4.0 |
| 166 | 0.6 |
| 167 | 3.2 |
| 168 | 0.8 |
| 169 | 34.8 |
| 170 | 4.9 |
| 171 | 0.3 |
| 172 | 0.3 |
| 173 | 1.9 |
| 174 | 0.4 |
| 175 | 0.9 |
| 176 | 0.3 |
| 177 | 0.3 |
| 178 | 0.9 |
| 179 | 10.8 |
| 180 | 1.4 |
| 181 | 2.7 |
| 182 | 0.5 |
| 183 | 1.4 |
| 184 | 0.2 |
| 185 | 0.5 |
| 186 | 0.2 |
| 187 | 0.4 |
| 188 | 16.7 |
| 189 | 3.0 |
| 190 | 0.4 |
| 191 | 0.6 |
| 192 | 0.7 |
| 193 | 11.1 |
| 194 | 1.6 |
| 195 | 0.1 |
| 196 | 3.2 |
| 197 | 0.7 |
| 198 | 0.2 |

In vivo effects of the compounds of formula I can be demonstrated with the measurement of Complete Freund's adjuvant (CFA)-induced mechanical allodynia in rats using von Frey hair test.

Complete Freund's adjuvant (CFA)-induced mechanical hypersensitivity in rats (da Costa et al., *Pain*, 2010, vol. 148, 431-437; Petrus et al., *Molecular Pain*, 2007, vol. 3, 40) is measured using von Frey hairs from 0.07 g to 26 g. A 50% response threshold (g) to light tactile stimuli is quantified by using the up-and-down paradigm (Dixon, *Ann Rev Pharmacol Toxicol*, 1980, vol. 20, 441-462; Chaplan et al., *Journal of Neuroscience Methods*, 1994, vol. 53, 55-63). Mechanical nociceptive threshold is determined before substance administrations (basal level threshold, day 0), 2 days after CFA (25 μg, i.pl.) injection and subsequently following experimental compound administration on day 2. Testing is performed during the light portion of the circadian cycle (between 06:00-18:00 h). Rats are placed in the observation chamber with a wire mesh bottom which allows full access to the paws. Habituation is allowed until chamber exploration and major grooming activities are ceased i.e. ca. 10 to 15 min. The area tested is the mid-plantar right hind paw. Testing is initiated with the 4 g von Frey hair presented perpendicular to the plantar surface with sufficient force to cause slight buckling against the paw, and held for approximately 8 s. A positive response is noted if the paw is sharply withdrawn and/or flinched immediately upon removal of the hair. Tactile stimuli are applied in a consecutive fashion, whether ascending or descending. In the absence of a paw withdrawal response (negative response) to the initially selected hair, a stronger stimulus is presented; in the event of paw withdrawal, the next weaker stimulus is chosen. The 50% threshold is determined by counting of the critical 6 data points according to Dixon (1980); all responses are noted and counting of these critical data points starts once the response threshold is first crossed. The resulting pattern of responses is tabulated as follows X=positive response, 0=negative response, and the 50% response threshold is interpolated using the formula $$50\% \text{ g threshold} = (10^{[X_f + k\delta]})/10{,}000$$

$X_f$=value (log) of the final von Frey hair used, k=tabular value (Dixon 1980, Chaplan et al. 1994) for the pattern of positive/negative responses, δ=mean difference (log) between stimuli. Based on the threshold values following parameter is calculated % Reversal=(Threshold post compound−Threshold post CFA)/(Basal level threshold−Threshold post CFA)*100%

In the repeated dosing set-up, tactile allodynia testing is initiated from 1 day after CFA up to 3 days after CFA. Thus, day 1 representing the acute effect of the experimental compound, and days 2 and 3 indicating the effect of repeated dosing of the experimental compound.

The compounds of formula I exhibit TRPA1 antagonism. The present disclosure thus provides compounds for use as a medicament. Compounds for use in the treatment of disorder, condition or disease mediated by TRPA1 receptor activity are also provided. Furthermore, a method for the treatment of disorder, condition, or disease mediated by TRPA1 receptor activity is provided. In said method an effective amount of at least one compound of formula I is administered to a mammal, such as human, in need of such treatment. The use of the compounds of formula I for the manufacture of a medicament for the treatment of disorder, condition, or disease mediated by TRPA1 receptor activity is also provided.

In one embodiment of the invention the aforementioned disorder, condition, or disease mediated by TRPA1 receptor activity is asthma, cough, allodynia, chronic obstructive pulmonary disease (COPD), tear gas irritation, pain in diabetic polyneuropathy, sleep deprivation-induced pain, sleep deprivation-induced allodynia, neurogenic inflammation, fibromyalgia, pruritus in diabetes, drug-induced pruritus, insect bite-induced pruritus, itch, neurogenic itch, neuropathic itch, psychogenic itch, mechanical hypersensitivity, migraine, neuropathic pain, nerve injury-induced neuropathic pain, postherpetic neuralgia, low back pain, parkinson pain, postherpetic pain, trigeminal neuralgia, neuropathy in diabetes, environmental chemical-induced neuropathy, neuropathy in parkinson disease, alcohol-induced neuropathy, cancer drug-induced neuropathy and pain, cancer drug-induced cold hypersensitivity, diabetic autonomic neuropathy, cardiovascular autonomic neuropathy, gastrointestinal autonomic neuropathy, polydipsia, psychogenic polydipsia, nocturia, overactive urinary bladder, erectile dysfunction, sudomotor dysfunction, primary headache, dental, pain, dental cold hypersensitivity, ear pain, eye pain, spinal cord injury-induced pain, poststroke pain, pancreatitis pain, inflammatory pain, visceral pain, gastric pain, abdominal pain, burn injury-induced pain and allodynia, central pain, coeliac pain, cold pain, cold hypersensitivity, frostbite-induced pain, labor pain, musculoskeletal pain, nausea, vomiting, drug-induced nausea and vomiting, radiation-induced pain and allodynia, opioid-resistant postoperative pain, acute pain, insect bite-induced pain, urticaria, hangover headache, neurocardiogenic syncope, diabetes, severe sepsis, septic shock, sepsis-induced cognitive dysfunction tai cognitive dysfunction following severe sepsis, stroke-induced cognitive dysfunction, cognitive dysfunction, epilepsy, multiple sclerosis, neurodegenerative diseases, delirium, spinal cord injury, gout pain, astrogliosis, acidosis-induced pain, metabolic acidosis-induced pain, acidosis-induced neuropathy, metabolic acidosis-induced neuropathy, allergic contact dermatitis, or diabetic retinopathy; for example neuropathic pain, pain in diabetic polyneuropathy, postoperative pain, cancer pain, migraine, asthma, cough, pain in osteoarthritis, pain in rheumatoid arthritis, inflammatory bowel disease, or diabetes.

The compounds of the present disclosure can be administered, for example, enterally, topically or parenterally by means of any pharmaceutical formulation useful for said administration and comprising at least one active compound of formula I in pharmaceutically acceptable and effective amounts together with pharmaceutically acceptable diluents, carriers, and/or excipients known in the art. The manufacture of such pharmaceutical formulations is known in the art.

The therapeutic dose to be given to a subject in need of the treatment will vary depending on the compound being administered, the species, the age and the sex of the subject being treated, the particular condition being treated, as well as the route and method of administration, and is easily determined by a person skilled in the art. Accordingly, the typical dosage for oral administration is from 10 ng/kg to 100 mg/kg per day and for parenteral administration from 1 ng/kg to 10 mg/kg for an adult mammal.

The compounds of the present disclosure are given to the subject as such or in combination with one or more other active ingredients, each in its own composition or some or all of the active ingredients combined in a single composition, and/or suitable pharmaceutical excipients. Suitable pharmaceutical excipients include conventionally used excipients and formulation aids, such as fillers, binders, disintegrating agents, lubricants, solvents, gel forming agents, emulsifiers, stabilizers, colorants, and/or preservatives.

The compounds of the present disclosure are formulated into dosage forms using commonly known pharmaceutical manufacturing methods. The dosage forms can be, for example, tablets, capsules, granules, suppositories, emulsions, suspensions or solutions. Depending on the route of administration and the galenic form, the amount of the active ingredient in a formulation can typically vary between 0.01% and 100% by weight.

A person skilled in the art will appreciate that the embodiments described herein can be modified without departing from the inventive concept. A person skilled in the art also understands that the present disclosure is not limited to the particular embodiments disclosed but is intended to also cover modifications of the embodiments that are within the scope of the present disclosure.

The invention claimed is:

1. A compound of Formula I,

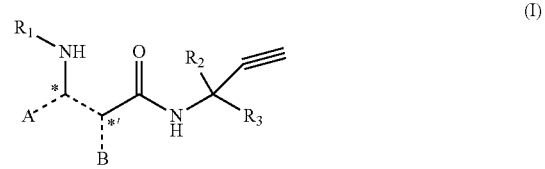

wherein

A and B form, together with the atoms to which they are attached,

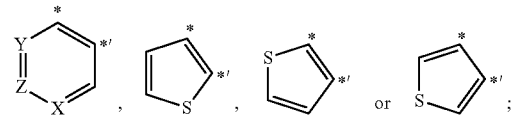

wherein the atoms marked with * and *' are bonded to the parent molecular moiety;

X is $CR_5$ or N;

Y is $CR_6$ or N;

Z is $CR_4$ or N, provided that when Y or X is N, then Z is not N;

$R_1$ is $(C_1$-$C_6)$alkyl, cyclo$(C_3$-$C_6)$alkyl, halo$(C_1$-$C_6)$alkyl, $(C_1$-$C_6)$alkoxy$(C_1$-$C_6)$alkyl, halo$(C_1$-$C_6)$alkoxy$(C_1$-

$C_6$)alkyl, $(C_1-C_6)$alkyl-S—$(C_1-C_6)$alkyl, heterocyclyl, heterocyclyl$(C_1-C_3)$alkyl, phenyl, phenyl$(C_1-C_3)$alkyl, or phenoxy$(C_1-C_6)$alkyl, wherein said cyclo$(C_3-C_6)$alkyl, heterocyclyl, or phenyl is unsubstituted or substituted with 1 or 2 substituent(s) each independently being halogen, $(C_1-C_5)$alkyl, halo$(C_1-C_5)$alkyl, $(C_1-C_5)$alkoxy, cyclo$(C_3-C_6)$alkyl, CN, halo$(C_1-C_5)$alkoxy, $(C_1-C_5)$alkyl-S—, $(C_1-C_5)$alkyl-(S=O)—, $(C_1-C_5)$alkyl-(O=S=O)—, $(C_1-C_3)$alkylamino or di$(C_1-C_3)$alkylamino;

$R_2$ is $(C_1-C_6)$alkyl;

$R_3$ is $(C_1-C_6)$alkyl;

$R_4$ is H, halogen, $(C_1-C_6)$alkyl, $(C_1-C_6)$alkoxy, halo$(C_1-C_6)$alkyl, halo$(C_1-C_6)$alkoxy, $(C_1-C_6)$alkoxy$(C_1-C_6)$alkoxy, $(C_1-C_6)$alkyl-S—, $(C_1-C_6)$alkylamino, halo$(C_1-C_6)$alkylamino, $(C_1-C_6)$alkyl(C=O), CN, or heterocyclyl;

$R_5$ is H, halogen, $(C_1-C_6)$alkyl, cyclo$(C_3-C_6)$alkyl, $(C_1-C_6)$alkoxy, halo$(C_1-C_6)$alkyl, $(C_1-C_6)$alkoxy$(C_1-C_6)$alkyl, halo$(C_1-C_6)$alkoxy, $(C_1-C_6)$alkoxy$(C_1-C_6)$alkoxy, $(C_1-C_6)$alkyl-S—, $(C_1-C_6)$alkyl-(S=O)—, $(C_1-C_6)$alkyl-(O=S=O)—, halo$(C_1-C_6)$alkyl-S—, halo$(C_1-C_6)$alkylamino, $(C_1-C_6)$alkyl(C=O), or CN; and $R_6$ is H, halogen, $(C_1-C_6)$alkyl, or halo$(C_1-C_6)$alkyl;

or $R_1$ and $R_6$ form, together with the atoms to which they are attached, a condensed 5 or 6 membered saturated or unsaturated heterocyclic ring containing, in addition to the nitrogen atom to which $R_1$ is attached, 0 or 1 further heteroatom selected from N, O, and S, wherein said heterocyclic ring is unsubstituted or substituted with 1 or 2 substituent(s) each independently being $(C_1-C_2)$alkyl or halogen;

or $R_4$ and $R_5$ form, together with the carbon ring atoms to which they are attached, a condensed 5, 6 or 7 membered saturated or unsaturated carbocyclic ring or a condensed 5, 6, or 7 membered saturated or unsaturated heterocyclic ring containing 1 or 2 heteroatom(s) selected from N, O, and S, wherein said carbocyclic or heterocyclic ring is unsubstituted or substituted with 1 or 2 substituent(s) each independently being $(C_1-C_2)$alkyl or halogen;

or a pharmaceutically acceptable salt thereof;

with the proviso that the compound is not 2-(methylamino)-N-(2-methylbut-3-yn-2-yl)benzamide or N-(2-methylbut-3-yn-2-yl)-2-(propylamino)benzamide.

2. The compound according to claim 1, wherein

A and B form, together with the atoms to which they are attached,

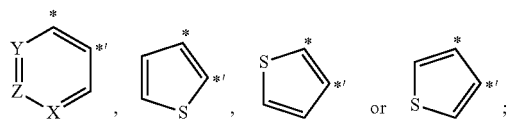

X is $CR_5$ or N;
Y is $CR_6$ or N;
Z is $CR_4$ or N;

$R_1$ is $(C_1-C_6)$alkyl, cyclo$(C_3-C_6)$alkyl, halo$(C_1-C_6)$alkyl, $(C_1-C_6)$alkoxy$(C_1-C_6)$alkyl, halo$(C_1-C_6)$alkoxy$(C_1-C_6)$alkyl, heterocyclyl, heterocyclyl$(C_1-C_3)$alkyl, phenyl, phenyl$(C_1-C_3)$alkyl, or phenoxy$(C_1-C_6)$alkyl, wherein said cyclo$(C_3-C_6)$alkyl, heterocyclyl, or phenyl is unsubstituted or substituted with 1 or 2 substituent(s) each independently being halogen, $(C_1-C_3)$alkyl, halo$(C_1-C_3)$alkyl, $(C_1-C_3)$alkoxy, cyclo$(C_3-C_6)$alkyl, or CN;

$R_2$ is $(C_1-C_6)$alkyl;

$R_3$ is $(C_1-C_6)$alkyl;

$R_4$ is H, halogen, $(C_1-C_6)$alkyl, $(C_1-C_6)$alkoxy, halo$(C_1-C_6)$alkyl, CN or heterocyclyl;

$R_5$ is H, halogen, $(C_1-C_6)$alkyl, $(C_1-C_6)$alkoxy, halo$(C_1-C_6)$alkyl, halo$(C_1-C_6)$alkoxy, $(C_1-C_6)$alkyl-S—, or CN; and $R_6$ is H or halogen;

or $R_1$ and $R_6$ form, together with the atoms to which they are attached, a condensed 5 or 6 membered saturated or unsaturated heterocyclic ring containing, in addition to the nitrogen atom to which $R_1$ is attached, 0 further heteroatoms, wherein said heterocyclic ring is unsubstituted or substituted with 2 substituent(s) each independently being $(C_1-C_2)$alkyl;

or $R_4$ and $R_5$ form, together with the carbon ring atoms to which they are attached, a condensed 5, 6 or 7 membered saturated heterocyclic ring containing 1 or 2 heteroatom(s) which are O, wherein said heterocyclic ring is unsubstituted.

3. The compound according to claim 1, wherein

A and B form, together with the atoms to which they are attached,

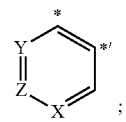

X is $CR_5$ or N;
Y is $CR_6$ or N;
Z is $CR_4$ or N;

$R_1$ is $(C_1-C_6)$alkyl, cyclo$(C_3-C_6)$alkyl, halo$(C_1-C_6)$alkyl, $(C_1-C_6)$alkoxy$(C_1-C_6)$alkyl, halo$(C_1-C_6)$alkoxy$(C_1-C_6)$alkyl, heterocyclyl, heterocyclyl$(C_1-C_3)$alkyl, phenyl, phenyl$(C_1-C_3)$alkyl, or phenoxy$(C_1-C_6)$alkyl, wherein said cyclo$(C_3-C_6)$alkyl, heterocyclyl, or phenyl is unsubstituted or substituted with 1 or 2 substituent(s) each independently being halogen, $(C_1-C_3)$alkyl, halo$(C_1-C_3)$alkyl, $(C_1-C_3)$alkoxy, or cyclo$(C_3-C_6)$alkyl;

$R_2$ is $(C_1-C_6)$alkyl;

$R_3$ is $(C_1-C_6)$alkyl;

$R_4$ is H, halogen, $(C_1-C_6)$alkyl, $(C_1-C_6)$alkoxy, halo$(C_1-C_6)$alkyl, CN or heterocyclyl;

$R_5$ is H, halogen, $(C_1-C_6)$alkyl, $(C_1-C_6)$alkoxy, halo$(C_1-C_6)$alkyl, halo$(C_1-C_6)$alkoxy, $(C_1-C_6)$alkyl-S—, or CN; and $R_6$ is H or halogen;

or $R_1$ and $R_6$ form, together with the atoms to which they are attached, a condensed 5 or 6 membered saturated or unsaturated heterocyclic ring containing, in addition to the nitrogen atom to which $R_1$ is attached, 0 further heteroatoms, wherein said heterocyclic ring is unsubstituted or substituted with 2 substituent(s) each independently being $(C_1-C_2)$alkyl;

or $R_4$ and $R_5$ form, together with the carbon ring atoms to which they are attached, a condensed 5, 6 or 7 membered saturated heterocyclic ring containing 1 or 2 heteroatom(s) which are O, wherein said heterocyclic ring is unsubstituted.

4. The compound according to claim 1, wherein
X is $CR_5$ or N;
Y is $CR_6$ or N;
Z is $CR_4$;
$R_1$ is $(C_1-C_6)$alkyl, cyclo$(C_3-C_6)$alkyl, halo$(C_1-C_6)$alkyl, $(C_1-C_6)$alkoxy$(C_1-C_6)$alkyl, halo$(C_1-C_6)$alkoxy$(C_1-C_6)$alkyl, or phenyl, wherein said cyclo$(C_3-C_6)$alkyl, or phenyl is unsubstituted or substituted with 1 or 2 substituent(s) each independently being halogen, $(C_1-C_3)$alkyl or $(C_1-C_3)$alkoxy;
$R_2$ is $(C_1-C_3)$alkyl;
$R_3$ is $(C_1-C_3)$alkyl;
$R_4$ is H, halogen, $(C_1-C_4)$alkoxy, or halo$(C_1-C_4)$alkyl;
$R_5$ is H, halogen, $(C_1-C_4)$alkyl, $(C_1-C_4)$alkoxy, halo$(C_1-C_4)$alkyl, halo$(C_1-C_4)$alkoxy, or $(C_1-C_4)$alkyl-S—; and
$R_6$ is H or halogen.

5. The compound according to claim 1, wherein
X is $CR_5$ or N;
Y is $CR_6$ or N;
Z is $CR_4$;
$R_1$ is, $(C_1-C_6)$alkyl, cyclo$(C_3-C_6)$alkyl, halo$(C_1-C_6)$alkyl, or phenyl, wherein said cyclo$(C_3-C_6)$alkyl, or phenyl is unsubstituted or substituted with 1 or 2 substituent(s) each independently being halogen, $(C_1-C_3)$alkyl or $(C_1-C_3)$alkoxy;
$R_2$ is $(C_1-C_3)$alkyl;
$R_3$ is $(C_1-C_3)$alkyl;
$R_4$ is H, halogen, $(C_1-C_4)$alkoxy or halo$(C_1-C_4)$alkyl;
$R_5$ is H, halogen, $(C_1-C_4)$alkyl, $(C_1-C_4)$alkoxy, halo$(C_1-C_4)$alkyl, halo$(C_1-C_4)$alkoxy or $(C_1-C_4)$alkyl-S—; and
$R_6$ is H or halogen.

6. The compound according to claim 1, wherein
X is $CR_5$;
Y is $CR_6$;
Z is $CR_4$;
$R_1$ is, $(C_1-C_6)$alkyl, cyclo$(C_3-C_6)$alkyl, halo$(C_1-C_6)$alkyl or phenyl, wherein said cyclo$(C_3-C_6)$alkyl, or phenyl is unsubstituted or substituted with 1 or 2 substituent(s) each independently being halogen, $(C_1-C_2)$alkyl or $(C_1-C_2)$alkoxy;
$R_2$ is $(C_1-C_2)$alkyl;
$R_3$ is $(C_1-C_2)$alkyl;
$R_4$ is H, halogen, $(C_1-C_2)$alkoxy or halo$(C_1-C_2)$alkyl;
$R_5$ is H, halogen, $(C_1-C_2)$alkyl, $(C_1-C_2)$alkoxy, halo$(C_1-C_2)$alkyl, halo$(C_1-C_2)$alkoxy or $(C_1-C_2)$alkyl-S—; and
$R_6$ is H or halogen.

7. The compound according to claim 1, wherein
X is $CR_5$;
Y is N;
Z is $CR_4$;
$R_1$ is, $(C_1-C_6)$alkyl, cyclo$(C_3-C_6)$alkyl, halo$(C_1-C_6)$alkyl or phenyl, wherein said cyclo$(C_3-C_6)$alkyl, or phenyl is unsubstituted or substituted with 1 or 2 substituent(s) each independently being halogen, $(C_1-C_2)$alkyl or $(C_1-C_2)$alkoxy;
$R_2$ is $(C_1-C_2)$alkyl;
$R_3$ is $(C_1-C_2)$alkyl;
$R_4$ is H, halogen, $(C_1-C_2)$alkoxy or halo$(C_1-C_2)$alkyl; and
$R_5$ is H, halogen, $(C_1-C_2)$alkyl, $(C_1-C_2)$alkoxy, halo$(C_1-C_2)$alkyl, halo$(C_1-C_2)$alkoxy or $(C_1-C_2)$alkyl-S—.

8. The compound according to claim 1, wherein
X is $CR_5$ or N;
Y is $CR_6$ or N;
Z is $CR_4$;
$R_1$ is phenyl, wherein said phenyl is unsubstituted or substituted with 1 or 2 substituent(s) each independently being halogen, $(C_1-C_3)$alkyl or $(C_1-C_3)$alkoxy;
$R_2$ is $(C_1-C_3)$alkyl;
$R_3$ is $(C_1-C_3)$alkyl;
$R_4$ is H, halogen, $(C_1-C_4)$alkoxy, or halo$(C_1-C_4)$alkyl;
$R_5$ is H, halogen, $(C_1-C_4)$alkyl, $(C_1-C_4)$alkoxy, halo$(C_1-C_4)$alkyl, halo$(C_1-C_4)$alkoxy, or $(C_1-C_4)$alkyl-S—; and
$R_6$ is H or halogen.

9. The compound according to claim 1, wherein
X is $CR_5$;
Y is N;
Z is $CR_4$;
$R_1$ is phenyl, wherein said phenyl is unsubstituted or substituted with 1 or 2 substituent(s) each independently being halogen, $(C_1-C_2)$alkyl or $(C_1-C_2)$alkoxy;
$R_2$ is $(C_1-C_2)$alkyl;
$R_3$ is $(C_1-C_2)$alkyl;
$R_4$ is H, halogen, $(C_1-C_2)$alkoxy or halo$(C_1-C_2)$alkyl; and
$R_5$ is H, halogen, $(C_1-C_2)$alkyl, $(C_1-C_2)$alkoxy, halo$(C_1-C_2)$alkyl, halo$(C_1-C_2)$alkoxy or $(C_1-C_2)$alkyl-S—.

10. The compound according to claim 1, wherein X is $CR_5$, Y is N, and Z is $CR_4$.

11. The compound according to claim 1, wherein X is $CR_5$, Y is $CR_6$, and Z is $CR_4$.

12. The compound according to claim 1, wherein the compound is 5-fluoro-N-(2-methylbut-3-yn-2-yl)-2-(3,3,3-trifluoropropylamino)nicotinamide, N-(2-methylbut-3-yn-2-yl)-5-(trifluoromethyl)-2-(3,3,3-trifluoropropylamino)nicotinamide, 5-chloro-N-(2-methylbut-3-yn-2-yl)-2-(propylamino)benzamide, 5-chloro-2-(isopropylamino)-N-(2-methylbut-3-yn-2-yl)benzamide, 5-chloro-2-(2,2-difluoroethylamino)-N-(2-methylbut-3-yn-2-yl)benzamide, N-(2-methylbut-3-yn-2-yl)-7-(3,3,3-trifluoropropylamino)-2,3-dihydrobenzo[b][1,4]dioxine-6-carboxamide, 6-(isobutylamino)-N-(2-methylbut-3-yn-2-yl)benzo[d][1,3]dioxole-5-carboxamide, 8-(isobutylamino)-N-(2-methylbut-3-yn-2-yl)-3,4-dihydro-2H-benzo[b][1,4]dioxepine-7-carboxamide, 7-(isobutylamino)-N-(2-methylbut-3-yn-2-yl)-2,3-dihydrobenzo[b][1,4]dioxine-6-carboxamide, 2-(2,2-difluoroethylamino)-N-(2-methylbut-3-yn-2-yl)-5-(trifluoromethyl)benzamide, N-(2-methylbut-3-yn-2-yl)-2-(trifluoromethyl)-4-(3,3,3-trifluoropropylamino) pyrimidine-5-carboxamide, N-(2-methylbut-3-yn-2-yl)-5-(trifluoromethyl)-2-(3,3,3trifluoropropyl-amino)benzamide, 4-chloro-N-(2-methylbut-3-yn-2-yl)-2-(propylamino)benzamide, 5-chloro-N-(2-methylbut-3-yn-2-yl)-2-(2,2,2-trifluoroethylamino)benzamide, 3-fluoro-N-(2-methylbut-3-yn-2-yl)-2-(3,3,3-trifluoropropylamino)benzamide, 3-fluoro-N-(2-methylbut-3-yn-2-yl)-2-(propylamino)benzamide, 2-(cyclobutylamino)-4,5-difluoro-N-(2-methylbut-3-yn-2-yl)benzamide, N-(2-methylbut-3-yn-2-yl)-2-(2,2,3,3,3-pentafluoropropylamino)-5-(trifluoro methyl)benzamide, N-(2-methylbut-3-yn-2-yl)-2-(2,2,3,3,3-pentafluoropropylamino) benzamide, 2-(2,2-difluoroethylamino)-5-fluoro-N-(3-methylpent-1-yn-3-yl)nicotinamide, 2-(cyclobutylamino)-3-fluoro-N-(2-methylbut-3-yn-2-yl)benzamide, 5-fluoro-N-(2-methylbut-3-yn-2-yl)-2-(2,2,2-trifluoroethylamino)-benzamide, 2-(cyclobutylamino)-N-(2-methylbut-3-yn-2-yl)-5-(trifluoromethyl)benzamide, 2-(cyclobutylamino)-5-fluoro-N-(2-methylbut-3-yn-2-yl)benzamide, 2-(cyclobutylamino)-5-fluoro-N-(2-methylbut-3-yn-2-yl) nicotinamide, 5-chloro-2-(isopropylamino)-N-(2-methylbut-3-yn-2-yl)nicotinamide, 5-chloro-2-(cyclobutylamino)-N-(2-methylbut-3-yn-2-yl)nicotinamide, 2-(isopropylamino)-N-(2-methylbut-3-yn-2-yl)-5-(trifluoromethyl)nicotinamide, 5-fluoro-N-(2-methylbut-3-yn-2-yl)-2-(2,2,3,3,3-pentafluoropropylamino)nicotinamide, 5-methyl-N-(2-methylbut-3-yn-2-yl)-2-(2,2,3,3,3-pentafluoropropylamino)benzamide, 5-fluoro-N-(2-methylbut-3- yn-2-yl)-2-(2,2,3,3,3-pentafluoropropylamino)benzamide, 5-chloro-2-(2,2-difluoroethyl-amino)-N-(2-methylbut-3-yn-2-yl)nicotinamide, 5-fluoro-N-(2-methylbut-3-yn-2-yl)-2-(2,2,2-trifluoroethylamino)nicotinamide, 5-chloro-N-(2-methylbut-3-yn-2-yl)-2-(2,2,2-trifluoroethylamino)nicotinamide, N-(2-methylbut-3-yn-2-yl)-2-(2,2,2-trifluoroethyl-amino)-5-(trifluoromethyl)nicotinamide, 5-cyano-2-(cyclobutylamino)-N-(2-methylbut-3-yn-2-yl)benzamide, 4-cyano-2-(cyclobutylamino)-N-(2-methylbut-3-yn-2-yl)benzamide, 4,5-difluoro-N-(2-methylbut-3-yn-2-yl-2-(2,2,2-trifluoroethylamino)-benzamide, N-(2-methylbut-3-yn-2-yl)-2-(2,2,2-trifluoroethylamino)-5-(trifluoromethyl)benzamide, 5-methyl-N-(2-methylbut-3-yn-2-yl)-2-(2,2,2-trifluoroethylamino)benzamide, 5-chloro-N-(2-methylbut-3-yn-2-yl)-2-(3,3,3-trifluoropropylamino)nicotinamide, 2-(butylamino)-4,5-difluoro-N-(2-methylbut-3-yn-2-yl)benzamide, 5-bromo-N-(3-ethylpent-1-yn-3-yl)-2-(2-methoxyethylamino)-benzamide, 5-chloro-N-(3-ethylpent-1-yn-3-yl)-2-(2-methoxyethylamino)benzamide, N-(3-ethylpent-1-yn-3-yl)-4,5-difluoro-2-(2-methoxyethyl-amino)benzamide, N-(3-ethylpent-1-yn-3-yl)-2-(2-methoxyethylamino)-5-(trifluoromethyl)benzamide, N-(3-ethylpent-1-yn-3-yl)-5-iodo-2-(2-methoxyethylamino)benzamide, 2-(methoxyethyl-amino)-N-(2-methylbut-3-yn-2-yl)-5-(trifluoromethyl)benzamide, 2-(butylamino)-5-fluoro-N-(2-methylbut-3-yn-2-yl)benzamide, 5-iodo-2(2-methoxyethylamino)-N-(2-methylbut-3-yn-2-yl)benzamide, 5-fluoro-2-(isobutylamino)-N-(2-methylbut-3-yn-2-yl)nicotinamide, 5-fluoro-2-(isopentylamino)-N-(2-methylbut-3-yn-2-yl)nicotinamide, 5-fluoro-N-(2-methylbut-3-yn-2-yl)-2-(2-(trifluoromethoxy)ethylamino)benzamide, 5-fluoro-N-(2-methylbut-3yn-2-yl)-2-(4,4,4-trifluorobutylamino)benzamide, 3,5-difluoro-N-(2-methylbut-3-yn-2-yl)-2-(3,3,3-trifluoropropylamino)benzamide, 2-(2,2-difluoroethylamino)-N-(2-methylbut-3-yn-2-yl)-5-(trifluoromethyl)nicotinamide, 2-(2,2-difluoropropylamino)-5-fluoro-N-(2-methylbut-3-yn-2-yl)nicotinamide, 2-(3,3-difluoropropylamino)-N-(2-methylbut-3-yn-2-yl)-5-(trifluoromethyl)nicotinamide, 5-chloro-2-(2,2-difluoropropylamino)-N-(2-methylbut-3-yn-2-yl)nicotinamide, 5-chloro-2-(3,3-difluoropropylamino)-N-(2-methylbut-3-yn-2-yl)nicotinamide, 4,5-difluoro-N-(2-methylbut-3-yn-2-yl)-2-(neopentylamino)benzamide, 4,5-difluoro-2-(isobutylamino)-N-(2-methylbut-3-yn-2-yl)benzamide, 4,5-difluoro-N-(2-methylbut-3-yn-2-yl)-2-(propylamino)benzamide, 2-(butylamino)-N-(2-methylbut-3-yn-2-yl)benzamide, 2-(ethylamino)-4,5-difluoro-N-(2-methylbut-3-yn-2-yl)benzamide, 4,5-difluoro-N-(2-methylbut-3-yn-2-yl)-2-(3,3,3-trifluoropropylamino)benzamide, 4,5-difluoro-2-(isopropylamino)-N-(2-methylbut-3-yn-2-yl)benzamide, N-(3,5-dimethylhex-1-yn-3-yl)-4,5-difluoro-2-(isobutylamino)benzamide, N-(3,4-dimethylpent-1-yn-3-yl)-4,5-difluoro-2-(isobutylamino)benzamide, 4,5-difluoro-2-(isobutylamino)-N-(3-methylhex-1-yn-3-yl)benzamide, 4-fluoro-N-(2-methylbut-3-yn-2-yl)-2-(3,3,3-trifluoropropyl-amino)benzamide, N-(2-methylbut-3-yn-2-yl)-4-(trifluoromethyl)-2-(3,3,3-trifluoropropylamino)benzamide, 4-methoxy-N-(2-methylbut-3-yn-2-yl)-2-(3,3,3-trifluoropropylamino)benzamide, 4-methoxy-N-(2-methylbut-3-yn-2-yl)-2-(propylamino)benzamide, N-(2-methylbut-3-yn-2-yl)-5-(trifluoromethoxy)-2-(3,3,3-trifluoropropylamino)benzamide, 5-methoxy-N-(2-methylbut-3-yn-2-yl)-2-(3,3,3-trifluoropropylamino)benzamide, 5-methyl-N-(2-methylbut-3-yn-2-yl)-2-(3,3,3-trifluoropropylamino)benzamide, N-(2-methylbut-3-yn-2-yl)-5-(methylthio)-2-(3,3,3-trifluoropropylamino)benzamide, N-(2-methylbut-3-yn-2-yl)-2-(3,3,3-trifluoropropyl-amino)benzamide, 2-(isobutylamino)-N-(2-methylbut-3-yn-2-yl)benzamide, N-(2-methylbut-3-yn-2-yl)-2-(neopentylamino)benzamide, 2-(tert-butylamino)-4,5-difluoro-N-(2-methylbut-3-yn-2-yl) benzamide, 4-fluoro-2-(isopropylamino)-N-(2-methylbut-3-yn-2-yl)benzamide, 2-(methylamino)-N-(2-methylbut-3-yn-2-yl)-4-(trifluoromethyl)-benzamide, 2-(methylamino)-N-(2-methylbut-3-yn-2-yl)-5-(trifluoromethoxy)-benzamide, 2-(cyclopropylamino)-4,5-difluoro-N-(2-methylbut-3-yn-2-yl)benzamide, N-(3,4-dimethylpent-1-yn-3-yl)-2-(ethylamino)-4,5-difluorobenzamide, 2-(isobutylamino)-4,5-dimethoxy-N-(2-methylbut-3-yn-2-yl)benzamide, 2-(2-methoxy-ethylamino)-N-(2-methylbut-3-yn-2-yl)-4-(trifluoromethyl)benzamide, 2-(cyclopropyl-amino)-4-fluoro-N-(2-methylbut-3-yn-2-yl)benzamide, 2-(cyclopropylamino)-5-fluoro-N-(2-methylbut-3-yn-2-yl)benzamide, 5-fluoro-2-(isopropylamino)-N-(2-methylbut-3-yn-2-yl)benzamide, 2-(isopropylamino)-5-methyl-N-(2-methylbut-3-yn-2-yl)benzamide, 4-methyl-N-(2-methylbut-3-yn-2-yl)-2-(3,3,3-trifluoropropylamino)benzamide, 5-chloro-3-fluoro-2-(isopropylamino)-N-(2-methylbut-3yn-2-yl)benzamide, 5-methoxy-N-(2-methylbut-3-yn-2-yl)-2-(4,4,4-trifluorobutylamino)benzamide, 2-(3-methoxy-benzylamino)-N-(2-methylbut-3-yn-2-yl)nicotinamide, 2-(3-fluorobenzylamino)-N-(2-methylbut-3-yn-2-yl)nicotinamide, N-(2-methylbut-3-yn-2-yl)-2-(propylamino)-6-(trifluoromethyl)nicotinamide, 2-(butylamino)-N-(2-methylbut-3-yl)nicotinamide, 2-(tert-butylamino)-N-(2-methylbut-3-yn-2-yl)nicotinamide, 2-(butylamino)-5-fluoro-N-(3-methylpent-1-yn-3-yl)benzamide, 2-(ethylamino)-N-(3-ethylpent-1-yn-3-yl)-5-fluorobenzamide, 5-fluoro-N-(2-methylbut-3-yn-2-yl)-2-(3,3,3-trifluoropropylamino)-benzamide, 2-(isobutylamino)-N-(2-methylbut-3-yn-2-yl)-6-(trifluoromethyl)-nicotinamide, 2-(isopropylamino)-N-(2-methylbut-3-yn-2-yl)-6-(trifluoromethyl)-nicotinamide, 2-(ethylamino)-N-(2-methylbut-3-yn-2-yl)-6-(trifluoromethyl)-nicotinamide, 4-(tert-butylamino)-N-(2-methylbut-3-yn-2-yl)-2-(trifluoromethyl)-pyrimidine-5-carboxamide, N-(2-methylbut-3-yn-2-yl)-4-(tert-pentylamino)-2-(trifluoromethyl)pyrimidine-5-carboxamide, 4-(isopropylamino)-N-(2-methylbut-3-yn-2-yl)-2-(trifluoromethyl)pyrimidine-5-carboxamide, 2-(tert-butylamino)-N-(2-methylbut-3-yn-2-yl)-6-(trifluoromethyl)nicotinamide, 6-chloro-2-(isopropylamino)-N-(2-methylbut-3-yn-2-yl)nicotinamide, 6-chloro-2-(ethylamino)-N-(2-methylbut-3-yn-2-yl)nicotinamide, 5-fluoro-2-(isopropylamino)-N-(2-methylbut-3-yn-2-yl)-6-morpholinonicotinamide, N-(2-methylbut-3-yn-2-yl)-2-(tetrahydro-2H-pyran-4-ylamino)-6-(trifluoromethyl)nicotinamide, N-(2-methylbut-3-yn-2-yl)-2-((tetrahydro-2H-pyran-4-yl)methylamino)-6-(trifluoromethyl)nicotinamide, 2-(cyclopropylamino)-N-(2-methylbut-3-yn-2-yl)-6-(trifluoromethyl)nicotinamide, 2,3-dimethyl-N-(2-methylbut-3-yn-2-yl)-1H-indole-7-carboxamide, N-(3-ethylpent-1-yn-3-yl)-1H-indole-7-carboxamide, N-(3-ethylpent-1-yn-3-yl)-1,2,3,4-tetrahydroquinoline-8-carboxamide, 2-(3-fluorophenylamino)-N-(2-methylbut-3-yn-2-yl)nicotinamide, 2-(2-fluorophenyl-amino)-N-(2-methylbut-3-yn-2-yl)nicotinamide, 2-(4,4-difluorocyclohexylamino)-N-(2-methylbut-3-yn-2-yl)nicotinamide, 5-bromo-N-(2-methylbut-3-yn-2-yl)-2-(propylamino)-benzamide, N-(2-methylbut-3-yn-2-yl)-2-(1,1-trifluoro-2-methyl-propan-2-ylamino)nicotinamide, N-(2-methylbut-3-yn-2-yl)-4-(propylamino)thiophene-3-carboxamide, N-(2-methylbut-3-yn-2-yl)-2-(phenylamino)nicotinamide, 2-(tert-butylamino)-N-(2-methylbut-3-yn-2-yl)-5-(trifluoromethyl)-nicotinamide, 5-chloro-N-(2-methylbut-3- yn-2-yl)-2-(phenylamino)nicotinamide, 2-(butylamino)-N-(2-methylbut-3-yn-2-yl)thiophene-3-carboxamide, 2-(4-fluorophenylamino)-N-(2-methylbut-3-yn-2-yl)nicotinamide, N-(2-methylbut-3-yn-2-yl)-4-(2,2,3,3-pentafluoropropylamino)-pyrimidine-5-carboxamide, 2-(3,3-difluorocyclobutylamino)-N-(2-methylbut-3-yn-2-yl)nicotinamide, 3-((4-chlorophenyl)amino-N-(2-methylbut-3-yn-2-yl)isonicotinamide, 2-(3,3-difluoropropylamino)-3,5-difluoro-N-(2-methylbut-3-yn-2-yl)benzamide, 3-(isobutylamino)-N-(2-methylbut-3-yn-2-yl)thiophene-2-carboxamide, 5-fluoro-N-(2-methylbut-3-yn-2-yl)-2-(3-methylisothiazol-5-ylamino)nicotinamide, 5-chloro-N-(2-methylbut-3-yn-2-yl)-2-(pyridin-3-ylamino)nicotinamide, 5-chloro-2-(3,3-difluoro-cyclobutylamino)-N-(2-methyl-but-3-yn-2-yl)nicotinamide, 2-(6-cyclopentylpyridin-3-ylamino)-5-fluoro-N-(2-methylbut-3-yn-2-yl)nicotinamide, 2-(3,3-difluorocyclobutyl-amino)-N-(2-methylbut-3-yn-2-yl)-5-(trifluoromethyl)nicotinamide, N-(2-methylbut-3-yn-2-yl)-2-(phenethylamino)nicotinamide, N-(2-methylbut-3-yn-2-yl)-2-(3-phenylpropylamino)nicotinamide, 5-fluoro-2-(3-(4-fluorophenoxy)propylamino)-N-(2-methylbut-3-yn-2-yl)nicotinamide, 5-fluoro-2-(2-(4-fluorophenoxy)ethylamino)-N-(2-methylbut-3-yn-2-yl)nicotinamide, 5-chloro-2-(3-ethoxypropylamino)-N-(2-methylbut-3-yn-2-yl)nicotinamide, 2-(2-tert-butoxyethylamino)-5-chloro-N-(2-methylbut-3-yn-2-yl)nicotinamide, 5-chloro-2-(2-ethoxyethylamino)-N-(2-methylbut-3-yn-2-yl)-nicotinamide, 2-(3-fluoro-4-methylphenylamino)-N-(2-methylbut-3-yn-2-yl)-nicotinamide, 2-(3-chloro-4-methoxyphenylamino)-N-(2-methylbut-3-yn-2-yl)-nicotinamide, 2-(3,5-difluorophenylamino)-N-(2-methylbut-3-yn-2yl)nicotinamide, 2-(3,3-difluorocyclobutylamino)-5-(difluoromethyl)-N-(2-methylbut-3yn-2yl)-nicotinamide, 5-bromo-2-(ethylamino)-N-(2-methylbut-3-yn-2-yl)nicotinamide, 5-ethoxy-N-(2-methylbut-3-yn-2-yl)-2-(propylamino)benzamide, 2-(tert-butylamino)-5-chloro-N-(2-methylbut-3-yn-2-yl)nicotinamide, 2-(3,3-difluorocyclobutylamino)-5-fluoro-N-(2-methylbut-3-yn-2-yl)nicotinamide, 5-fluoro-2-(4-fluorophenylamino)-N-(2-methylbut-3-yn-2-yl)nicotinamide, 5-fluoro-N-(2-methylbut-3-yn-2-yl)-2-(1,1,1-trifluoropropan-2-ylamino)nicotinamide, 4-(4-chlorophenylamino)-N-(2-methylbut-3-yn-2-yl)nicotinamide, 5-fluoro-N-(2-methylbut-3-yn-2-yl)-2-(phenylamino)-nicotinamide, N-(2-methylbut-3-yn-2-yl)-4-(4-(trifluoromethyl)phenylamino)-pyrimidine-5-carboxamide, 2-(tert-butylamino)-5-fluoro-N-(2-methylbut-3-yn-2-yl)nicotinamide, 2-(3,3-difluorocyclobutylamino)-N-(3-ethylpent-1-yn-3-yl)-5-fluoronicotinamide, 2-(3,3-difluorocyclobutylamino)-5-fluoro-N-(3-methylpent-1-yn-3-yl)nicotinamide, 2-(3-fluoro-5-methoxyphenylamino)-N-(2-methylbut-3-yn-2-yl)-nicotinamide, 2-(3-fluoro-5-methoxyphenylamino)-N-(3-methylpent-1-yn-3-yl)-nicotinamide, 2-(3-chloro-5-methoxyphenylamino)-N-(2-methylbut-3-yn-2-yl)-nicotinamide, 2-(3-chloro-5-methoxyphenylamino)-N-(3-methylpent-1-yn-3-yl)-nicotinamide, 2-(2-fluoro-3-methoxyphenylamino)-N-(2-methylbut-3-yn-2-yl)-nicotinamide, 2-(2-fluoro-3-methoxyphenylamino)-N-(3-methylpent-1-yn-3-yl)-nicotinamide, 5-fluoro-2-(4-fluorophenylamino)-N-(3-methylpent-1-yn-3-yl)-nicotinamide, 5-fluoro-N-(3-methylpent-1-yn-3-yl)-2-(phenylamino)nicotinamide, 2-(2,4-difluorophenylamino)-N-(2-methylbut-3-yn-2-yl)nicotinamide, 2-(2,4-difluorophenylamino)-N-(3-methylpent-1-yn-3-yl)nicotinamide, 5-fluoro-2-(3-fluorophenylamino)-N-(2-methylbut-3-yn-2-yl)nicotinamide 5-fluoro-2-(3-fluorophenylamino)-N-(3-methylpent-1-yn-3-yl)nicotinamide, 5-chloro-2-(3,3-difluorocyclobutylamino)-N-(3-methylpent-1-yn-3-yl)nicotinamide, 2-(3-cyanophenyl-amino)-5-fluoro-N-(3-methylpent-1-yn-3-yl)nicotinamide, 2-(2-fluoro-5-methoxy-phenylamino)-N-(2-methylbut-3-yn-2-yl)nicotinamide, 2-(2-fluoro-5-methoxyphenyl-amino)-N-(3-methylpent-1-yn-3-yl)nicotinamide, 2-(3-cyano-4-fluorophenylamino)-N-(2-methylbut-3-yn-2-yl)nicotinamide, 2-(3-cyano-4-fluorophenylamino)-N-(3-methylpent-1-yn-3-yl)nicotinamide, 2-(3-cyano-5-fluorophenylamino)-N-(2-methylbut-3-yn-2-yl)nicotinamide, 2-(3-fluorophenylamino)-N-(3-methylpent-1-yn-3-yl)-nicotinamide, 2-(2-fluorophenylamino)-N-(3-methylpent-1-yn-3-yl)nicotinamide, 2-(3,5-difluorophenylamino)-N-(3-methylpent-1-yn-3-yl)nicotinamide, 2-(3-cyano-5-fluorophenylamino)-N-(3-methylpent-1-yn-3-yl)nicotinamide, 2-(2-chloro-5-methoxyphenylamino)-N-(2-methylbut-3-yn-2-yl)nicotinamide, 2-(2-chloro-5-methoxyphenylamino)-N-(3-methylpent-1-yn-3-yl)nicotinamide, N-(3-methylpent-1-yn-3-yl)-2-(phenylamino)nicotinamide, 2-(4,4-difluorocyclohexylamino)-N-(3-methylpent-1-yn-3-yl)nicotinamide, 2-(3-chloro-4-methoxyphenylamino)-N-(3-methylpent-1-yn-3-yl)nicotinamide, 2-(4-fluoro-3-methoxyphenylamino)-N-(2-methylbut-3-yn-2-yl)-nicotinamide, 2-(4-fluoro-3-methoxyphenylamino)-N-(3-methylpent-1-yn-3-yl)-nicotinamide, 2-(3,4-difluorophenylamino)-N-(3-methylpent-1-yn-3-yl)nicotinamide, 2-(4-chloro-3-methoxyphenylamino)-N-(2-methylbut-3-yn-2-yl)nicotinamide, 2-(4-chloro-3-methoxyphenylamino)-N-(3-methylpent-1-yn-3-yl)nicotinamide, or 2-(4-fluorophenylamino)-N-(3-methylpent-1-yn-3-yl)nicotinamide.

13. A method for the treatment of neuropathic pain, postoperative pain, cancer pain, migraine, asthma, COPD, cough, pain in osteoarthritis, pain in rheumatoid arthritis, or inflammatory bowel disease comprising administering an effective amount of a compound according to claim 12 to a patient in need thereof.

14. A method for the treatment of neuropathic pain, postoperative pain, cancer pain, migraine, asthma, COPD, cough, pain in osteoarthritis, pain in rheumatoid arthritis, or inflammatory bowel disease comprising administering an effective amount of a compound according to claim 1 to a patient in need thereof.

15. A pharmaceutical composition comprising an affective amount of at least one compound according to claim 1 and at least one pharmaceutically acceptable carrier, diluent, or excipient.

16. The method according to claim 13, wherein the neuropathic pain is pain in diabetic polyneuropathy.

17. The method according to claim 14, wherein the neuropathic pain is pain in diabetic polyneuropathy.

\* \* \* \* \*

UNITED STATES PATENT AND TRADEMARK OFFICE
CERTIFICATE OF CORRECTION

PATENT NO. : 9,533,952 B2
APPLICATION NO. : 14/674940
DATED : January 3, 2017
INVENTOR(S) : Riina Arvela et al.

Page 1 of 1

It is certified that error appears in the above-identified patent and that said Letters Patent is hereby corrected as shown below:

In the Claims

Claim 12, Column 154, Line 62, "(1,1-trifluoro-2-methyl -propan-2-" should read
-- (1,1,1-trifluoro-2-methyl -propan-2- --.

Claim 12, Column 155, Lines 4-5, "-4-(2,2,3,3-pentafluoropropylamino" should read -- "-4-(2,2,3,3,3-pentafluoropropylamino --.

Claim 12, Column 155, Line 32, "methylbut-3-yn-2yl" should read -- methylbut-3-yn-2-yl --.

Claim 12, Column 155, Line 34, "methylbut-3yn-2yl" should read -- methylbut-3-yn-2-yl --.

Signed and Sealed this
Thirtieth Day of May, 2017

Michelle K. Lee
*Director of the United States Patent and Trademark Office*